US009521868B2

(12) United States Patent
Cobbett et al.

(10) Patent No.: US 9,521,868 B2
(45) Date of Patent: Dec. 20, 2016

(54) ATHLETIC BAND WITH REMOVABLE MODULE

(71) Applicant: NIKE, Inc., Beaverton, OR (US)

(72) Inventors: Jamian R. Cobbett, Portland, OR (US); Monica Judge, Portland, OR (US); Summer Schneider, Portland, OR (US); Kevin C. Sze, Portland, OR (US); Ariana B. Manesh, Portland, OR (US); Simon Quay, Portland, OR (US); Bill Webb, San Francisco, CA (US); Quin Fitzgerald, San Francisco, CA (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 14/946,674

(22) Filed: Nov. 19, 2015

(65) Prior Publication Data
US 2016/0136882 A1 May 19, 2016

Related U.S. Application Data

(60) Provisional application No. 62/215,497, filed on Sep. 8, 2015, provisional application No. 62/168,357, filed
(Continued)

(51) Int. Cl.
*A41D 20/00* (2006.01)
*A41D 1/00* (2006.01)
(Continued)

(52) U.S. Cl.
CPC .............. *A41D 1/005* (2013.01); *A41D 1/002* (2013.01); *A41D 20/00* (2013.01); *A41D 27/205* (2013.01);
(Continued)

(58) Field of Classification Search
None
See application file for complete search history.

(56) References Cited

U.S. PATENT DOCUMENTS 1,531,994 A    5/1925   Starmer
4,462,116 A *  7/1984   Sanzone .................. A45C 1/04
                                              2/160
(Continued)

FOREIGN PATENT DOCUMENTS

EP    1559335 A2    8/2005
EP    2260910 A1    12/2010
(Continued)

OTHER PUBLICATIONS

Feb. 18, 2016—(WO) Internation Search Report/Written Opinion—App PCT/US15/61691.
(Continued)

*Primary Examiner* — Barbara J Musser
(74) *Attorney, Agent, or Firm* — Banner & Witcoff, Ltd.

(57) ABSTRACT

A manufacturing method uses a main body piece formed of an elastic fabric material and having a first portion having a first end, a second portion having a second end opposite the first end, and two side ends extending between the first and second ends. A bonding material is placed in contact with the first and/or second portions, arranged in lines extending in a direction between the first and second ends. The lines are spaced from each other in a second direction extending between the side ends. The main body piece is folded so that the first portion confronts the second portion, defining a fold line, where the bonding material is positioned between the first and second portions. The folded main body piece is then heat pressed and bent so the side ends are connected together to form a band having a tubular body defining a central passage.

29 Claims, 91 Drawing Sheets

Related U.S. Application Data on May 29, 2015, provisional application No. 62/168,502, filed on May 29, 2015, provisional application No. 62/146,029, filed on Apr. 10, 2015, provisional application No. 62/100,782, filed on Jan. 7, 2015, provisional application No. 62/082,113, filed on Nov. 19, 2014.

(51) Int. Cl.

| | | |
|---|---|---|
| A63B 24/00 | (2006.01) | |
| G08B 6/00 | (2006.01) | |
| G06F 3/02 | (2006.01) | |
| G06F 3/01 | (2006.01) | |
| G06F 1/16 | (2006.01) | |
| A61B 5/0205 | (2006.01) | |
| A61B 5/024 | (2006.01) | |
| A61B 5/11 | (2006.01) | |
| A61B 5/00 | (2006.01) | |
| A41D 27/20 | (2006.01) | |
| B29C 65/02 | (2006.01) | |
| B29C 65/52 | (2006.01) | |
| B29C 65/78 | (2006.01) | |
| B29C 65/00 | (2006.01) | |
| A41H 43/04 | (2006.01) | |
| G06F 19/00 | (2011.01) | |
| B29L 29/00 | (2006.01) | |
| B29L 31/48 | (2006.01) | |
| A45F 5/00 | (2006.01) | |

(52) U.S. Cl.
CPC .............. *A41H 43/04* (2013.01); *A61B 5/0205* (2013.01); *A61B 5/02416* (2013.01); *A61B 5/1118* (2013.01); *A61B 5/4866* (2013.01); *A61B 5/681* (2013.01); *A61B 5/6804* (2013.01); *A61B 5/6824* (2013.01); *A61B 5/6831* (2013.01); *A61B 5/7207* (2013.01); *A61B 5/7221* (2013.01); *A63B 24/0062* (2013.01); *B29C 65/02* (2013.01); *B29C 65/52* (2013.01); *B29C 65/7832* (2013.01); *B29C 66/4324* (2013.01); *B29C 66/71* (2013.01); *B29C 66/729* (2013.01); *G06F 1/163* (2013.01); *G06F 3/016* (2013.01); *G06F 3/0227* (2013.01); *G06F 19/3481* (2013.01); *G08B 6/00* (2013.01); *A41D 2300/52* (2013.01); *A45F 2005/008* (2013.01); *A45F 2200/05* (2013.01); *A61B 2560/0223* (2013.01); *B29K 2623/06* (2013.01); *B29K 2913/00* (2013.01); *B29K 2995/0046* (2013.01); *B29L 2029/00* (2013.01); *B29L 2031/48* (2013.01)

(56) References Cited

U.S. PATENT DOCUMENTS

| | | | |
|---|---|---|---|
| 5,353,793 A | | 10/1994 | Bornn |
| 5,547,115 A | | 8/1996 | Ambrosius et al. |
| 6,178,343 B1 | | 1/2001 | Bindszus et al. |
| 6,425,137 B1 | * | 7/2002 | Fakhrai ................... A45C 1/04 2/170 |
| 8,381,989 B2 | * | 2/2013 | O'Neill ................ A44C 5/0015 235/487 |
| 9,141,087 B2 | | 9/2015 | Brown et al. |
| 2002/0124295 A1 | | 9/2002 | Fenwick et al. |
| 2004/0010199 A1 | | 1/2004 | Hashimoto et al. |
| 2004/0171464 A1 | | 9/2004 | Ashby et al. |
| 2005/0119833 A1 | | 6/2005 | Nanikashvili |
| 2007/0021269 A1 | | 1/2007 | Shum |
| 2007/0261703 A1 | | 11/2007 | Gheneva et al. |
| 2007/0300174 A1 | | 12/2007 | Macbeth et al. |
| 2008/0058668 A1 | | 3/2008 | Seyed Momen et al. |
| 2009/0012542 A1 | | 1/2009 | N'diaye et al. |
| 2009/0292178 A1 | | 11/2009 | Ellis et al. |
| 2010/0010357 A1 | | 1/2010 | Ostrowiecki |
| 2010/0032462 A1 | | 2/2010 | Cameron et al. |
| 2010/0268056 A1 | | 10/2010 | Picard et al. |
| 2011/0205161 A1 | | 8/2011 | Myers et al. |
| 2012/0229248 A1 | | 9/2012 | Parshionikar et al. |
| 2013/0237882 A1 | | 9/2013 | Niemimaki |
| 2013/0267854 A1 | | 10/2013 | Johnson et al. |
| 2014/0107493 A1 | | 4/2014 | Yuen et al. |
| 2014/0176944 A1 | | 6/2014 | Addison et al. |
| 2014/0213863 A1 | | 7/2014 | Loseu et al. |
| 2014/0213917 A1 | | 7/2014 | Hobeika et al. |
| 2014/0316305 A1 | | 10/2014 | Venkatraman et al. |
| 2015/0031964 A1 | | 1/2015 | Bly et al. |
| 2015/0164349 A1 | | 6/2015 | Gopalakrishnan et al. |
| 2015/0169074 A1 | | 6/2015 | Ataee et al. |
| 2015/0182160 A1 | | 7/2015 | Kim et al. |
| 2015/0190072 A1 | | 7/2015 | Armstrong |
| 2015/0257708 A1 | | 9/2015 | Winokur et al. |
| 2015/0370333 A1 | | 12/2015 | Ataee et al. |

FOREIGN PATENT DOCUMENTS

| | | |
|---|---|---|
| WO | 0115286 A1 | 3/2001 |
| WO | 2010015030 A1 | 2/2010 |
| WO | 2014037874 A1 | 3/2014 |

OTHER PUBLICATIONS

Feb. 18, 2016—(WO) International Search Report/Written Opinion—App PCT/US15/61675.
Feb. 18, 2016—(WO) International Search Report/Written Opinion—App PCT/US15/61676.
Shekharappa et al, Correlation between body mass index and cardiovascular parameters in obese and non-obese in different age groups, 2011, Internatinal Journal of Biological & Medical Research, 2(2): 551-555.
Weight Loss Resources, BMI Calculator, 2004, Web, Retreived from: http://www.weightlossresources.co.uk/body_weight/healthy_weight/bmi_calculator.htm.
CNET, First look: Withings Pulse a sleek wireless pedometer and heart rate monitor, 2013, Web Video. Retrieved from: https://www.youtube.comiwatch?v=j8L61s0fYmM.
Ratas, Review of Withings Pulse, 2013, Web, Retrieved from: http://technogog.com/review/reviewofwithingspulse/.
Cambridge University Engineering Department, Materials Data Book, 2003, Web, Rerieved from: http://www.mdpeng.cam.ac.uk/web/library/enginfo/dueddatabooks/materials.pdf.
May 4, 2016—(WO) ISR & WO—App PCT/US15/61694.
Funada S et al: "Body mass index and cardiovascular disease mortality in Japan: The Ohsaki Study", Preventive Medicine, Academic Press, XX, vol. 47, No. 1, Jul. 1, 2009, pp. 66-70.
Apr. 29, 2016—(WO) ISR & WO—App No. PCT/US2015/061644.
Jun. 7, 2016—(WO) ISR & WO—App No. PCT/US2015/061670.

* cited by examiner

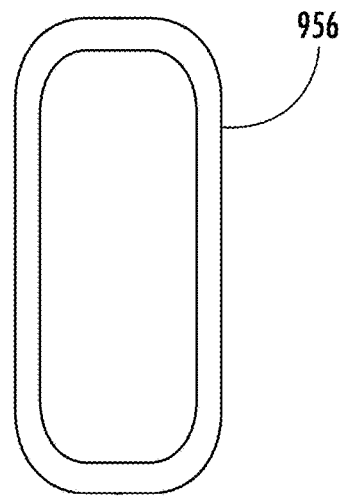
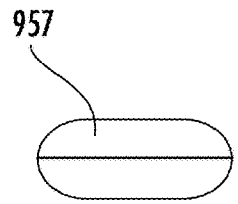
FIG. 26  FIG. 27
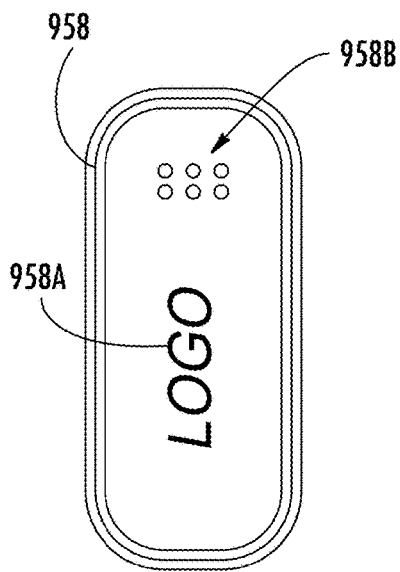
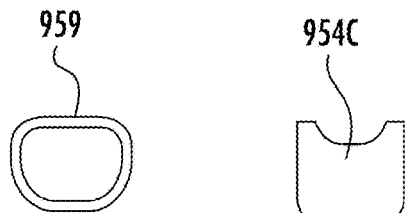
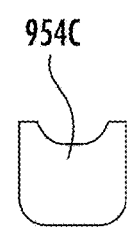
FIG. 28  FIG. 29  FIG. 30

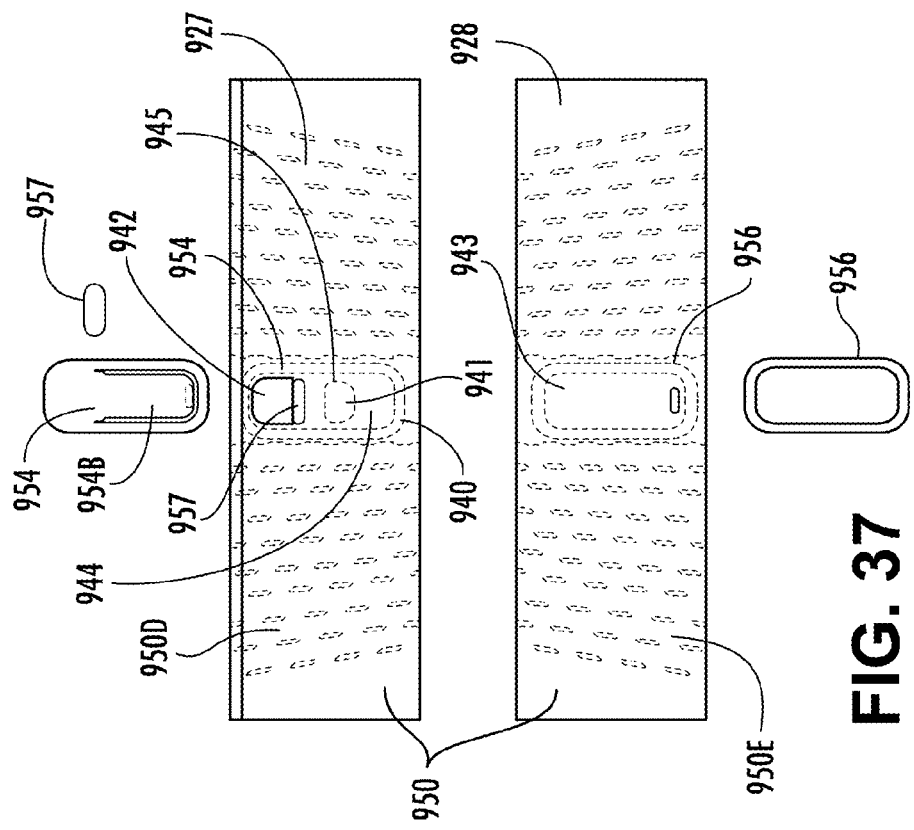
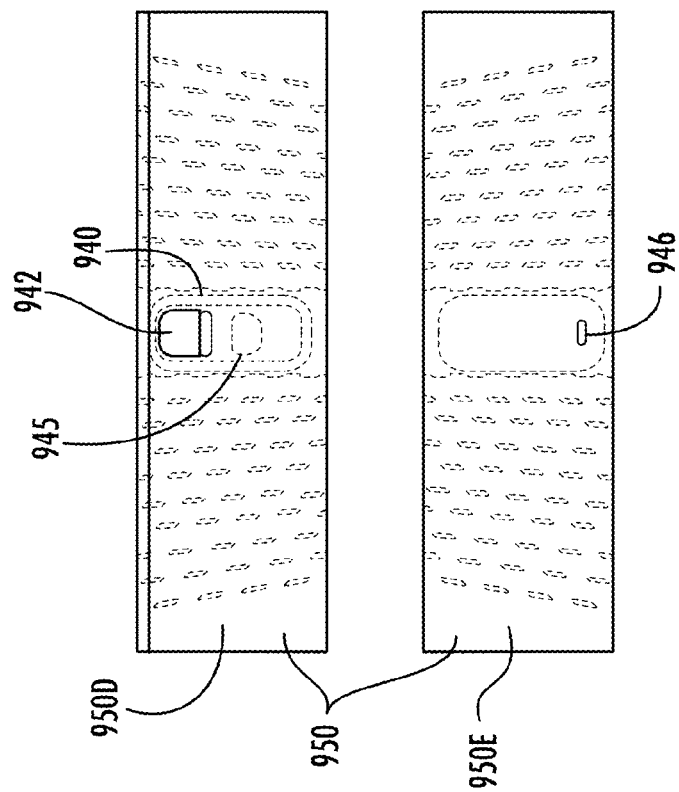
FIG. 37
FIG. 36

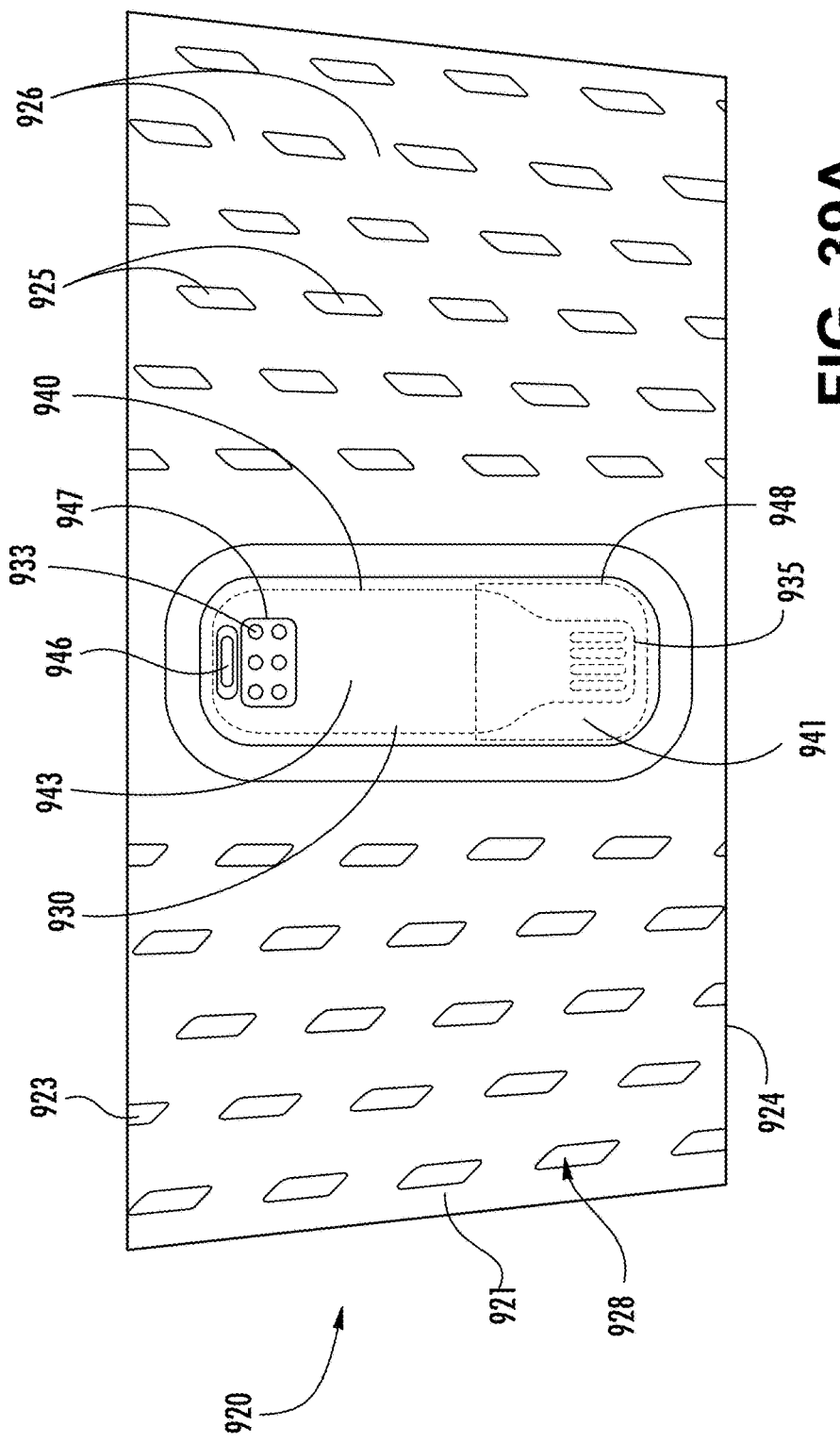

ATHLETIC BAND WITH REMOVABLE MODULE

CROSS-REFERENCE TO RELATED APPLICATIONS

This application is a non-provisional of and claims priority to U.S. Provisional Application No. 62/082,113, filed Nov. 19, 2014; U.S. Provisional Application No. 62/100,782, filed Jan. 7, 2015; U.S. Provisional Application No. 62/146,029, filed Apr. 10, 2015; U.S. Provisional Application No. 62/168,357, filed May 29, 2015; U.S. Provisional Application No. 62/168,502, filed May 29, 2015; and U.S. Provisional Application No. 62/215,497, filed Sep. 8, 2015, which prior applications are incorporated herein by reference and made part hereof.

FIELD OF THE INVENTION

The present invention relates to apparel. Aspects of the disclosure concern, more particularly, an article of apparel that incorporates an electronic device that is retained within the article of apparel yet operable, and may be partially viewable, from outside the article of apparel.

BACKGROUND OF THE INVENTION

When engaged in a physical activity, such as running, an athlete wants to maintain a focus on the activity. Although many mobile devices may be updated to include "apps" or modules that provide athletic or fitness-related information, they are often ineffective for many athletes, including those involved in intense physical activities. Removing an electronic device, such as a mobile phone or music player from a pocket to operate the device can be distracting to the athlete. In addition, the athlete may drop the device while fumbling to remove or replace the device from a pocket. Further, many athletes, including but not limited to professional, semi-professional, and league players are bound by rules and regulations which can greatly restrict the materials worn by the athlete during a game or tournament. Unfortunately, historically acceptable apparel was not designed to allow reliable reception of athletic sensing devices. This disclosure addresses these and other shortcomings of the prior art.

BRIEF SUMMARY

Aspects of the present disclosure include an article of apparel, such as an armband, wristband, shirt, or jacket that is configured to retain an electronic module. The article of apparel has a pocket having an opening to permit insertion and removal of an electronic module.

Aspects of the disclosure relate to a manufacturing method that includes providing a main body piece formed of an elastic fabric material, the main body piece having a first portion having a first end and a second portion having a second end opposite the first end and two side ends extending between the first and second ends. A bonding material is placed in contact with at least one of the first and second portions, where the bonding material is arranged in a plurality of lines extending in a first direction between the first and second ends, and where the lines are spaced from each other in a second direction extending between the side ends. The lines may be curved, straight, or a combination of the two in various configurations. The main body piece is folded by moving the first and second ends together to define a folded main body piece, such that the first portion confronts the second portion, defining a fold line between the first and second portions, where the bonding material contacts the first and second portions and is positioned between the first and second portions. The folded main body piece is heat pressed to seal the bonding material between the first and second portions. The folded main body piece is bent and the side ends are connected together to form a band having a tubular body defining a central passage extending in an axial direction. The band is configured to be worn on a user's body such that a portion of the user's body is received in the central passage, wherein the lines of the bonding material in the band extend in the axial direction.

According to one aspect the method also includes placing a plug between the first and second portions during the heat pressing, such that the plug defines a pocket connected to the band and having an access opening configured to receive an electronic module therein. In one configuration, the main body piece has a hole through the first portion, and the hole defines the access opening. The main body piece may be folded such that the first portion forms an inner surface of the band, and the access opening is located on the inner surface of the band. The main body piece may also have a second hole through the first portion, and the second hole defines a sensor opening in the pocket on the inner surface of the band, the sensor opening configured to permit a sensor permit a sensor of the electronic module to be placed in close proximity to skin of the user's body. Further, the main body piece may have a second hole through the second portion, where the second hole defines a display hole in an outer surface of the band configured to permit viewing a display of the electronic module through the second portion.

According to another aspect, the method includes placing an additional piece of the elastic fabric material in contact with one of the first and second portions to further define a pocket as described above. The additional piece of the elastic fabric material may be a trim piece positioned on an exterior surface of the folded main body piece and extending around the pocket, with the additional piece further having a tongue connected to the trim piece and extending from the trim piece into the access opening.

According to a further aspect, a plurality of additional pieces of the elastic fabric material are placed in contact with at least one of the first and second portions to further define the pocket as described above.

According to yet another aspect, each of the lines of bonding material is a broken line including a plurality of line segments separated by a plurality of gaps. The gaps in each line are staggered with respect to the gaps in each adjacent line, or more specifically, the gaps of a first line may be offset from the gaps of a second line adjacent to the first line, such that the gaps of the first line are aligned with the line segments of the second line, and the gaps of the second line are aligned with the line segments of the first line.

According to a still further aspect, the method includes applying a graphic to an outer surface of the band.

According to an additional aspect, the side ends are cut in an angular shape before the side ends are connected together, such that the band has a varying width.

According to another aspect, a first trim strip is connected to the band to cover the first and second ends, and a second trim strip is connected to the band to cover the side ends.

Additional aspects of the disclosure relate to a manufacturing method including providing a main body piece formed of an elastic fabric material, the main body piece having a first portion having a first end and a second portion having a second end opposite the first end and two side ends extending between the first and second ends, where the main body piece has a hole through the first portion. A bonding material is placed in contact with at least one of the first and second portions, where the bonding material is arranged in a plurality of lines extending in a first direction between the first and second ends, where the lines are spaced from each other in a second direction extending between the side ends, and where each of the lines of bonding material is a broken line including a plurality of line segments separated by a plurality of gaps. The lines may be curved, straight, or a combination of the two in various configurations. The main body piece is folded by moving the first and second ends together to define a folded main body piece, such that the first portion confronts the second portion, defining a fold line between the first and second portions, where the bonding material contacts the first and second portions and is positioned between the first and second portions, and where a first trim strip is connected to the folded main body piece to cover the first and second ends. The folded main body piece is heat pressed to seal the bonding material between the first and second portions, the heat pressing including placing a plug between the first and second portions during the heat pressing and pressing the folded main body piece between opposed dies, such that the plug defines a pocket connected to the band and the hole defines an access opening on the inner surface of the band configured to receive an electronic module therein. The folded main body piece is bent and the side ends are connected together to form a band having a tubular body defining a central passage extending in an axial direction, where the first portion forms an inner surface of the band, such that the access opening is positioned on the inner surface. A second trim strip is connected to the band to cover the side ends. The band is configured to be worn on a user's body such that a portion of the user's body is received in the central passage, where the lines of the bonding material in the band extend in the axial direction.

According to one aspect, the main body piece has a second hole through the first portion, and the second hole defines a sensor opening in the pocket on the inner surface of the band. The sensor opening is configured to permit a sensor permit a sensor of the electronic module to be placed in close proximity to skin of the user's body.

Further aspects of the disclosure relate to a manufacturing method including providing a main body piece formed of an elastic fabric material, the main body piece having a first portion having a first end and a second portion having a second end opposite the first end and two side ends extending between the first and second ends, the main body piece having a hole through the first portion. A housing is placed in contact with the main body piece, the housing being made from a polymer material having a rigidity greater than the elastic fabric material, with the housing defining a cavity and having an access opening permitting access to the cavity. The main body piece is folded by moving the first and second ends together and connecting the first and second ends together to define a folded main body piece, such that the first portion confronts the second portion, defining a fold line between the first and second portions. The housing is positioned between the first and second portions and a portion of the housing including the access opening is received in the hole through the first portion, such that the access opening is accessible. The folded main body piece is bent and the side ends are connected together to form a band having a tubular body defining a central passage extending in an axial direction. The band is configured to be worn on a user's body such that a portion of the user's body is received in the central passage, and the housing defines a pocket that is configured to removably receive an electronic module through the access opening.

According to one aspect, the side ends are cut in an angular shape before the side ends are connected together, such that the band has a varying width.

According to another aspect, a first trim strip is connected to the band to cover the first and second ends, and a second trim strip is connected to the band to cover the side ends.

According to a further aspect, the housing has a flange extending outwardly around at least a portion of a periphery of the housing, where the flange is positioned between the first and second portions after the main body piece is folded. Two opposed mold pieces may be applied to the folded main body piece to heat press the first and second portions around the flange of the housing. Additionally, a trim piece may be applied to the folded main body piece around the hole, where the mold pieces heat press the trim piece to the folded main body piece. The mold pieces may each have an opening so that the mold pieces are configured to press only around the flange.

According to yet another aspect, the main body piece has a second hole through the second portion, and the housing has a window, where the second hole defines a display hole in an outer surface of the band that is aligned with the window and configured to permit viewing a display of the electronic module through the second portion. A bonding material may be placed between the housing and the second portion around the window to bond the second portion to the housing such that the second hole is aligned with the window.

According to a still further aspect, the method also includes applying a graphic to an outer surface of the band.

Still further aspects of the disclosure relate to a manufacturing method including providing a main body piece formed of an elastic fabric material, the main body piece having a first portion having a first end and a second portion having a second end opposite the first end and two side ends extending between the first and second ends, the main body piece having a hole through the first portion. A housing is placed in contact with the main body piece, the housing being made from a polymer material having a rigidity greater than the elastic fabric material, the housing defining a cavity and having an access opening permitting access to the cavity, the housing further having a flange extending outwardly around at least a portion of a periphery of the housing. The main body piece is folded by moving the first and second ends together and the first and second ends are connected together to define a folded main body piece, such that the first portion confronts the second portion, defining a fold line between the first and second portions, wherein a first trim strip is connected to the folded main body piece to cover the first and second ends, and where the flange of the housing is positioned between the first and second portions and a portion of the housing including the access opening is received in the hole through the first portion, such that the access opening is accessible. The folded main body piece is bent and the side ends are connected together to form a band having a tubular body defining a central passage extending in an axial direction, where the first portion forms an inner surface of the band, such that the access opening is positioned on the inner surface, and where a second trim strip is connected to the band to cover the side ends. The band is configured to be worn on a user's body such that a portion of the user's body is received in the central passage, and the housing defines a pocket that is configured to removably receive an electronic module through the access opening.

Other aspects of the disclosure may include any features or combinations of features described above.

Still other features and advantages of the disclosure will be apparent from the following specification taken in conjunction with the following drawings.

BRIEF DESCRIPTION OF THE DRAWINGS

FIGS. 18-30 are top views of components for manufacturing a band according to aspects of the disclosure;

FIGS. 31-38 are plan views schematically illustrating a method of manufacturing a band according to aspects of the disclosure, using the components of FIGS. 18-30;

FIG. 39A is a top view and a side view of another embodiment of a band according to aspects of the disclosure;

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
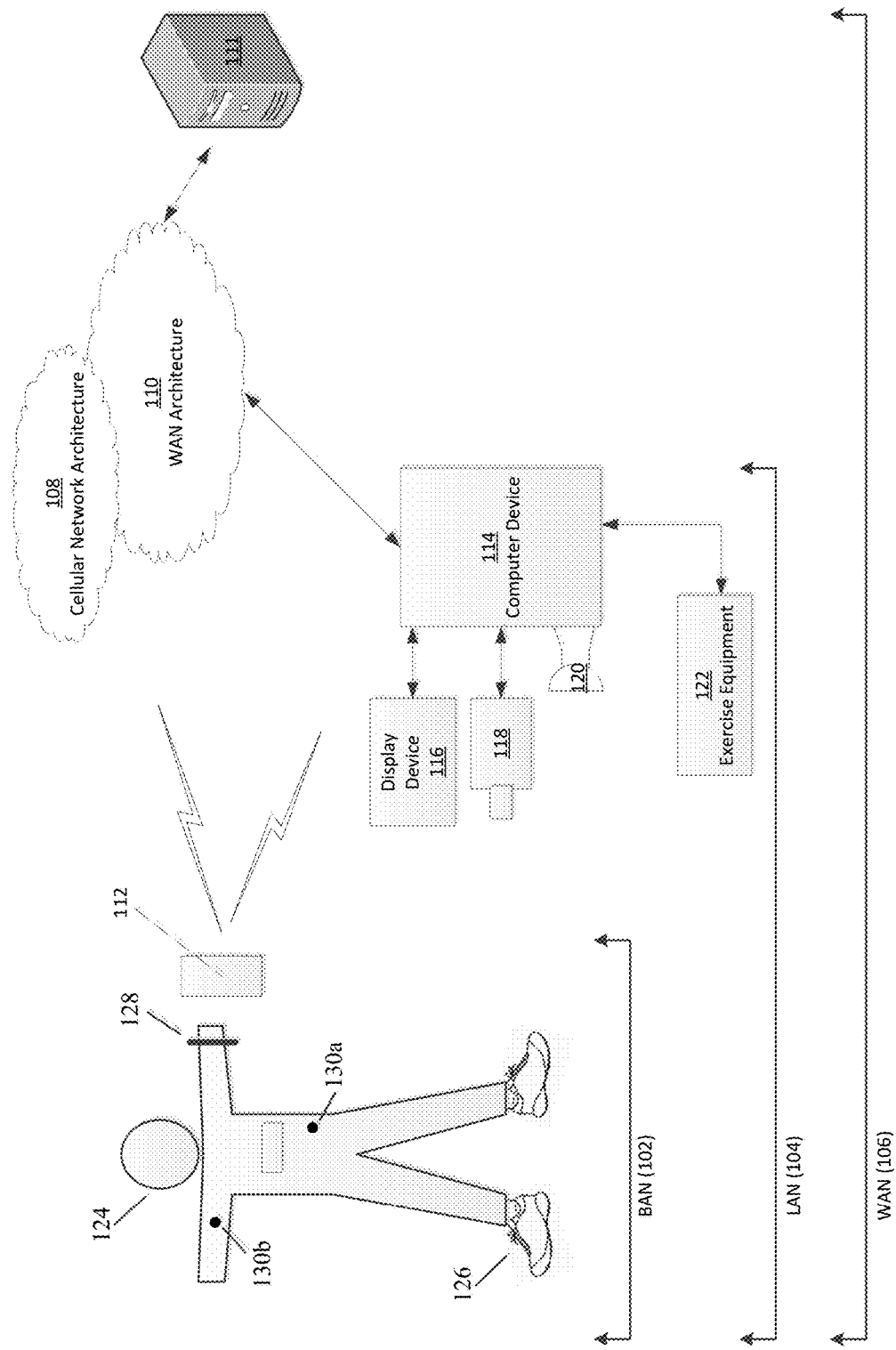
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
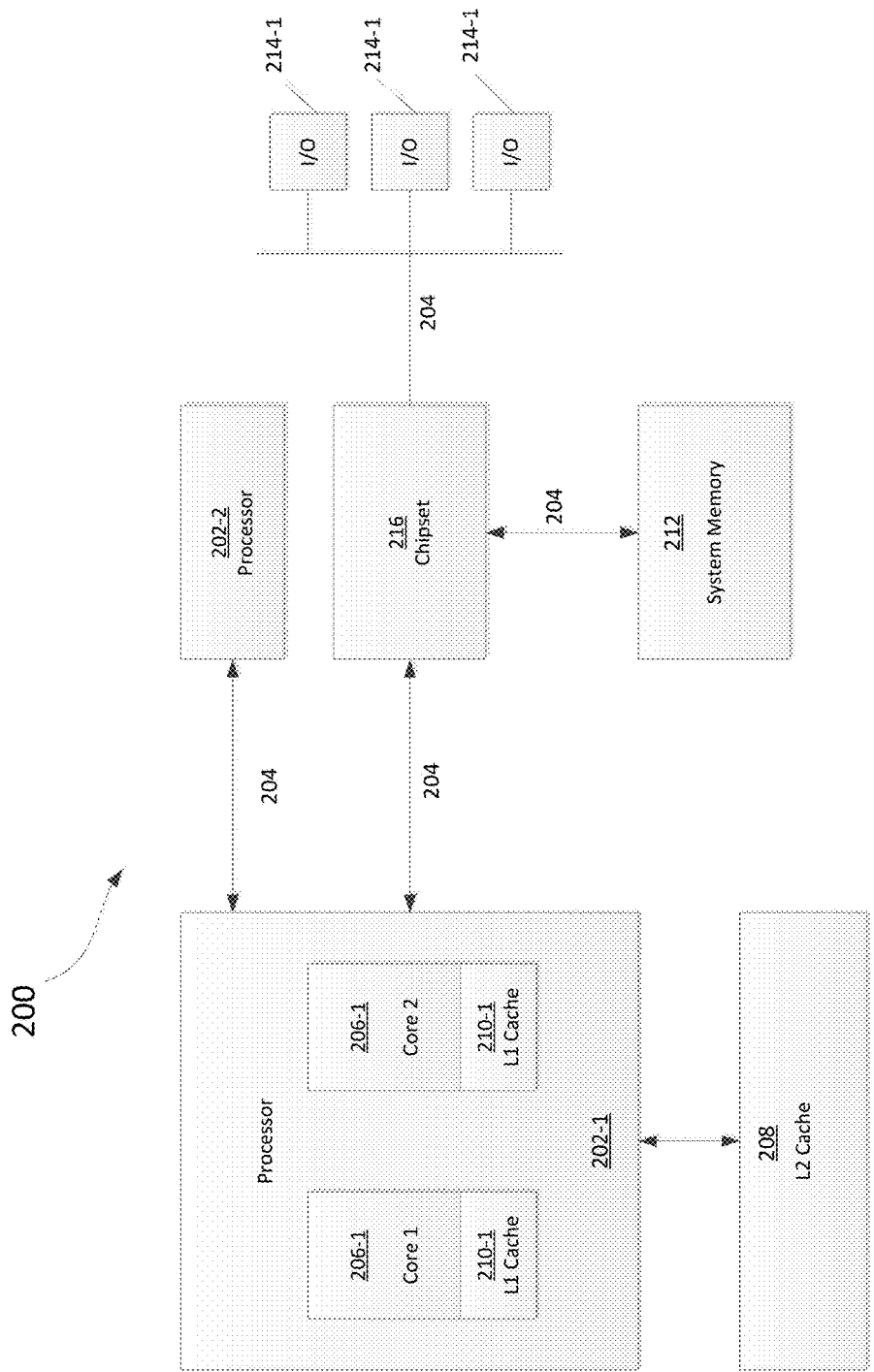
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking web site or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
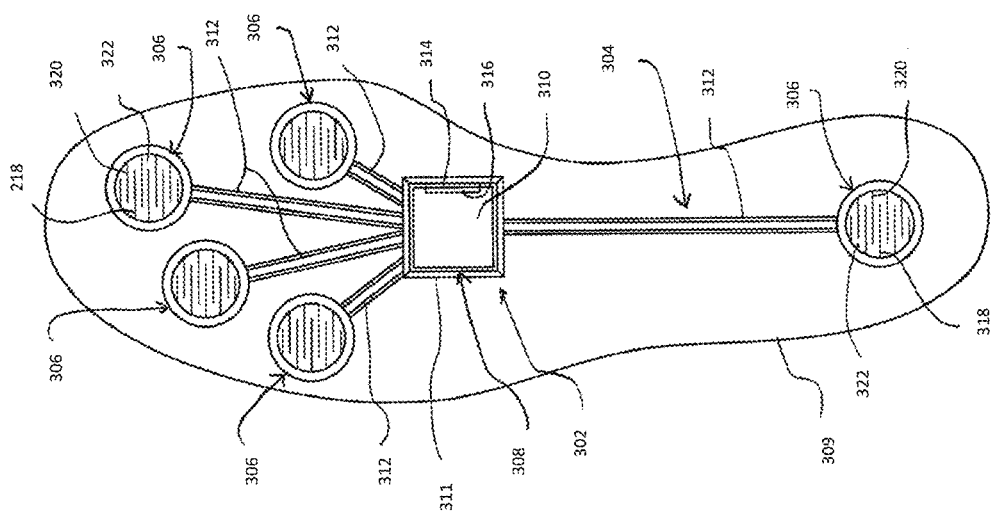
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
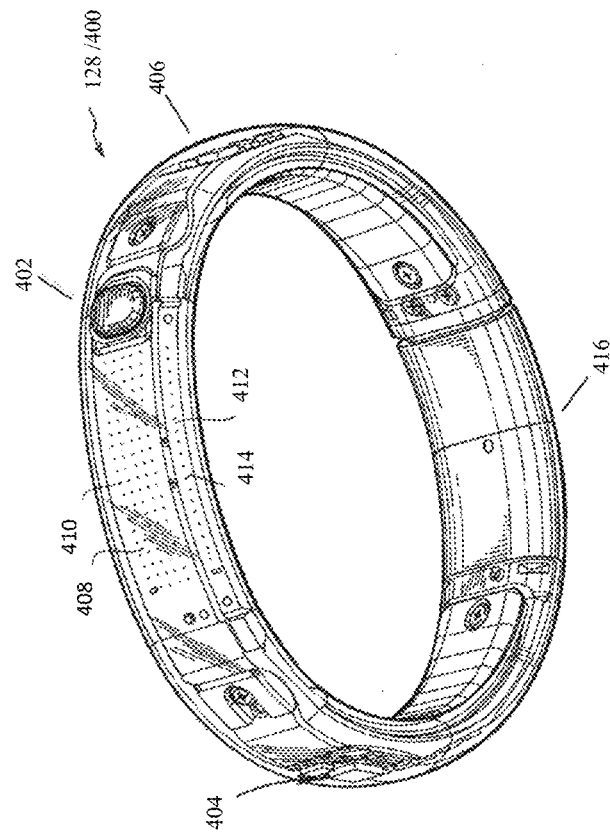
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
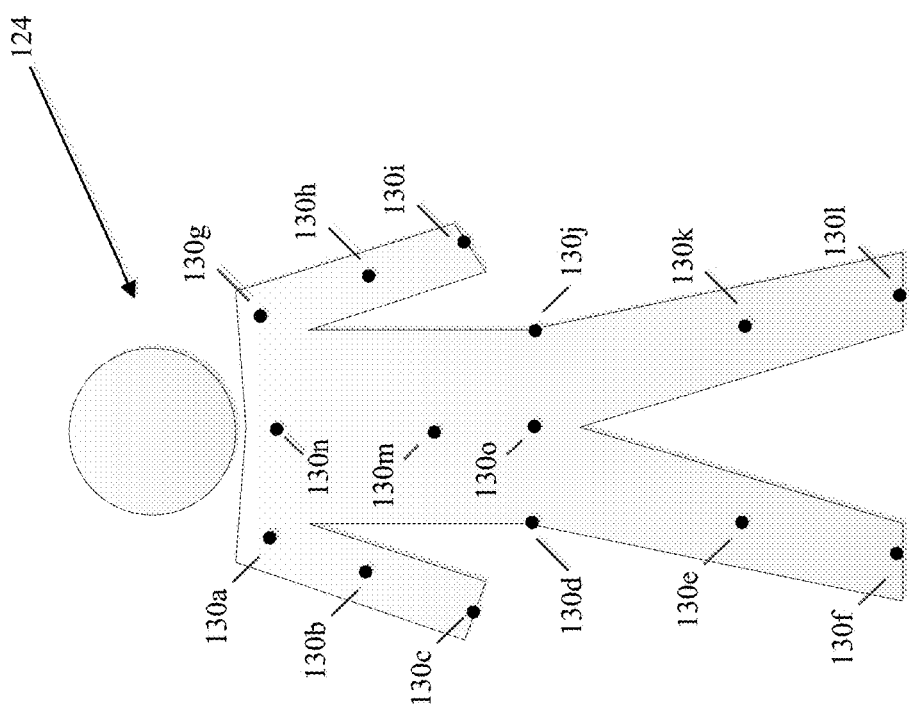
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 1306n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple sensor locations, such as sensors 130m-130o, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130m-130o may serve as a point for a center of moment location of user 124. In another embodiment, one or more locations may serve as a center of moment of specific body parts or regions.

II. Athletic Band with Removable Module

Aspects of this disclosure relate to a system that may measure one or more attributes (e.g., physiological, biomedical, athletic, with the understanding that these may be overlapping examples) of a user during physical movements. In one embodiment, systems and methods may measure one or more attributes of a user while performing intense physical exercise or movements. For example, users may be participating in professional sporting activities, including but not limited to: American football, football, basketball, swimming, or a combination thereof. In one embodiment, systems and methods may consistently provide measurements from a user during exercises in which the system experiences impact forces and/or acceleration magnitudes commonly encountered during intensive activity, such as engaging in professional sports.

Certain aspects relate to a modular system that may firmly retain or otherwise hold at least one sensor against a user's skin during intense physical activities. In one embodiment, the system may be configured to retain a heart rate sensor against a user's skin during the intense physical activity in a manner that allows accurate readings during the activity. The band may further secure at least one sensor against the skin and allow for less than 1 mm of movement of the sensor with respect to the user's skin during the athletic activity or during movements commonly associated with the average forces and/or acceleration magnitudes of the specific athletic activity. In yet another embodiment, the band may be configured such that a removable sensor moves less than 0.5 mm with respect to the surface of the user's skin during the athletic activity. The system may comprise a band 920 configured to be secured against the user's skin or clothing. In one embodiment, the band is configured to be an armband, however, may be configured as a wristband, waistband, or other configuration. In one embodiment, the band 920 is configured to be worn between the user's elbow and wrist. In another embodiment, the band is configured to be worn in a location between the elbow and the shoulder.

Band 920 may be any suitable article of apparel that can be attached to the body such as, but not limited to, bands such as armbands, wristbands, leg bands, and belts. In addition, the article of apparel may be any suitable article of apparel that can be worn on the body such as shirts, jackets, coats, sweatshirts, vests, shorts, and pants, and various other articles of clothing.

In one embodiment, the band 920 may be configured without fasteners configured to retain the band around the arm. In one embodiment, the band may exhibit a modulus of elasticity that allows the band to be retained around an appendage of the user (e.g., arm) in a manner that fasteners are not required to secure the band 920 to the appendage to obtain accurate sensor readings during the activity, which may be intense athletic activity. In yet another embodiment, fasteners may be utilized to connect at least a portion or portions of the band together for attachment to the appendage. Any suitable fasteners may be used such as Velcro, snaps, buttons, buckles, and zippers as is within the skill of the art.

In another aspect of the invention, as shown in the figures herein, a wrist band or armband may be a continuous tubular band made of an elastic material that can be pulled onto the wrist or arm. As discussed below, a pocket (e.g., pocket 940) may be attached to, or formed integrally with, the band 920. As further discussed below, band 920 may be configured to comprise a "pocket" configured to retain an electronic module. In this regard, the band may form a seal or other surface around a portion of the user's skin in a manner that distributes forces such that at least a portion of the band 920 is held against the user's skin with a less force per unit area compared to any surface of an electronic module 930 held in the pocket 940 is pressed against the skin when the user is wearing the band 920. Band 920 may further be configured such that a certain portion of ambient light is blocked from contacting the user's skin under the band 920. In this regard, band 920 may block light in one or more specific regions and/or over the entire area covered by the band during normal use. In one embodiment, at least 75% of ambient light is blocked from reaching the area of the band immediate proximate to where a sensor extends from an aperture of the band and contacts the surface of the user's skin.

Figure 11:
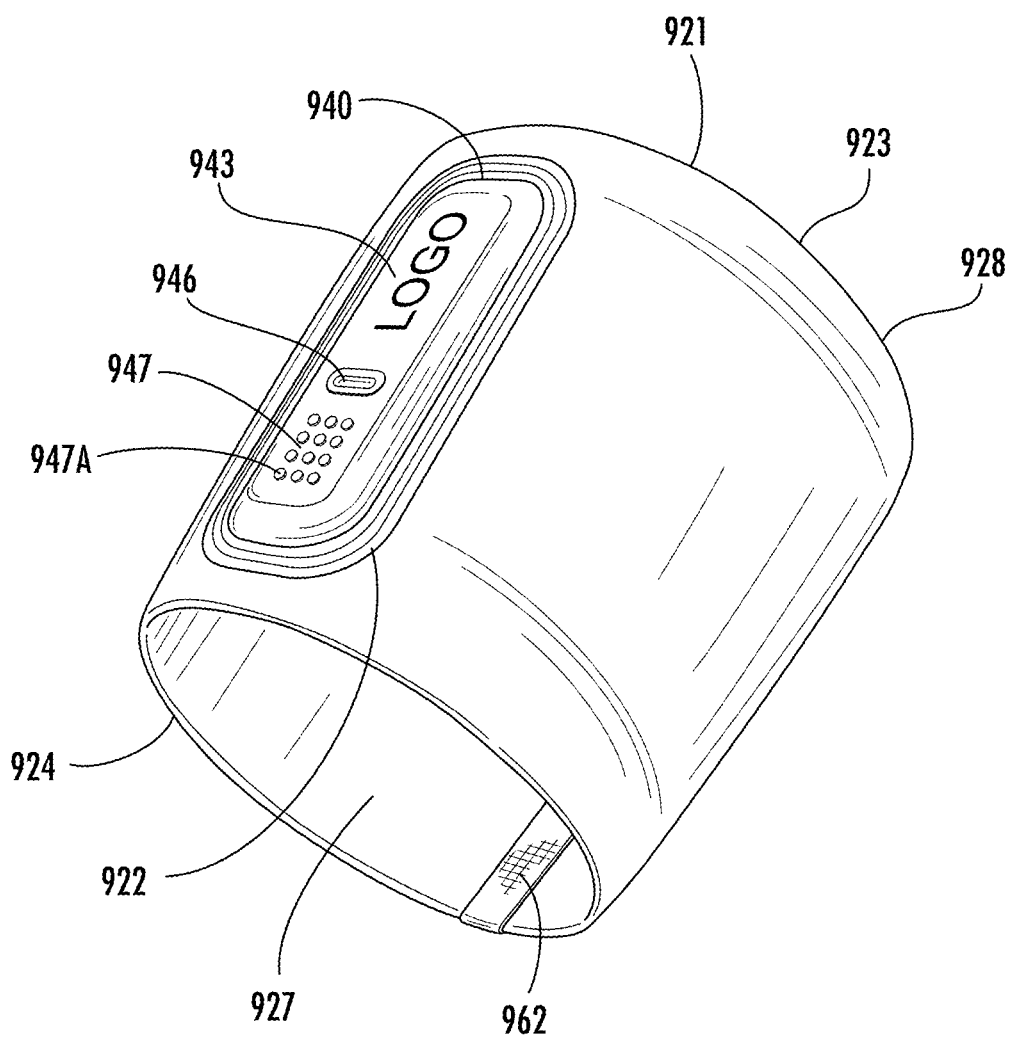
FIG. 11 is a perspective view of one embodiment of a band according to aspects of the disclosure.
Figure 12:
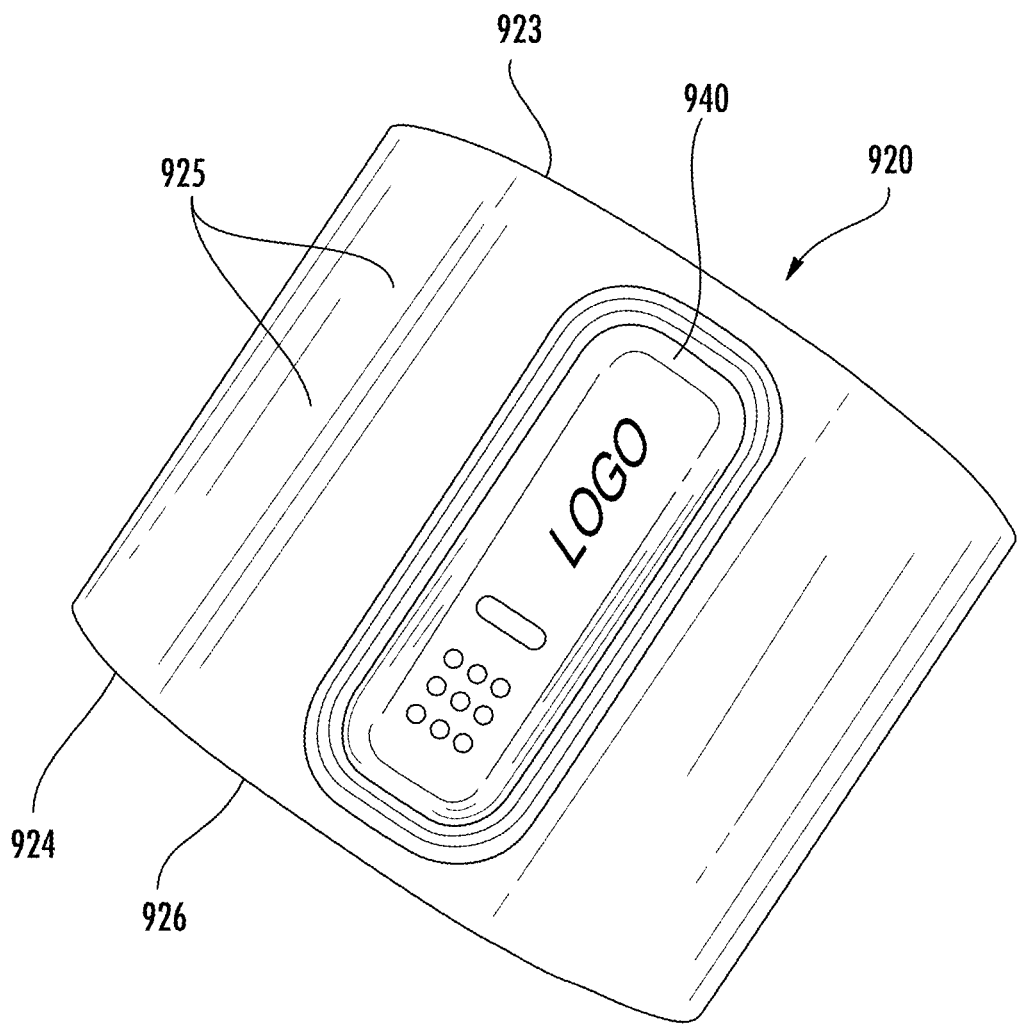
FIG. 12 is a top view of the band of FIG. 11.
Figure 39B:
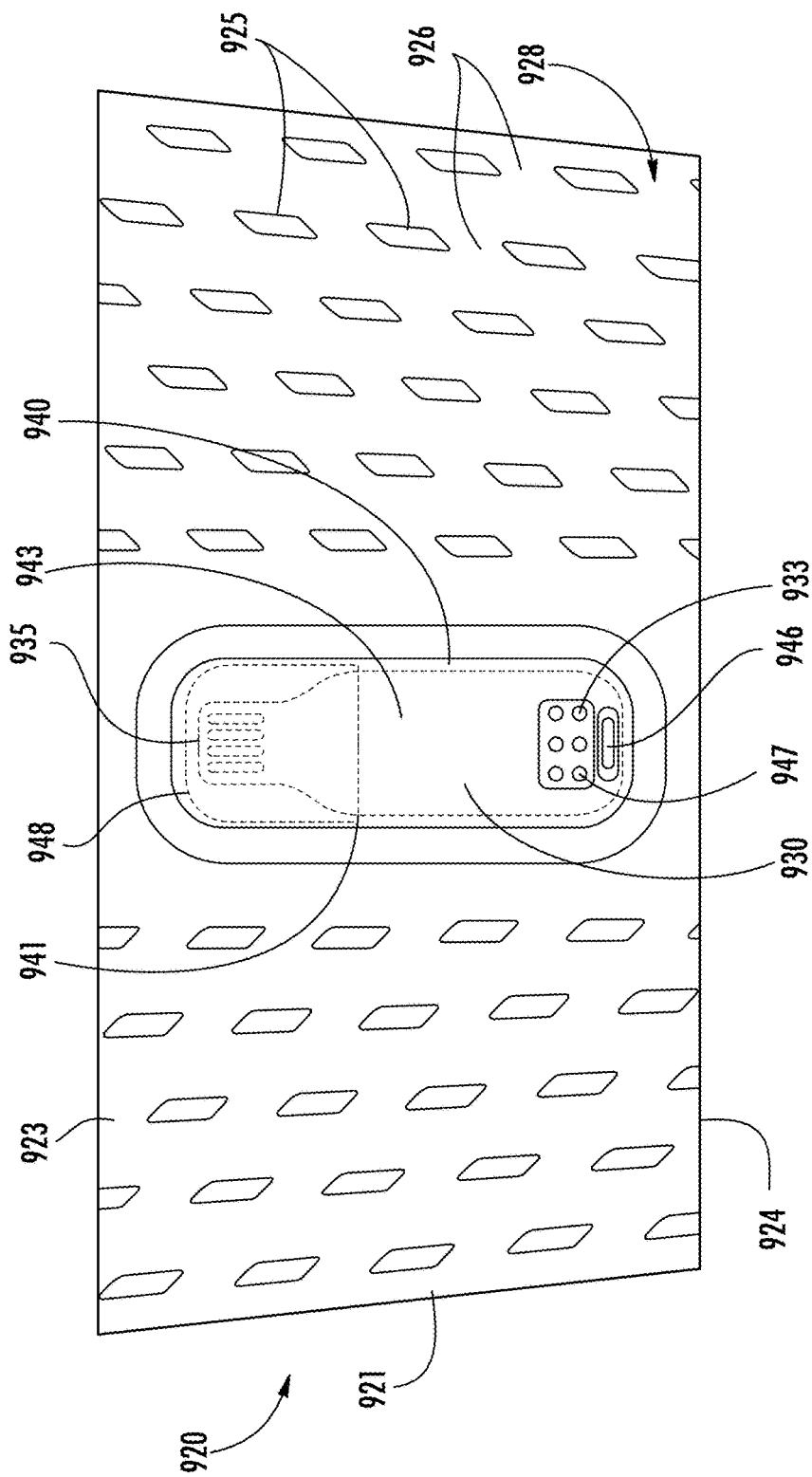
FIG. 39B is a top view and a side view of another embodiment of a band according to aspects of the disclosure.
Figure 96:
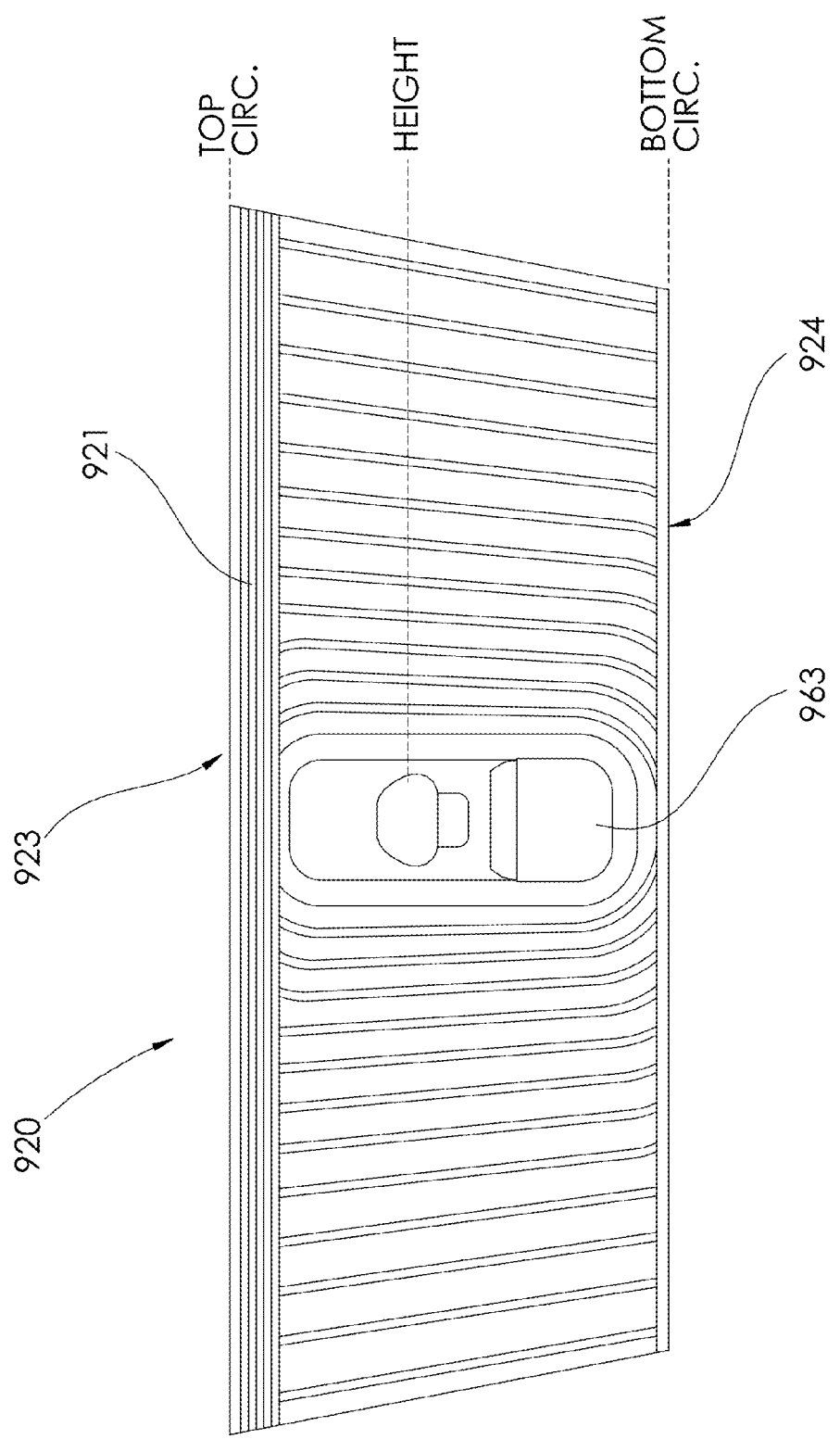
FIG. 96 is a bottom view of another embodiment of a band according to aspects of the disclosure, illustrating certain physical dimensions of the band.

Generally, the device includes a band 920 configured to be worn by or otherwise attached to the body of a user and a module 930 configured to be connected to the band 920, in order to be worn by or otherwise attached to the user. The band 920 may be an armband in one embodiment, as illustrated in FIGS. 11-12, which is configured to be worn on the upper forearm of the user, just below the elbow. FIGS. 39A-B also illustrate embodiments similar to the embodiments of FIGS. 11-12. The band 920 in this embodiment includes a tubular body 921 defining a central passage 922, such that the user's arm is received through the passage 922 and the tubular body 921 wraps around the arm. The tubular body 921 is somewhat frusto-conical in shape in the embodiment shown, with a wider top end 923 configured to be positioned closer to the elbow, and an opposite narrower bottom end 924 configured to be positioned closer to the wrist, where the arm is typically smaller. The frusto-conical shape of the tubular body 921 may assist in resisting slipping of the band 920 when worn on the user's forearm during activity. Without being bound to a particular theory, evidence indicates that the tendency of the band 920 to slip decreases with a decrease in the proportional difference between the size of the top end 923 and the size of the bottom end 924 (e.g., the "slope" of a cross-section of the tubular body 921). FIG. 96 illustrates how the slope of an edge 994 of the tubular body 921 can be determined, with respect to the Axis X. In other words, the closer the size of the bottom end 924 is relative to the top end 923, the less likely slippage is to occur (within limits). Evidence also indicates that larger-size bands 920 are more likely to slip than smaller-size bands 920. Accordingly, larger-size bands 920 may be provided with a smaller difference between the diameter of the top end 923 and the bottom end 924 relative to that of smaller-size bands 920 in one embodiment, in order to reduce slippage in the larger-size bands 920.

Various different "slopes" defined on the tubular body 921 may be relevant to the degree of slippage of the band 920. FIG. 96 illustrates multiple different slopes that may be calculated relative to the Axis X, which is perpendicular to the top and bottom ends 923, 924, using a reference point Height H in the calculation of the slopes. The Height H represents a circumferential line that is parallel to the ends 923, 924 of the band 920 and is positioned approximately 70% of the distance between the bottom end 924 and the top end 923, i.e., the approximate location of the sensor 932 when the module 930 is positioned within the housing 963. It is understood that reference point Height H may be located differently if the band 920 is configured differently, in order to create a different sensor 932 position. It has been found that the overall slope of the tubular body 921 and the Slope B (between the bottom end 924 and the Height H) have the greatest effect on slippage, and as these slopes approach zero, the reported incidence of slippage is reduced. In the embodiment shown in FIG. 96, the Slope A and Slope B are equal to each other, and are also equal to the overall slope of the tubular body 921. In other embodiments, Slope A and Slope B may be different from each other, and one or both of Slope A and Slope B may be different from the overall slope of the tubular body 921. It is understood that any of these slopes may be an "average" slope, and that the tubular body 921 may have a curvilinear or other non-linear edge profile.

Figure 96A:
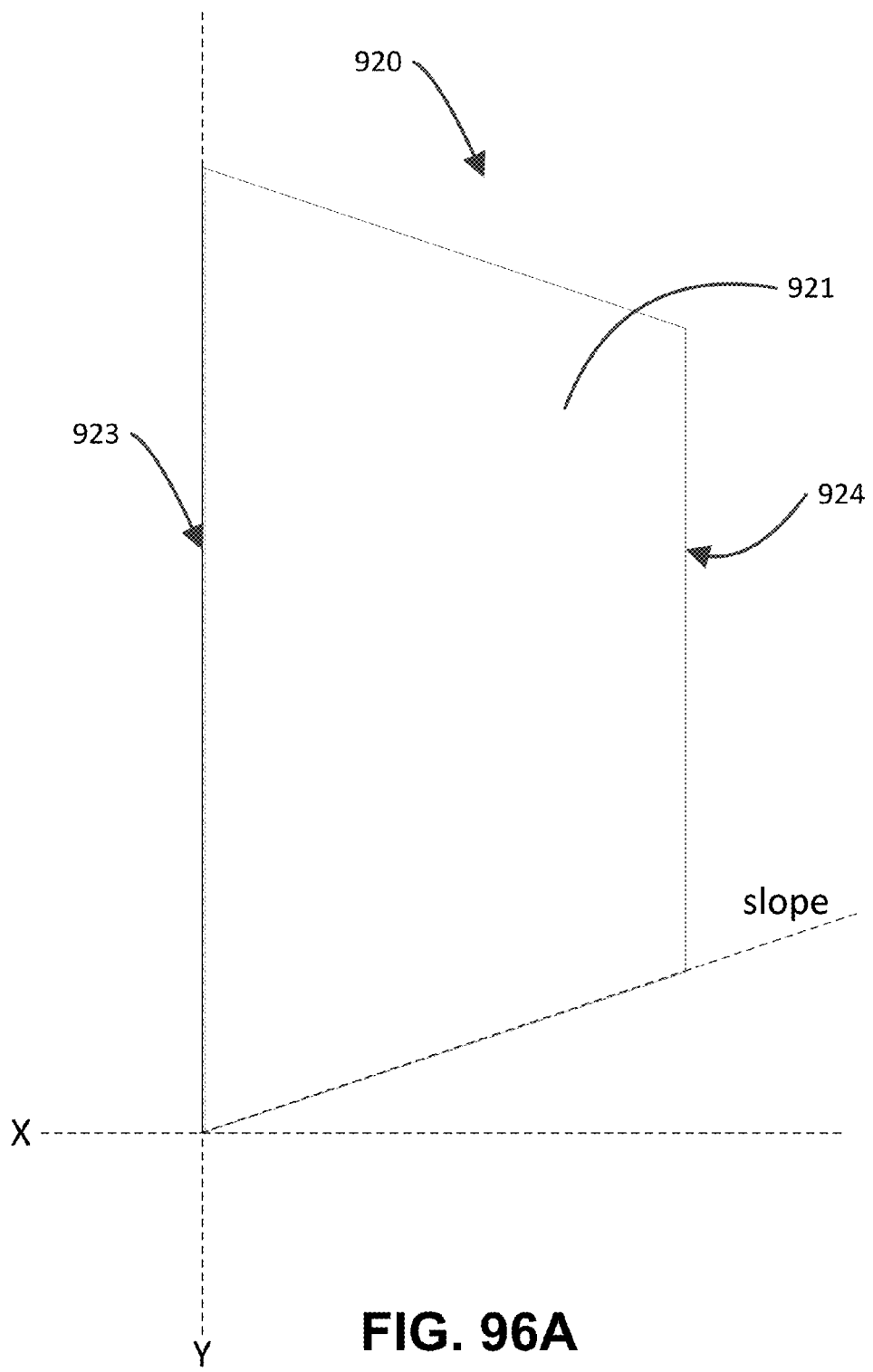
FIG. 96A is a schematic view of one embodiment of a band according to aspects of the disclosure, illustrating the calculation of the slope of the band.

As stated above, the overall slope of the tubular body 921 may affect the fit and slippage probability of the band 920. The overall (average) slope of the tubular body 921 may be calculated by drawing a straight virtual line between the intersection point of the Axis X and the top end 923 of the band 920 and the end point of the bottom end 924 of the band 920, as shown in FIG. 96A. A short-hand way to perform this calculation is to use the difference in circumference or diameter between any two points along the height of the tubular body 921 (e.g., between the top end 923 and the bottom end 924) to determine the slope. This virtual line may be considered to be the combination of the lines Slope A and Slope B in FIG. 96, although Slope A and Slope B may be different from each other in other embodiments. Slope A or Slope B may also affect the fit and slippage probability of the band 920, and these slopes may be calculated as averages in the same manner described above with respect to the overall slope of the tubular body 921. In one embodiment, the overall slope of the tubular body 921, the Slope A, and/or the Slope B may be from 0-0.75, or about 0.65. In another embodiment, the overall slope of the tubular body 921, the Slope A, and/or the Slope B may be from 0-0.5, or about 0.4. In a further embodiment, the overall slope of the tubular body 921, the Slope A, and/or the Slope B may be from 0-0.3, or from 0-0.15. For smaller sizes of bands 920 (e.g., maximum diameter of 200 mm or below), the overall slope of the tubular body 921, the Slope A, and/or the Slope B may be closer to zero than for larger sizes. It is understood that if the overall slope of the tubular body 921 is zero, the dimensions of the top and bottom ends 923, 924 may be equal or approximately equal, such that the top end 923 is not wider than the bottom end 924.

In another embodiment, a similarly structured band 920 may be configured to be worn elsewhere on the body. For example, the band 920 may be configured to be worn elsewhere on the arm, such as on the upper arm, the wrist, the hand, etc. As another example, the band 920 may be configured to be wrap around a different body part of the user, such as various locations on the leg, neck, torso, head, etc. It is understood that the dimensions and contours of the band 920 may be adjusted for wrapping around different body parts.

In one embodiment, the band 920 may be formed of a flexible, elastic material that can stretch to allow the user to comfortably wear the band 920 and to place the band 920 on and off of the user's body, e.g., an elastic fabric. The band 920 may be made from two or more layers of material that are joined together, and which may be part of a single piece folded over to create multiple layers. FIGS. 11-12 illustrate one embodiment of the band 920, and FIGS. 14-17, 39A-B, and 68-70C illustrate similar embodiments with some different features, as described herein.

In the embodiments shown in FIGS. 11-17 and 39A-B, the band 920 is made from a piece of fabric that is folded over onto itself to form two layers and joined by adhesive applied between the two layers. The adhesive may be formed into a pattern in some embodiments, which may be visible in the finished product, creating a distinct visual appearance. The adhesive pattern may also be functional, such as in controlling the maximum degree of stretching of the band 920, controlling the locations of stretching or other deformation of the band 920, enhancing the durability of the band 920, and/or other functions. As shown in FIGS. 12, 14, and 39A-B, the adhesive is applied in a plurality of lines 925 extending in the axial direction (i.e., between the ends 923, 924) along the band 920 and spaced circumferentially from each other. In these configurations, radial stretching of the band 920 occurs between the lines 925, and the adhesive lines 925 provide low-stretch areas. The bands 920 in FIGS. 12, 14, and 39A-B have broken or discontinuous adhesive lines 925 (i.e., line segments), having one or more gaps 926 along each line 925. Additionally, the gaps 926 of each line 925 in this embodiment are offset or staggered from the gaps 926 of the adjacent lines 925. In another embodiment, the band 920 may have solid adhesive lines 925 (which may be straight and/or curved), such as in FIGS. 40A-B, or one or more solid blocks of adhesive. The configurations of the adhesive lines 925 in FIGS. 12, 14, 39A-B, and 40A-B provides several advantages. First, the lines 925 extending axially allows most of the radial stretching of the band to occur between the lines 925, so that the modulus or elastic response of the elastic material of the band 920 controls the amount of stretching. Additionally, the lines 925 extending axially permits the adhesive of the lines 925 to have a more significant influence on the modulus or elastic response of the band 920 in the axial direction, thus limiting the amount of axial stretching that occurs. This is beneficial to avoid excess stretching as the band 920 is pulled onto the user's body (e.g., forearm), so that the band 920 slides as desired, rather than wasting user-exerted energy by stretching the band. The "offset" of the gaps 926 also helps limit axial stretching. Further, the intermittent application of the adhesive lines 925 provides greater breathability, as the fabric of the band material is typically more breathable than the adhesive. In another embodiment, the band 920 is made from a piece of fabric that is folded over onto itself to form two layers and joined around the ends 923, 924, such as by adhesive, stitching, etc.

Figure 38:
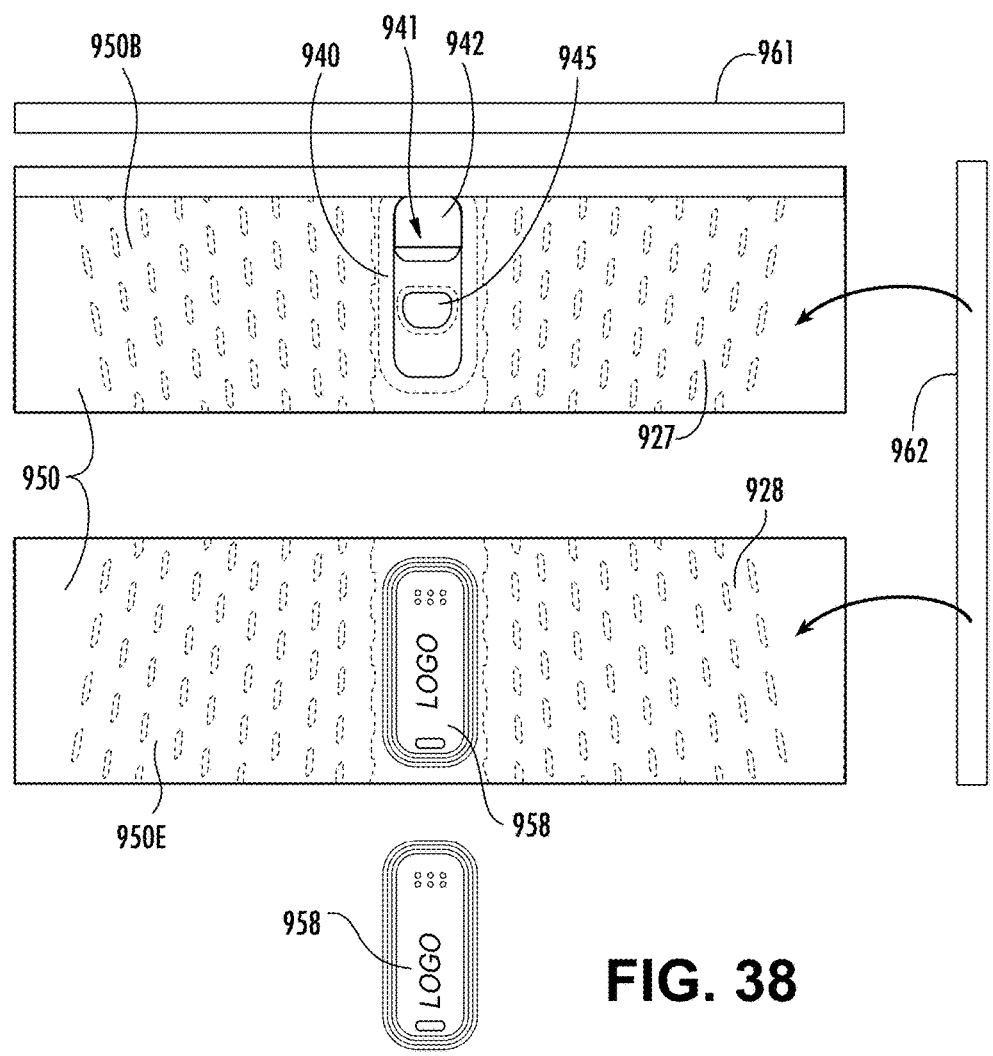

The band 920 is generally configured to hold an electronic module 930, which may be removable from the band 920. In one embodiment, the band 920 has a pocket 940 defining a cavity 941 configured to receive the module 930 in a removable configuration. In one embodiment, as illustrated in FIGS. 11-12, the pocket 940 is accessible from an inner surface 927 of the band 920 that is configured to confront and/or contact the user's body. FIGS. 36-38 illustrate components of the pocket 940 as well. In this configuration, the pocket 940 has an access opening 942 defined on the inner side 927 of the band 920, and the module 930 can be inserted and removed through the opening 942. The band 920 may be flipped inside-out in order to facilitate this access. The pocket 940 in each embodiment shown in FIGS. 11-17 and 36-39A-B has an outer wall 943 that forms part of the outer surface 928 of the band 920 and an inner wall 944 that forms part of the inner surface 927 of the band 920, with the cavity 941 defined between the walls 943, 944. These walls 943, 944 are at least somewhat flexible in one embodiment, and may be made of a single layer and/or piece or multiple layers and/or pieces. In other embodiments, the walls 943, 944 may be rigid, and may be made of the same material or a different material as other portions of the band 920. The access opening 942 is defined within the inner wall 944 at one end of the cavity 941 in the embodiment of FIGS. 11-14 and 36-39A-B, such that the module 930 is inserted by inserting one end of the module 930 (the USB connector 135 in one embodiment) into the opening 942 and then pushing the rest of the module 930 through the opening 942 and into the cavity 941.

FIGS. 39A-B illustrate embodiments of the band 920 with the module 930 inserted into the pocket 940. In FIG. 39A, the pocket 940 is configured for insertion of the module 930 with the light 934 and the button 933 positioned nearer the top end 923 of the band 920 (i.e., nearer the user's elbow) and the connector 935 positioned nearer the bottom end 924 of the band 920 (i.e., nearer the user's wrist). This is similar to the configuration of FIG. 14. In FIG. 39B, the pocket 940 is configured for insertion of the module 930 with the light 934 and the button 933 positioned nearer the bottom end 924 of the band 920 (i.e., nearer the user's wrist) and the connector 935 positioned nearer the top end 923 of the band 920 (i.e., nearer the user's elbow). This is similar to the configuration of FIGS. 11-12. It is understood that the access opening 942 (not shown in FIGS. 39A-B) may be located near the top end 923 in FIG. 39A and near the bottom end 924 in FIG. 39B. The configuration in FIG. 39B may provide greater ergonomics and ease of use. For example, viewing the light 934 and pushing the button 933 may require less movement and more natural movement when these components are located nearer the wrist. Also, the force of pushing the button 933 compresses the user's arm, and if the button 933 is nearer the wrist where the bone is closer to the skin, there is less soft tissue that can compress under the force of the button pushing. In the configuration of FIG. 39B, the protective shell 948 (described below) protects the connector 935, as it is located in an area where users may grip to pull the band 920 on the arm.

Figure 13A:
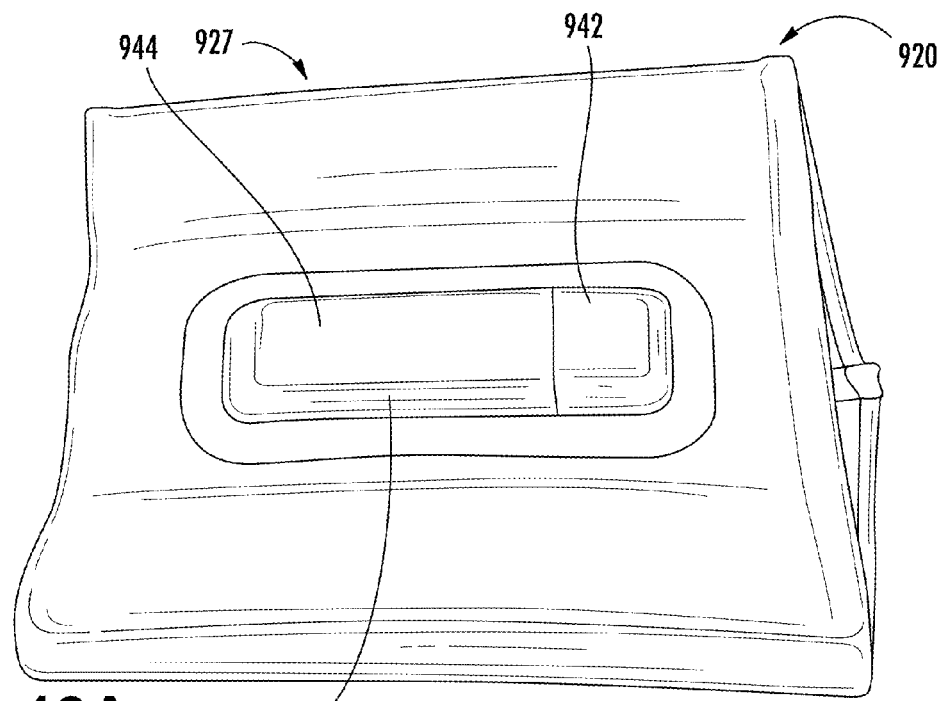
FIGS. 13A-B are perspective views of another embodiment of a band according to aspects of the disclosure, turned inside-out.
Figure 13B:
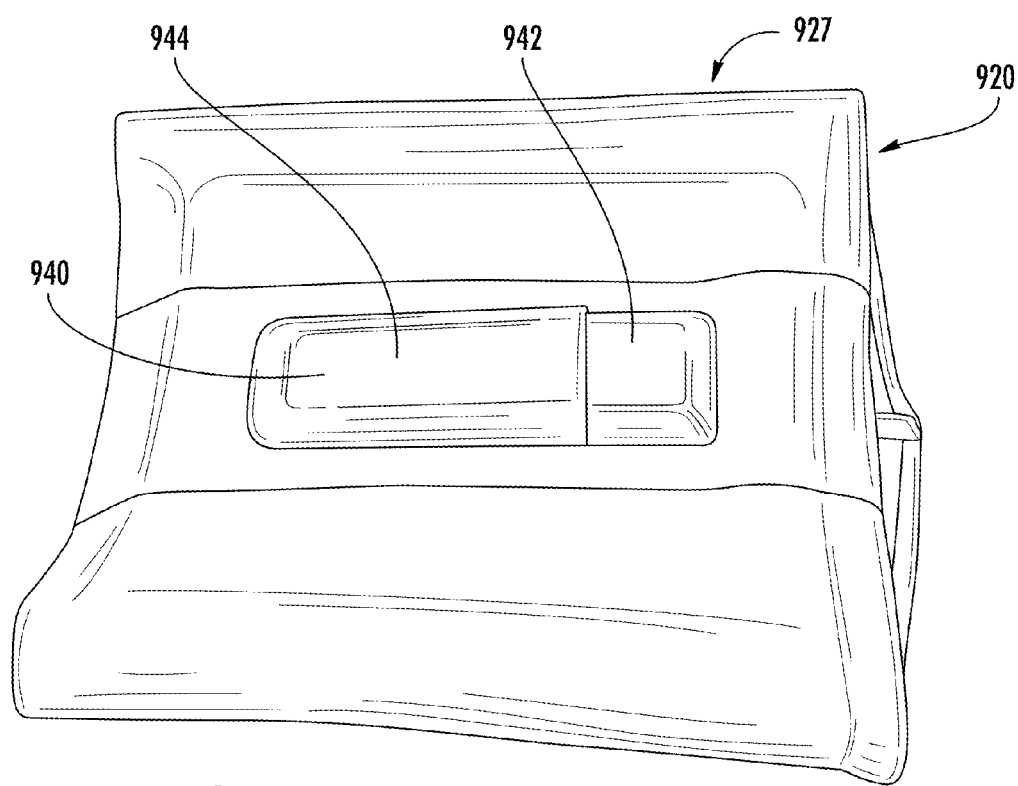
Figure 14:
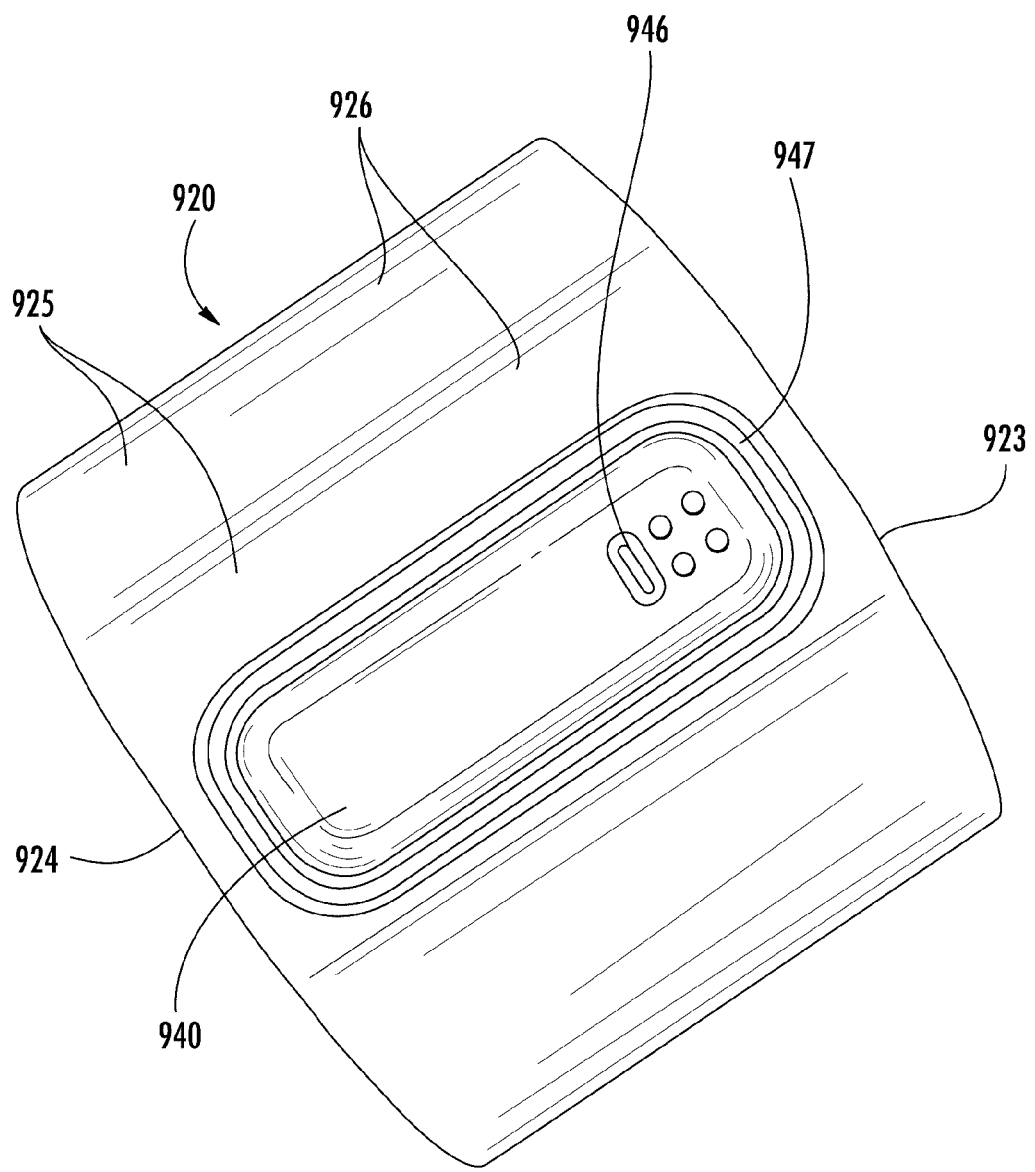
FIG. 14 is a top view of another embodiment of a band according to aspects of the disclosure.

FIGS. 13A-B illustrate another configuration for inserting the module 930 into a pocket 940 with an access opening 942 on the inner surface 927 of the band 920.

The pocket 940 may also include one or more sensor openings 945 configured to permit the sensor(s) 932 of the module 930 an unimpeded path to sense the user's body directly, such as by contacting the user's body (e.g., a heart rate sensor) or otherwise interacting directly with the user's body (e.g., an optical, heat, or other radiation-based sensor). In the embodiment illustrated in FIGS. 36-38, the pocket 940 has a single sensor opening 945 on the inner wall 944 that is separate from the access opening 942. In other embodiments, the sensor opening 945 may be contiguous with the access opening 942, such that only a single opening is defined in the inner wall 944, and/or the pocket 940 may have multiple sensor openings 945. One example of this configuration is illustrated in FIGS. 68-70C and 78-82.

The outer wall 943 of the pocket is configured to cover the module 930, and may be configured to permit reading and/or manipulation of the module through the outer wall 943. For example, the outer wall 943 may include one or more windows 946 to permit viewing of a display of the module 930. Such a window 946 may be an opening in the outer wall 943 or a transparent or translucent portion that allows viewing of a light or lighted display therethrough. In the embodiments shown in FIGS. 11-14 39A-B, and 68-70C, the outer wall 943 has a window 946 to permit viewing of a single light, and may additionally or alternately have one or more windows 946 configured to permit viewing of a plurality of LEDs on the module 930 (i.e., a readable display). It is understood that the pocket 940 may have one or more windows 946 configured to be complementary with the structure of the module 930.

As another example, the outer wall 943 may have one or more button portions 947 that are configured to allow manipulation of one or more buttons 933 of the module 930 through the outer wall 943. It is understood that "buttons" may include mechanical/electrical buttons, a touch-screen interface, or other manually operable components. The button portion 947 may simply be a flexible portion of the outer wall 943 that permits the user to press the button portion 947 to activate the button 933 of the module 930, as shown in FIGS. 11-14. The outer wall 943 may further have one or more flex zones (not shown) to control flexing of the outer wall 943 and/or portions of the band 920, such as a concave or indented portion having greater flexibility. In another embodiment, the button portion 947 may have a button mechanism (or mechanisms) that actuates the button(s) 933 of the module 930. In a further embodiment, the button portion 947 may double as a window 946, such as if the module 930 has a button with a light on it (see FIG. 42) or if the module 930 has a lighted touch-screen display. The outer wall 943 may further have indicia 947A, such as indications of the location(s) of the button(s) 933 on the module 930, logos, instructions, etc.

Figure 16:
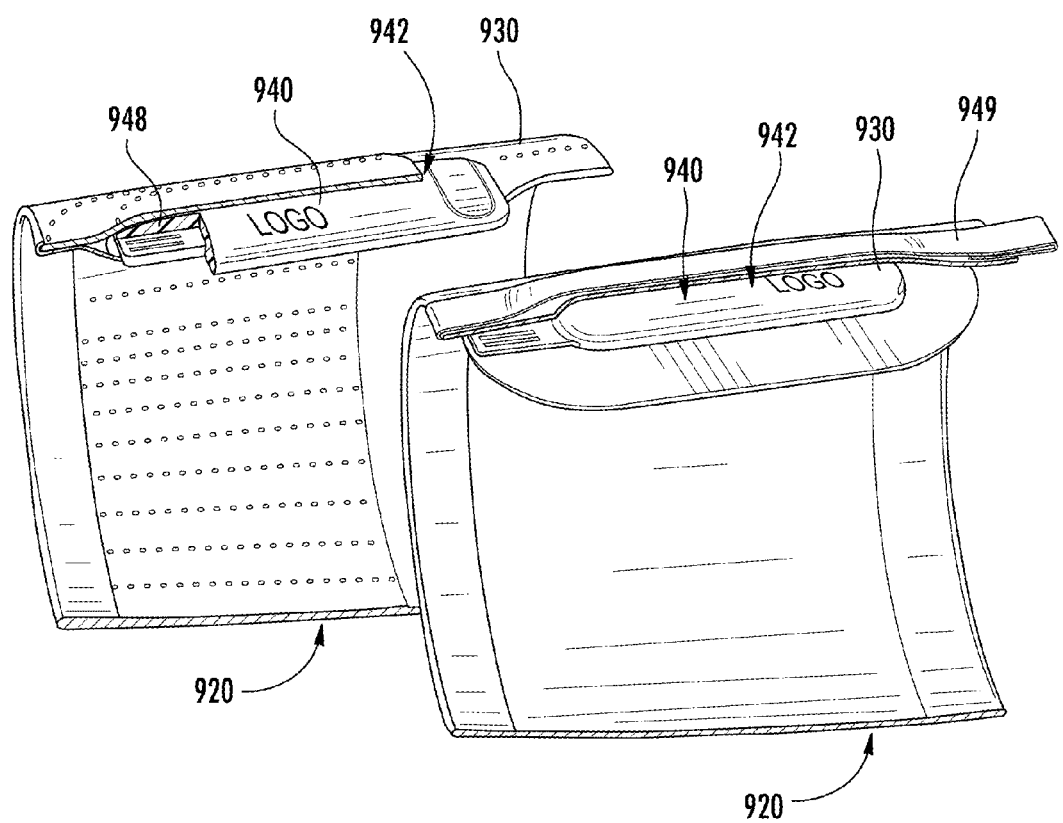
FIG. 16 shows two cross-section views of two additional embodiments of a band according to aspects of the disclosure.

The pocket 940 may further include a protective shell 948 within the cavity 941 to protect at least a portion of the module 930. The shell 948 may be formed of a rigid material, such as a rigid plastic or fiber reinforced polymer (e.g., thermoplastic polyurethane), a metallic material, or other material. In the embodiment of FIGS. 11-14, the walls 943, 944 of the pocket 940 are flexible, and the shell 948 is received within the cavity 941 and positioned at the end opposite the access opening 942. In this configuration, the shell 948 receives and protects the USB connector 935 of the module 930. The shell 948 may further have structure to retain the module 930 once the module 930 is inserted, such as a friction fit configuration, complementary interlocking structure with the module 930, etc. The shell 948 may also have structures that produce audible and/or tactile indications when the module 930 is fully inserted, in order to indicate to the user that the module 930 is fully inserted. These audible/tactile indications may be used with or without the locking structure, and may interact with the connector 935. The shell 948 may be retained within the pocket 940 by adhesive or other bonding material, friction fit, various mechanical connection techniques, etc. In other embodiments, the shell 948 may cover a greater or smaller proportion of the module 930, or the pocket 940 may have no shell at all. FIG. 16 also illustrates a protective shell 948 in one configuration.

Figure 15A:
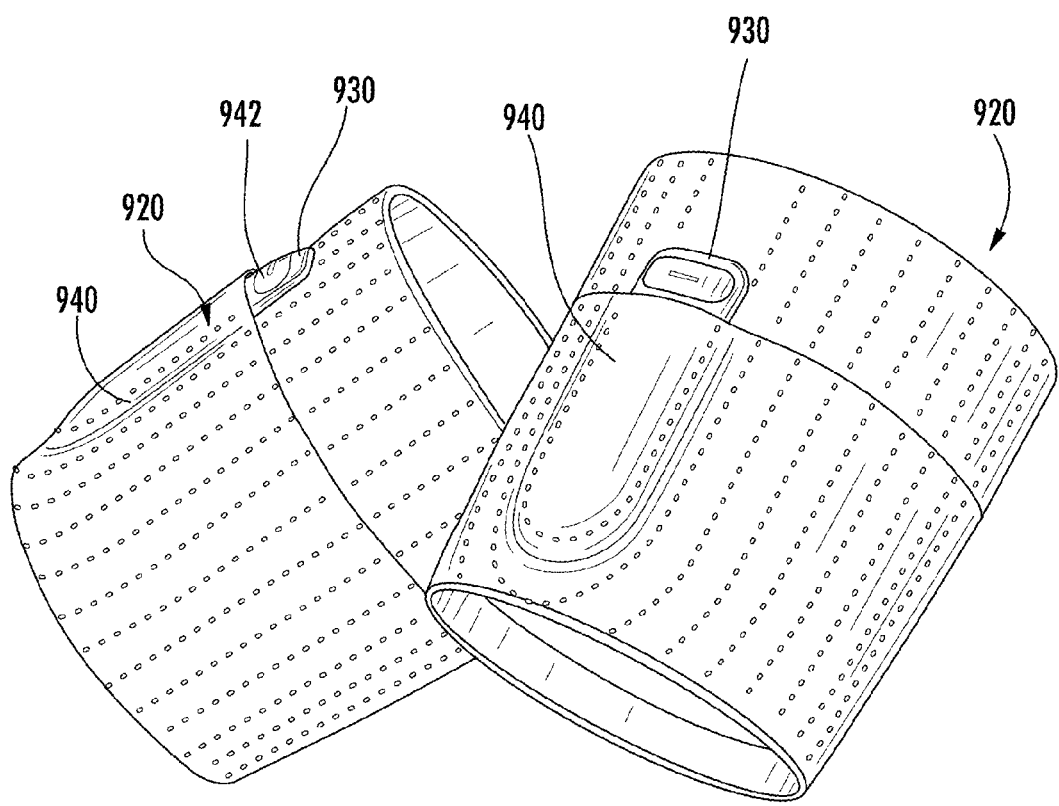
FIG. 15A is a perspective view and a side view of another embodiment of a band according to aspects of the disclosure.
Figure 15B:
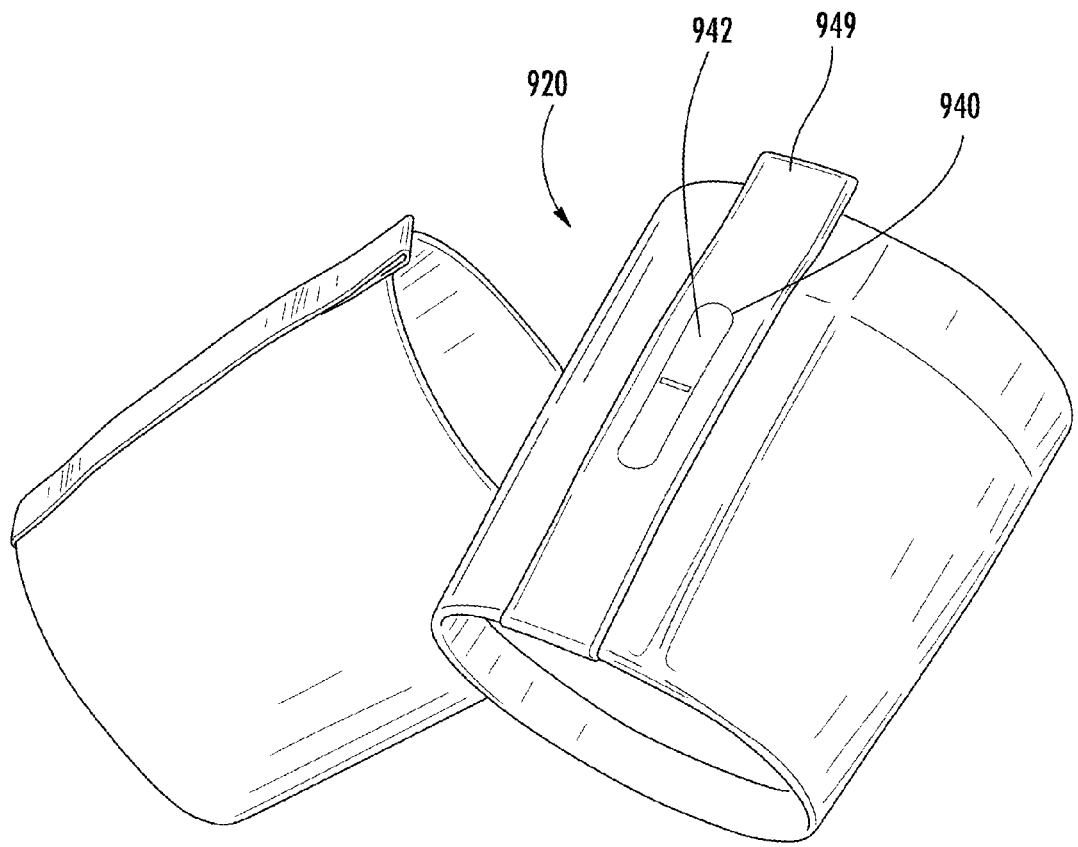
FIG. 15B is a perspective view and a side view of another embodiment of a band according to aspects of the disclosure.
Figure 17:
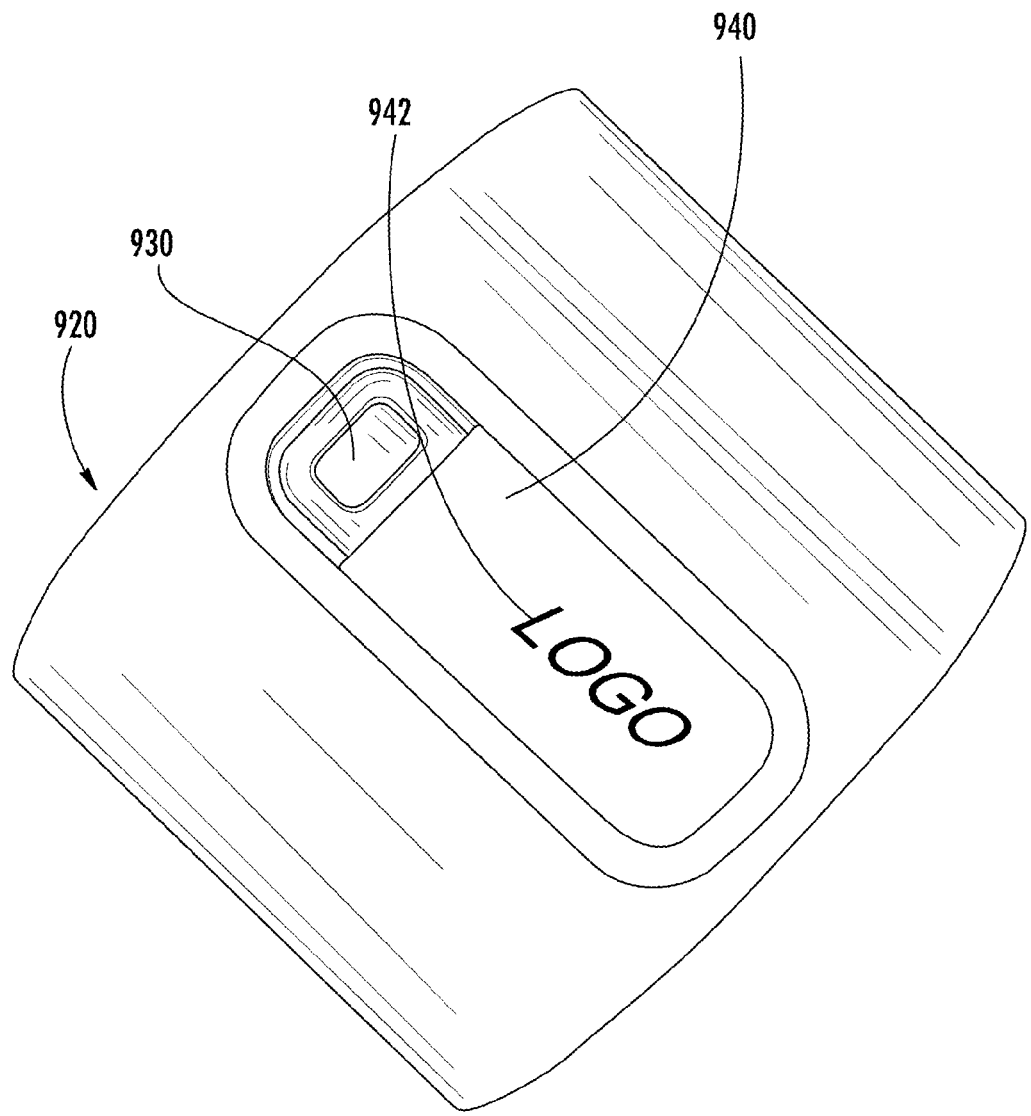
FIG. 17 is a top view and a side view of another embodiment of a band according to aspects of the disclosure.

In other embodiments, illustrated in FIGS. 15A-17, the band 920 may have the access opening 942 on the exterior of the band 920. For example, FIG. 15A illustrates an embodiment where the access opening 942 is exposed on the outer surface 928 of the band 920, and the module 930 can be inserted through the access opening 942 into the cavity 941. The module 930 in this embodiment is inserted similarly to the technique described above, by inserting the end of the module 930 first through the opening 942. As another example, FIG. 15B illustrates an embodiment where the access opening 942 is much larger and is nearly the same size as the cavity 941. In this embodiment, the entire module 930 is pushed downward into the cavity 941 through the opening 942, and then a securing member 949 is used to secure the module 930 within the pocket 940. The securing member 949 in this embodiment is a strap with a releasable connection, such as hook-and-loop material, a mechanical fastener (e.g., a snap or button), or other releasable connection. In other embodiments, the securing member 949 may have a different configuration, such as a cap, a flap, a tab, or other structure. FIG. 16 illustrates cross-sections of both of these embodiments. FIG. 17 illustrates an embodiment where the module 930 is inserted similarly to the embodiment of FIG. 15A.

Figure 18:
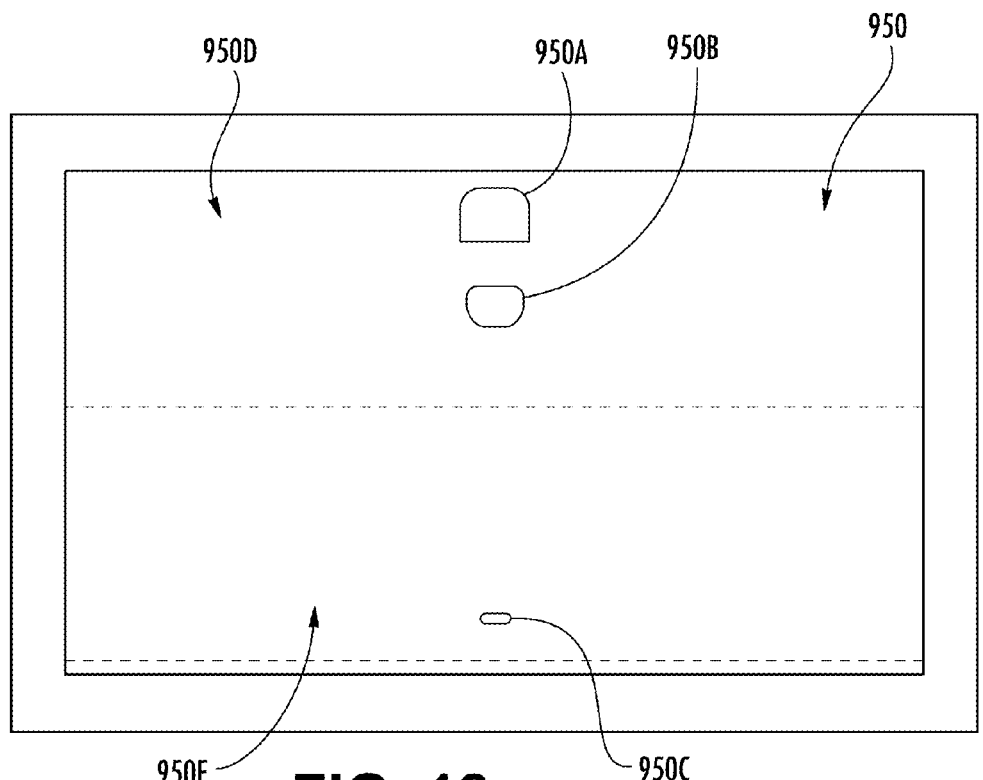
Figure 19:
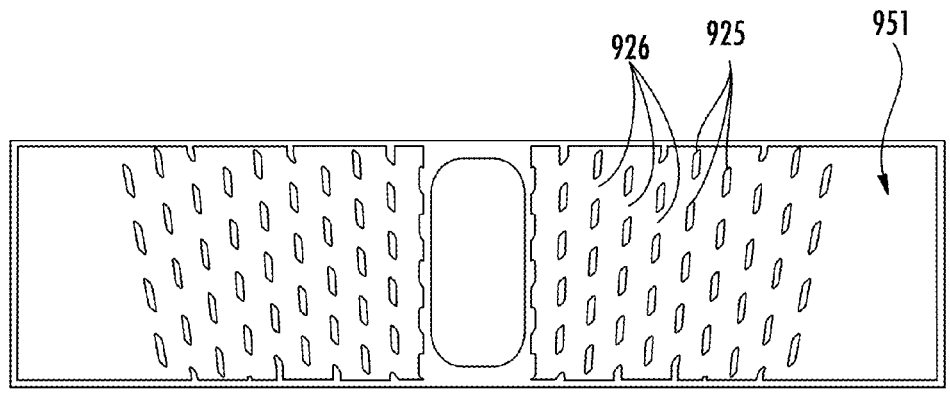
Figure 20:
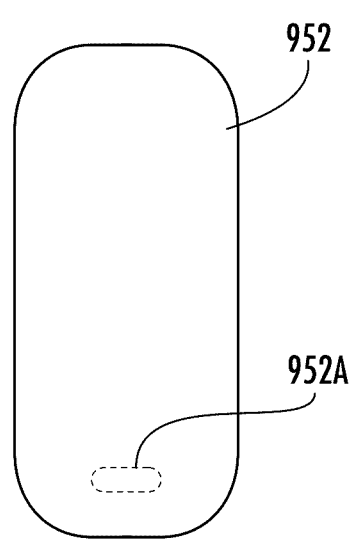
Figure 21:
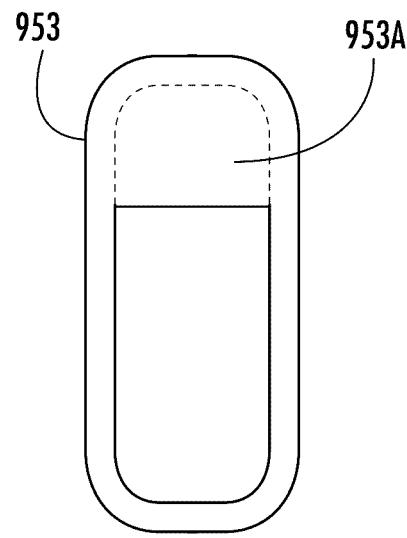
Figure 22:
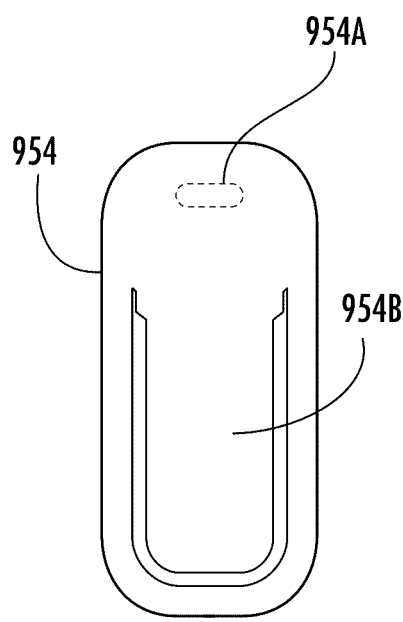
Figure 23:
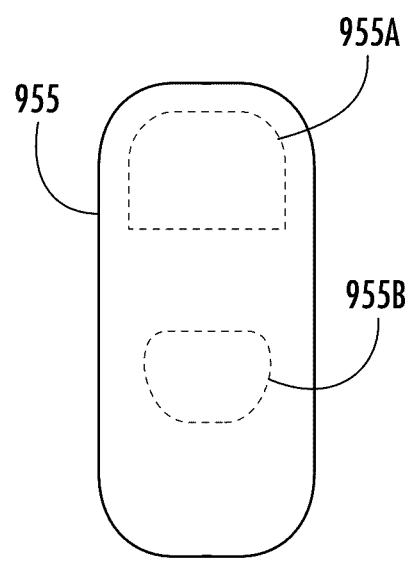
Figure 24:
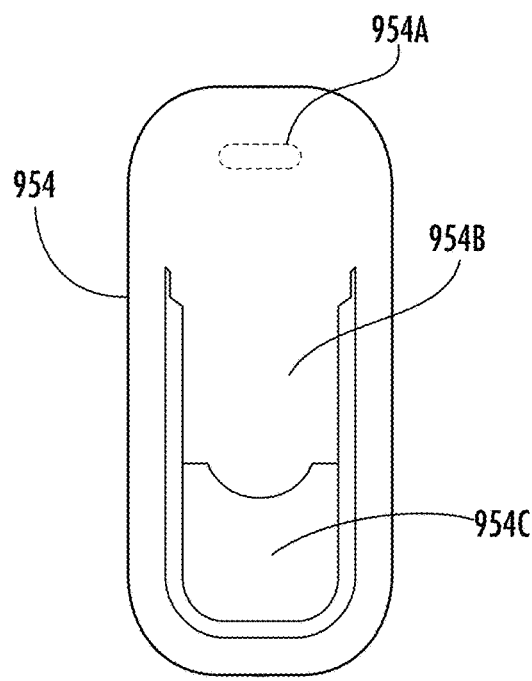
Figure 25:
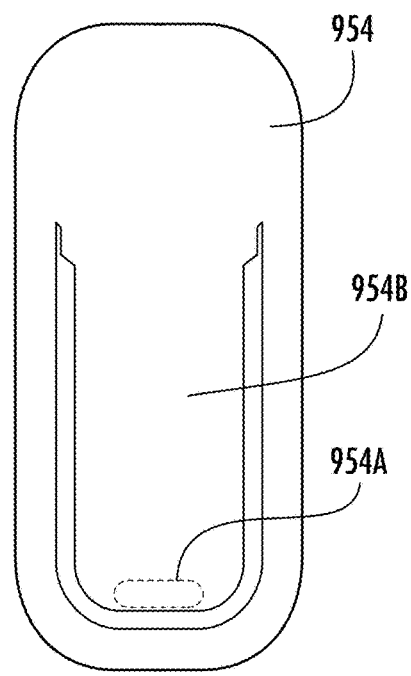
Figure 40A:
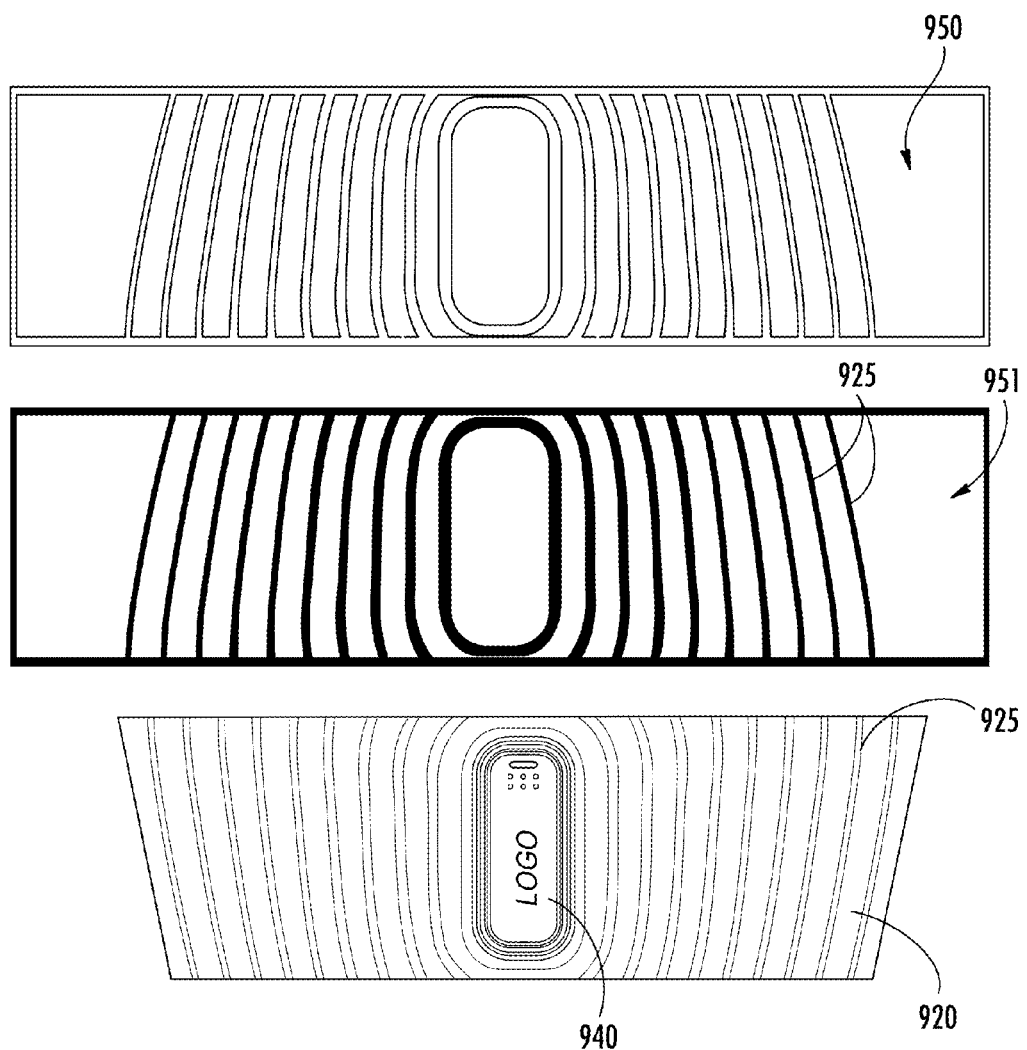
FIG. 40A is a top view of another embodiment of a band according to aspects of the disclosure, with some components used in manufacturing the band.
Figure 40B:
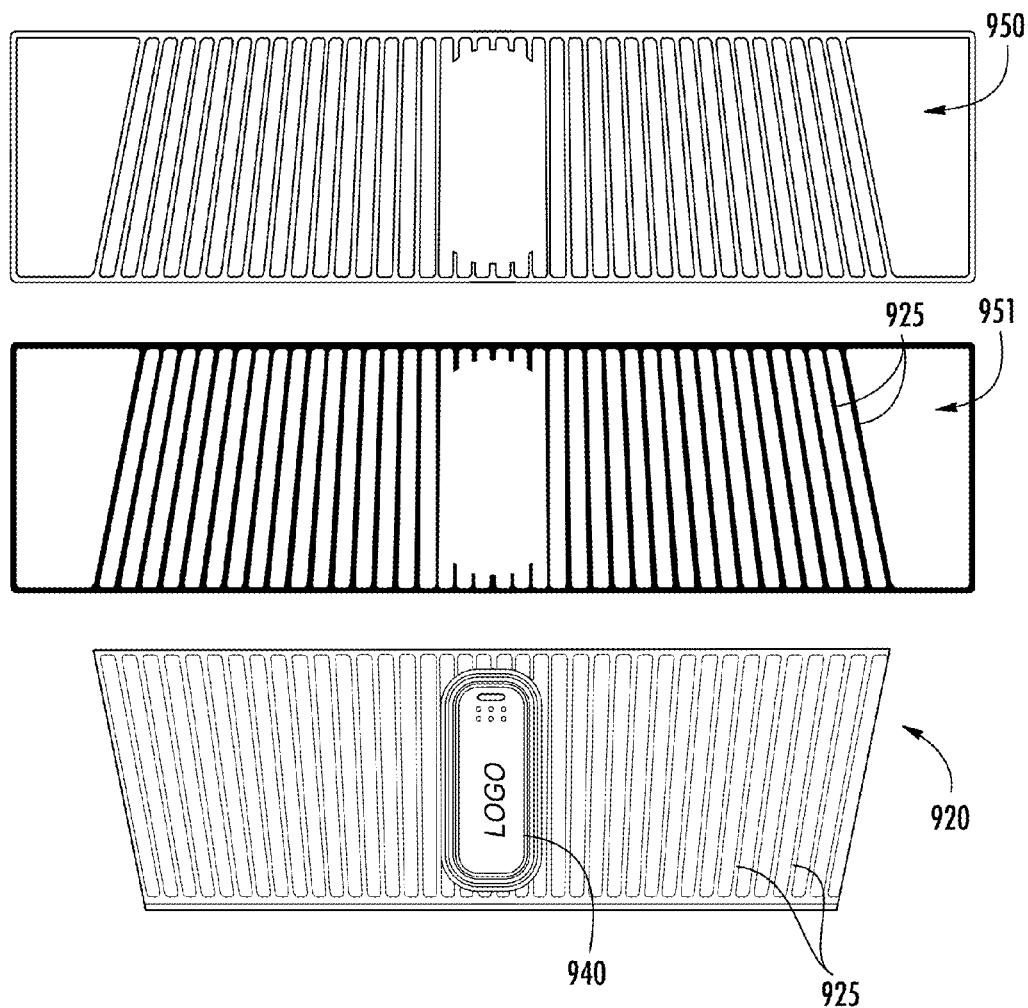
FIG. 40B is a top view of another embodiment of a band according to aspects of the disclosure, with some components used in manufacturing the band.

The band 920 may be assembled by using a heat press operation, with heat-activated films bonding the pieces of the band 920 together. FIGS. 18-38 illustrate one embodiment of a method of assembly/manufacturing of the band 920. In this embodiment, a main body piece 950 is formed (e.g., cut) from an elastic fabric material, as shown in FIG. 18, with fold lines indicated by broken lines. The main body piece 950 has a first hole 950A for the opening 942, a second hole 950B for the sensor opening 945, and a third hole 950C forming part of a window 946. The central fold line divides the main body piece 950 into an inner portion 950D forming the inner surface 927 of the band 920 and an outer portion 950E forming the outer surface 928 of the band 920. FIG. 19 illustrates a main bonding panel 951 of heat-activated film or adhesive film (referred to as a "bonding material"), with the lines 925 and gaps 926 formed thereon by etching or cutting. FIGS. 40A-B illustrate alternate embodiments of the main bonding panel 951 and the resultant band 920. FIGS. 20-21 illustrate an outer pocket interior piece 952 with a light hole 952A forming part of a window 946 and an interior pocket edge bonding piece 953 with a hole 953A for the opening 942, both of which are made from a bonding material. FIGS. 22-23 illustrate an inner pocket trim and outer pocket structure piece 954 and an inner pocket structure piece 955, both of which are made from a fabric material with a bonding material backing. The inner pocket trim and outer pocket structure piece 954 has a light hole 954A and a tongue 954B that is cut out of the middle thereof. FIGS. 24-25 both illustrate alternate embodiments of the inner pocket trim and outer pocket structure piece 954. FIG. 24 illustrates a piece 954 that has an adhesive or bonding material 954C positioned on the tongue 954B for bonding to the shell 948 within the pocket 940. FIG. 25 illustrates a piece 954 that has a differently located light hole. The inner pocket structure piece 955 has a first hole 955A for the opening 942 and a second hole 955B for the sensor opening 945. FIGS. 26-27 illustrate an outer pocket trim piece 956 and a pocket edge trim piece 957, both of which are made from a fabric material with a bonding material backing. FIG. 28 illustrates a graphics piece 958, which may include a logo 958A or other indicia 958B, as well as optionally a light hole which may form part of a window 946. The graphics piece 958 may be made from a heat-activatable material. FIG. 29 illustrates a frame piece 959 that may be placed around the holes 950B, 955B for the sensor opening 945, which may be made from a polycarbonate material. FIG. 30 illustrates the bonding material 954C for the shell 948, as also shown in FIG. 24. It is understood that the various pieces of bonding material described herein, including pieces 951, 952, 953, etc., may be made from the same or different bonding materials, and may have the same or different thicknesses and/or functional properties. It is also understood that the broken lines in FIGS. 20-25 indicate cut lines that are made after the pieces are placed in position on the band 920 during assembly.

Figure 32:
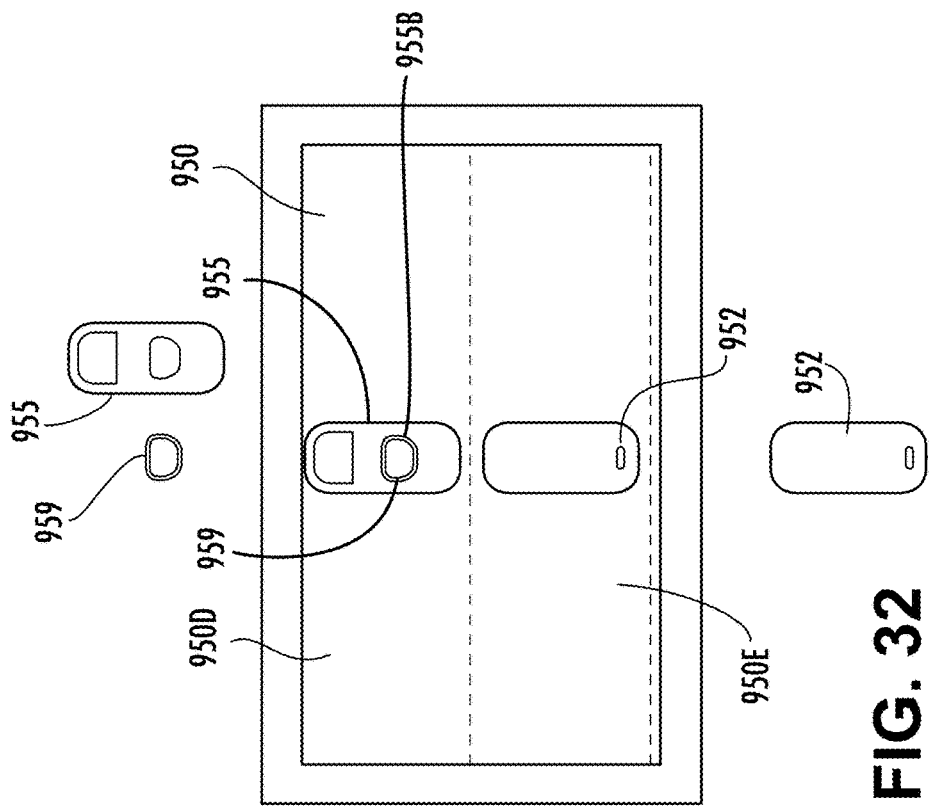
Figure 31:
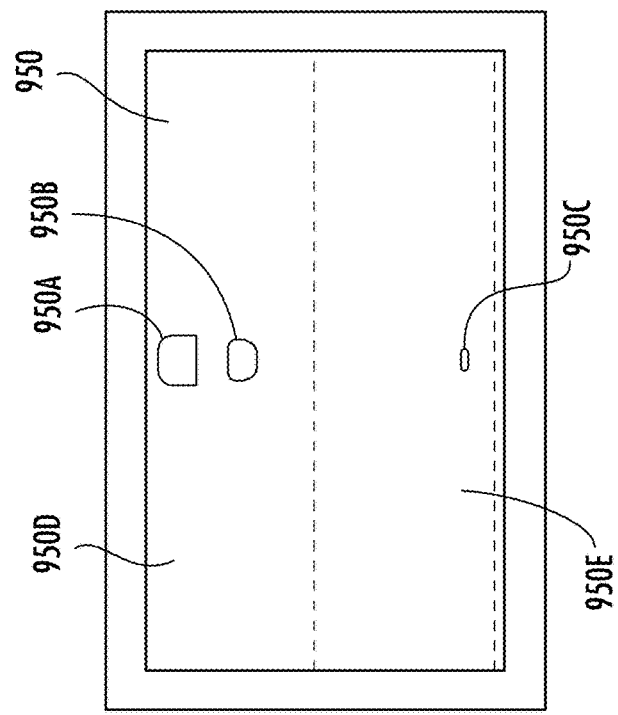
Figure 34:
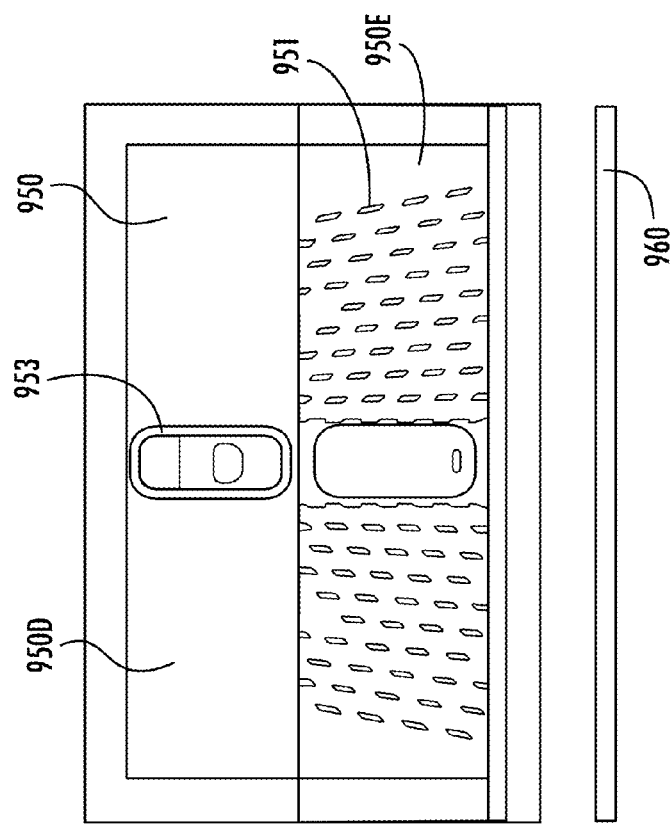
Figure 33:
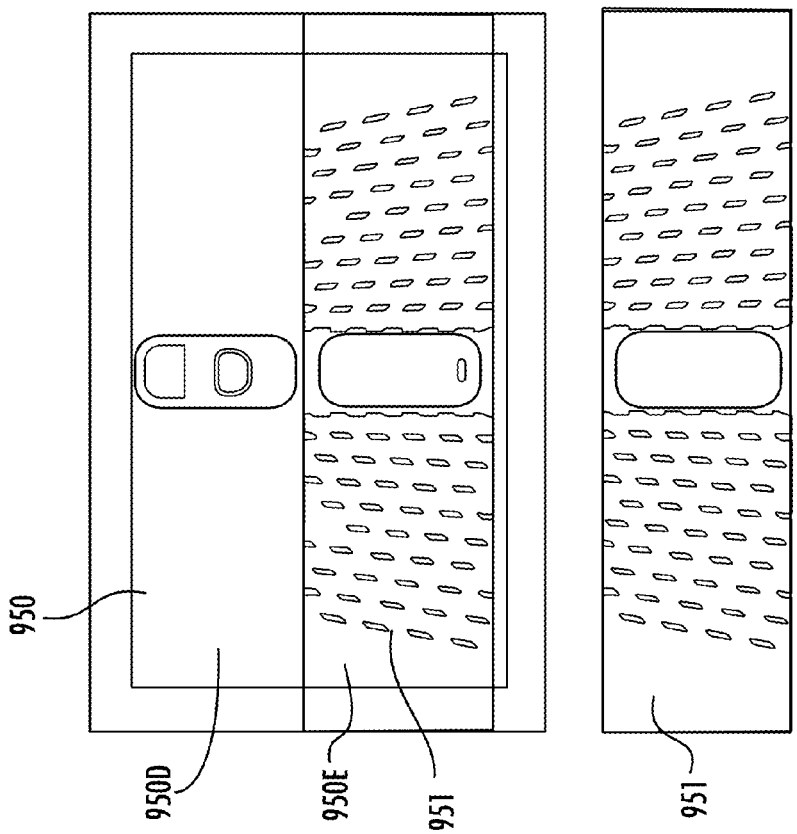
Figure 35:
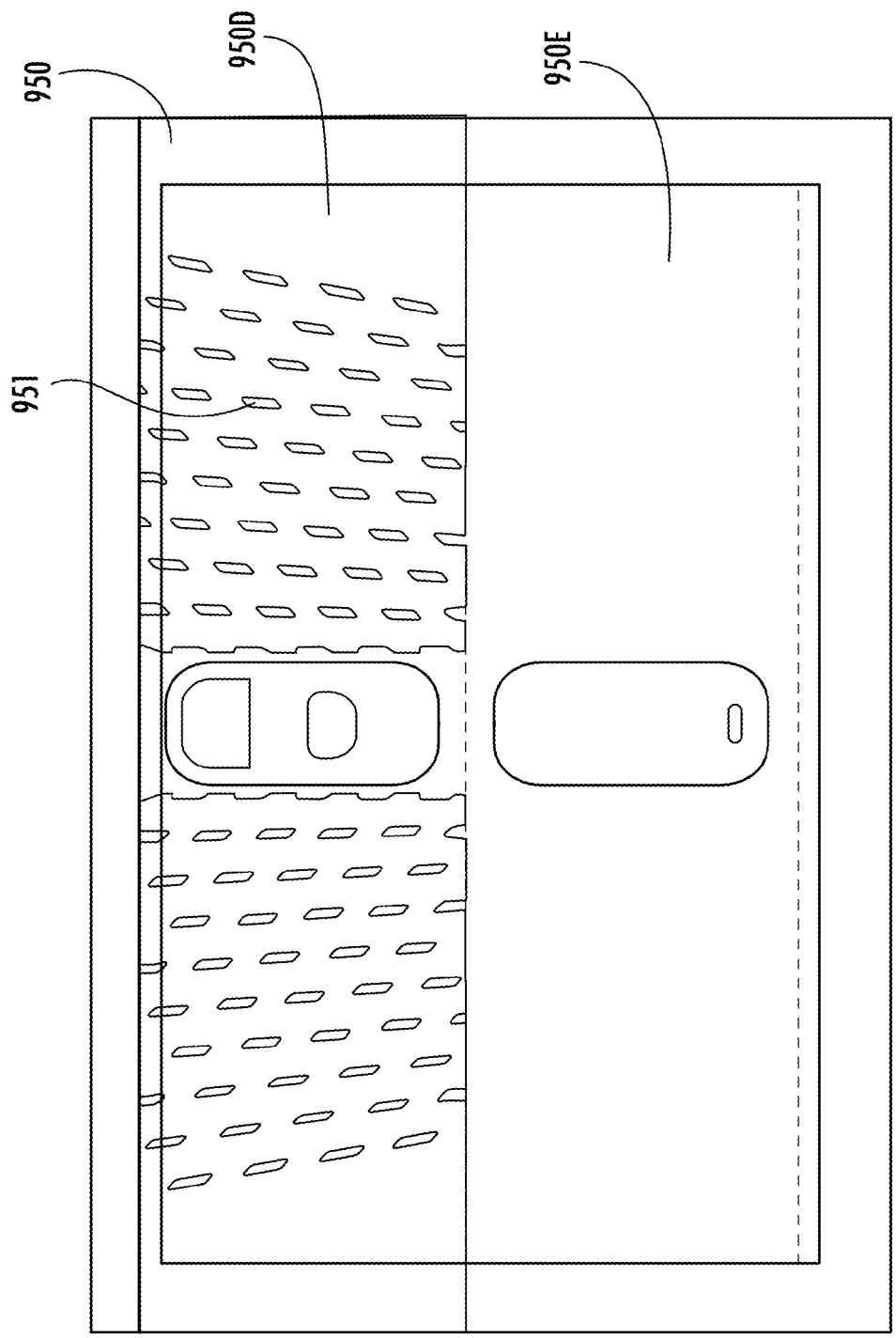

Assembly of these components may be performed using a heat press, which seals the bonding material. The assembly starts with the main bonding panel 950, as shown in FIG. 31. In FIG. 32, the outer pocket interior piece 952 is placed on the outer portion 950E of the main body panel 950 and the inner pocket structure piece 955 is placed on the inner portion 950D main body panel 950, and a slight tackiness of the bonding material may retain these places in place. The frame piece 959 may additionally be placed around the opening 955B in the inner pocket structure piece 955 to protect and reinforce the sensor opening 945 after assembly. In another embodiment, the frame piece 959 may be replace by an adhesive rimming. In FIG. 33, the main bonding panel 951 is applied to the outer portion 950E of the main body piece 950, and may be retained by tackiness. As alternately shown in FIG. 35, the main bonding panel 951 may be applied to the inner portion 950D of the main body piece 950. The main bonding panel 951 may be applied to the main body piece 950 and then removed to leave only the lines 925 of bonding material defined by the etching/cutting. As shown in FIG. 34, the interior pocket edge bonding piece 953 is placed on the inner portion 950D of the main body piece 950, with the hole 953A properly located where the display of the module 930 may be. A strip 960 of bonding material is then placed across the edge of the outer portion 950E of the main body piece, which bonds the edges of the inner and outer sides 950D-E together after folding. In FIG. 36, the main body piece 950 is folded over so that the inner and outer portions 950D-E confront each other and can be bonded together by the main bonding panel 951 and the strip 960. FIG. 36 illustrates both the inner portion 950D and the outer portion 950E, now on opposite surfaces of the main body piece 950. Outer portions of the main body piece 950 may be cut away and/or folded inwardly to make the final shape of the band 920 in this step, as well.

In FIG. 37, the inner pocket trim and outer pocket structure piece 954 is placed on the inner portion 950D, so that the piece 954 is on the outer surface and the tongue 954B extends through the opening 942 and into the cavity 941, between the inner and outer portions 950D-E of the main body piece 950. The outer pocket trim piece 956 is placed on the outer portion 950E, as also shown in FIG. 37. The pocket edge trim piece 957 is placed along an edge of the access opening 942, as further shown in FIG. 37, such that the piece 957 folds over the edge. After this point in assembly, the pieces are heat-pressed by using a specially-designed mold. One embodiment of the mold 970 includes a first mold plate or piece 971 in contact with the inner portion 950D and a second mold plate or piece 972 in contact with the outer portion 950E, where the plates 971, 972 are pressed together to heat-press the assembly and mold the pocket 940, as described in greater detail below and shown in FIGS. 64-67. A plug is inserted through the opening 942 during the heat pressing, to form the inner shape of the pocket 940. During the heat pressing, the bonding materials are heat-activated to bond the adjacent surfaces together, and may add some local rigidity to the structure as well. This local rigidity is particularly advantageous for retaining the shape of the pocket 940 and for limiting axial stretching as described elsewhere herein. In this configuration, the assembled pieces 950, 952, 953, 954, 955, 956, 957 define the pocket 940, the cavity 941, the access opening 942, and the sensor opening 945. The inner portion 950D of the main body piece 950 combines with other pieces (e.g., the inner pocket structure piece 955) to define the inner wall 944, and the outer portion 950E combines with other pieces (e.g., the outer pocket interior piece 952 and the tongue 954B) to define the outer wall 943.

Figure 65:
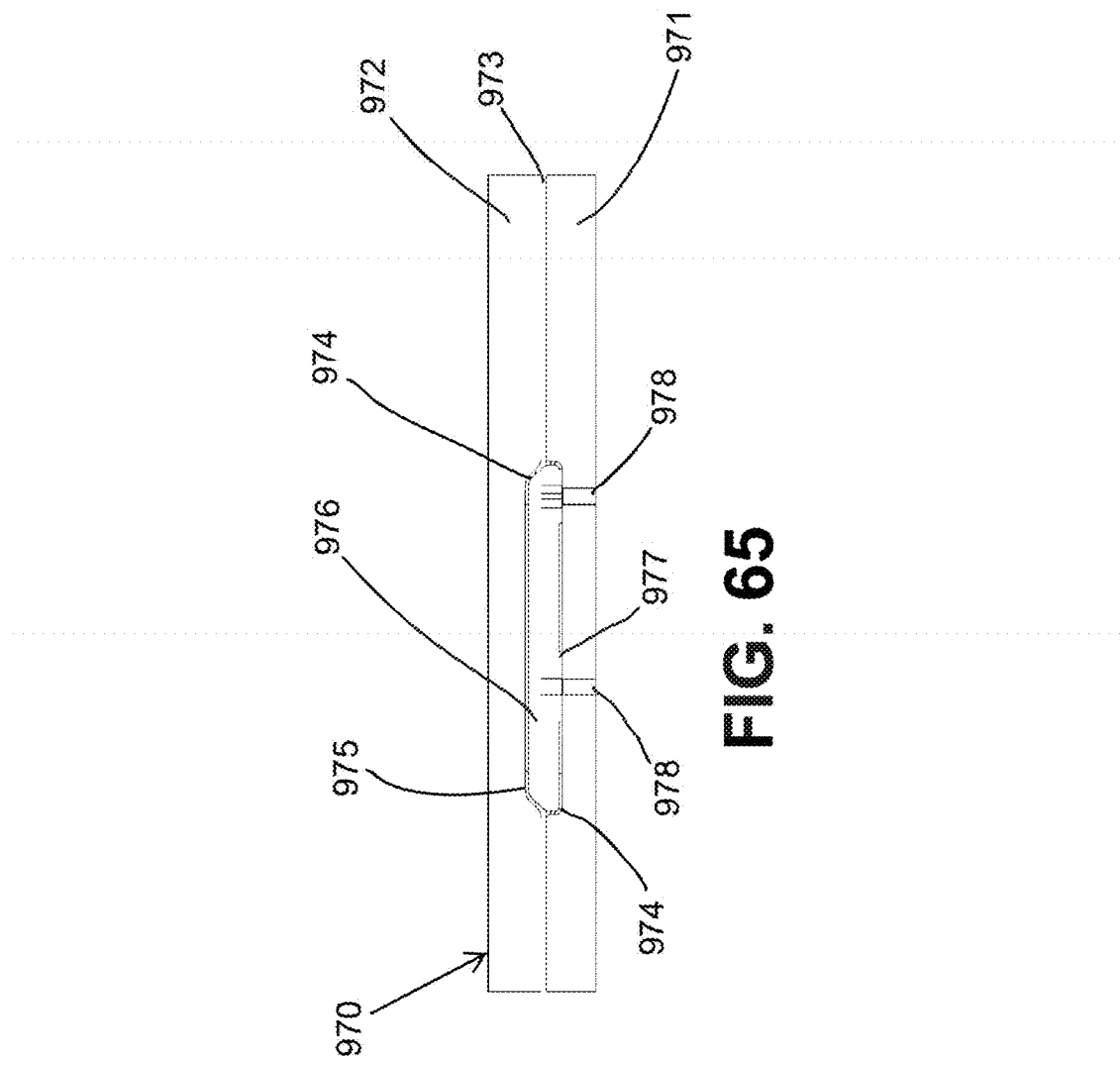
FIG. 65 is a cross-sectional view of the mold of FIG. 64 along a longitudinal axis.
Figure 66:
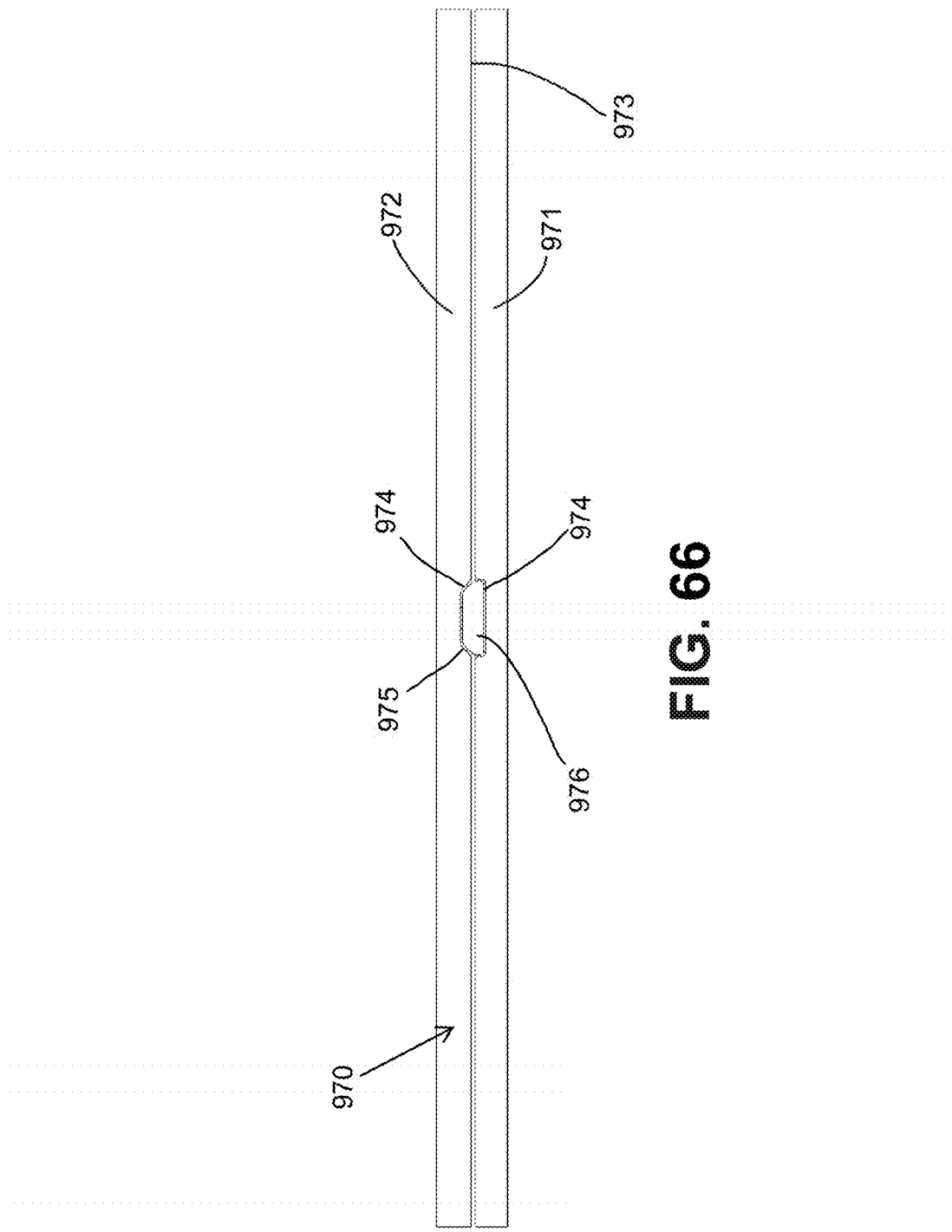
FIG. 66 is a cross-sectional view of the mold of FIG. 64 along a lateral axis.
Figure 67:
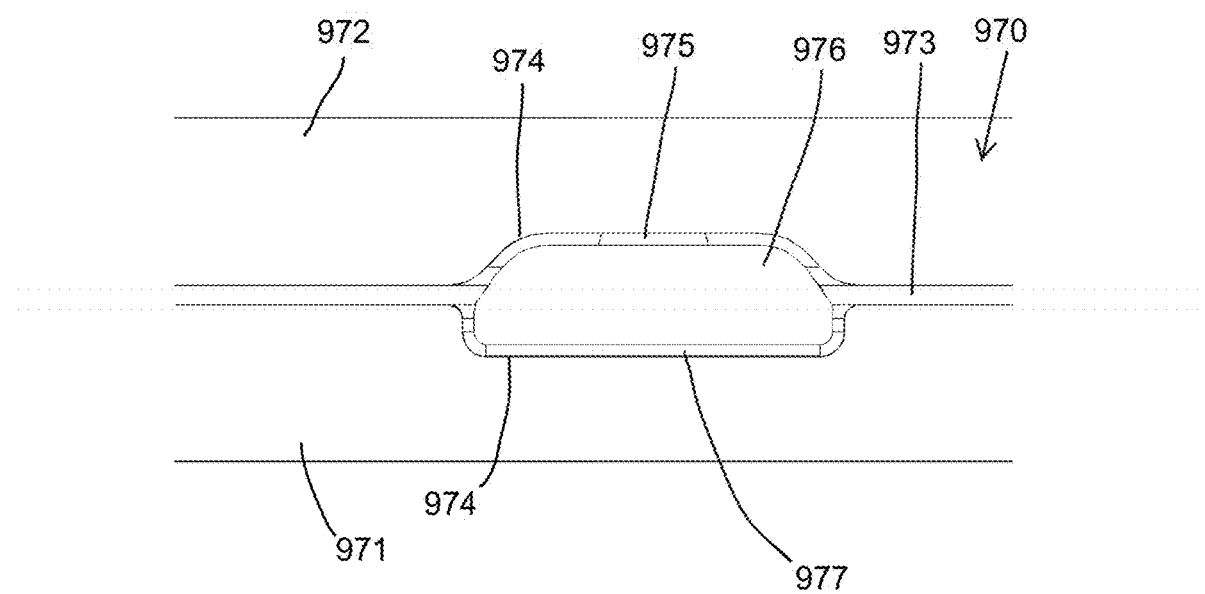
FIG. 67 is a magnified view of a portion of the mold as shown in FIG. 66.

FIGS. 64-67 illustrate an example embodiment of a mold 970 that can be used to manufacture the band 920 using the components and techniques described herein and illustrated in FIGS. 18-40B. The mold 970 includes two mold plates 971, 972 that are pressed together around the assembled inner and outer portions 950D-E as shown in FIG. 37, such that these components are received in a mold cavity 973 between the mold plates 971, 972 in an assembled manner. In the configuration shown in FIGS. 64-67, the first plate 971 contacts the inner portion 950D and the second plate 972 contacts the outer portion 950E. The mold plates 971, 972 each have an enlarged portion 974 that creates a secondary cavity 975 within the mold cavity 973, for molding the pocket 940. One or both plates 971, 972 may include one or more holes 978 to permit gases to escape during molding. A plug 976 is inserted between the inner and outer portions 950D-E during the heat pressing, to form the inner shape of the pocket 940, as shown in FIGS. 65-67. As illustrated in FIGS. 65 and 67, the plug 976 includes a projection 977 that extends through the sensor opening 945 during the molding process. After the heat pressing is completed, the mold plates 971, 972 are separated, the plug 976 is removed from the pocket 940 (such as through the opening 942), and the assembled band 920 is removed from the mold 970. Additional manufacturing steps may then be taken, as shown in FIG. 38. It is understood that the structure and configuration of the mold 970 and the components thereof may be changed for bands 920 having different sizes, shapes, structures, etc.

After the complete, the assembly is removed from the mold, and the final structure of the band 920 is assembled as a flat piece, as shown in FIG. 38. The protective shell 948 may be placed in position in the cavity 941 after the heat pressing is complete, and may be connected by the adhesive or bonding material 954C in one embodiment. The graphics piece 958 may be connected to the outer surface 928 of the band 920, such as by heat pressing, heat sealing, adhesive or other bonding material, etc. Additionally, a seam bonding strip 961 is placed along the edge where the folded ends of the inner and outer portions 950D-E meet, in order to cover the edges. A band closure trim strip 962 is used to bond the ends of the main body piece 950 together to form the tubular body 921. It is understood that the sides of the main body portion 950 may be cut or trimmed to shape, such as an angular shape to create a "slope" of the band 920, before connection to form the tubular body 921. These strips 961, 962 may be connected by heat pressing, heat sealing, adhesive or other bonding material, knitting/stitching, or other technique. This forms the final structure of the band 920 with the pocket 940 defined on the inner surface 927. The strips 961, 962 may further form effective locations for gripping the band 920 to pull the band 920 onto the user's arm, and in particular, the closure trim strip 962 may provide an effective area, due to it having lower stretching capability than the other locations of the band 920. FIG. 39A illustrates the band 920 constructed as shown in FIGS. 18-38 with the module 940 received in the pocket 940, and FIG. 39B illustrates a similar band 920, as described elsewhere herein. It is understood that similar processes and components may be used to form a band 920 with a different configuration, such as an opening 942 on the outer surface 928, a pocket 940 in a different location or orientation, a differently configured band 920 for use on a different body part, etc. It is also understood that the components described as being connected together herein may be connected by other techniques in other embodiments, such as other types of adhesives/bonding materials, mechanical fasteners, knitting/stitching/sewing, etc.

Figure 68:
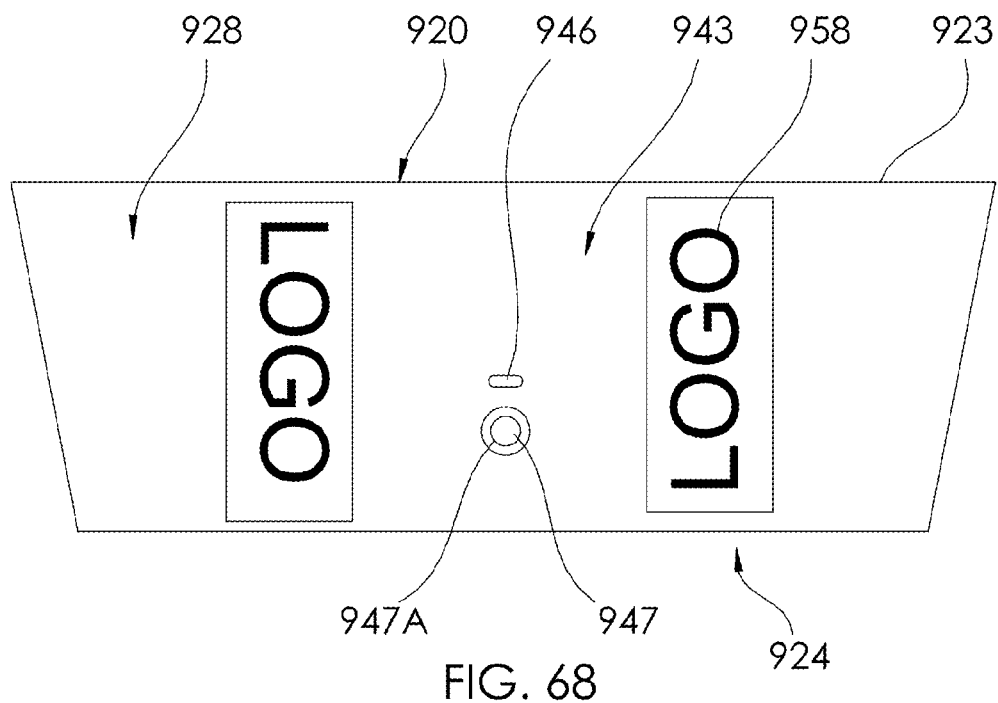
FIG. 68 is a top view of another embodiment of a band according to aspects of the disclosure.
Figure 69:
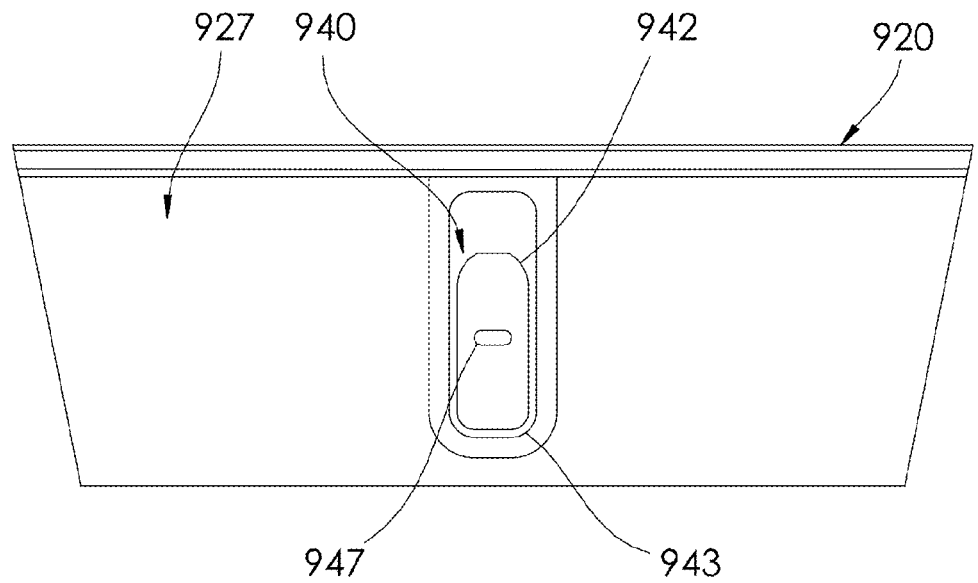
FIG. 69 is a top view of the band of FIG. 68, turned inside-out.
Figure 70A:
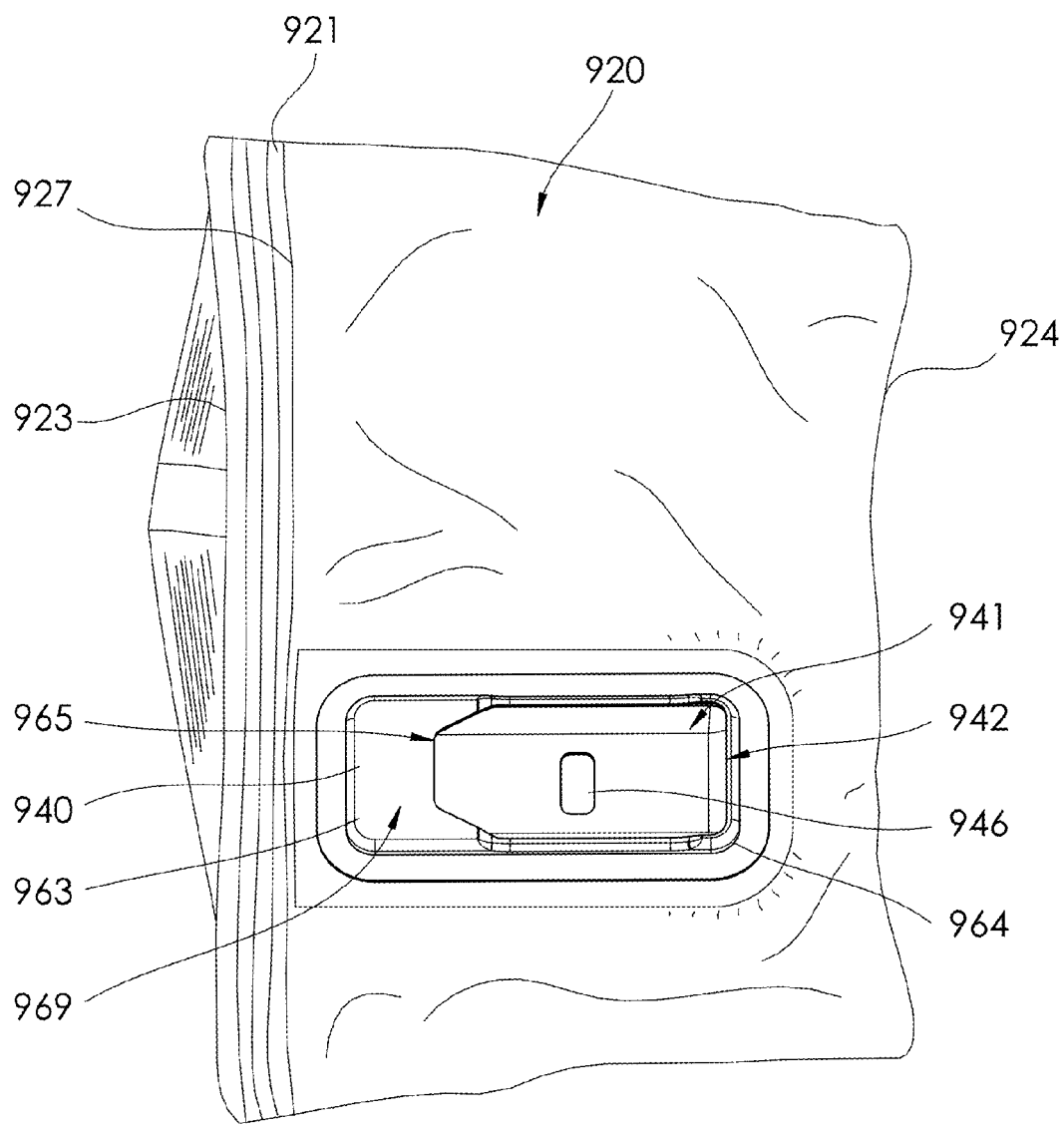
FIG. 70A is top view of the band of FIG. 68, turned inside out.
Figure 70B:
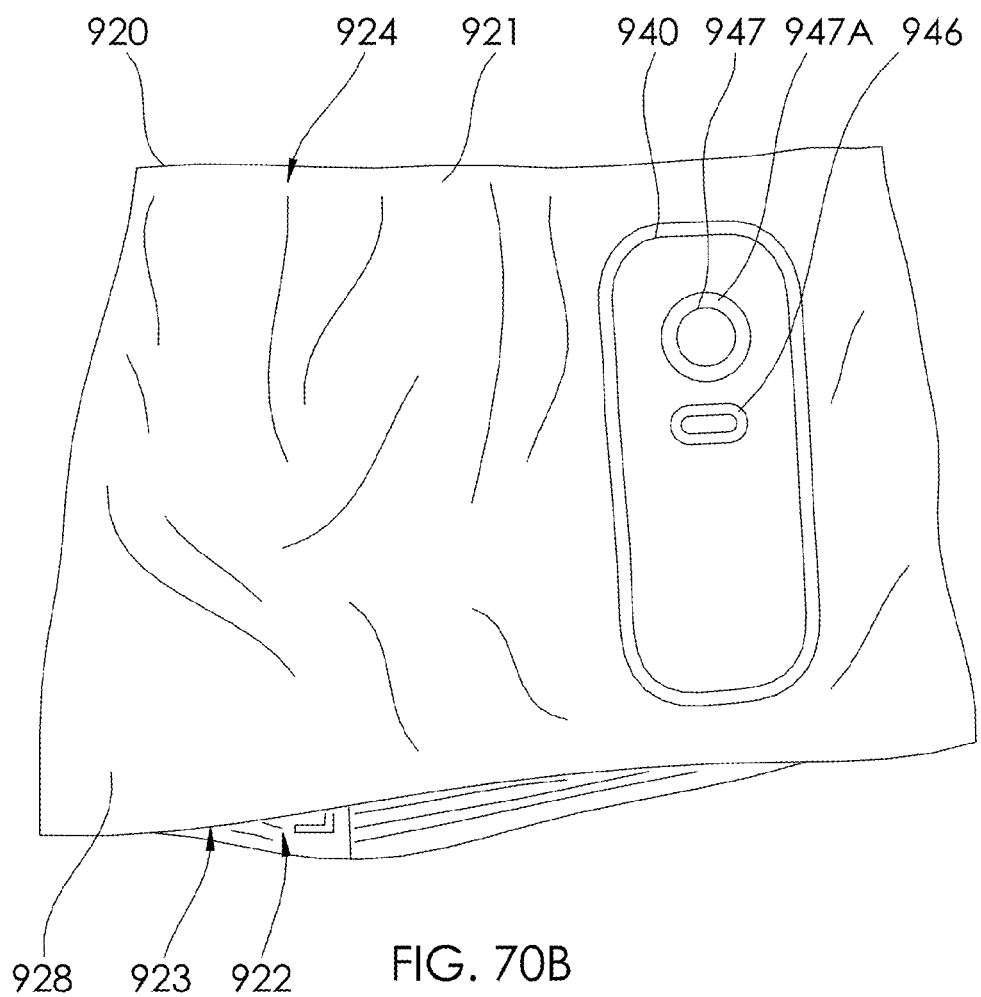
FIG. 70B is top view of the band of FIG. 68.
Figure 70C:
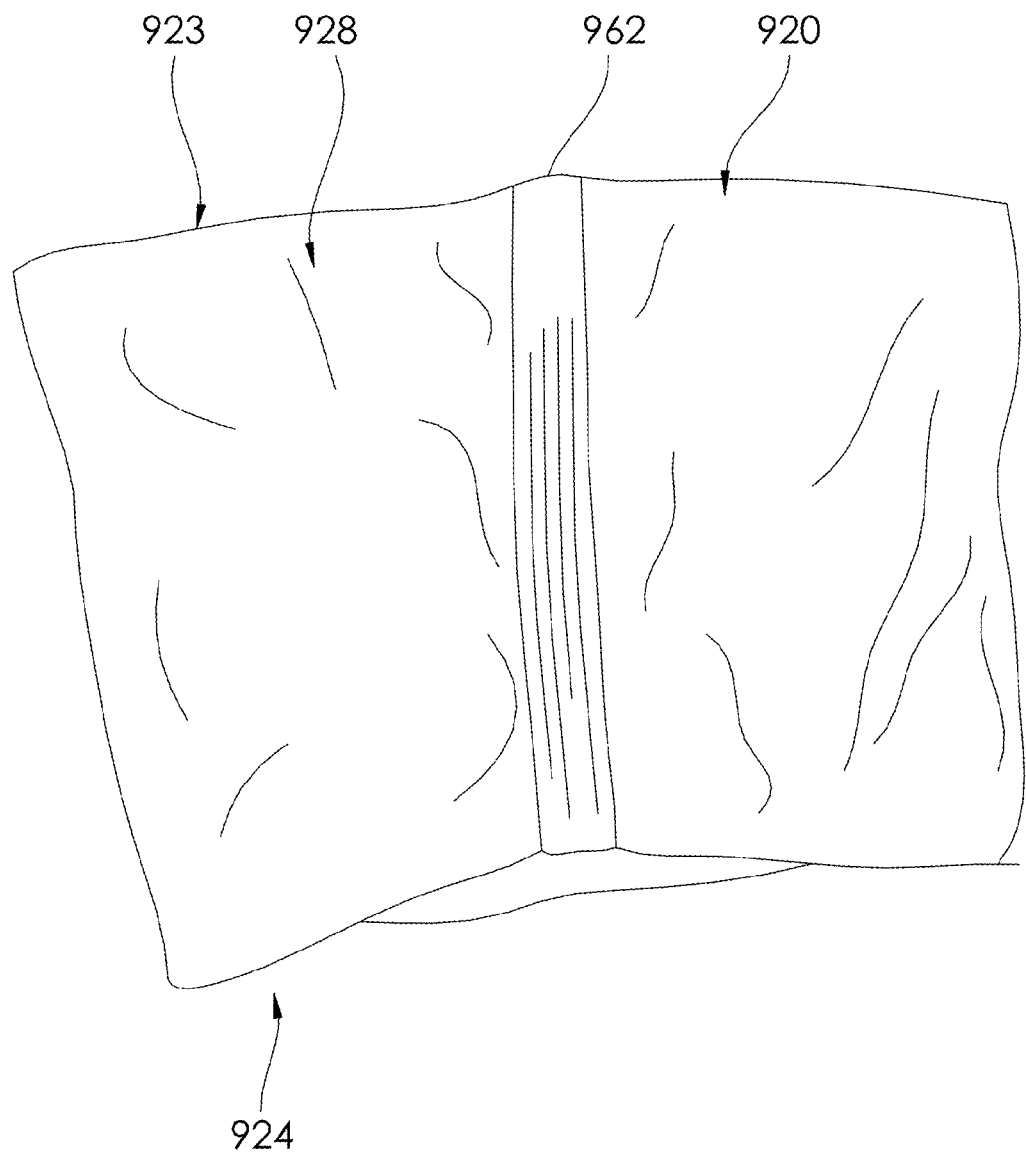
FIG. 70C is bottom view of the band of FIG. 68.
Figure 71:
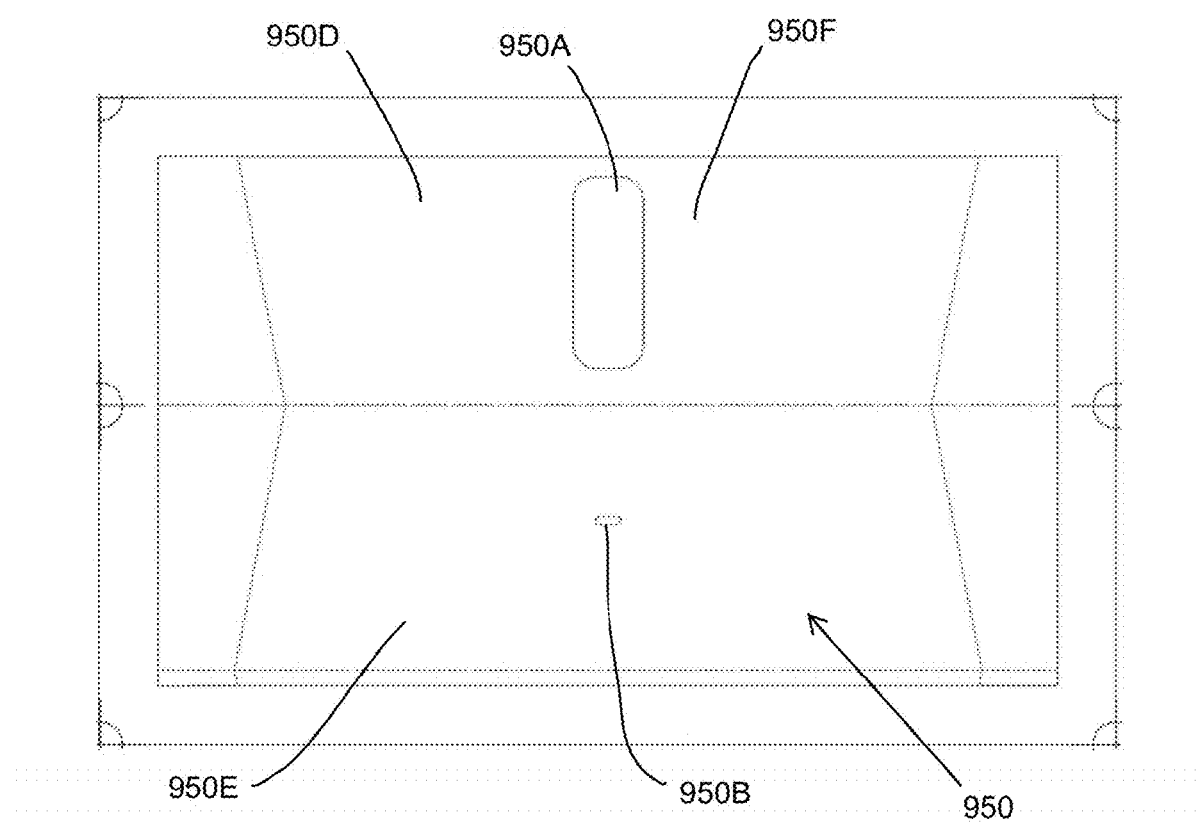
FIGS. 71-73 are top views of components for manufacturing the band as shown in FIGS. 68-70C.

FIGS. 68-70C illustrate another embodiment of a band 920 that, in certain embodiments may include one or more components in common with the bands 920 described elsewhere herein and shown, e.g., in FIGS. 11-17 and 39A-B. By way of illustrating certain embodiments, reference numbers used in FIGS. 68-93 are consistent with the reference numbers used in connection with FIGS. 1-67, unless otherwise noted below, and not all reference numbers may be described again with respect to FIGS. 68-93 for the sake of brevity. FIG. 68 illustrates the outer side 928 of the band 920, and FIG. 69 illustrates the inner side 927 of the band 920. For example, the band 920 has a pocket 940 configured for insertion of the module 930 with the display 934 and the button 933 positioned nearer the bottom end 924 of the band 920 (i.e., nearer the user's wrist) and the connector 935 positioned nearer the top end 923 of the band 920 (i.e., nearer the user's elbow), similar to the configuration of FIG. 39B. In another embodiment, the pocket 940 may be arranged differently, such as an arrangement similar to the configuration of FIG. 39A. The module 930 is not shown in FIGS. 68-70C. The outer wall 943 of the pocket has a button portion 947 configured to interact with the button 933 on the module 930 and a window 946 configured to permit viewing of the light 934 through the outer wall 943. The pocket 940 has an opening 942 on the inner wall 944 that extends into the cavity 941 and is configured to act as both a sensor opening and access opening. In other words, the opening 942 is large enough to permit insertion of the module 930 into the cavity 941 through the opening 942, and a portion of the opening 942 permits the projection 939 of the module 930 to extend through to permit the sensor(s) 932 to be in close proximity to the user's body.

Figure 78:
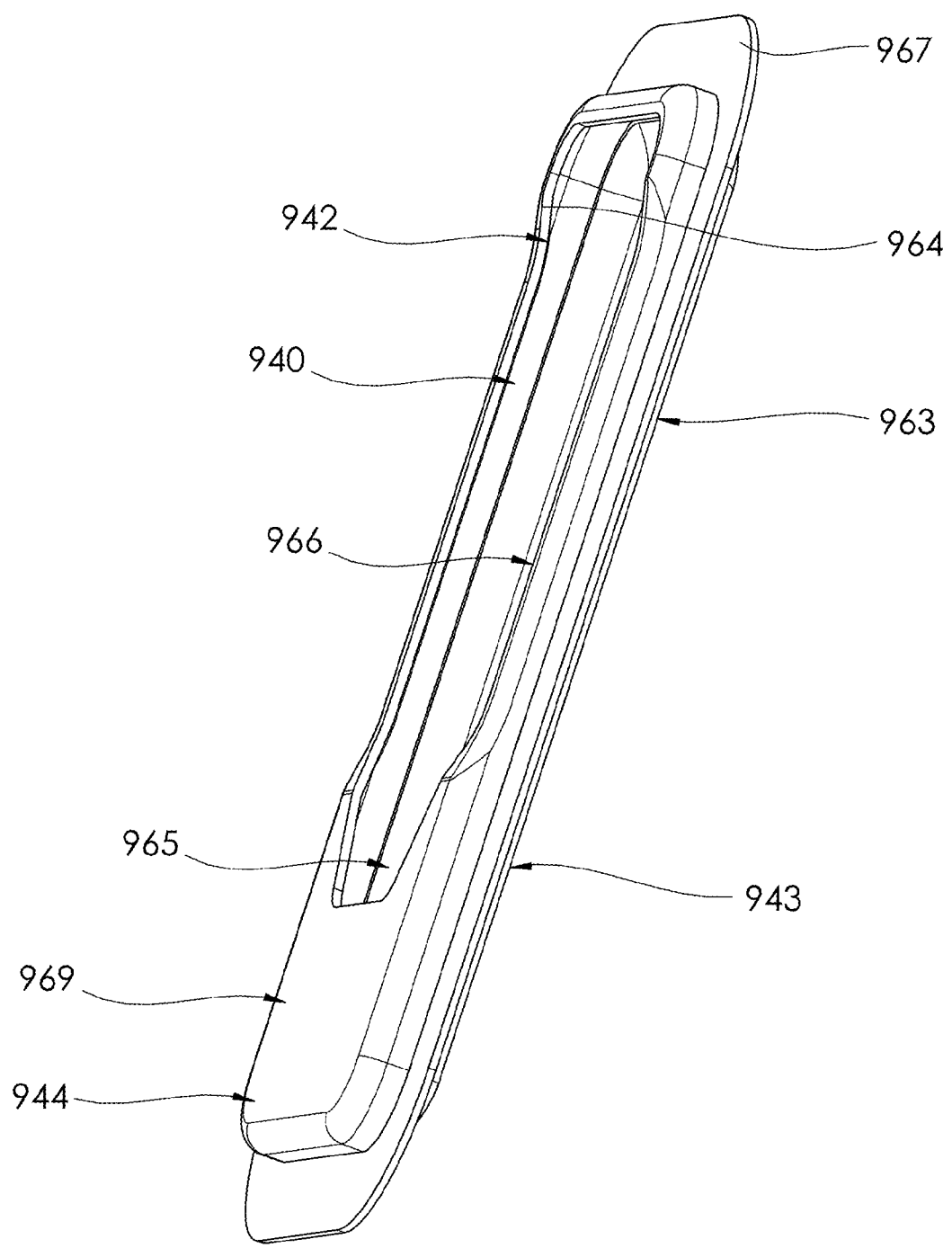
FIG. 78 is a side view of the housing of FIG. 74.
Figure 79:
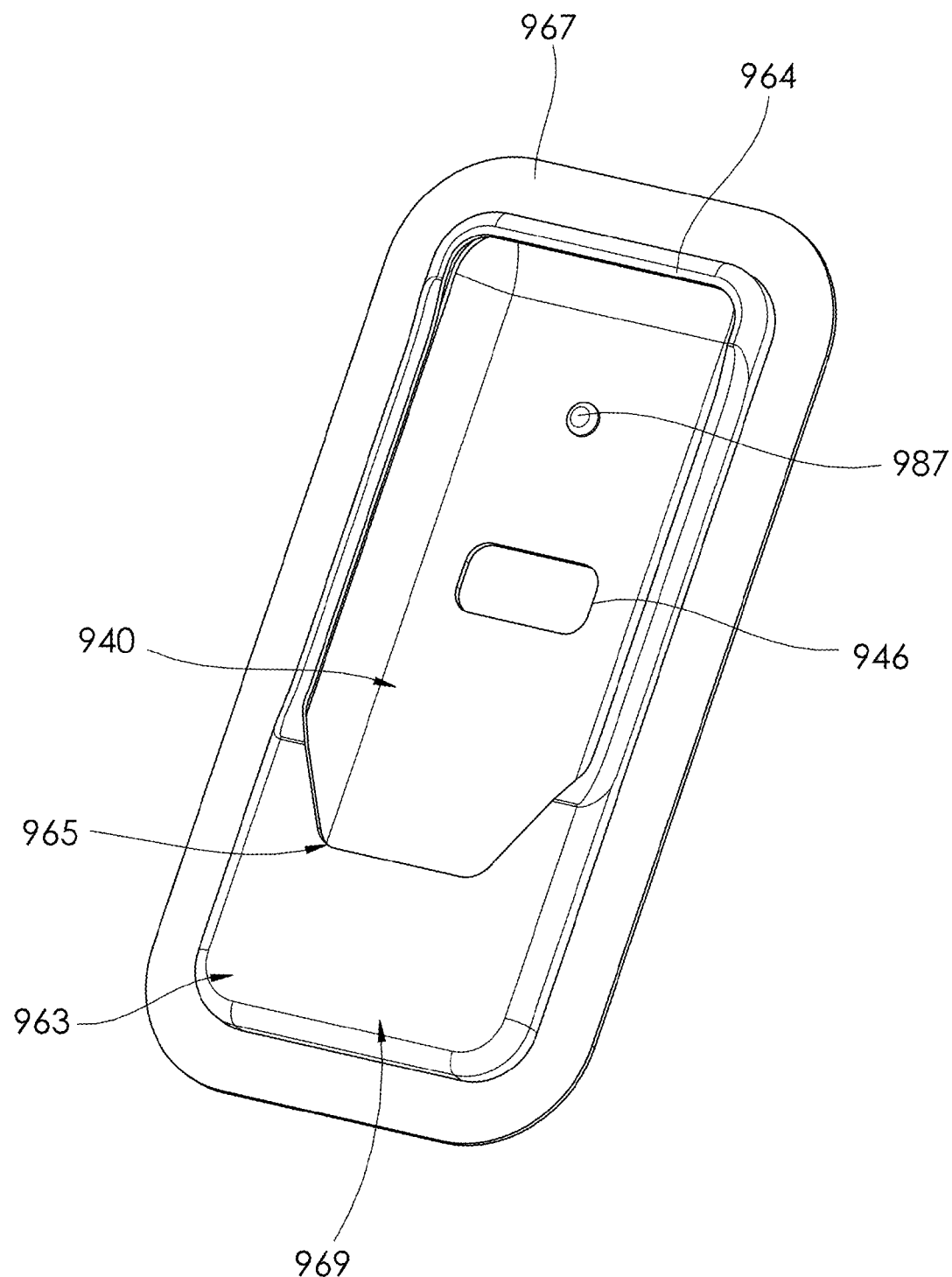
FIG. 79 is a bottom perspective view of the housing of FIG. 74.
Figure 80:
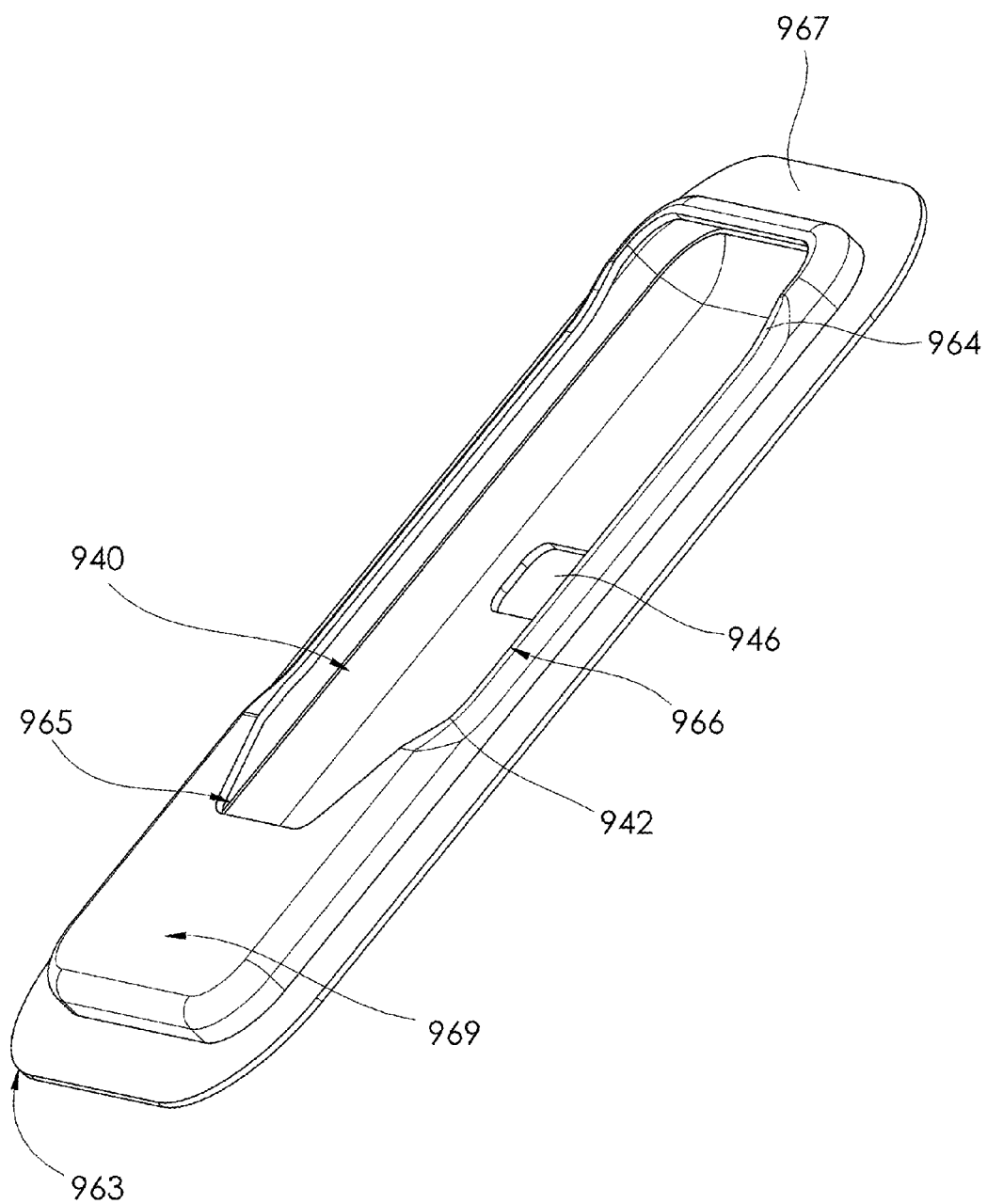
FIG. 80 is a bottom perspective view of the housing of FIG. 74.
Figure 81:
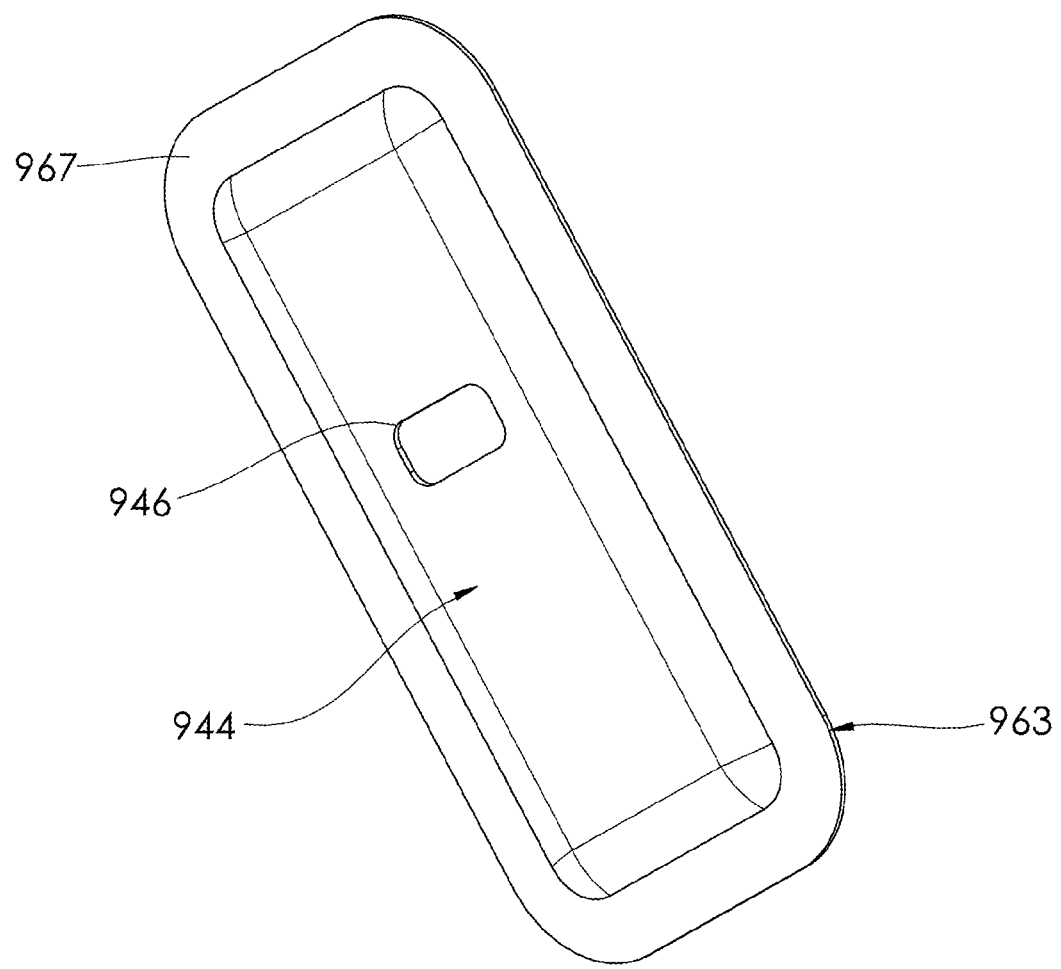
FIG. 81 is a top perspective view of the housing of FIG. 74.
Figure 82:
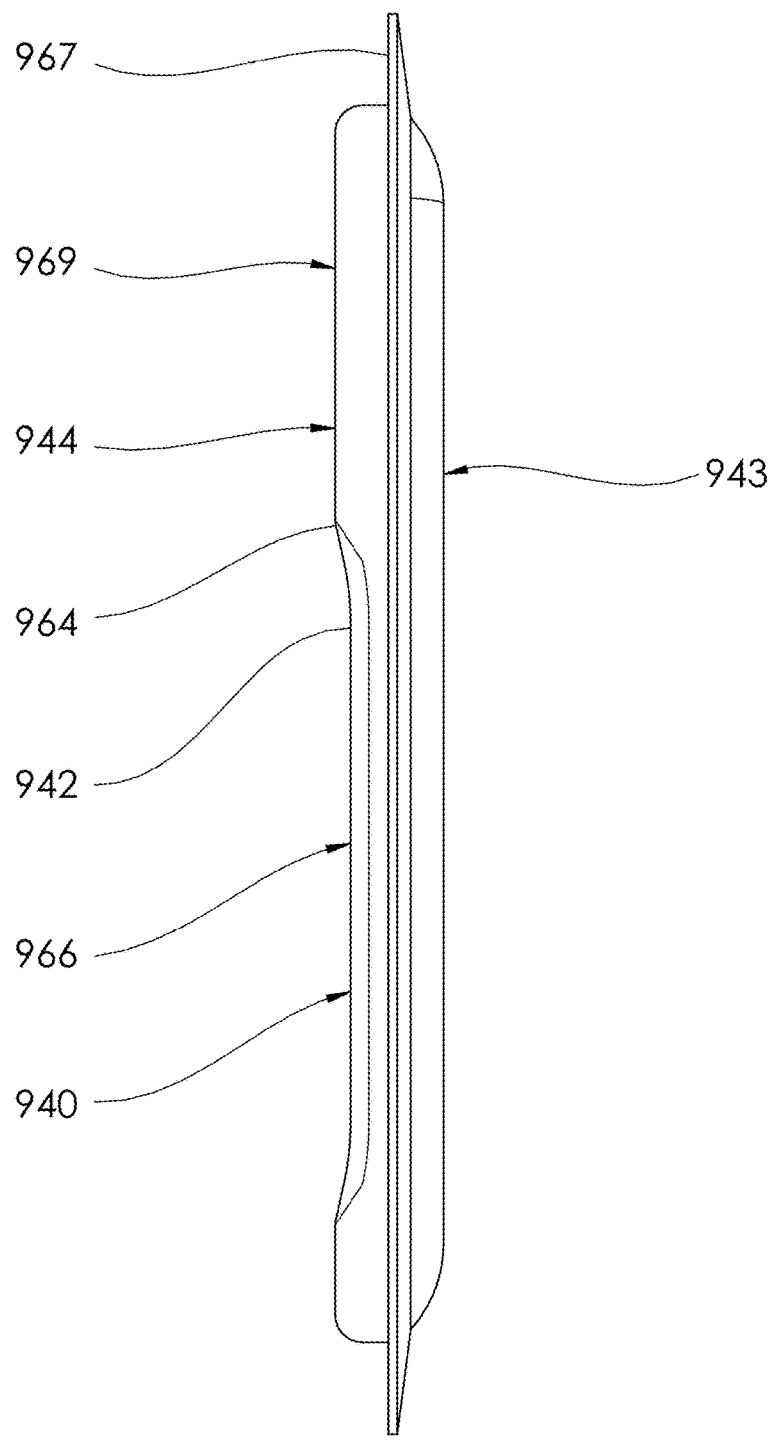
FIG. 82 is a side view of the housing of FIG. 74.

The band 920 in FIGS. 68-70C utilizes a housing 963 that is formed separately from the band 920 and is connected to the band 920 to form the pocket 940. One embodiment of the housing 963 is shown in FIGS. 74-75 and 78-82. The housing 963 may be made of a thermoplastic polyurethane (TPU) material and is formed in a single piece (e.g., by injection molding) in one embodiment, but may be partially or completely made from other materials, multiple pieces, and/or other techniques in other embodiments. The housing 963 in this embodiment is a moderately rigid shell that completely defines the cavity 941 and defines the opening 942 on the inner wall 944 and the window 946 on the outer wall 943. In one embodiment, the rigidity of the housing 963 may be sufficiently rigid to protect the module 930, and sufficiently flexible to permit manipulation of the button 933 by pressing on the button portion 947 of the band 920. The rigidity of the housing 963 may be greater than the rigidity of the fabric material forming the band 920. The housing 963 may also have a protrusion 987 on the outer wall 943 in one embodiment, to facilitate manipulation of the button 933 by the button portion 947 on the outer surface 928 of the band 920 and/or to enhance the "feel" of the button 933, as shown in FIG. 79. The protrusion 987 may lightly engage the button 933 or be in close proximity to the button 933, so that manipulation of the button 933 requires a small amount of movement/flexing of the adjacent portions of the housing 963. The embodiment of FIG. 79 has the protrusion 987 formed as a dome-shaped protrusion formed of an epoxy material applied to the inner surface of the outer wall 943. In other embodiments, the protrusion may be formed differently, such as being integrally formed (e.g., molded) with the housing 963, or may be structured or located differently. As shown in FIGS. 78-82, the housing 963 in the illustrated embodiment has a lip 964 that extends inwardly around the opening 942 and functions to retain the module 930 within the pocket 940. The opening 942 has a narrowed portion 965 that is configured to engage with the projection 939 of the module 930 to hold the projection 939 in place, and the lip 964 has recessed portions 966 located around the narrowed portion 965, as shown in FIGS. 78, 80, and 82. The recessed portions 966 permit the projection 939 to extend farther outwardly relative to the lip 964, in order to have better access to the user's skin. The housing 963 also has a wall 969 configured to form a pocket enclosing and holding the connector(s) 935 of the module 930.

In one embodiment, the housing 963 further has a flange 967 that extends outwardly around at least a portion of the periphery of the housing 963 and is configured for connection to the band 920. In the embodiment shown in FIGS. 74-75 and 78-82, the flange 967 extends generally in a single plane around the entire periphery of the housing 963. In other embodiments, the flange 967 may have a different configuration (e.g., intermittent), or may not be present. Generally, the exterior surfaces of the housing 963 shown in FIGS. 74-75 and 78-82 are smoothly contoured, both for aesthetics and for increased comfort when the housing 963 engages the user's body.

The window 946 of the housing 963 may be an empty passage in one embodiment, or may have a transparent filler in another embodiment, in order to resist ingress of material from the outer surface 928 of the band 920. In further embodiments, the window 946 may include a light-scattering and/or light-collecting structure, to enhance transmission of the light through the window 946, making light from the display 934 appear brighter at the outer surface 928 of the band 920 from a wide variety of angles. For example, the window 946 may include a clear silicon print aligned with the window 946 in one embodiment. As another example, the window 946 may have a silkscreen fabric or fine weave of material aligned with the window 946 in another embodiment. As a further example, the window 946 may have a film connected over the window 946 in yet another embodiment, such as a polycarbonate film that is connected by adhesive or sonic welding. It is understood that these structures may be located within the window 946 and/or positioned over the inner and/or outer surfaces of the window 946, in various embodiments. This may be particularly advantageous when used with a housing 963 as shown in FIGS. 78-82, which may have a significant wall thickness between the display 934, which may make the light darker or more difficult to detect from peripheral angles.

FIGS. 71-91 illustrate one embodiment of a set of components and a method for manufacturing the band 920 as shown in FIGS. 68-70C, which may be made from a piece of fabric that is folded over onto itself to form two layers and joined by stitching and/or adhesive applied between the two layers. It is understood that the band 920 may be made from two or more separate pieces joined together in another embodiment. The band 920 may use a heat press operation in assembly, with heat-activated films bonding the pieces of the band 920 together. The embodiment of the method shown in FIGS. 83-91 utilizes more localized heat pressing, and does not involve heat pressing the entire band 920 as in the method of FIGS. 18-38 and 64-67. FIGS. 71-82 illustrate components that may be used in the method illustrated in FIGS. 83-91, which are described in greater detail below with respect to FIGS. 83-91.

Figure 83:
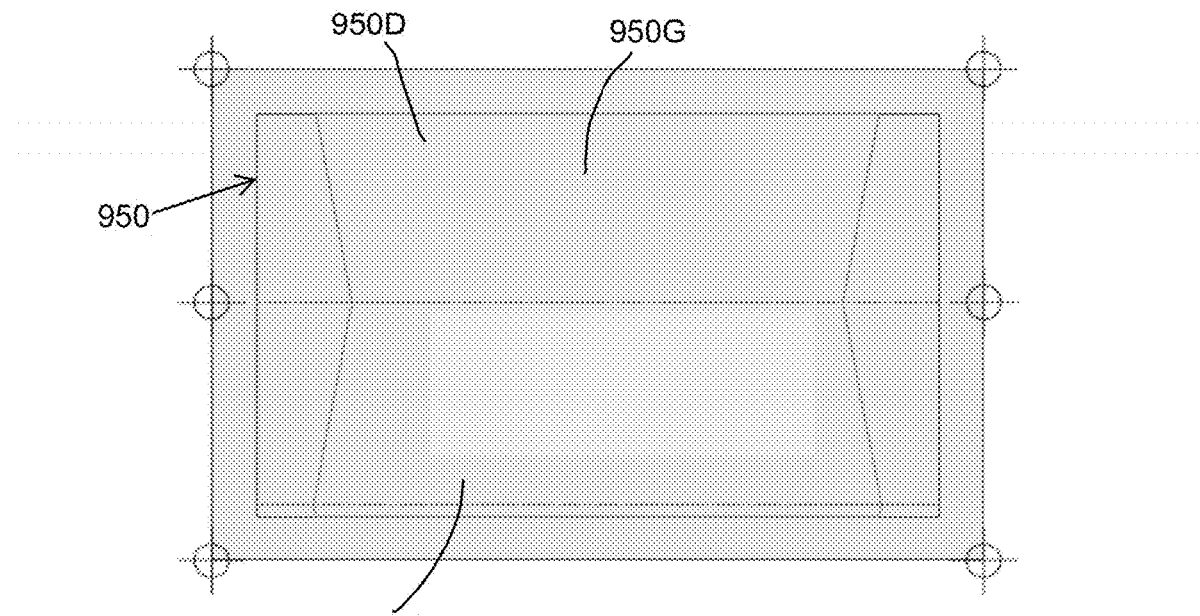
FIGS. 83-91 are plan views schematically illustrating a method of manufacturing a band according to aspects of the disclosure, using the components and housing of FIGS. 71-82.
Figure 84:
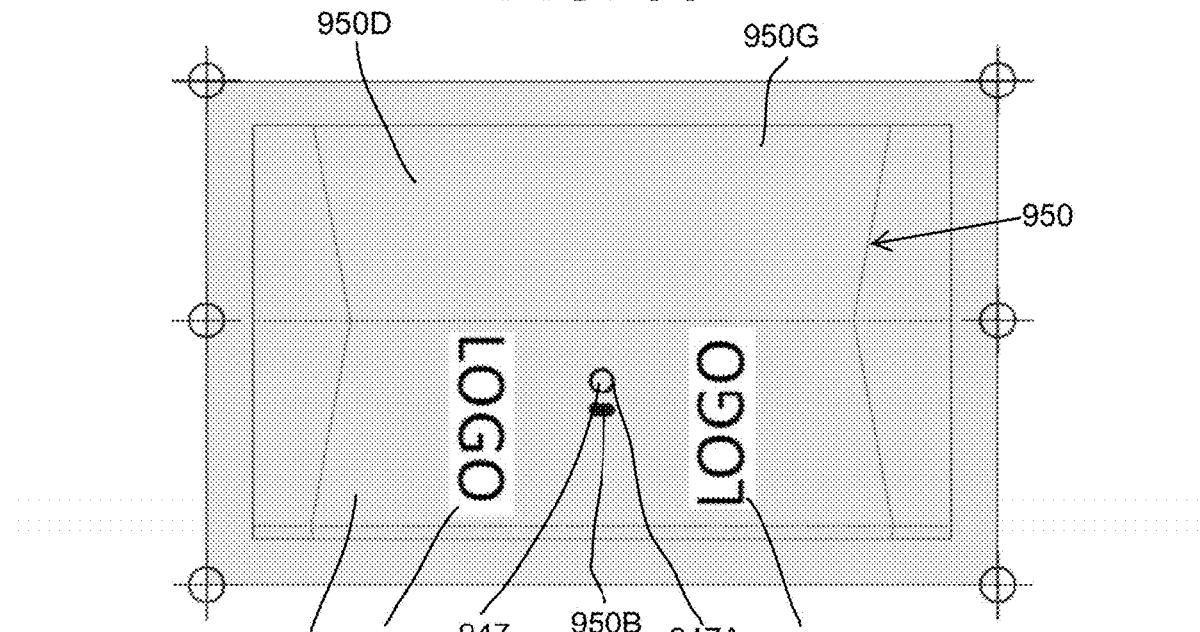
Figure 85:
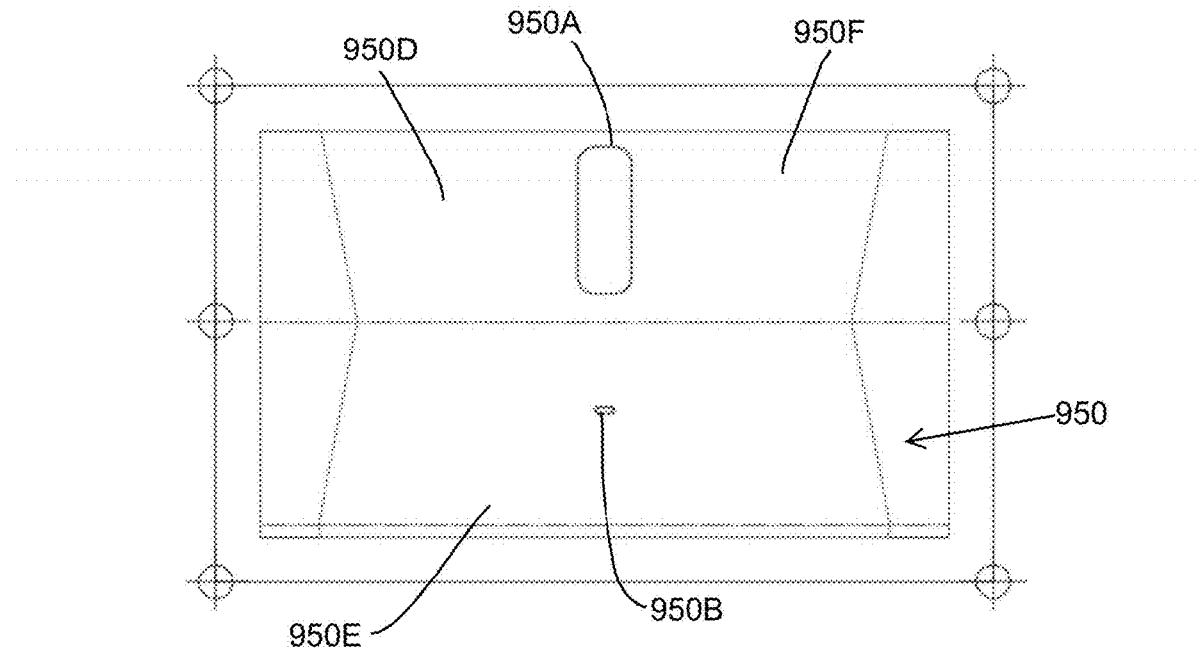

In the embodiment of FIGS. 71-91, a main body piece 950 is formed (e.g., cut) from an fabric material with elastic properties (e.g., a polyethylene-based material), as shown in FIG. 83, with fold lines indicated by broken lines. Graphics 958 may be applied to the outer surface 928 of the band 920, such as by screen printing as shown in FIG. 84, if desired. The main body piece 950 has a first hole 950A for the housing 963 to extend through the band 920 and be accessible from the inner surface 927 of the band 920 and a second hole 950B aligned with and/or forming part of the window 946. The holes 950A-B may be formed in the main body piece 950 by cutting or laser etching in one embodiment, as shown in FIG. 85, and may be formed before or after application of the graphics (if graphics are applied). The central fold line divides the main body piece 950 into a first or inner portion 950D forming the inner surface 927 of the band 920 and a second or outer portion 950E forming the outer surface 928 of the band 920, and the main body piece 950 has an inside surface 950F and an outside surface 950G (illustrated by shading in FIGS. 83-91. The outside surface 950G forms the inner and outer surfaces 927, 928 of the band 920 after assembly, and the inside surface 950F is folded over on itself during manufacturing and forms no portion of the inner and outer surfaces 927, 928 of the band 920. It is understood that graphics 958 that are configured to be visible on the inner or outer surface 927, 928 of the band 920 may be applied to the outside surface 950G of the main body piece 950.

Figure 86:
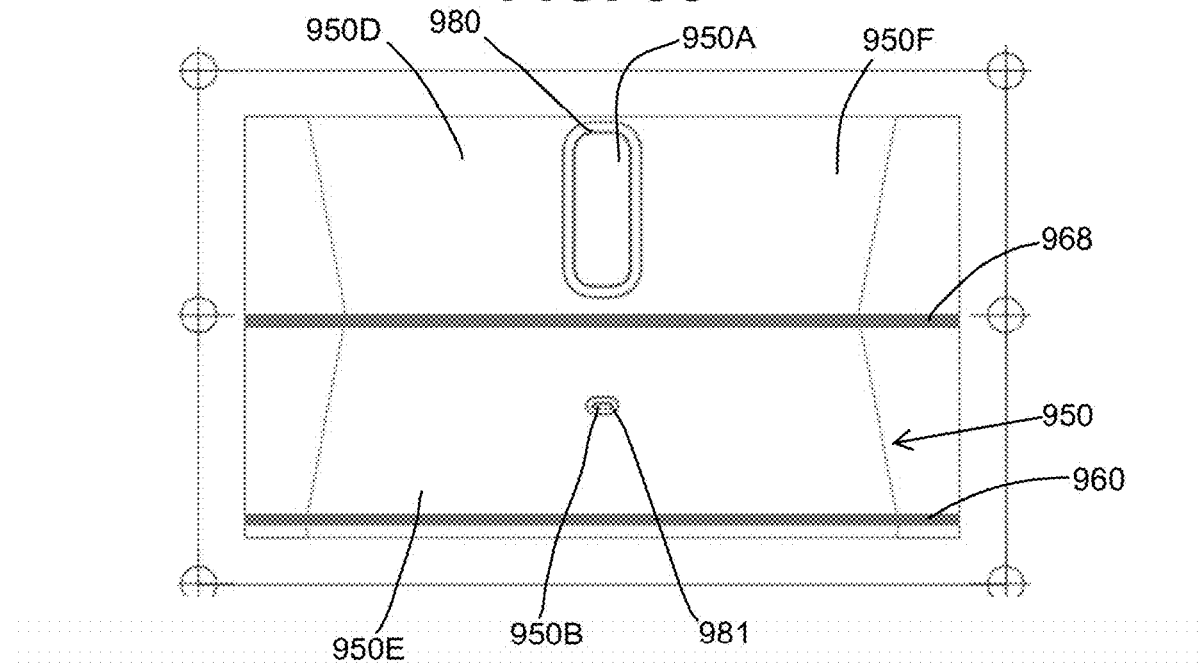

As shown in FIG. 86, an frame bond 980 is applied around the first hole 950A on the inside surface 950F of the first portion 950D and is configured for bonding to the flange 967 of the housing 963, and a light alignment bond 981 is applied around the second hole 950B on the inside surface 950F of the second portion 950E and is configured for bonding to the housing 963 around the window 946. In this configuration, the light alignment bond 981 resists displacement of the hole 950B with respect to the window 946, which may cover the window 946 and block light passage. Although the light alignment bond 981 is shown as being applied in FIG. 86, in one embodiment, the light alignment bond 981 may be applied at the stage illustrated in FIG. 89, immediately before folding the inner and outer portions 950D-E together. These bonds 980, 981 may initially be lightly bonded by slight application of heat and pressure in one embodiment, to hold the components in place during assembly, and then may be normally bonded later during assembly. A strip 960 of bonding material is also placed across the edge of the inside surface 950F of the outer portion 950E of the main body piece 950, configured to bond the edges of the inner and outer sides 950D-E together after folding, as shown in FIG. 86. Another bonding strip 968 may also be placed on the inside surface 950F along the central fold line, in order to provide additional strength and structural support to the bottom end 924 of the finished band 920, as also shown in FIG. 86.

Figure 87:
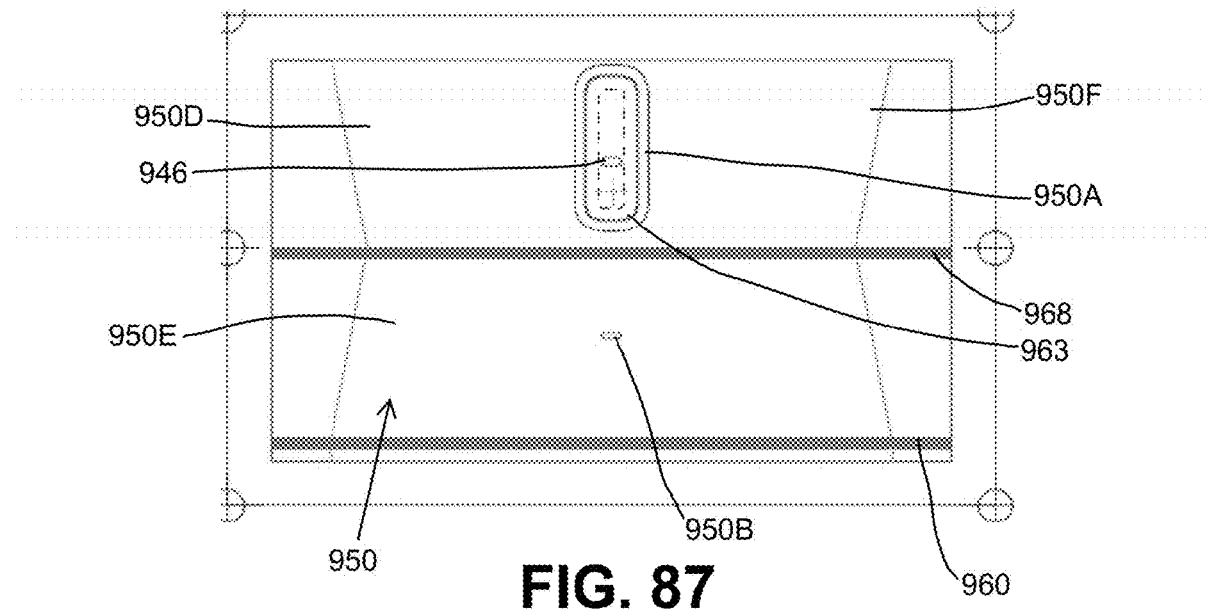
Figure 88:
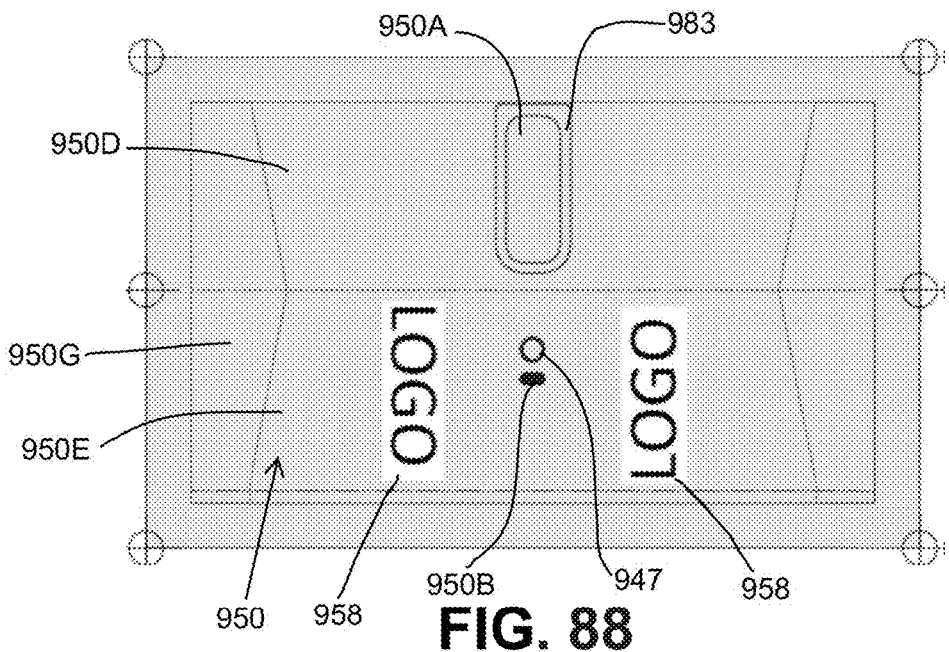

The housing 963 may then be connected to the band 920, such that the flange 967 sits around the periphery of the hole 950A and the portion of the housing 963 including the opening 942 projects through the hole 950A, as shown in FIG. 87. The flange 967 may be connected to the inside surface 950F of the main body piece 950 by stitching around part or all of the flange 967 and/or bonding to the frame bond 980 in one embodiment. As described above, in one embodiment, the flange 967 may be lightly bonded to the inside surface 950F by the frame bond 980 prior to stitching, and then more strongly bonded later on during assembly. After the housing 963 is connected to the band 920, a trim piece 983 may be connected on the outside surface 950G of the inner portion 950D of the main body portion 950, as shown in FIG. 88. This trim piece 983 forms part of the inner surface 927 of the band 920 and covers the connection between the housing 963 and the main body portion 950. The trim piece 983 may be formed of a heat-activated material as described herein and may be heat pressed into place in one embodiment, and the trim piece 983 may be lightly pressed at first and then more strongly pressed at a later time, or may be fully pressed initially, in various embodiments.

Figures 72, 73:
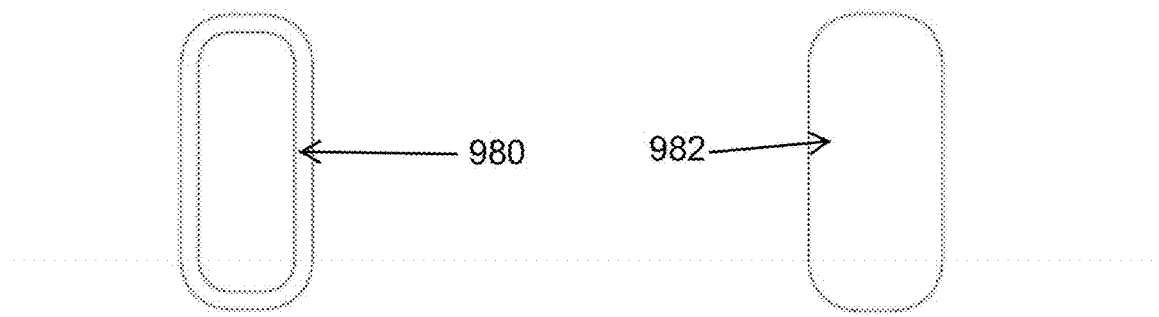
Figures 74, 75:
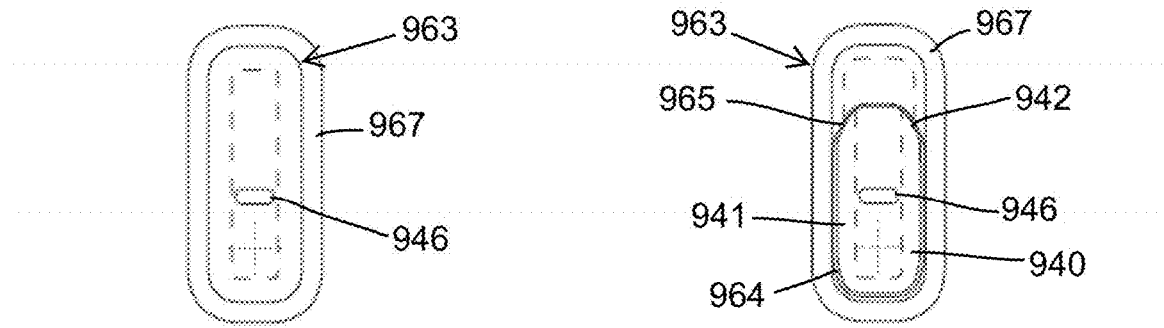
FIG. 74 is a top view of a housing of the band as shown in FIGS. 68-70C.
FIG. 75 is a bottom view of the housing of FIG. 74.
Figures 76, 77:
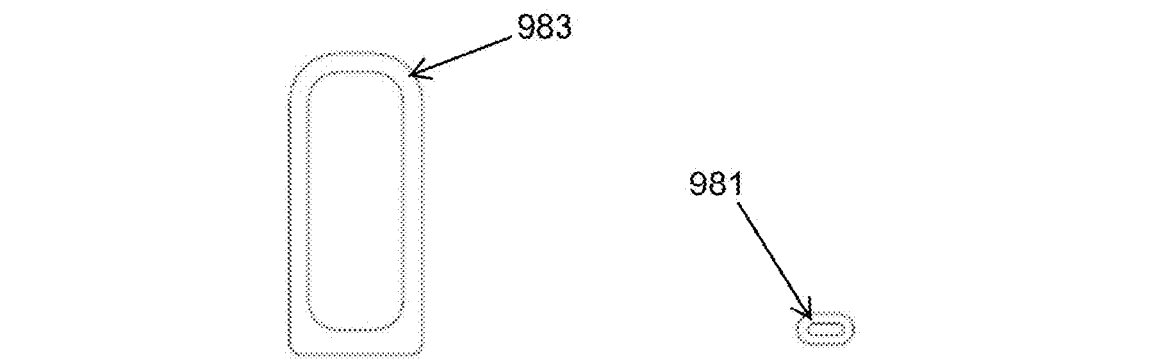
FIGS. 76-77 are top views of additional components for manufacturing the band as shown in FIGS. 68-70C.

In one embodiment, a support piece 982 as shown in FIG. 73 may also be positioned between the housing 963 and the inside surface 950F of the outer portion 950E of the main body piece 950 prior to folding of the main body piece 950. The method illustrated in FIGS. 83-91 does not include this support piece 982, and the support piece 982 (if used) may be connected to the housing 963 and the main body piece 950 between the steps in FIGS. 88 and 89 in one embodiment. The support piece 982 may be formed of a heat-activated material as described herein and may be heat pressed into place. The support piece 982 may have a hole (not shown) cut in alignment with the window 946. This support piece 982 may be included if graphics are printed on or around the areas of the band 920 located over the pocket 940 and housing 963, e.g., as in FIGS. 40A-B, to resist stretching or distortion of the graphics. If no graphics are printed in this location, the support piece 982 may not be included.

Figure 97:
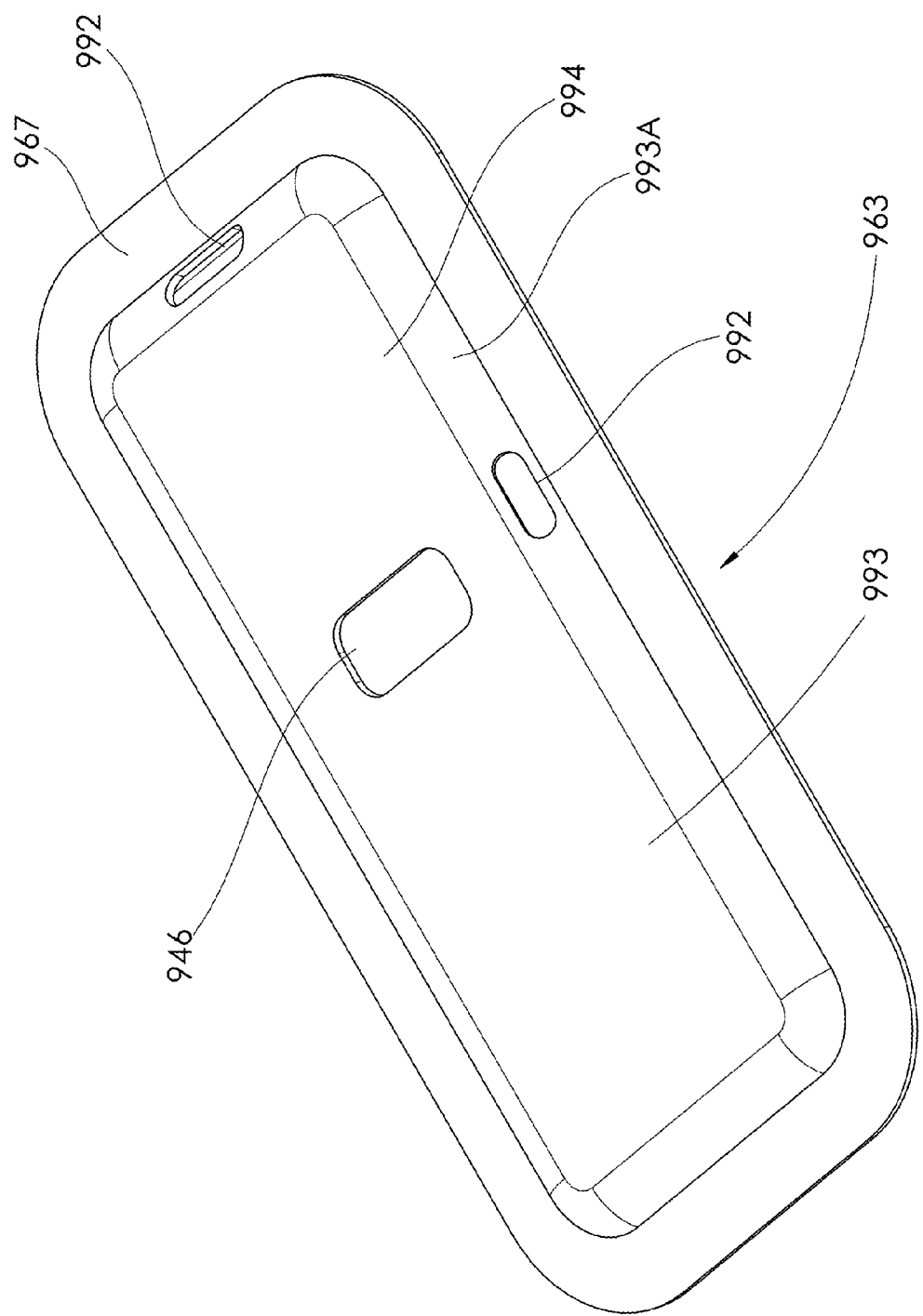
FIG. 97 is a top perspective view of another embodiment of a housing usable in manufacturing a band according to aspects of the disclosure.
Figure 98:
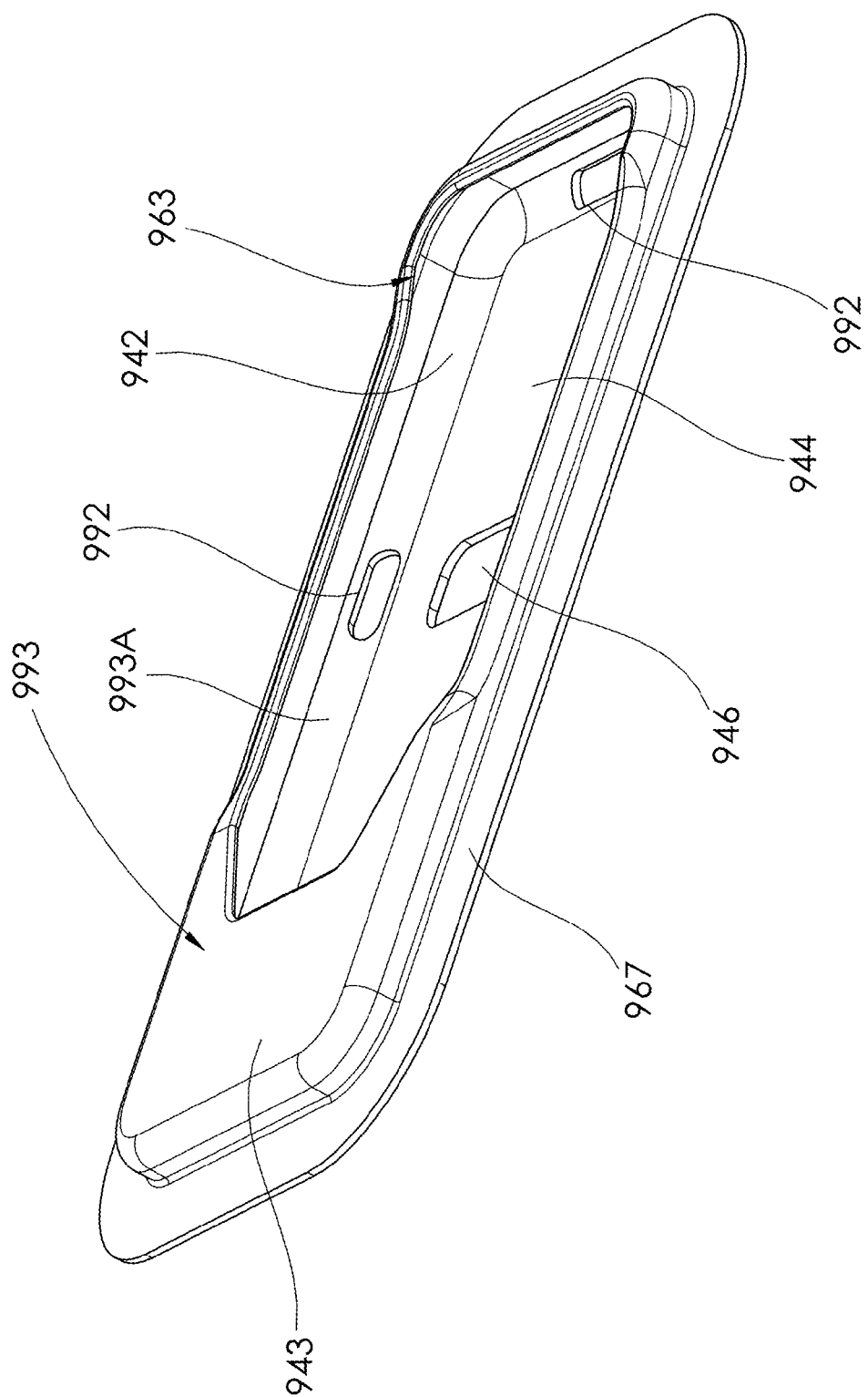
FIG. 98 is a bottom perspective view of the housing of FIG. 97.
Figure 99:
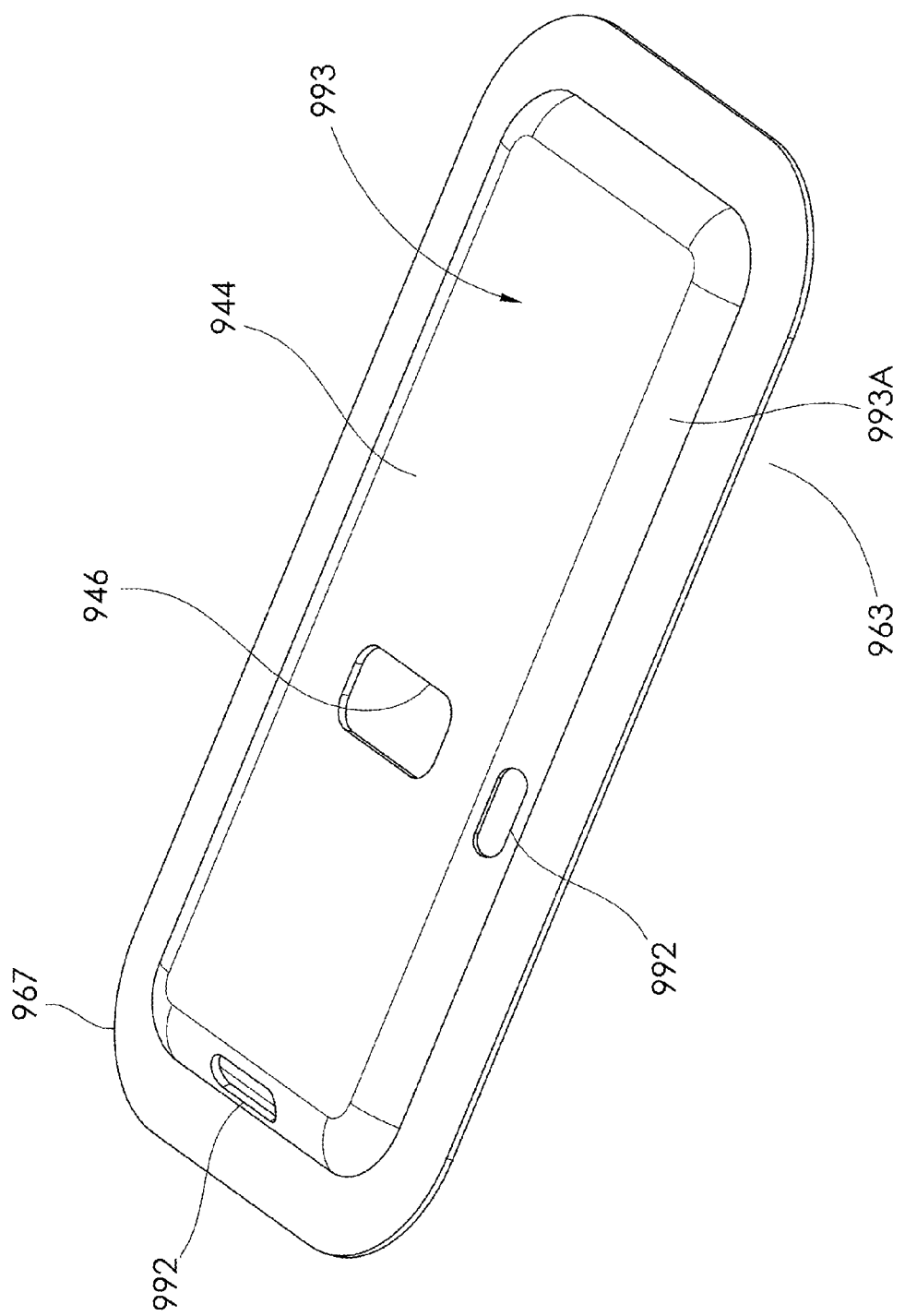
FIG. 99 is a top perspective view of the housing of FIG. 97.
Figure 100:
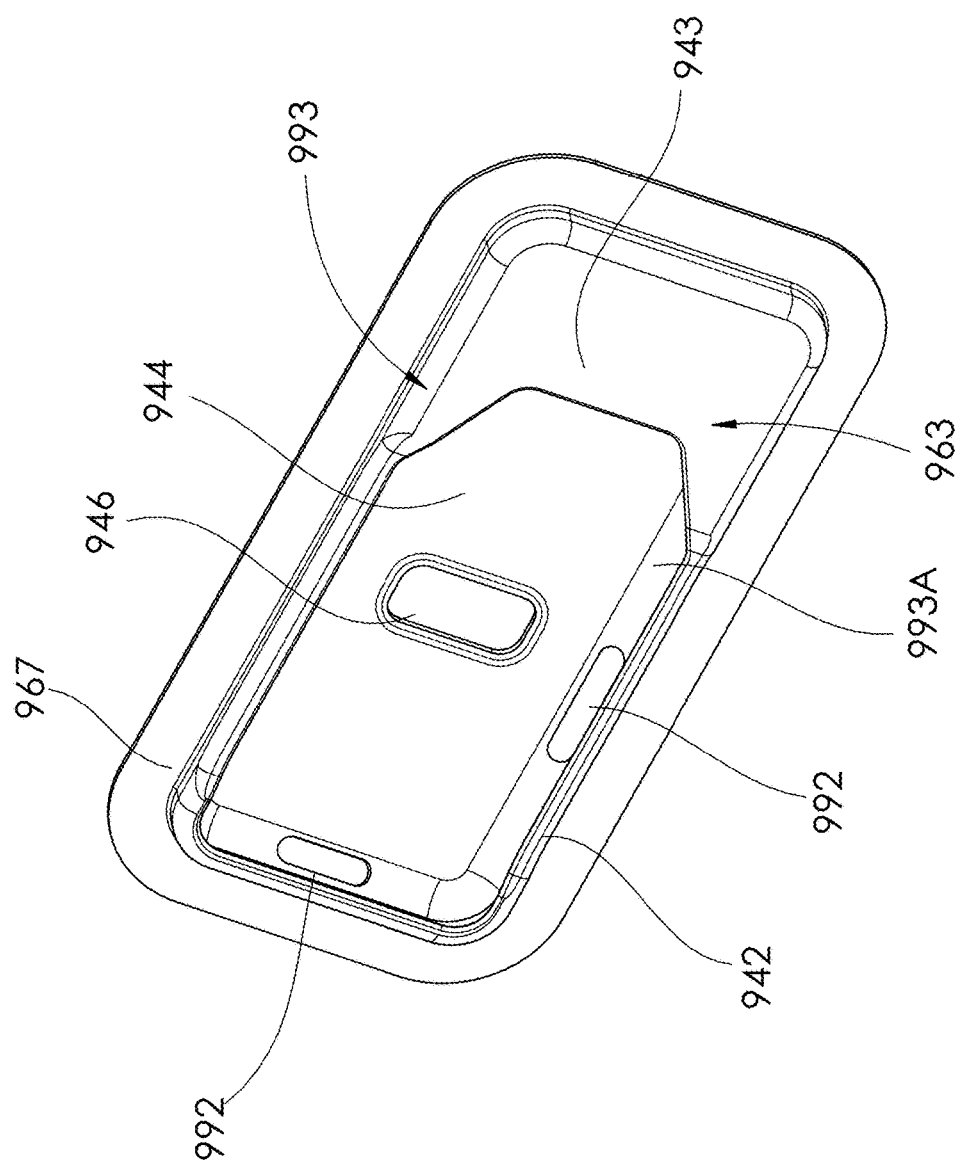
FIG. 100 is a bottom perspective view of another embodiment of a housing usable in manufacturing a band according to aspects of the disclosure.
Figure 101:
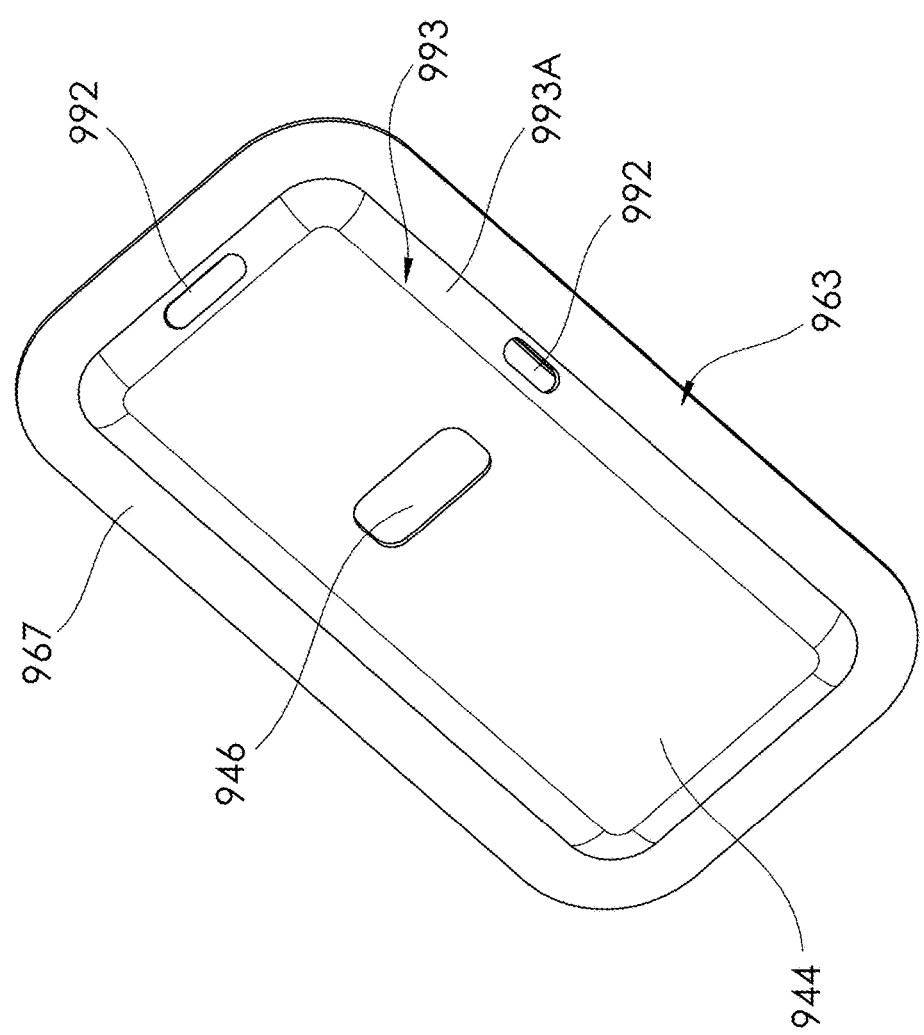
FIG. 101 is a top perspective view of the housing of FIG. 100.

FIGS. 97-99 illustrate an embodiment of a housing 963 that is usable in manufacturing a band 920 according to various embodiments described herein. FIGS. 100-101 illustrate another embodiment of a housing 963 that is configured in a similar manner to the housing 963 in FIGS. 97-99, and the descriptions herein with respect to FIGS. 97-99 apply equally to FIGS. 100-101 unless stated otherwise. The housing 963 in FIGS. 97-99 includes one or more slots 992 extending through one or more of the walls 993 of the housing 963. It is understood that the walls 993 of the housing 963 define the cavity 941 and may include the outer wall 943, the inner wall 944, and potentially other walls as well.

The slots 992 may help avoid accumulation of moisture (e.g., sweat) within the housing 963 during use, by allowing the moisture to escape easily from the housing 963. In one embodiment, the housing 963 may include at least one slot 992 that is located at the end of the housing 963 positioned closest to the bottom end 924 of the band 920, i.e., the end of the housing 963 that is configured to be at the bottom when the band 920 is worn on a user's arm in a normal standing position. The housing 963 in FIGS. 97-99 has a slot 992 on the bottom end of the outer wall 943 in this position, when the housing 963 is mounted on the band 920 in the orientation shown in FIGS. 69-70A, 91, and 96. In this position, the downward-facing slot 992 promotes increased moisture passage, because gravity tends to force moisture toward the slot 992. Centrifugal force generated by swinging the arm during exercise may also force moisture toward the downward-facing slot 992. The housing 963 may also have one or more additional slots 992 in other locations in various embodiments. For example, the housing 963 may also have slots 992 in one or both of the left and right sides of the inner wall 944, as in the embodiment of FIGS. 97-99. These side slots 992 may also promote increased moisture passage through gravity and/or centrifugal force, as one of these slots 992 will be downward-facing when the user's arm is bent at a 90° angle, as is common during running and many other exercises.

The housing 992 may have additional slots 992 and/or slots 992 located in different positions in other embodiments, which may or may not be positioned in locations where gravity and/or centrifugal force promote flow of moisture. For example, if the housing 963 is positioned in a different orientation in another embodiment, e.g., oriented similarly to the embodiment in FIG. 39A, then the end of the housing 963 that is downward-facing may be different. In such an embodiment, the slot(s) 992 may be located differently, in order to promote increased moisture passage, e.g., by having a slot 992 at the opposite end of the housing 963 as the end slot 992 in FIGS. 97-99. In a further embodiment, the housing 963 may have slots 992 located at the bottom-left and bottom-right corners. Still further configurations may be used in other embodiments.

The slots 992 in the embodiment of FIGS. 97-99 are formed in the outer wall 943 of the housing 963. These slots 992 may be considered to be formed at least partially or entirely in side walls 993A of the housing 963 that form part of the outer wall 943 and extend transversely to the flange 967. In this position, the slots 992 are positioned only on the portions of the housing 963 that are located outwardly (toward the outer side 928 of the band 920) from the flange 967. This configuration permits moisture to pass from inside the housing 963 to the exterior of the housing and to be absorbed by the material of the band 920. In other embodiments, the slots 992 may additionally or alternately be located elsewhere. For example, the housing 963 may include one or more slots 992 in the inner wall 944 that allow moisture to pass to the exterior the band 920, or the housing 963 may have other exposed surfaces (such as in a differently-configured band 920) that may have slots 992 therein. Additionally, the size(s) of the slot(s) 992 may affect the moisture passage properties, as larger slots 992 can assist in breaking any meniscus that may form from moisture accumulation. In one embodiment, the slot 992 at the end of the housing 963 may be at least 50% of the width of the wall 993 in which it is located (i.e., not including the flange 967), and the slot(s) 992 on the side walls 993 of the housing 963 may each be at least 20% of the length of the side wall 993 in which it is located. Further, the housing 963 may have a surfactant applied to the inner surfaces of the housing 963, in order to enhance the ability of moisture to travel toward the holes and break up any meniscus that may form. The use of a surfactant may enable the use of smaller slots 992.

The slots 992 may be formed using any of a number of different forming techniques, in various embodiments. For example, in one embodiment, the slot(s) 992 may be formed in the housing 963 after the housing is formed, such as by using laser cutting, mechanical cutting, thermal cutting, or other cutting techniques; machining techniques; or other material removal techniques. In another embodiment, the slot(s) 992 may be formed as part of the forming process, such as by pressing or molding the material of the housing 963 with a tool configured to form the slot(s) 992. For example, a single-piece, injection molded TPU housing 963 as described above may be injection molded into a cavity that forms the slot(s) 992. Other techniques known in the art may be used as well.

Figure 94:
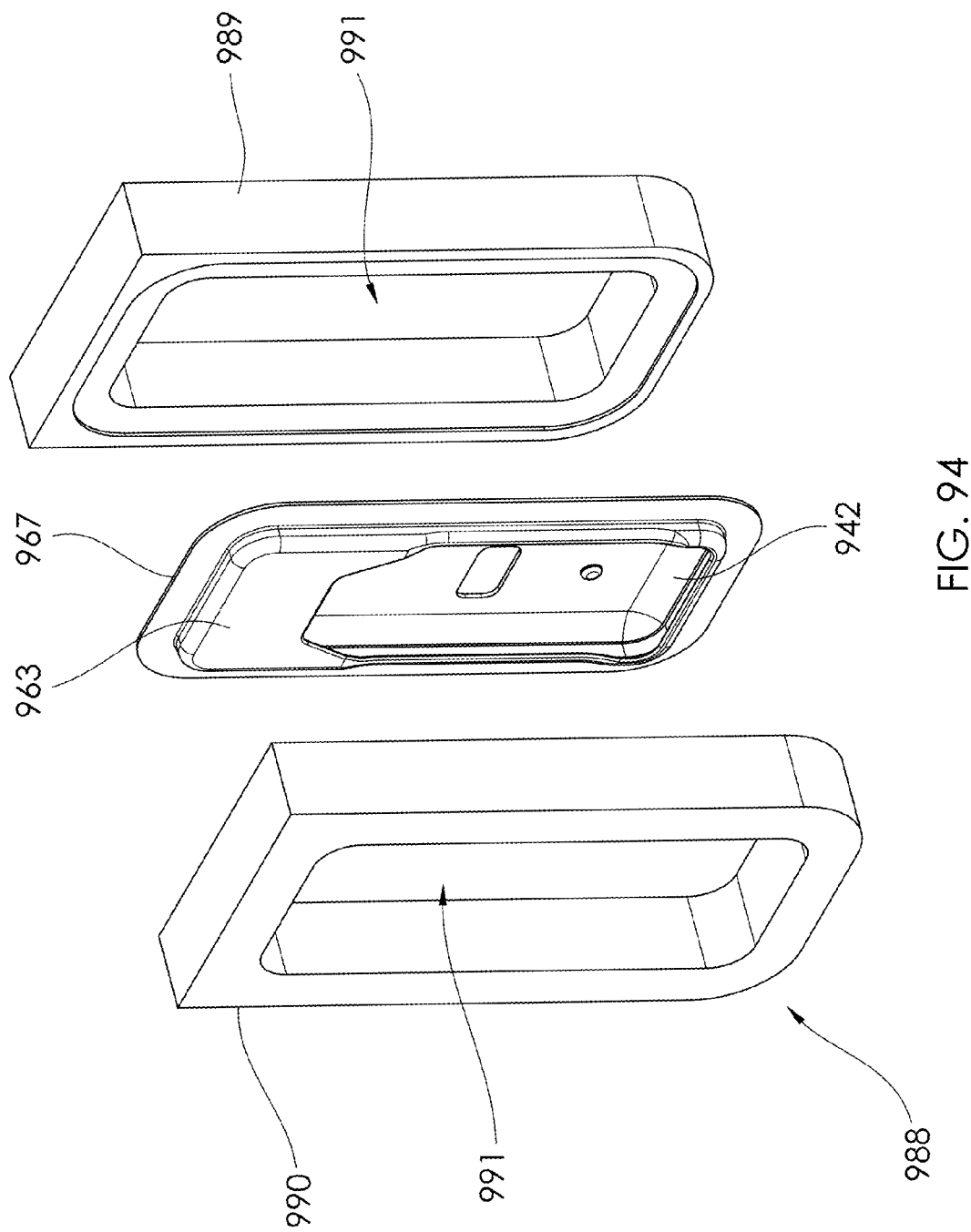
FIG. 94 is a perspective view schematically illustrating one embodiment of a mold for heat pressing a portion of a band according to aspects of the disclosure, along with the housing of FIG. 74, which is usable in connection with the method of FIGS. 83-91.
Figure 95:
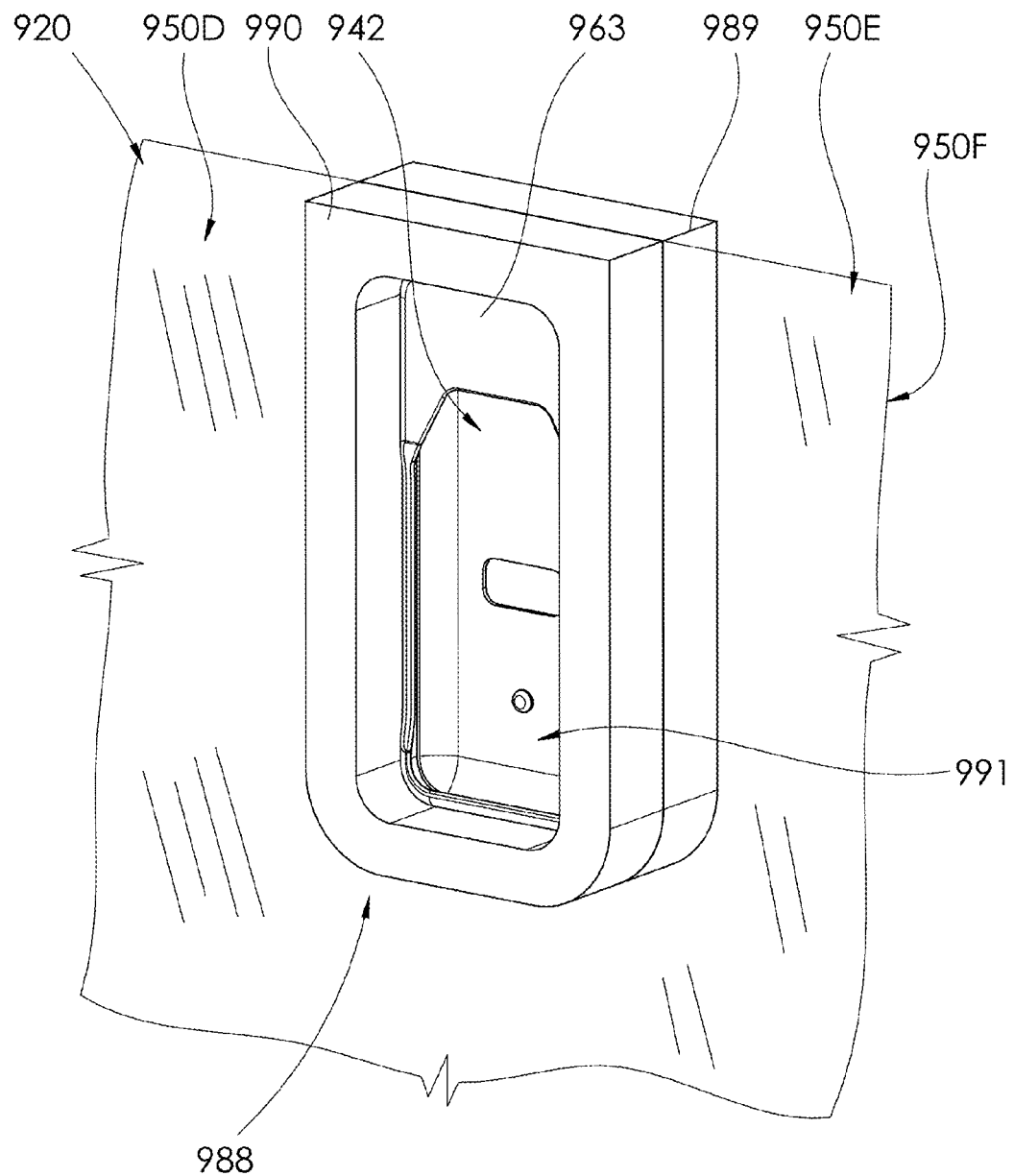
FIG. 95 is a perspective view schematically illustrating use of the mold of FIG. 94 in operation.

FIGS. 94-95 illustrate one embodiment of a heat press assembly 988 configured for heat pressing around the flange 967 of the housing 963 after the housing 963 is connected to the band 920, e.g., by stitching, as described herein with respect to FIG. 87. The heat press assembly 988 as shown in FIGS. 94-95 includes two opposed mold pieces 989, 990 that are configured for heat pressing around the flange 967 of the housing 963. The band 920 is illustrated schematically in FIG. 95, to show that the heat press assembly 988 is configured for heat pressing the band 920 along with the housing 963. In operation, the first mold piece 989 is positioned on the inside surface 950F of the inner portion 950D of the main body piece 950, and the second mold piece 989 is positioned on the outside surface 950G of the inner portion 950D of the main body piece 950. The mold pieces 989, 990 are annular in shape, each having an internal opening 991, so that the mold pieces 989, 990 are configured to press only around the flange 967 of the housing 963. In this configuration, the main body of the housing 963 is received within the opening 991, so that the mold pieces 989, 990 do not press the main body of the housing 963 or the adjacent portions of the band 920, which localizes the heat application and avoids creating unwanted marks or discolorations on the non-pressed portions of the band 920 and housing 963. The trim piece 983 shown in FIG. 88 may be applied prior to operation of the heat press assembly 988 in one embodiment, and the shapes of the mold pieces 988, 989 conform to the shape of the trim piece 983 as shown. The heat press assembly 988 may be applied to the band 920 and housing 963 following the assembly steps shown in FIGS. 87 and 88, and before the band 920 is folded over in FIG. 89 (discussed below). Additional pieces of heat-sealable material may be used in various positions, in connection with the heat press assembly 988. For example, the support piece 982 in FIG. 73 may also be applied before operation of the heat press assembly 988, as discussed herein. It is understood that the configuration of the mold pieces 988, 989 may vary depending on the shapes and configurations of the housing 963 and the trim piece 983 (or other pieces of heat sealable material that may be used).

Figure 89:
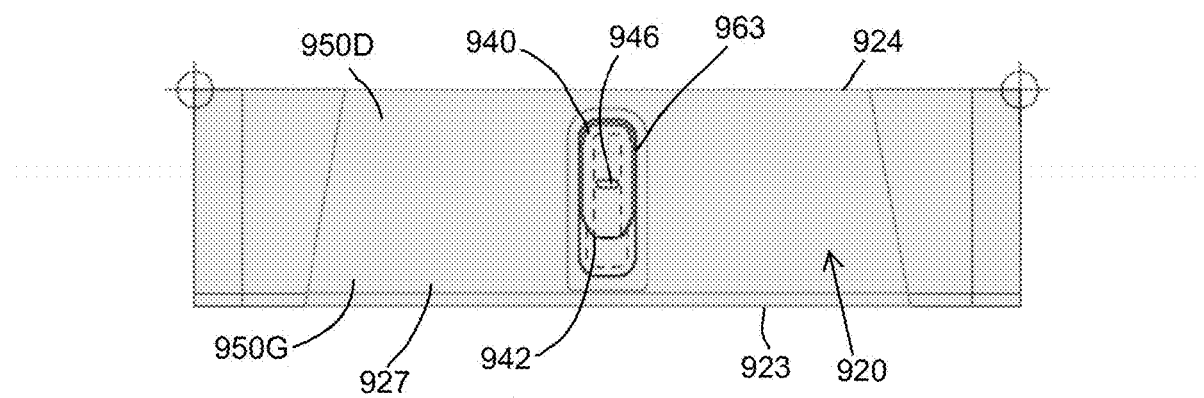
Figure 90:
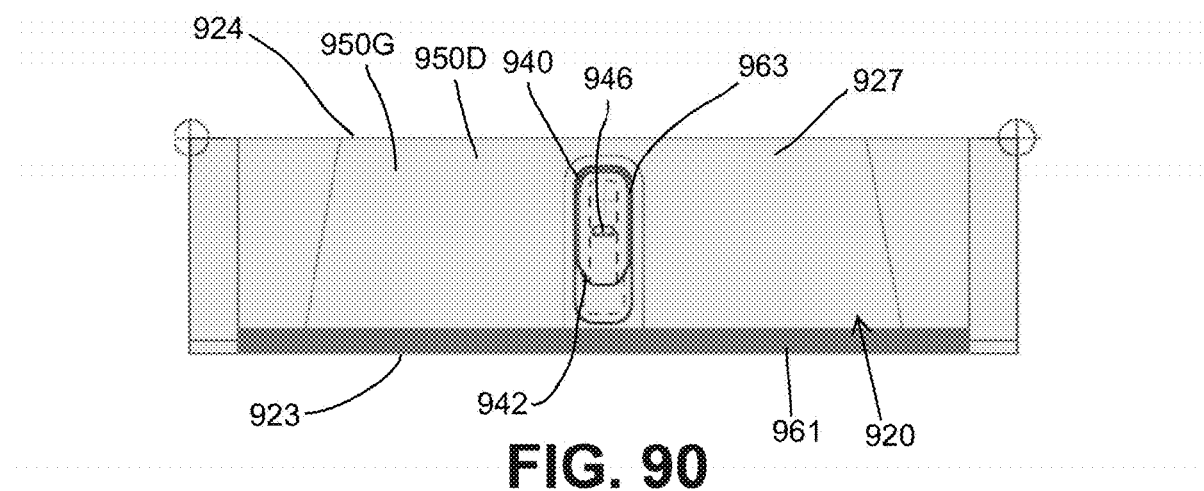
Figure 91:
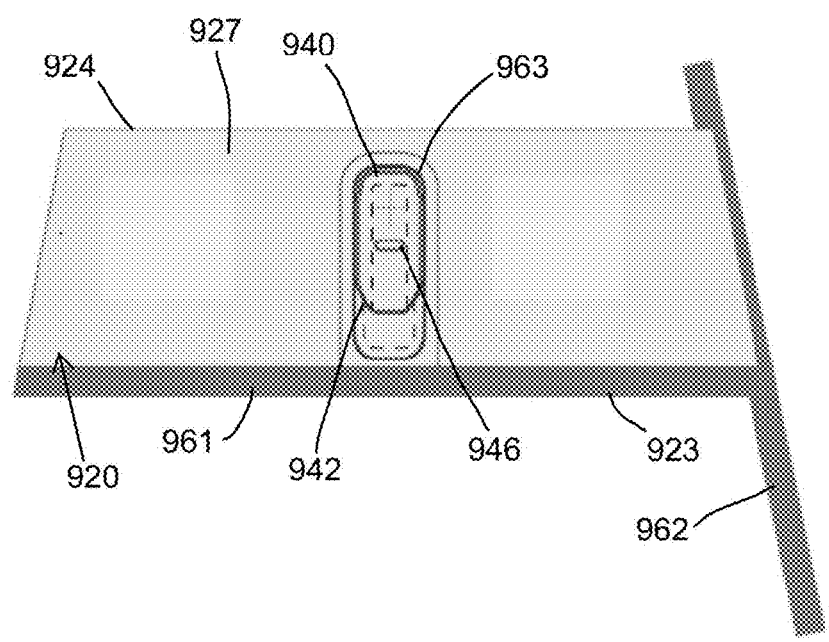

The main body piece 950 is then folded over so that the inner and outer portions 950D-E confront each other, as shown in FIG. 89. The outside surface 950G of the inner and outer portions 950D-E forms the inner and outer surfaces 927, 928 of the band 920, respectively, and the inside surface 950F is located internally within the band 920 in this configuration. A seam bonding strip 961 is placed along the edge where the folded ends of the inner and outer portions 950D-E meet, in order to cover the edges, as shown in FIG. 90. In one embodiment, the strips 960, 961, 968, frame bond 980, the trim piece 983, the light alignment bond 981, and optionally the support piece 982 (if present) may be bonded completely at this point in the process, such as by localized bonding techniques. For example, the bonding may be accomplished by bonding each piece individually and sequentially, or by a heat press with tool surfaces configured to press the desired pieces at the desired locations and not to press other locations of the band 920. The main body portion 950 may be cut to size at this point in the process, such as by cutting the ends 950 of the main body piece 950 to form angled edges, as seen in FIG. 91. A band closure trim strip 962 may be used to bond the ends of the main body piece 950 together to form the tubular body 921, as shown in FIG. 91. In one embodiment, the ends of the main body piece 950 are first wrapped to form the tubular body 921 and then stitched together along the seam, then the band closure trim strip 962 is applied to cover the stitching and secure the connection. The band closure trim strip 962 wraps around both the inner and outer surfaces 927, 928 of the band 920 when assembled, and one embodiment of the band closure strip can be seen in greater detail in FIG. 70C. In one embodiment, the closure trim strip 962 is locally heat pressed subsequent to the additional heat pressing operation described above. After stitching and connection of the trim strip 962, the final structure of the band 920 is formed, with the pocket 940 defined on the inner surface 927.

Figure 92:
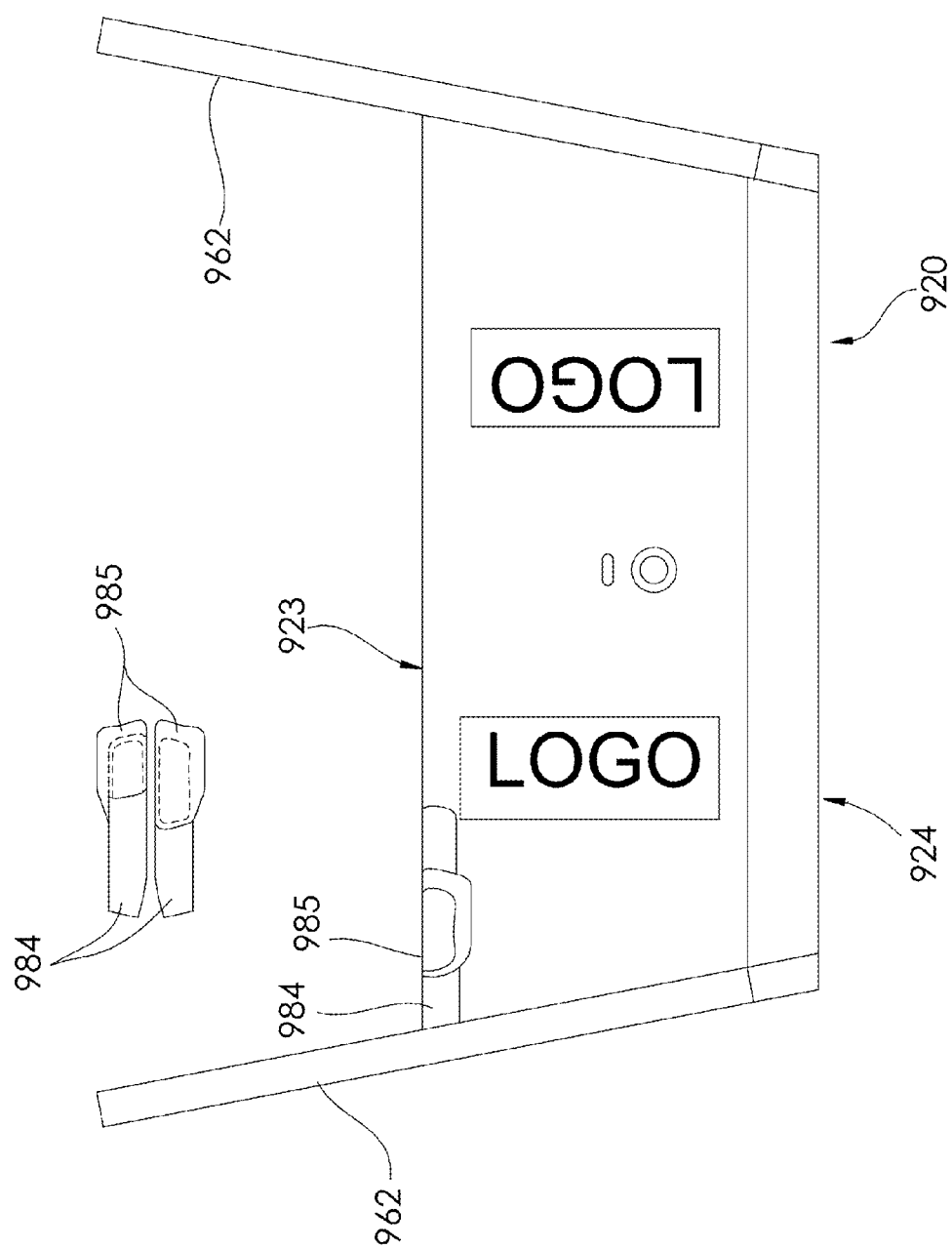
FIG. 92 is a top view of another embodiment of a band according to aspects of the disclosure, with a portion of the band shown in greater detail in an inset.
Figure 93:
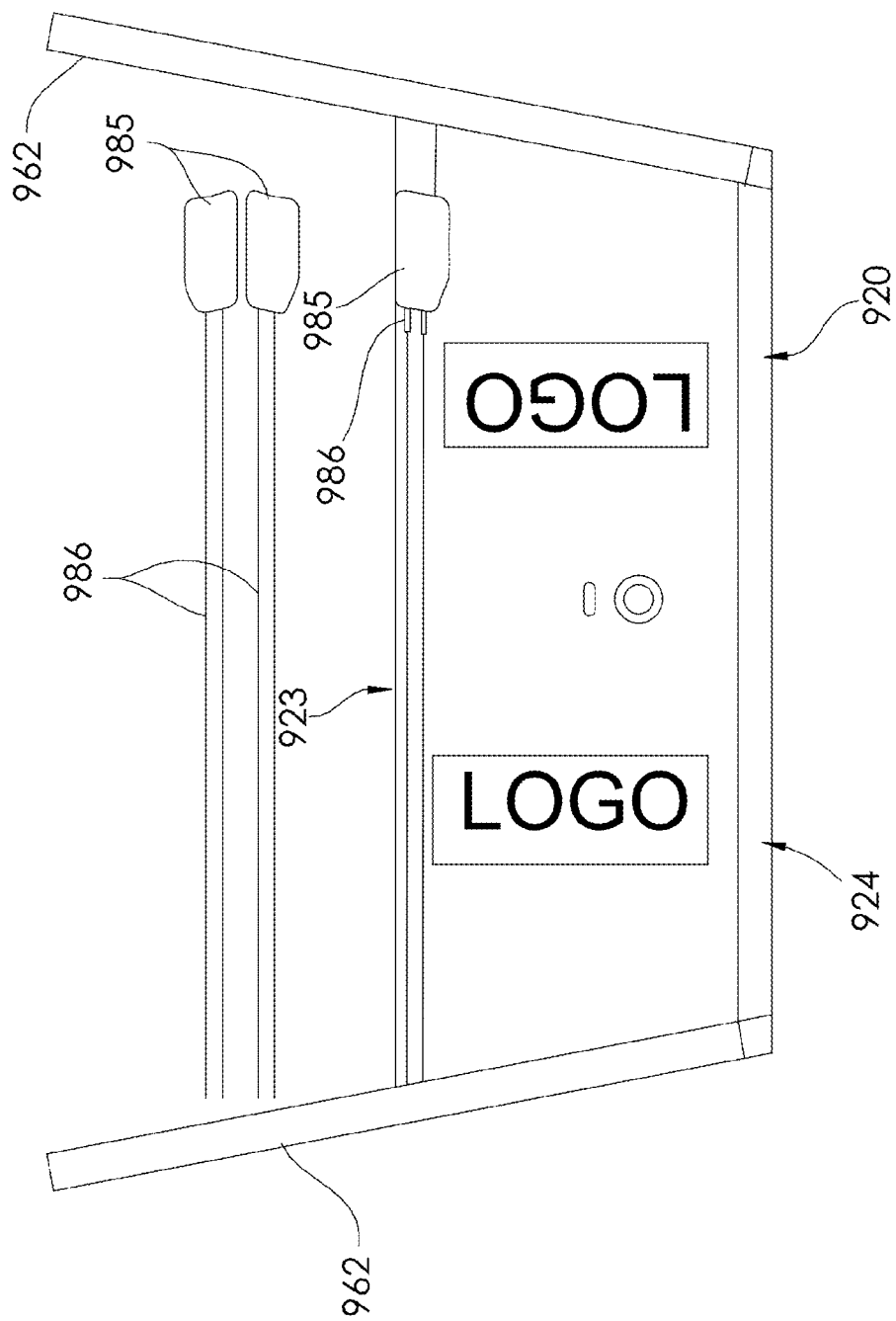
FIG. 93 is a top view of another embodiment of a band according to aspects of the disclosure, with a portion of the band shown in greater detail in an inset.

The band 920 may further be provided with an adjustment mechanism in one embodiment, to make the size (i.e., circumference) of the tubular body 921 adjustable. Examples of such adjustment mechanisms may include an adjustable fastening structure such that the band 920 can be wrapped around a portion of the user's body and fastened to form the tubular shape, or a foldable tab or flap that may be fastened in different positions to tighten or loosen the band 920. Fastening structures that may be used for such an adjustment mechanism include hook and loop (i.e., Velcro), snaps, clips, buckles, ties, etc. Other examples of such adjustment mechanisms include tightening strips or straps or a drawstring, which may be fastened as described above. Further examples of adjustment mechanisms may be used in other embodiments. FIGS. 92-93 illustrate example embodiments of structures that may be used for such adjustment mechanisms. For example, FIG. 92 illustrates a band 920 with an elastic tab 984 that is fixed proximate the edge of the band 920 at one end and has a releasable connector 985 (Velcro in this embodiment) at the opposite end. The elastic tab 984 can be stretched and reconnected to increase compression locally, thereby making the band 920 fit tighter on the user's body. The tab 984 is connected at the top end 923 of the band 920 in this embodiment, but could be located elsewhere in other embodiments. As another example, FIG. 93 illustrates a band 920 with an elastic cord or drawstring 986 that extends along most of the length of the band 920, with one end fixed near one edge of the band 920 and the other end having a releasable connector 985 (Velcro in this embodiment) near the opposite edge of the band 920. The cord 986 is connected at the top end 923 of the band 920 in this embodiment, but could be located elsewhere in other embodiments. The cord 986 can be stretched and reconnected to increase compression along almost the entire length of the top end 923 of the band 920. Further different embodiments of adjustment mechanisms may be used in other embodiments.

Figure 41:
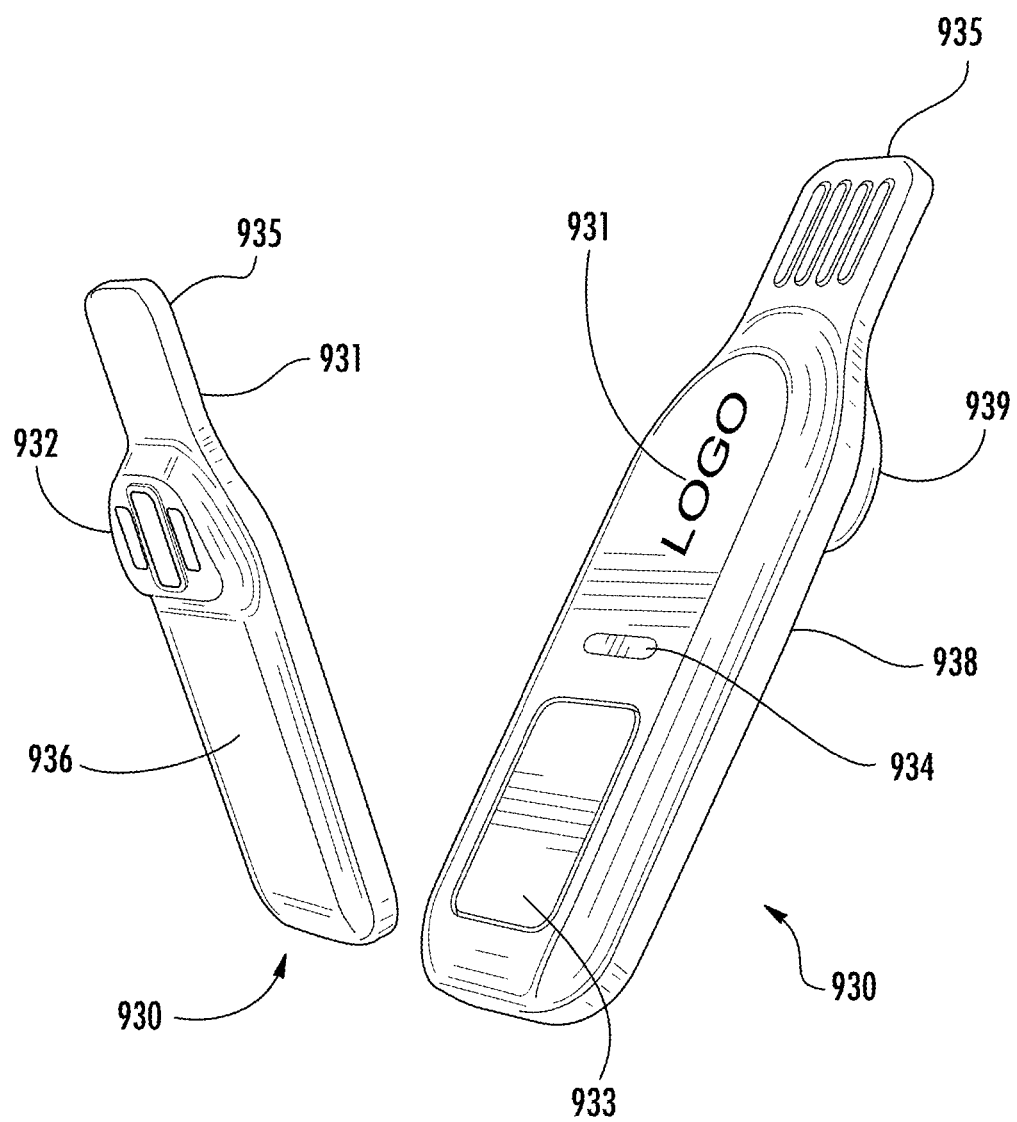
FIG. 41 shows top perspective and bottom perspective views of one embodiment of a module according to aspects of the disclosure.

FIG. 41 shows perspective side views of a module 930 that may be used in association with apparel or other devices, such as being insertable within an armband that may be used during intense physical activity. Module 930 may include one or more mechanical, electric, and/or electro-mechanical components, such as computer components, that are described elsewhere herein, as well as a casing 931 forming a structural configuration for the module 930. Module 930 may comprise at least one of a processor, a non-transitory computer-readable medium, sensor and/or a transceiver. One or more components may be similar to and/or identical to any component shown and described above in FIGS. 1-5. Those skilled in the art will appreciate that module 930 and the casing 931 may have multiple different structural configurations and the illustrations are merely exemplary.

In the embodiment of FIG. 41, the module 930 has at least one sensor 932, which may be in the form of, for example, a heart rate sensor or other sensor for sensing another physiological parameter of the user. Module 930 may be configured to contact the skin of the user during wear while the module 930 is secured within the band or apparatus. For example, the heart rate sensor 932 in this illustrated embodiment is an optical sensor that works best in contact or close proximity with the skin. As shown in FIG. 41, the casing 931 of module 930 has a projection 939 on the underside 936, and the sensor 932 is mounted on the end of the projection 939. The projection 939 extends the sensor 932 farther away from the surrounding surfaces of the casing 931, permitting greater capability for forming continuous contact with the user's body. Band 920 may have an aperture that allows a front surface of the protrusion to contact the user's skin, however, the remainder of underside 938 is held within the band 920 or at least is separated from the user's skin by at least one layer of a material. In one embodiment, the layer of material may be configured to wick away moisture (e.g., such as sweat) away from the sensing surface on the user's skin. In other embodiments, it may be configured to prevent moisture, light, and/or physical materials from contacting the sensing surface or location during the physical activity. In one embodiment, it may selectively block light of certain wavelengths. In certain embodiments, at least 95% of ambient light is blocked within the immediate vicinity of the sensing surface. In another embodiment, at least 99% of the ambient light is blocked. This may be advantageous for optical sensors, such as optical heart rate sensors. Those skilled in the art will appreciate that other sensors, including those sensors described above in relation to FIGS. 1-5, may be used—either alone in combination with each other or other sensors—without departing from the scope of this disclosure.

In one general embodiment, the module 930 may include one or more user input interfaces, such as for example, buttons 933 to provide user-actuated input. An example user input interface may consist of single mechanical button, e.g., button 933, which is shown on the top side 937 opposite the underside 936. Yet in other embodiments, display feature 934 may be configured as a user-input interface. Those skilled in the art will appreciate that one or more user-actuated inputs may also be received through one or more transceivers of the module 930. For example, a system may be configured such that a user may be able to enter a user input onto an electronic mobile device which may mimic using buttons 933 or, alternatively, perform different functions than available in a specific instance of actuating buttons 933. Module 933 may further comprise one or more display features 934.

In one embodiment, the pocket 940 of the band or apparatus may be configured to receive module 930 having a display feature 934 on surface that provides at least one visual indicia to a user. Display features 934 may be a simple light source, such as a light emitting diode. In a specific embodiment, the color, intensity, or pattern of illumination of at least one light source in display features may be used to provide a visual indication to the user. Those skilled in the art will further appreciate that more complex display devices, such as LED, OLED, LCD, etc. may be utilized. Other output mechanisms, such as audible and tactile are within the scope of this disclosure.

Module 930 may further include one or more connectors 935 for charging and/or connection to an external device. In one embodiment, connectors 935 may include a serial bus connection, such as that may comply with one or more Universal Serial Bus (USB) standards. In one embodiment, connectors 935 may be configured to provide at least of the same electronic information to an external device that may be transmitted via one or more transceivers of the module 930.

When the module 930 in the embodiment of FIG. 41 is received within the pocket 940 illustrated in FIGS. 11-12 and 36-39B, connector 935 is received within the shell 948, the underside 936 of the casing 931 is positioned in contact with the inner wall 944 of the pocket 940, and the top side 937 of the casing 931 is positioned in contact with the outer wall 943 of the pocket 940. In this arrangement, the projection 939 extends through the sensor opening 945 to place the sensor 932 in closer proximity with the user's body, the button 933 is positioned adjacent the button portion 947 on the outer wall 943, and the light 934 is positioned in alignment with the window 946 to permit viewing of the light 934 through the outer wall 943. The projection 939 extending through the sensor opening 945 and also in certain embodiments may assist in holding the module 930 in place. In this configuration the end of the module 930 opposite the connector 935 protrudes slightly from the access opening 942, in order to facilitate gripping for removal of the module 930.

The casing 931 may have a structural configuration to increase comfort of wearing the module 930 in close proximity to the user's skin. For example, the casing 931 has a flat configuration to create a thin profile, making the module 930 less noticeable when being worn on the user's body. As another example, the casing 931 may have curved contours on the underside 936 and the top side 937, as well as curved or beveled edges, in order to enhance comfort.

Figure 42:
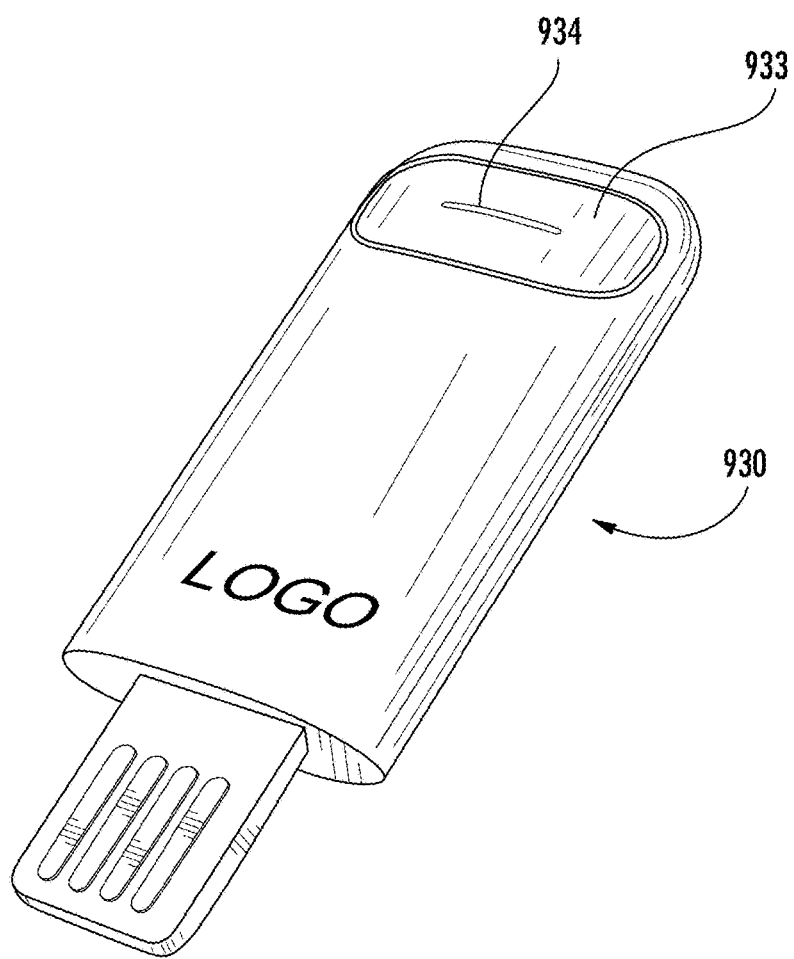
FIG. 42 is a top view of another embodiment of a module according to aspects of the disclosure.
Figure 43:
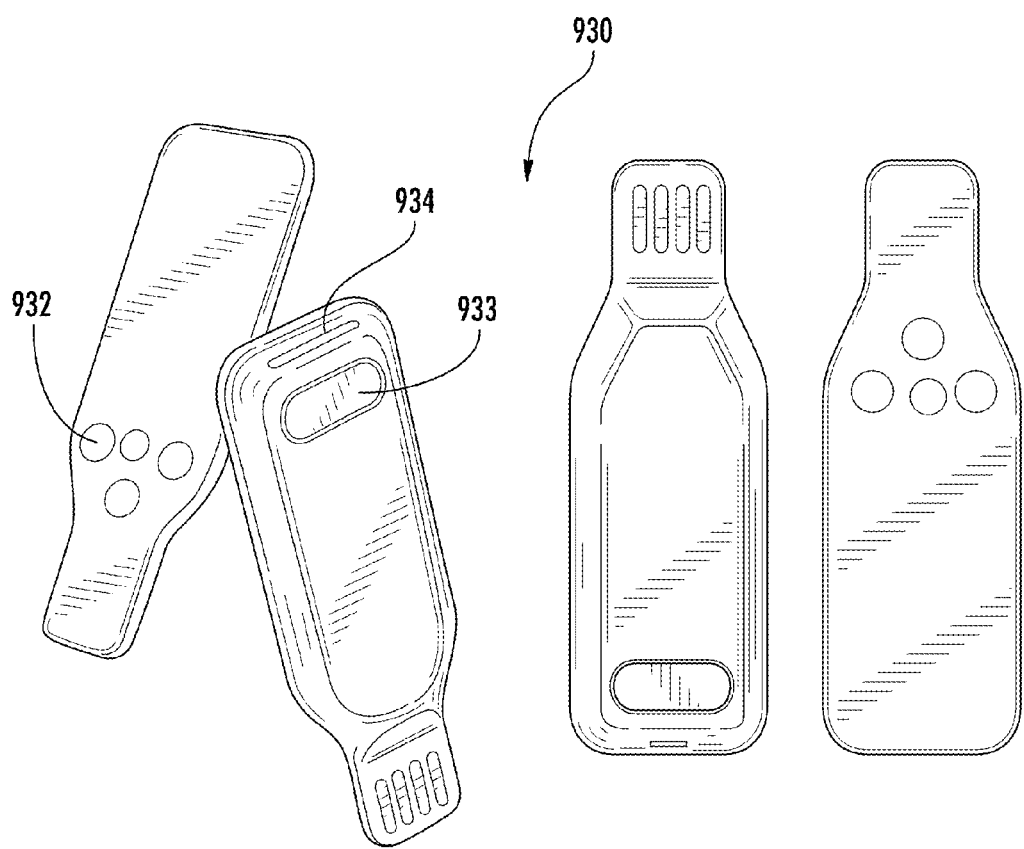
FIG. 43 shows bottom perspective, top perspective, top, and bottom views, from left to right, of another embodiment of a module according to aspects of the disclosure.
Figure 44:
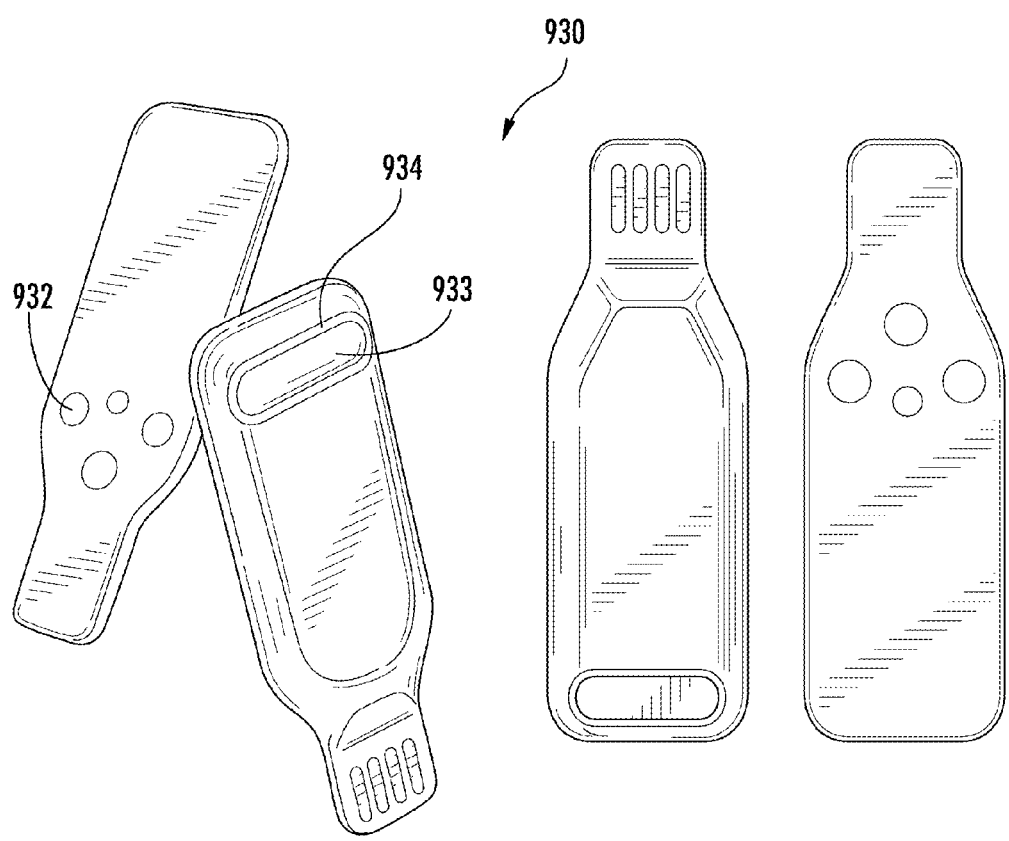
FIG. 44 shows bottom perspective, top perspective, top, and bottom views, from left to right, of another embodiment of a module according to aspects of the disclosure.
Figure 45:
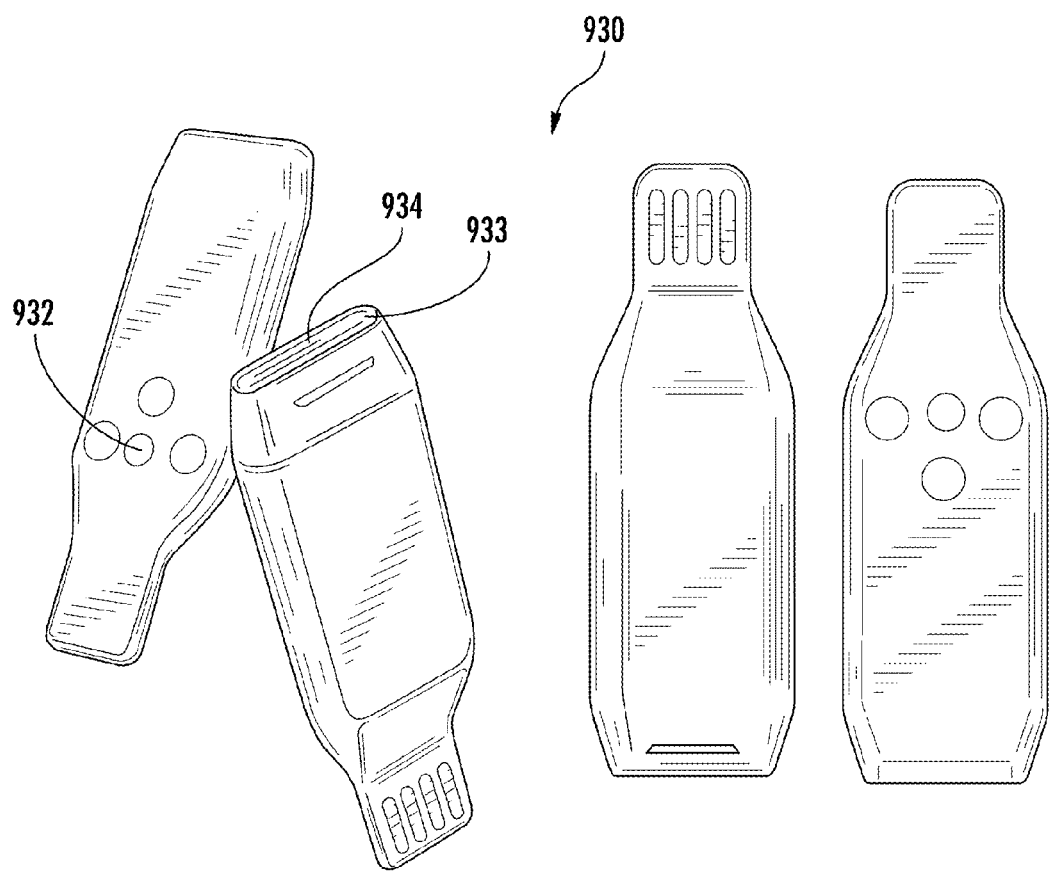
FIG. 45 shows bottom perspective, top perspective, top, and bottom views, from left to right, of another embodiment of a module according to aspects of the disclosure.
Figure 46:
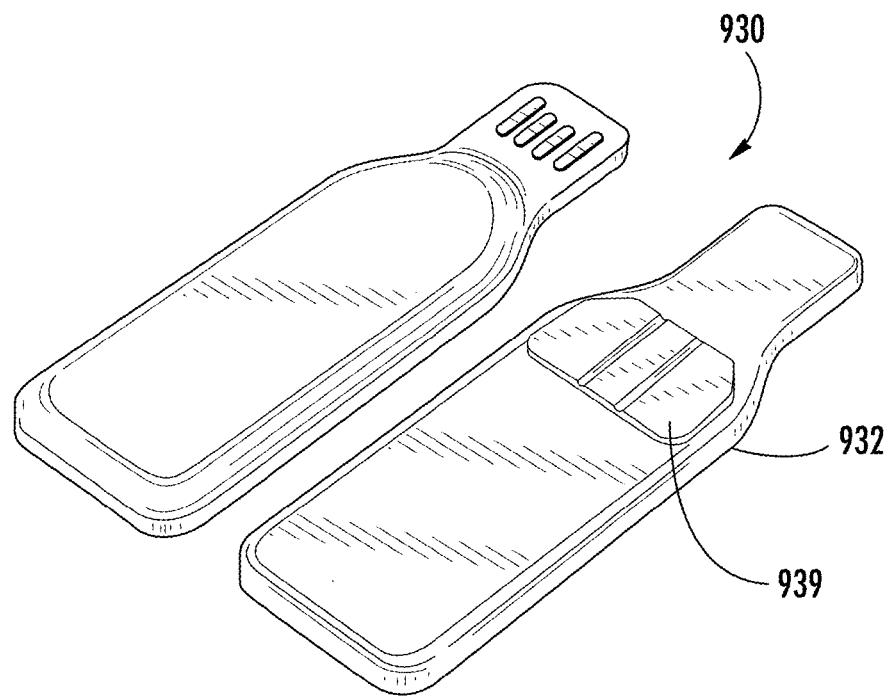
FIG. 46 shows top perspective and bottom perspective views, from left to right, of another embodiment of a module according to aspects of the disclosure.
Figure 47:
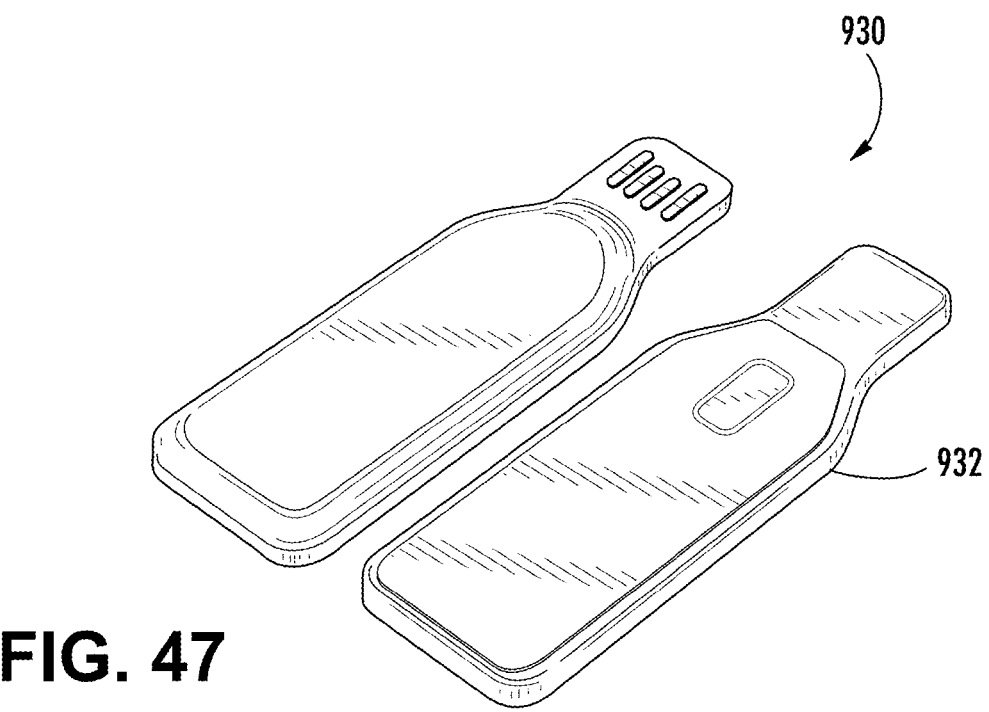
FIG. 47 shows top perspective and bottom perspective views, from left to right, of another embodiment of a module according to aspects of the disclosure.
Figure 48:
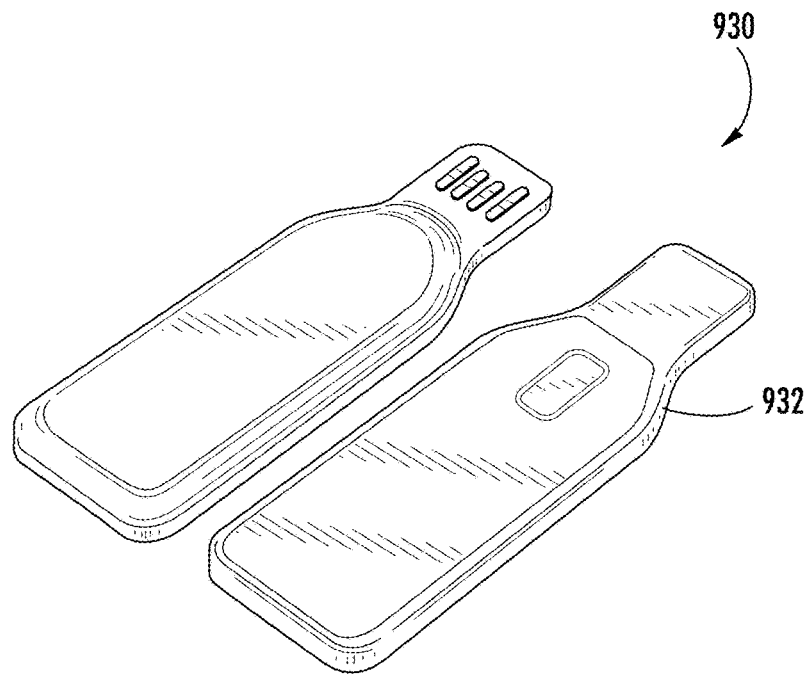
FIG. 48 shows top perspective and bottom perspective views, from left to right, of another embodiment of a module according to aspects of the disclosure.
Figure 49:
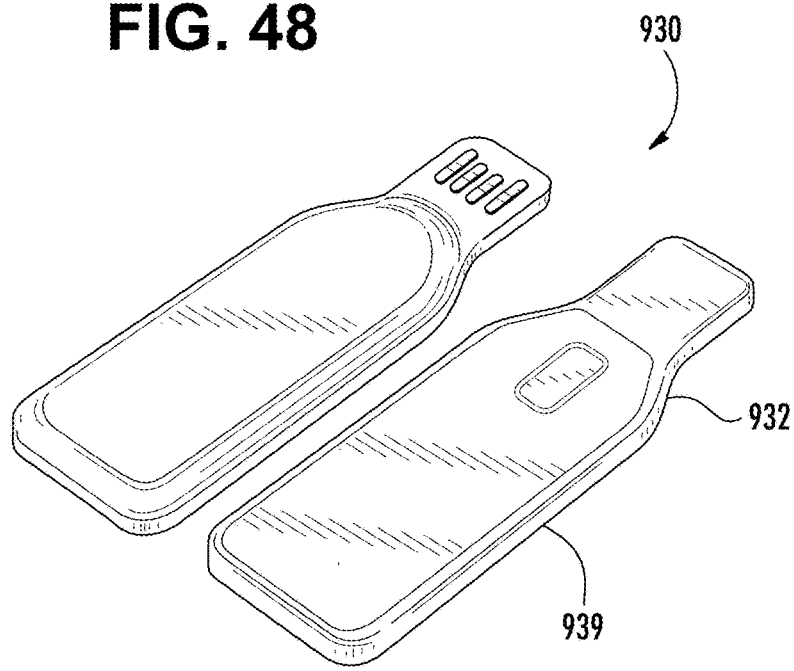
FIG. 49 shows top perspective and bottom perspective views, from left to right, of another embodiment of a module according to aspects of the disclosure.
Figure 50:
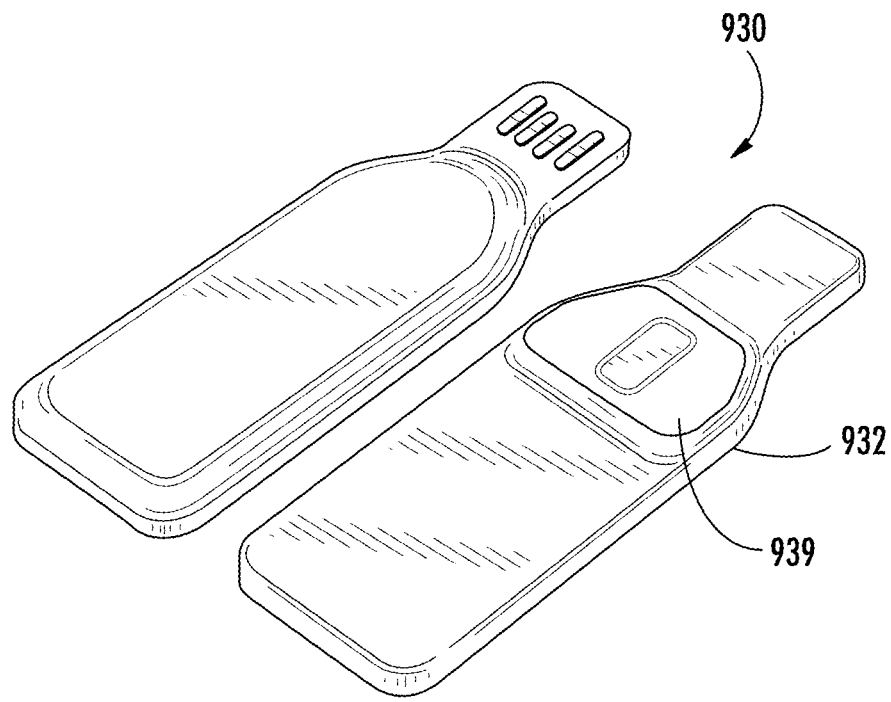
FIG. 50 shows top perspective and bottom perspective views, from left to right, of another embodiment of a module according to aspects of the disclosure.
Figure 51:
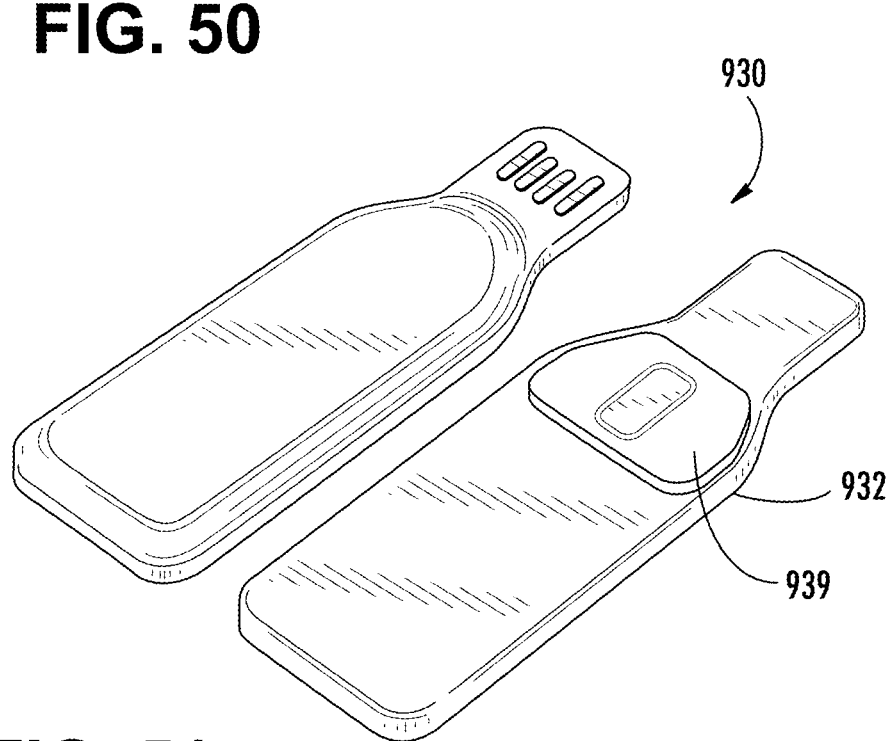
FIG. 51 shows top perspective and bottom perspective views, from left to right, of another embodiment of a module according to aspects of the disclosure.
Figure 52:
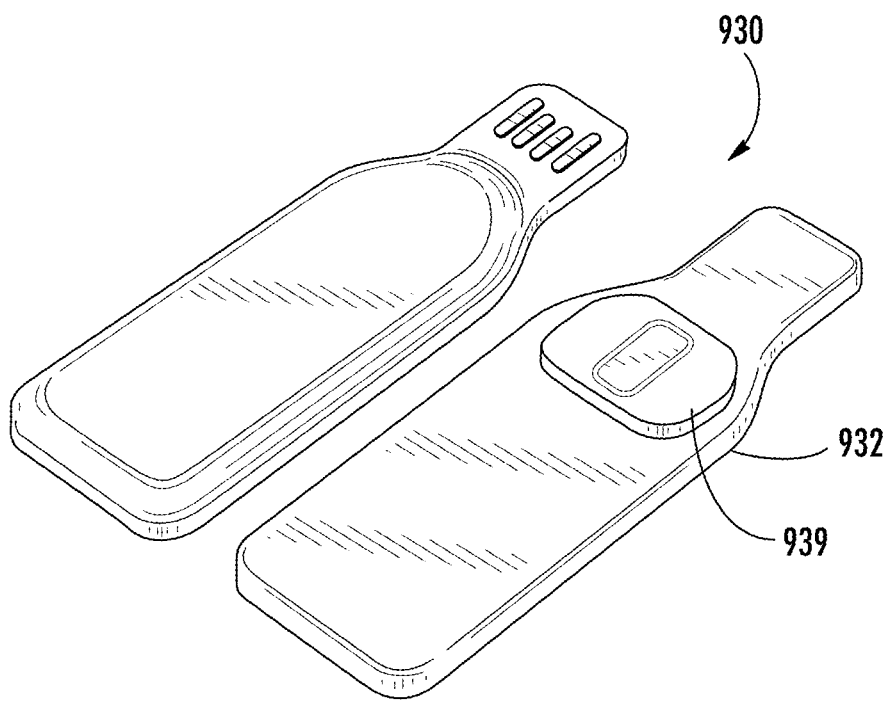
FIG. 52 shows top perspective and bottom perspective views, from left to right, of another embodiment of a module according to aspects of the disclosure.
Figure 53:
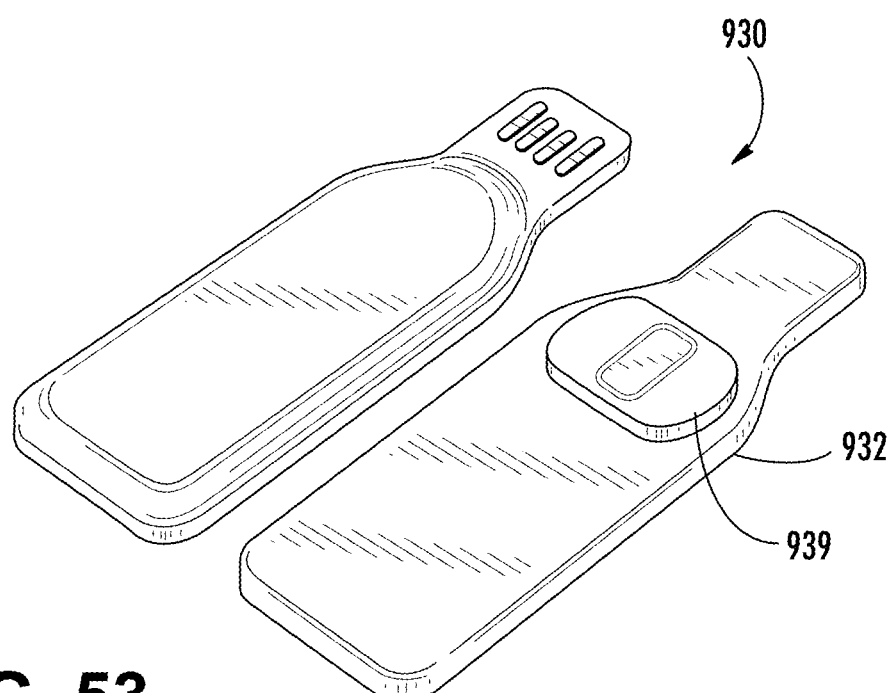
FIG. 53 shows top perspective and bottom perspective views, from left to right, of another embodiment of a module according to aspects of the disclosure.
Figure 54:
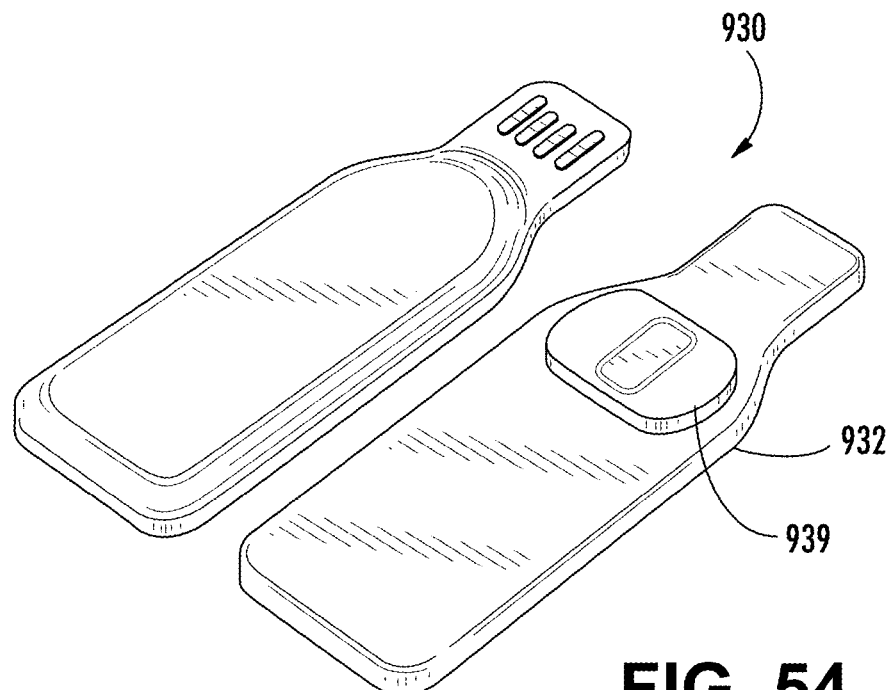
FIG. 54 shows top perspective and bottom perspective views, from left to right, of another embodiment of a module according to aspects of the disclosure.
Figure 55:
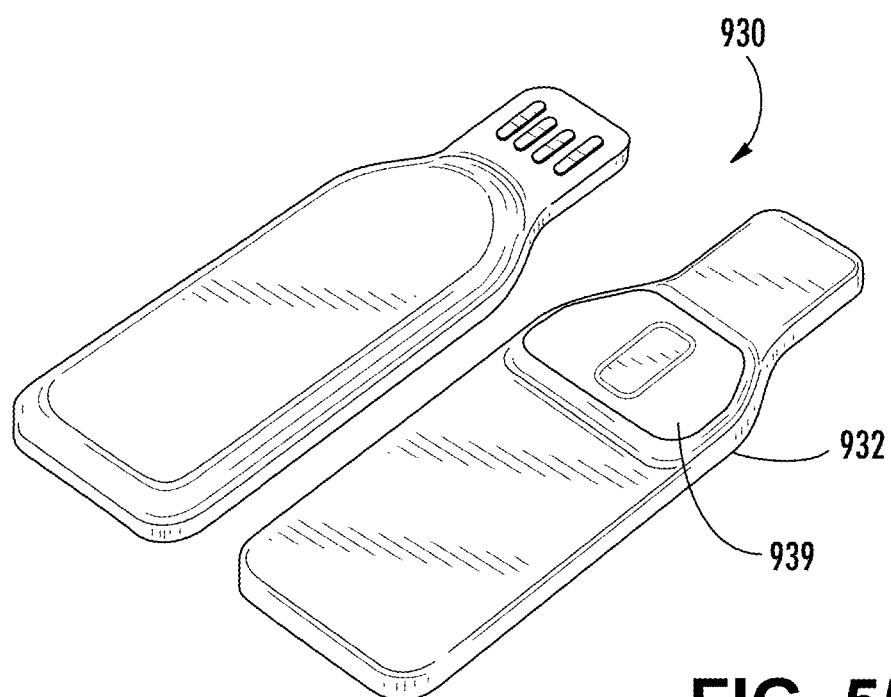
FIG. 55 shows top perspective and bottom perspective views, from left to right, of another embodiment of a module according to aspects of the disclosure.
Figure 56:
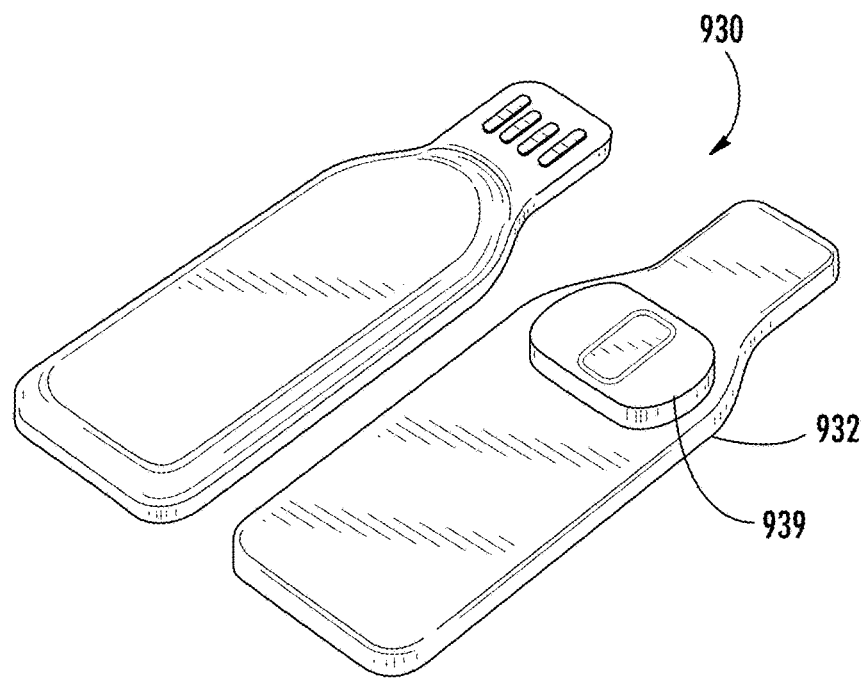
FIG. 56 shows top perspective and bottom perspective views, from left to right, of another embodiment of a module according to aspects of the disclosure.
Figure 57:
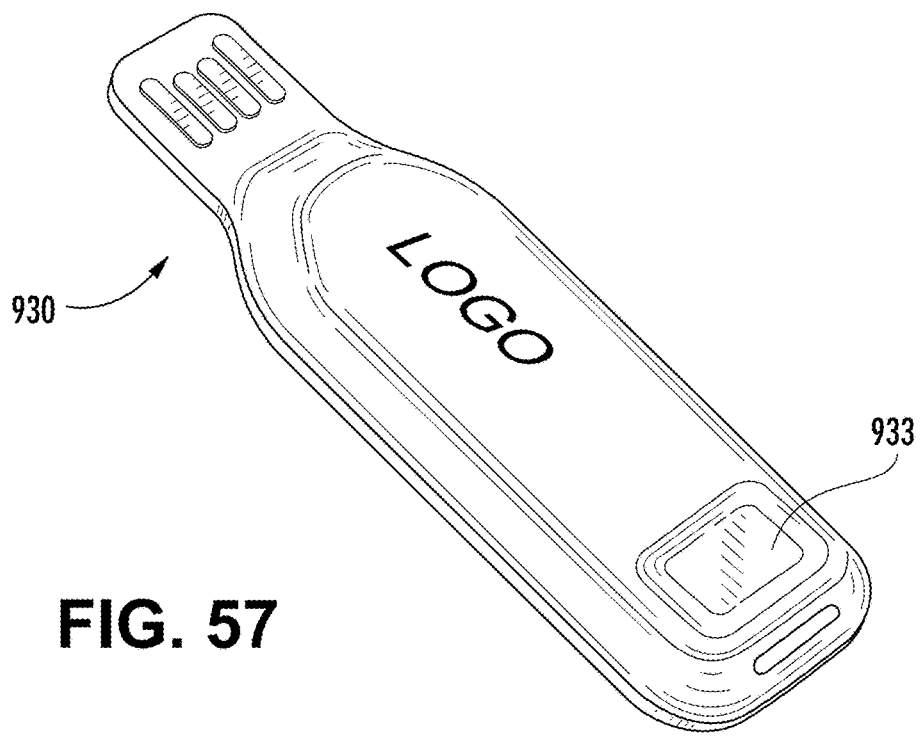
FIG. 57 is a top perspective view of another embodiment of a module according to aspects of the disclosure.
Figure 58:
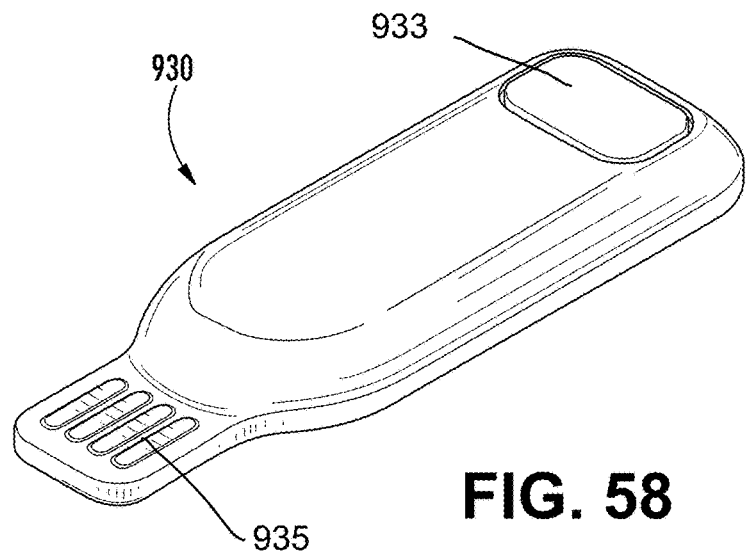
FIG. 58 is a top perspective view of another embodiment of a module according to aspects of the disclosure.
Figure 59:
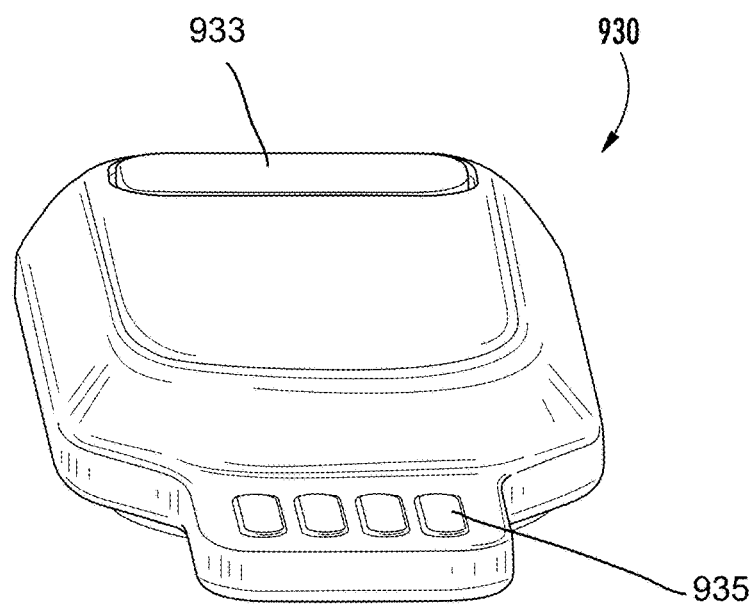
FIG. 59 is a front view of the module of FIG. 58.

FIGS. 42-59 illustrate several additional embodiments of various modules 930 with casings 931 that are differently configured. For example, FIG. 42 illustrates a module 930 with a flat-ended casing 931 and a button 933 that has a display feature (e.g., light source) 934 thereon. FIG. 43 illustrate a module 930 with a light 934 near the end opposite the connector 935, a single button 933, and no projection at the sensor 932. FIG. 44 illustrates a module 930 similar to that of FIG. 43, except with a light 934 surrounding the button 933. FIG. 45 illustrates a module 930 with a lighted button 933, 934 located on the end opposite the connector 935, rather than on the top side 937. FIGS. 46-59 illustrate various different embodiments having examples of projections 939 that are shaped, sized, and configured in many different ways. FIG. 57 illustrates a module 930 where the button 933 is recessed from the top side 937. Still further examples of modules with different configurations and arrangements of features are contemplated.

Figure 60:
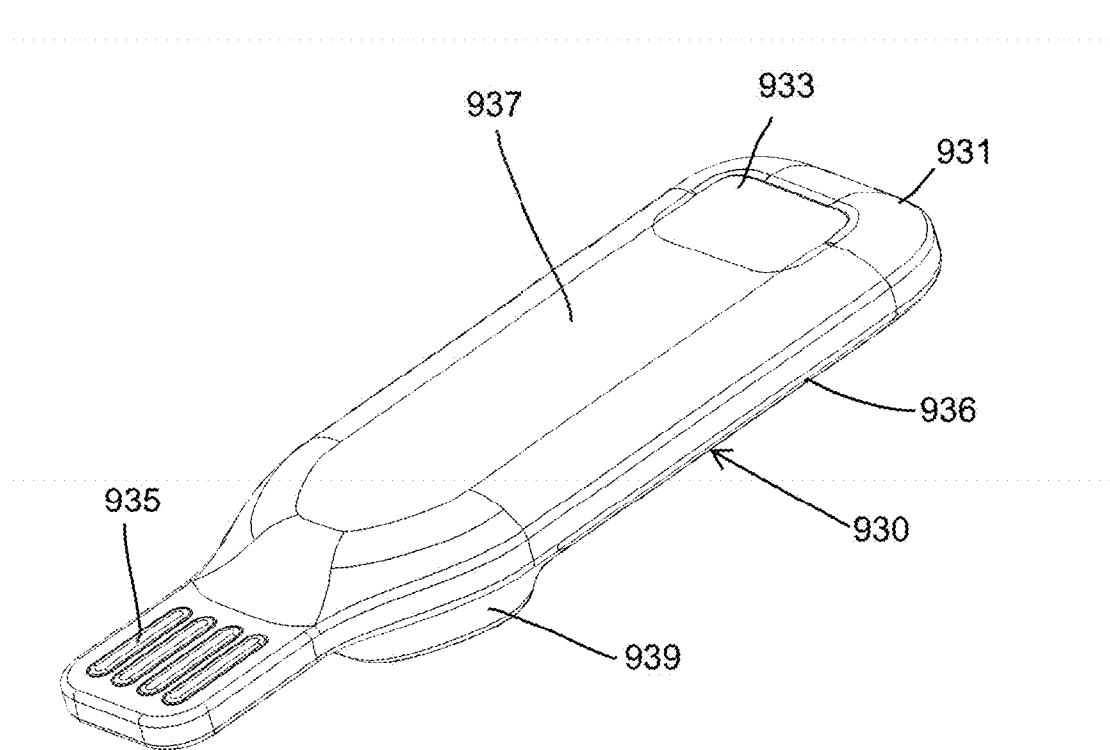
FIG. 60 is a top perspective view of another embodiment of a module according to aspects of the disclosure.
Figure 61:
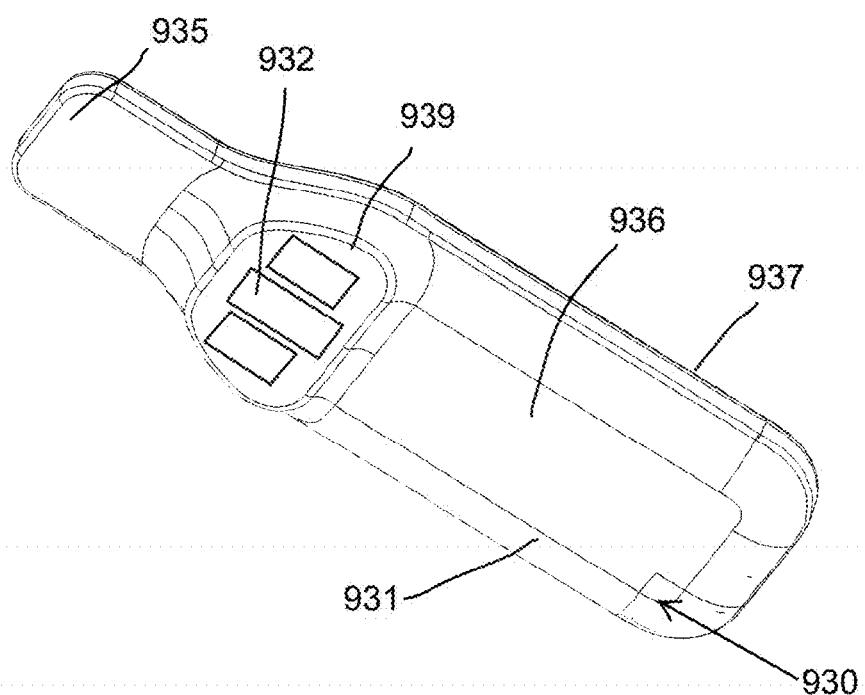
FIG. 61 is a bottom perspective view of the module of FIG. 60.
Figure 62:
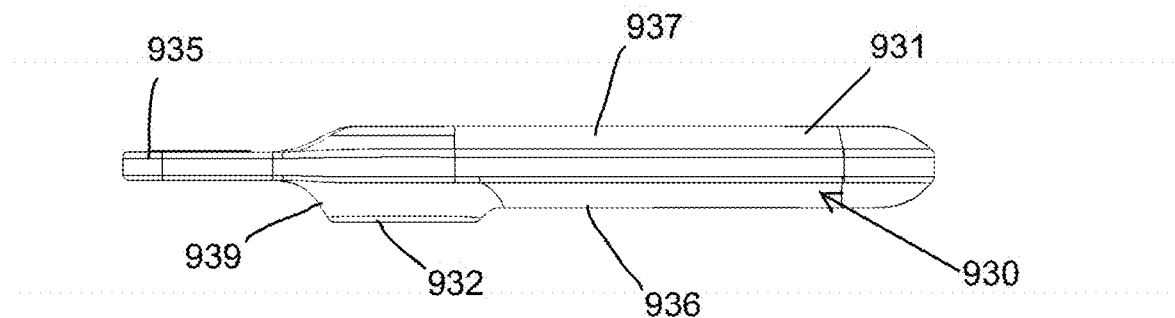
FIG. 62 is a side view of the module of FIG. 60.
Figure 63:
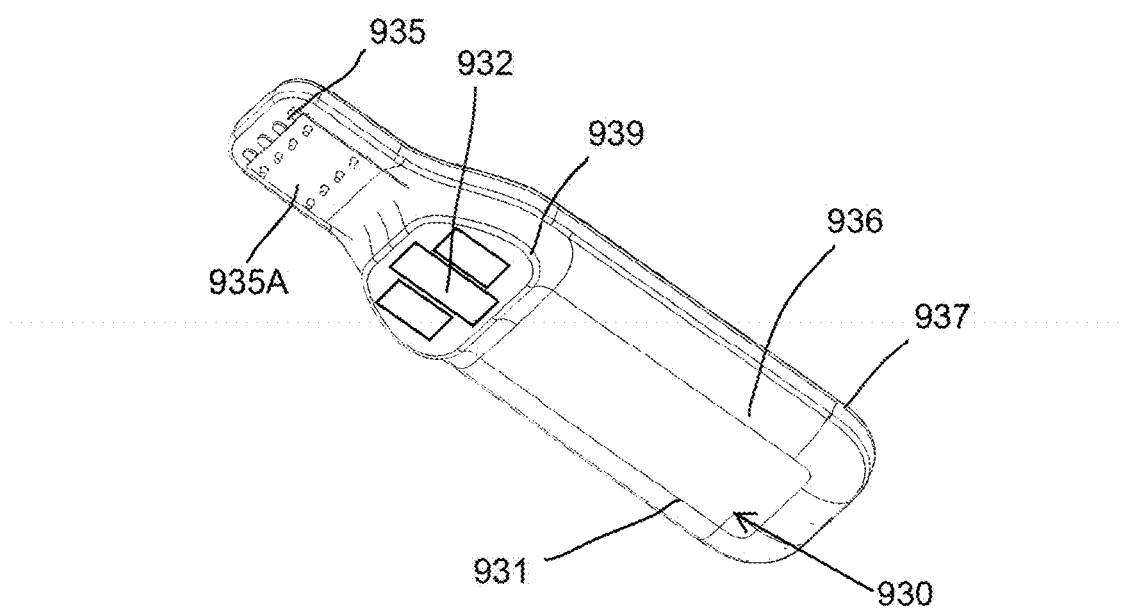
FIG. 63 is a bottom perspective view of the module of FIG. 60, with a retaining structure connected to the module.
Figure 64:
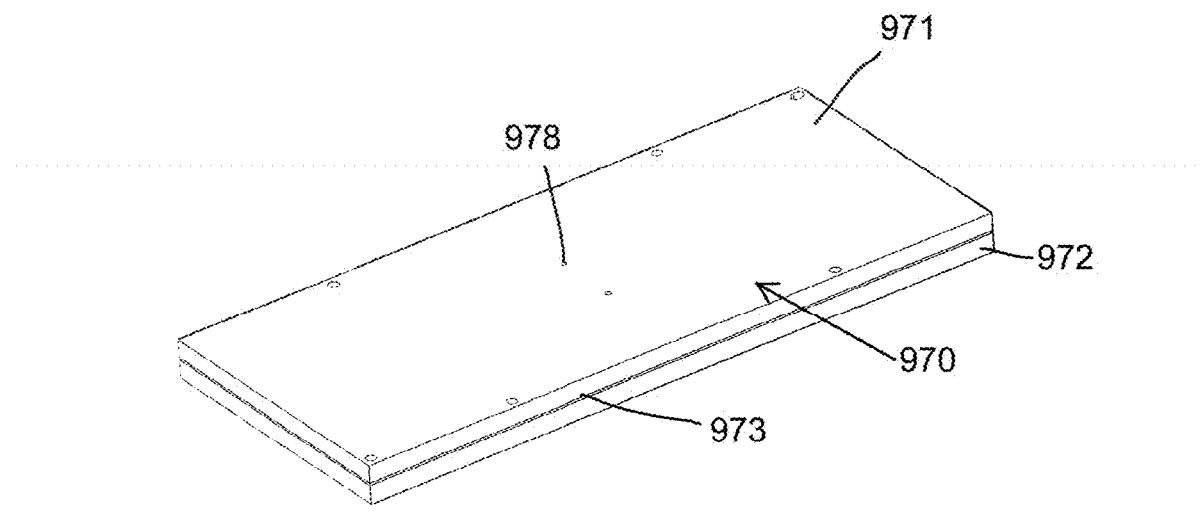
FIG. 64 is a perspective view of one embodiment of a mold for manufacturing a band according to aspects of the disclosure.

FIGS. 60-63 illustrate an additional embodiment of a module 930 with a casing 931 that has a projection 939 on the underside 936, with a sensor (e.g., a heart rate sensor) mounted on the end of the projection 939, similar to the embodiment of FIG. 41. The module 930 includes one or more user input interfaces, such as a button 933 on the top side 937, as seen in FIG. 60. The casing 931 of the module 930 in the embodiment of FIGS. 60-63 has curved or beveled edges, in order to enhance comfort. In another embodiment, as shown in FIG. 63, the module 930 may also include a retaining structure 935A on the underside of the USB connector 935. This retaining structure 935A may assist in retaining the connector 935 within the pocket 948, e.g., by engaging the shell 948. It is understood that this module 930 may be utilized as described herein, and may have additional or alternate features as described herein. The housing 963 of the band 920 as illustrated in FIGS. 68-70 and 78-82 is configured to fit the module 930 illustrated in FIGS. 60-63.

In certain embodiments, computer-executable instructions may be used to calibrate a device or system, such as to account for the location, orientation, or configuration of a sensor or group of sensors. As one example, module 930 may include a heart rate sensor. The heart rate sensor may be configured such that when correctly orientated on or in the band, the heart rate sensor is located or oriented a certain way with respect to the user. For example, if the heart rate sensor is an optical heart rate sensor, it may be within a distance range to the skin (with respect to multiple axes and location). Further, one or more sensors may be configured such that when correctly oriented within the band (e.g., placed within the pocket, a contact of a sensor is configured to be in communication with the user (e.g., their skin or alternatively their clothing). Too much variance with respect to the orientation or location of the sensor may result in inaccurate and/or imprecise data. In certain embodiments, one or more sensor measurements, either raw or calculated, may be utilized to determine a proper or preferred orientation(s) or location(s) of the sensor(s).

The measurements may be based on one or more remote or local sensors on the device to be oriented, such as module 930. For example, in certain embodiments, a user's Body Mass Index (BMI) or another parameter may be calculated. The calculation may be based, at least in part, on one or more sensors located on the device to be oriented. Based upon the sensor measurement(s), a UI, which may be on the device itself, a remote device, and/or a device in electronic communication with the device to be oriented (or re-oriented) may prompt and/or guide a user to re-orient the device. In other embodiments, it may provide a user input device to provide user inputs for orientation. For example, unlike prior art devices which may merely detect a weak or imprecise value and recommend or request the orientation of the sensor or device, embodiments disclosed herein may use data to intelligently determine the problem and/or solution. In one embodiment, a user's BMI or other data may be used to determine that the user should wear the device at another location and/or alter its orientation. For example, if a user's BMI is within the normal range (e.g., commonly accepted as 20-25), however, heart rate data is utilized in the calculation of a parameter that is below a threshold, then in certain embodiments, additional analysis may be performed to consider whether the heart rate sensor should be adjusted. As explained in more detail below, further embodiments relate to augmenting one or more calculations of parameters used in the calculations.

Systems and methods may be implemented to reduce inaccuracies and/or imprecise data collection. In one embodiment, the band may be configured to be worn within a range of locations, such as on a user's appendage or extremity. With respect to a "lower arm" usage example, the lower arm may be considered the distance between an elbow joint and the carpus of an arm or appendage, and may further be logically divided into a proximate region and a distal region. For example, the proximate region of the lower arm would include a portion (e.g., up to half) of the lower arm closest to the user's shoulder; and likewise, a distal region would include a portion (e.g., up to the remaining half) of the lower arm connecting to the carpus. In this regard, the band 920 may be configured to be worn in the proximate region of the lower arm. In one embodiment, the entire band is configured to be retained within a proximate half of the lower arm. In one embodiment, the band is configured to be retained at a specific location during athletic activities, such as with respect to the distance of the lower (or upper arm), a sensor measurement location is configured to move less than 1% or 0.5% of the distance along the lower arm. In yet other embodiments, the band may be configured to move within a specific distance with respect to the distance along the lower arm, however, at least one sensor (such as a sensor of the module 930) may be configured to move a smaller distance. For example, in one embodiment, the band 920 may be configured to permit movement of about 1 mm along the length of the lower arm, however, the module, or a sensing surface of the module, may be configured to only permit 0.55 mm movement along the same axis. As discussed above, one or more measurements may dictate altering this range, the distance from the sensor to the skin, as well as other locational dimensions and/or orientations. In one embodiment, the band 920 is configured to retain a sensing surface (or sensing location) of the module at least a predefined distance from the carpus. This may be due to the mechanical properties of the band 920, the module 930, and/or as a result of a sensor providing an indication of an incorrect and/or correct usage of the band 920 and/or module 930. In yet another embodiment, the sensing surface is at least located 20% of the distance away from the carpus. In another embodiment, the band may be configured to retain a sensing surface of the band at least a predefined distance of the distance from the elbow joint (or equivalent).

In one embodiment, one or more sensors of the module (alone and/or with other external sensors) may be utilized to detect the location of the module 930, a sensing surface of the module, a sensing location, and/or the band 920. This may be done directly or indirectly. In certain embodiments, one or more non-transitory computer-readable mediums may comprise computer-executable instructions, then when executed by a processor cause the processor to at least conduct a location calibration routine. The computer-readable medium(s) may be located entirely on the module, an external electronic device, such as a mobile or cellular device, and/or combinations thereof. One or more calibration routines may be automatically initiated, such as by being triggered by sensing one or more criteria (e.g. with a sensor of the module) or through a manual initiation, such as by a user initiating the routine.

Movements during the athletic activity will naturally cause physical movements of anatomical structures, including joints and flexing muscles. As one example, flexing muscles may cause relative and absolute changes in locations and orientation of sensor sensing surfaces and/or sensing locations. As discussed herein, having the band, sensing surfaces, and/or sensing locations located in positions to reduce or eliminate flexure-causing inaccuracies will improve the utility of such sensing systems when compared with prior-art systems. For example, the device (or location(s)) may be positioned to reduce or eliminate forearm tension in one embodiment. In another embodiment, systems and methods may be implemented to identify the extent of actual and/or anticipated flexure or anatomical movement. In further embodiments, one or more calibration or correction factors may be applied to sensor readings based upon flexure or other anatomical movements. In one embodiment, only flexure of one muscle or group of muscles may be considered. This may be the case even when other muscles' flexure is present.

Figure 6:
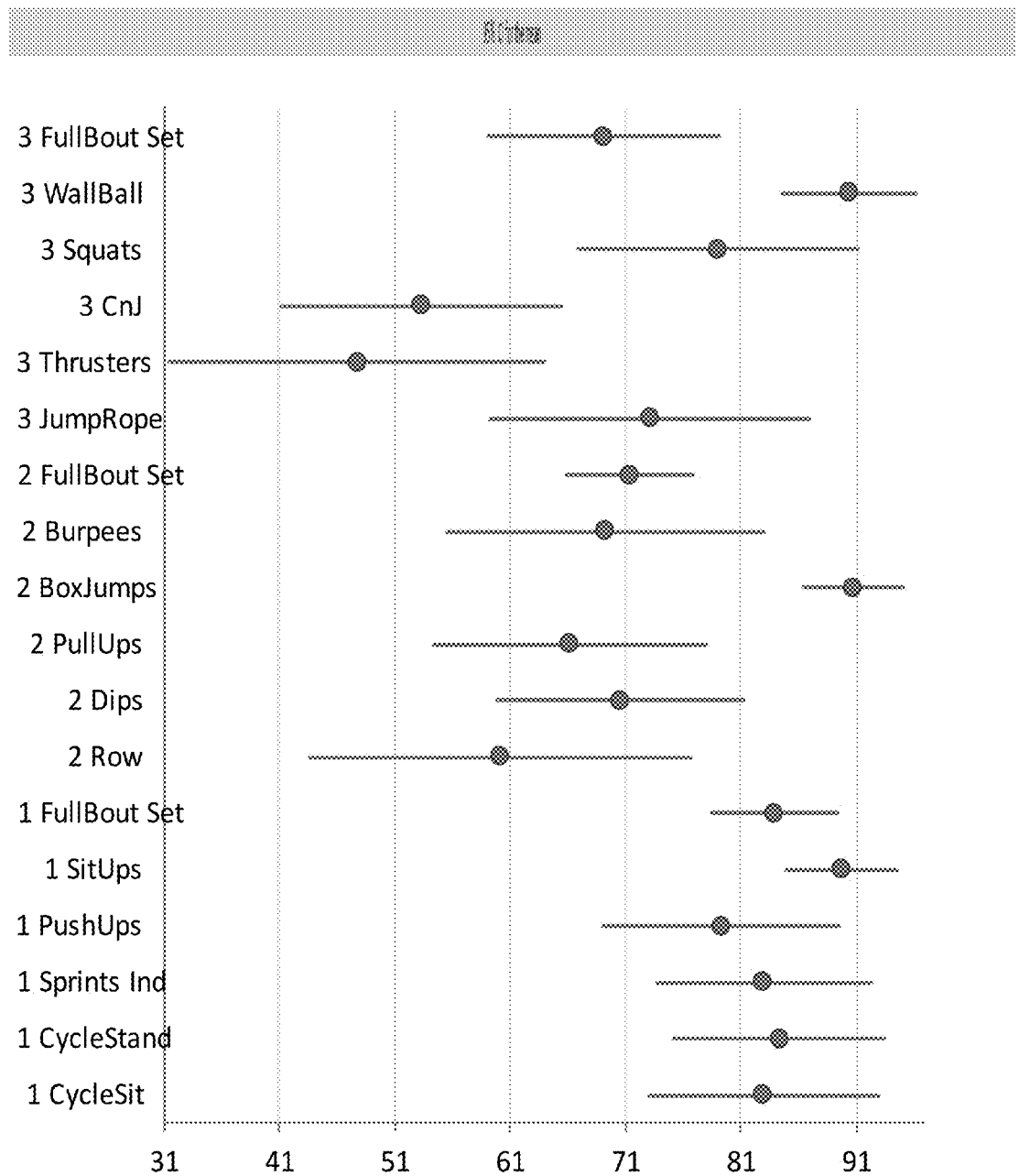
FIG. 6 shows a chart comparing different exercises to the mean of a sensor's output based upon different movements.

FIG. 6 shows a chart comparing different exercises to the mean of a heart rate sensor's output based upon different movements. Specifically, looking to FIG. 6, the Y-axis comprises a plurality of different exercises. The exercises are categorized into three sections, which are indicated by the numeral 1, 2, or 3 preceding each description. The numerals are merely used to distinguish different groups and has no other significance to FIG. 6 for purposes of this disclosure. By distinguishing the exercises, a "Fullbout Set" exercise could be provided which includes each exercise in the categories (1, 2, and 3). The X-axis of the chart shown in FIG. 6 shows the confidence interval for the mean heart rate measurement. As seen in FIG. 6, exercises generally known to cause tension in the forearm muscles scored lower than other exercises that cause lesser tension in the same muscles. For examples, "CnJ", "Thruster", and Row" all require a greater tension in forearm muscles when compared to "BoxJumps".

Certain embodiments, therefore, may be used to detect movements and/or account for some movements. In further embodiments, a calibration may be performed before a specific type of athletic activity to ensure variations are within a specified range. The range may be determined by demographic information, the type of activity to be performed, known correction factors or limitations, among others or combinations thereof. In one embodiment, a user may be prompted to perform a movement to trigger a known tension (or range of tension) within a specific muscle or group of muscles. In one embodiment, systems and methods may be implemented to cause a user to flex a certain muscle or group of muscles. For example, a user may be prompted to perform a specific athletic activity or group of activities, including one or more activities shown in FIG. 6. In one embodiment, sensor readings may be used to determine an individual's flex, which may be influenced by a user's anatomical and/or physiological characteristics. In one embodiment, a computer-readable medium may comprise computer-executable instructions that when processed by a processor, may combine the outcome of the sensor readings during calibration with other factors, which also may be stored entirely or partly on the module 930. Examples include demographic information, such as a user's sex, weight, age, and/or other attributes.

In further embodiments, other attributes such as a user's BMI and/or other demographic, physiological, biological, and/or anatomical parameters may be utilized in accordance with certain embodiments to augment processing of sensor data, such as for example an optical heart rate sensor Optical properties of light utilized in optical heart rate measurements, including the light's transmittance, reflectance, backscatter, and/or other properties, alone, in combination, and/or synergistically may be influenced by a user's build, such as muscle mass, lipids making up adipose tissue, water, electrolyte levels, and/or other content or properties of such contents. As discussed below, locational distribution of such contents may play a role. Aspects of this disclosure relate to systems that may receive an indication of an athletic parameter, e.g., BMI, adipose tissue presence (either proximate or within the range of the optical light waves being transmitted or received by the measurements, or alternatively systemic or regionally, such as along the forearm, back arm, waist, buttocks, etc.), and/or hydration levels, and adjust one or more aspects relating to heart rate measurements, such as, but not limited to: (1) changing or augmenting an algorithm or process used to obtain the measurements, such as for example, the weights assigned to the measurements of heart rate measurements or using a different wavelength and/or frequency of measurements; (2) determining whether to use or not use heart rate (or data from a specific sensor) as a measurement; (3) adjusting how heart rate may be calculated (e.g., from a different sensor or collection of sensors) including automatically altering the locational properties of the sensor or prompting the relocation of the sensor, and/or (4) re-interpreting heart rate measurements from one or more processes, which may collectively or individually be referred to as adjusting or augmenting a heart rate measurement protocol.

Figure 7:
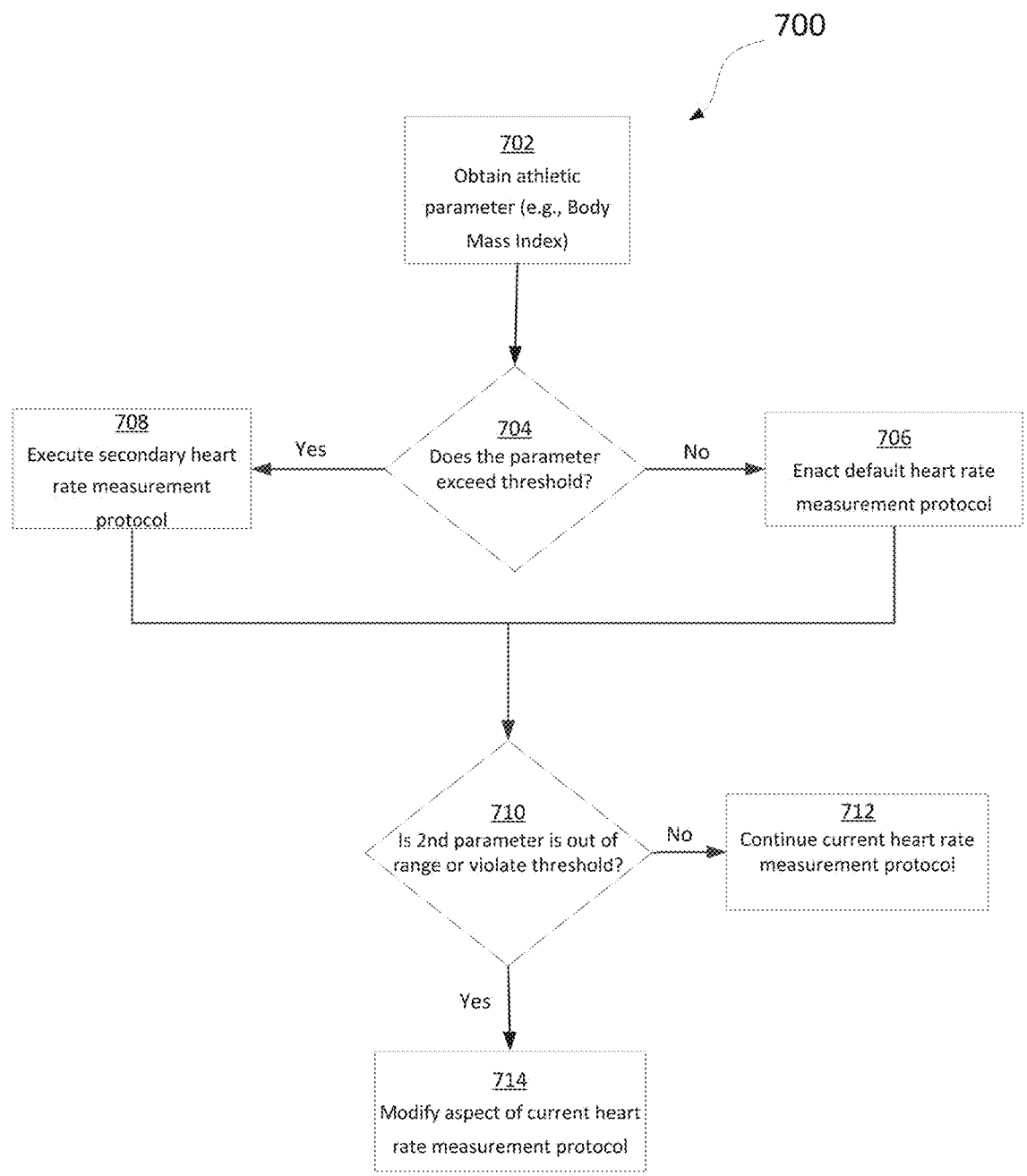
FIG. 7 is a flowchart that may be utilized in the creation or modification of a heart-rate measurement protocol in accordance with certain embodiments.

As one illustrative example, FIG. 7 shows flowchart 700 that may be implemented to augment one or more processes. As shown in flowchart 700, an athletic parameter (e.g., such as BMI) may be obtained or determined, such as by a processor located on module 930 (e.g., block 702). The parameter may be a single parameter from a single sensor or a plurality of parameters from one or more sensors. In further embodiments, a single parameter may be calculated or determined from several sub-parameters. In certain embodiments, the parameter may be predetermined, such as the user's gender, weight, and/or height. However, weight or other parameters that may be predetermined in previous calculations may be confirmed or refreshed using sensor data. In an example embodiment measuring BMI, the most-widely accepted calculation is to divide body weight (kg) by height$^2$ (m$^2$), thus BMI=weight/height$^2$. The parameter(s) of block 702 may be utilized as a threshold level (e.g., decision 704). If criteria is met, e.g., threshold or range rules are within operational criteria, then a default heart rate measurement protocol may be enacted (e.g., block 706). The protocol may be a specific algorithm and/or use specific wavelengths of light and/or light intensity to obtain readings. In certain embodiments, values exceeding (or not meeting) a threshold value or not within a range of values may cause a processor to execute a secondary heart rate measurement protocol (e.g., block 708), which may for example prompt a different algorithm to be implemented or another process to be augmented, such as for example, weights or confidences assigned to heart rate measurements, the utilization of heart rate as a measurement, adjusting how heart rate may be calculated, and/or interpreting heart rate measurements from one or more processes, as well as any other alteration of a heart rate measurement protocol provide herein. Using BMI as an example parameter, a BMI value of about 25 (which is commonly accepted as the dividing line between "normal" and "overweight") may be a threshold, in yet another embodiment, a BMI of about 20 (which is commonly accepted as the dividing line between "underweight" and "normal") may be utilized. Those skilled in the art will appreciate that multiple thresholds or ranges may be used, which may be higher, lower, and/or in-between these values. Generally, as described above, a user's BMI is calculated by dividing the body weight (kg) by height (m$^2$), thus BMI=weight/height. Given its inputs, BMI values may be artificially inflated or deflated based on an individual's specific build or other factors, some of which are described herein. In certain embodiments, other criteria may be utilized to weight or augment a BMI score. In further embodiments, other criteria may be used independently of BMI. BMI may not be used in certain embodiments, and a different metric may potentially be used in its place.

Figure 8:
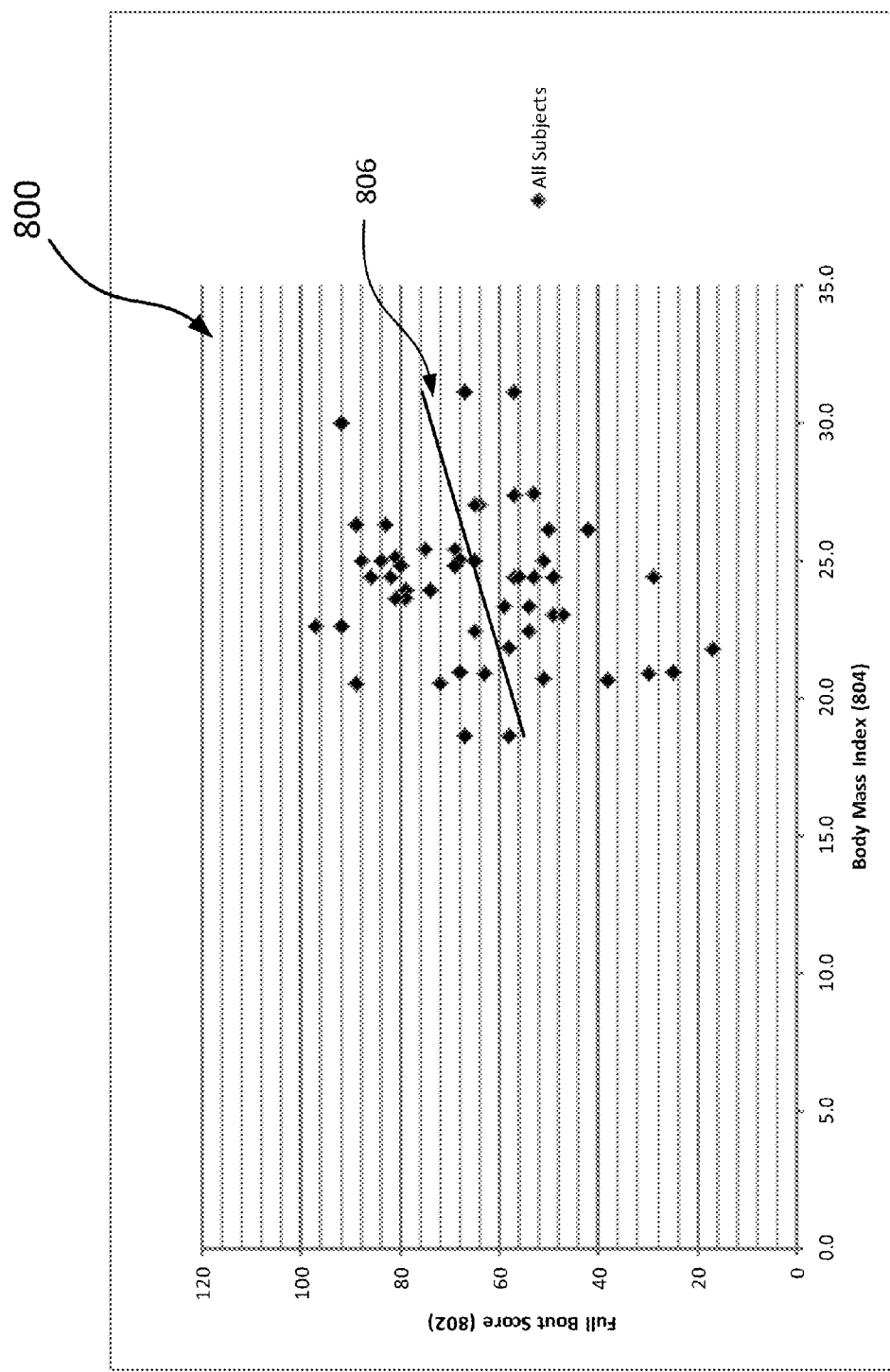
FIG. 8 is a chart correlating Body Mass Index (BMI) with a performance score amongst a full population sample, in accordance with various examples disclosed herein.
Figure 9:
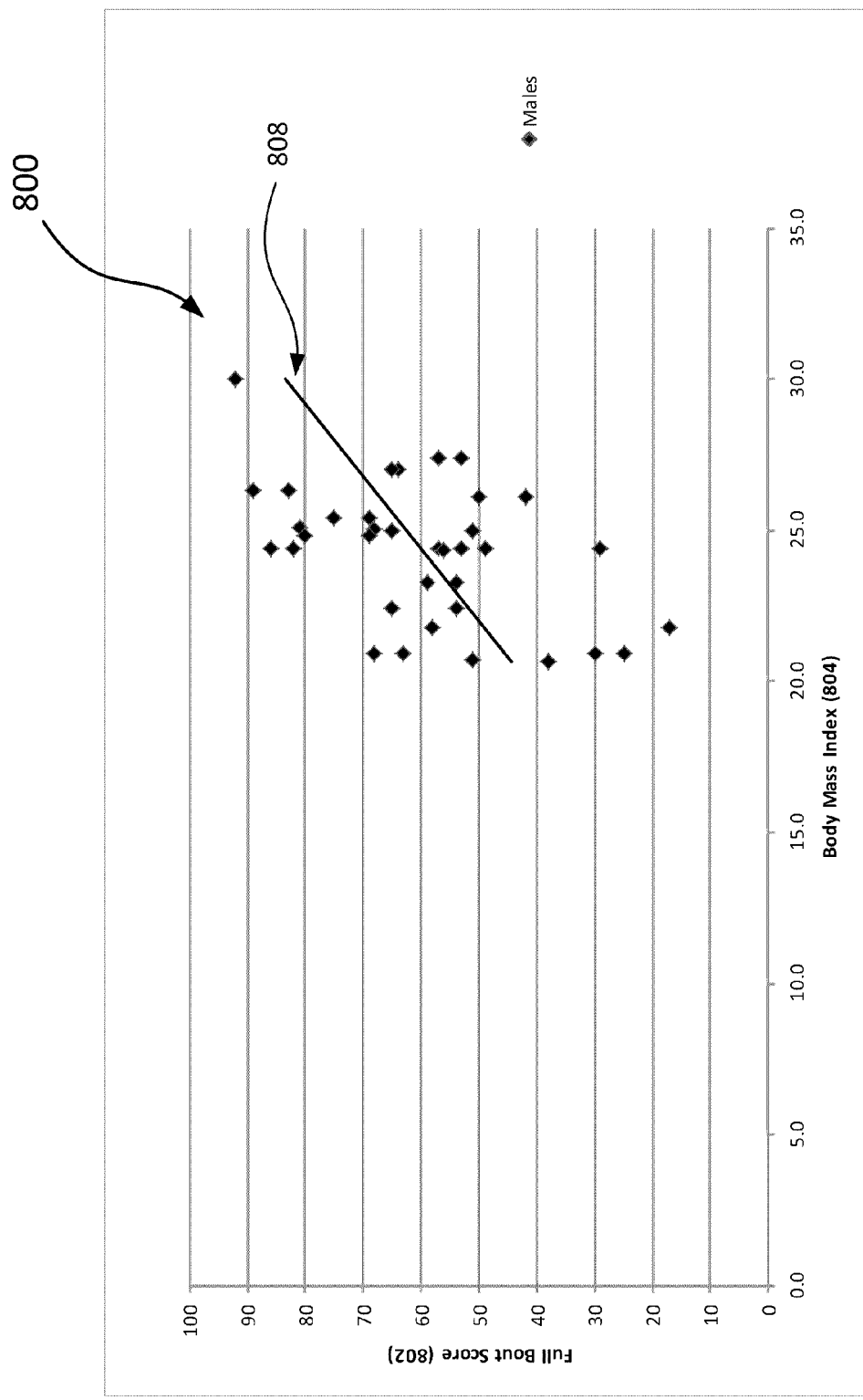
FIG. 9 is a chart correlating BMI with the performance score amongst male individuals of the population sample of FIG. 8, in accordance with various examples disclosed herein.
Figure 10:
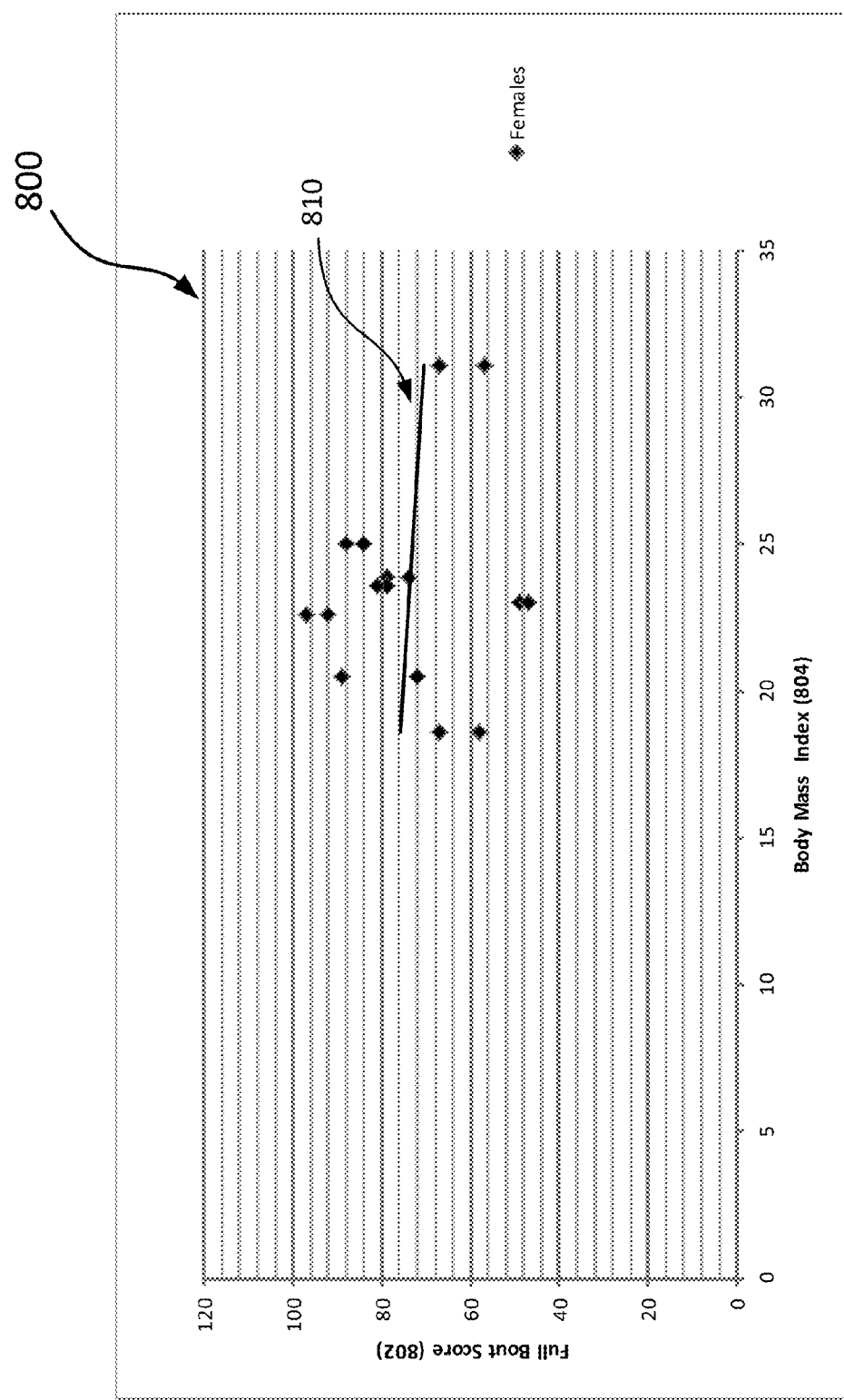
FIG. 10 is a chart correlating BMI with the performance score amongst female individuals of the population sample of FIG. 8, in accordance with various examples disclosed herein.

In this regard, the inventors have determined that individuals with lean body structures may be more susceptible to imprecise and/or inaccurate heart rate readings from optical heart rate monitors, even when blocking ambient light and controlling for other variables. For example, as shown in FIGS. 8-10, chart 800 shows an example parameter (e.g., BMI) along the x-axis (element 802) plotted against a performance score (e.g., a bout score) that may be calculated by a processor, based at least in part on heart rate measurements using an optical heart rate sensor, plotted along the y-axis (element 804). Looking first to FIG. 8, line 806, the correlation of the BMI parameter to the bout score, may be expressed as a best fit using the following: Bout Score=1.6327BMI+24.811. In this specific embodiment, line 806 exhibits an $R^2$ value=0.0609. Looking to chart 800 of FIG. 8, performance scores among individuals with lower BMI scores show more variance than the individuals with higher BMI scores. Further, each performance score below 40 (with respect to y-axis 804) was collected from an individual having a BMI<25. FIGS. 9 and 10 show sub-populations of the data presented in FIG. 8, specifically, in the illustrative example, FIG. 9 shows the respective data points obtained from male individuals and FIG. 10 shows respective data points obtained from female individuals. As shown in FIG. 9, line 808, a correlation of the BMI parameter to the performance score (e.g., bout score) may be expressed as a best fit using Bout Score=4.1962BMI−42.305. In this specific embodiment, $R^2$ may be=0.3001. As shown in FIG. 10, line 810, a correlation of the BMI parameter to the example performance score (e.g., bout score) may be expressed as a best fit using Bout Score=−0.4258x+83.772. In this specific embodiment $R^2$ may be=0.0098. Gender differences exist with respect to adipose tissue and the storage of lipids, including locational distribution, quantity, and other variables. Therefore, in one embodiment, block 702 may determine gender, age, or other parameters (alone or in combination) to determine to implement a first algorithm may be utilized to measure heart rate from user's with a BMI (and/or other parameters) below a threshold and a second algorithm may be used to measure heart rate from users above and/or meeting the threshold (e.g., blocks 706 and 708). A plurality of thresholds may be used.

In certain embodiments, decision 710 may be implemented after block 702 to determine if a second parameter is out of range or violating a threshold. The second parameter may be any parameter, including those discussed herein, including a derivation of the first parameter. If there is not a threshold violation and/or criteria is being met, the current in-place heart rate measurement protocol may be left intact (e.g. block 712). Alternatively, if decision 710 is in the negative, certain embodiments may modify one or more aspects of the current protocol (e.g., block 714). For example, a different optical wavelength may be used to detect heart rate on one or more individuals meeting one or more criteria, such as any discussed herein or known in the art. In yet further embodiments, a scalar may be applied to heart rate measurements obtained from those individuals meeting one or more criteria. Environmental cues and data, such as from light sensors, temperature sensors, and the like may further provide immediate and/or long term sensor data that may provide insights to the user's adipose tissue, muscle mass, etc. Further, in certain embodiments, distance between the sensor and the user's skin may be adjusted automatically or requested to be done manually based upon altering a protocol.

In yet another embodiment, one or more correction factors and/or calibration values may be altered or created based upon detecting the athletic activity a user is performing. The detection may be based, partly or wholly on sensor readings from the module 930. In one embodiment, external data may be received and utilized, such as for example from a user's electronic mobile device and/or another fitness device. In one embodiment, data from a user's schedule, past athletic data, friend's data, historical analysis, manual user input, locational data, and/or combinations thereof and others may be used to determine an athletic activity. In one embodiment, for example, it may be determined that a user is performing or is likely to perform an athletic activity that is associated with more elevated flexion values, and therefore, one or more instructions may be executed, such as confirming the band 930, module 940, and/or another apparatus is within a certain location or within an operational state, such as but not including adjusting one or more sensing parameters. In yet another embodiment, the user may be required to conduct one or more different movements or activities to recalibrate the band 920. In further embodiments, the user may be prompted to locate the band 920 or module 930 at a specific location. In still further embodiments, the user may be prompted to use a specific module. For example, replaceable modules may be interchanged for increased sensitivity, different sensing characteristics, and/or comfort based upon different factors for different activities (and/or user preference).

In various embodiments, the user may get feedback to reposition the module 930, band 920 and/or to conduct one or more analytics. Further, the system may provide feedback to indicate ranges or percentages of the user, such as to let the user decide whether the ranges/percentages are acceptable or rather to reposition or switch out components of the system.

Additional Hardware

FIGS. 102-111 illustrate embodiments for use with a band 920 that includes some or all of the features of the band 920 illustrated in FIGS. 68-70C, and may be manufactured in a manner similar to the method illustrated in FIGS. 71-91. Thus, the features and manufacturing techniques of the band 920 of FIGS. 102-111 that are similar to those already described will not necessarily be described again for the sake of brevity. Similar components described already may be referred to using similar reference numbers.

Figure 111:
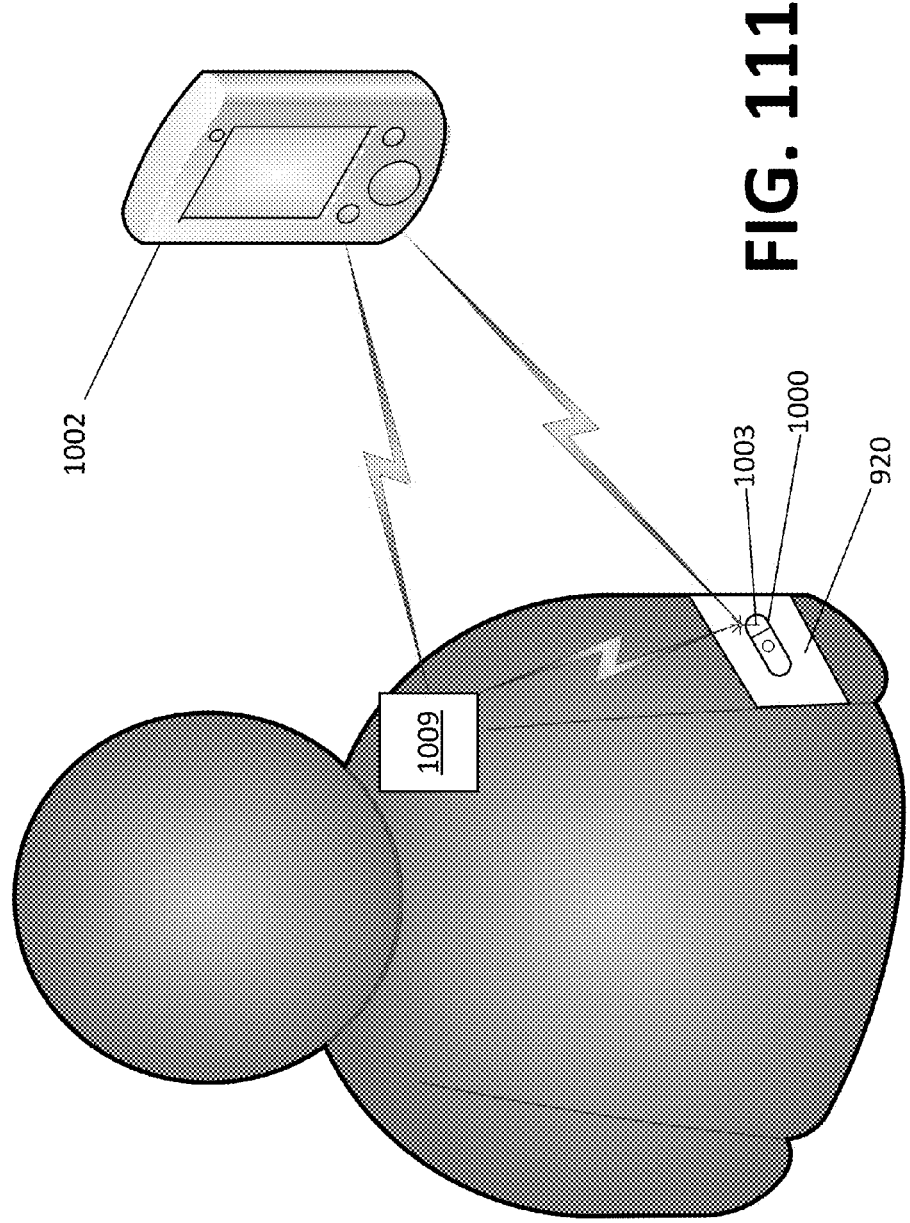
FIG. 111 is a schematic view illustrating another embodiment of a band with an additional input device connected to the band, with the band being worn on an arm of a user, and with the additional input device being in communication with one or more external devices.

In the embodiments of FIGS. 102-111, the band 920 includes a input device 1000 connected to the housing 963 and/or otherwise received within the pocket 940 and configured for connection to the module 930 when the module 930 is received within the pocket 940. The input device 1000 has one or more buttons 1001 thereon that are accessible from the outer surface 928 of the band 920, such as through the outer wall 943 of the band 920. The input device 1000 is configured for communication with an external device 1002, as shown in FIG. 111, and may have any of the components of the computer device 200 described above. In one embodiment, the input device 1000 includes a wireless transmitter 1003 (which may be part of a transceiver) configured for communication with the external device 1002, a port 1004 for connection to the connector 935 of the module 930, and potentially a small memory and/or processor for operation of the button(s) 1001, transmitter 1003, and port 1004. In one embodiment, the input device 1000 may include no internal operating system or significant software, and the input device 1000 may be configured to simply transmit a signal that the button 1001 was pressed, along with the sequence and/or length of the button press(es) 1001.

The button(s) 1001 of the input device 1000 may be one of a number of different types, including a tactile/mechanical button, a touchscreen, a heat-sensitive button, or other device capable of registering a touch by the user. It is understood that some types of buttons 1001 may require a window or other passage through the outer wall 943 of the band 920 for operation. In the embodiments of FIGS. 102-111, the input device 1000 includes tactile buttons 1001. The input device 1000 may include one or more additional buttons 1001, as illustrated in FIGS. 102-110 and described below. For example, each of the embodiments in FIGS. 102-109 has a main button 1001A and an optional additional volume control button 1001B. Various techniques and methods of operation of the button(s) 1001 are also described below. The band 920 may also have indicia 1008 on the outer surface 928 to inform the user where to press to activate the button(s) 1001, as shown in FIG. 109.

The transmitter 1003, which may be part of a transceiver as stated above, is configured for wireless communication with one or more external devices 1002, as illustrated in FIG. 111. It is understood that any of the embodiments of FIGS. 102-111 may have such a transmitter 1003. In one embodiment, the transmitter 1003 may be a Bluetooth or Bluetooth Low Energy (BTLE) transmitter. In other embodiments, the transmitter 1003 may use different transmissions, frequencies, protocols, etc., such as a Wi-Fi transmitter.

The port 1004 may include any connecting structure, and the configuration of the port 1004 may depend on the configuration of the module 930 to which it is connected. In the embodiment of FIGS. 102-111, the port 1004 is a USB or USB-compatible port configured to connect with the USB connector 935 on the module 930 of FIGS. 60-63. It is understood that the port 1004 may not include all of the hardware of a typical USB port in one embodiment, as the port 1004 may be configured only to draw power from the module 930 for operation of the input device 1000, and not to exchange data with the module 930. In another embodiment, the input device 1000 may be configured to operate as a wireless communications interface between the module 930 and the external device 1002, e.g., by receiving and/or transmitting data from/to the module 930 through the port 1004 and receiving and/or transmitting data from/to the external device 1002 through the transmitter 1003.

The input device 1000 may further include haptic feedback features, such as a vibration motor or other haptic feedback mechanism 1009 (shown schematically in FIG. 106), to communicate various signals (e.g., alerts) to the user. The input device 1000 may be configured for providing different types of haptic feedbacks, such as a steady vibration, pulsed vibration, etc. The input device 1000 may receive signals from the external device 1002 to generate specific haptic feedback. In one embodiment, the resolution of when to generate haptic feedback and which haptic feedback to generate is performed by the external device 1002, such that the input device needs only to receive the signal and generate the haptic feedback. The external device 1002 may utilize user settings for providing specific haptic feedback in the event of a specific occurrence, e.g., an incoming phone call, an emergency alert, an activity milestone reached, or other event. Haptic feedback may be used in connection with the various applications and functions described below.

Figure 102:
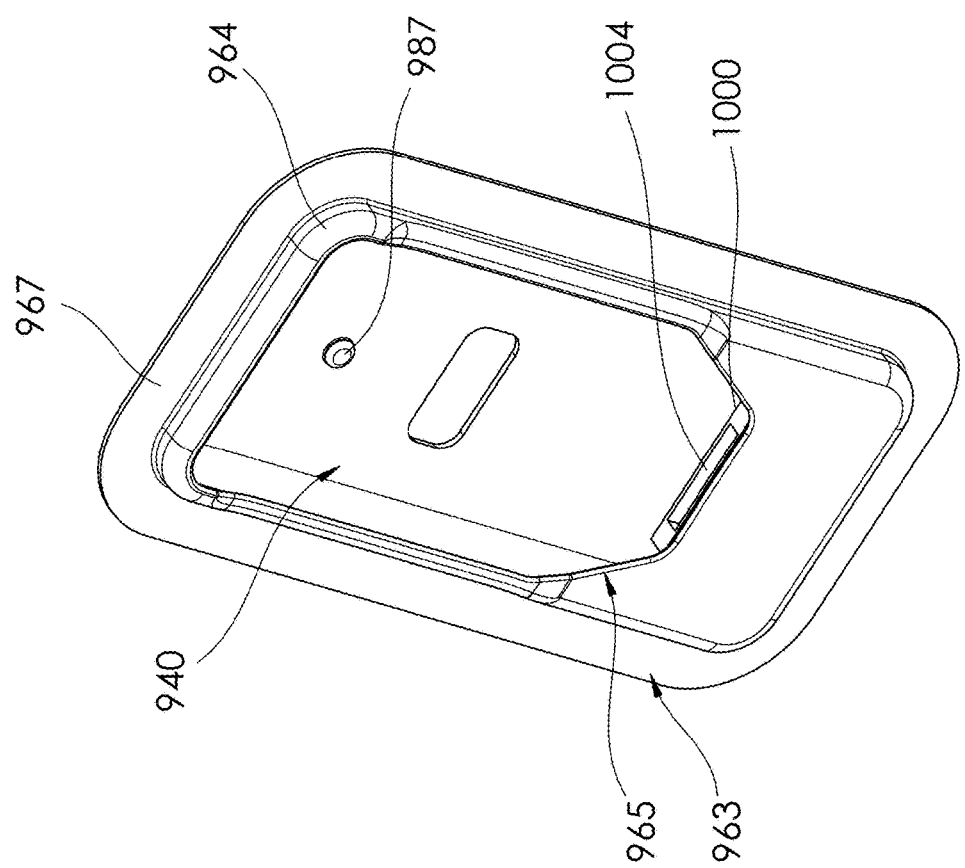
FIG. 102 is a bottom perspective view of one embodiment of a housing and additional input device that is usable in connection with a band and module according to aspects of the disclosure.
Figure 103:
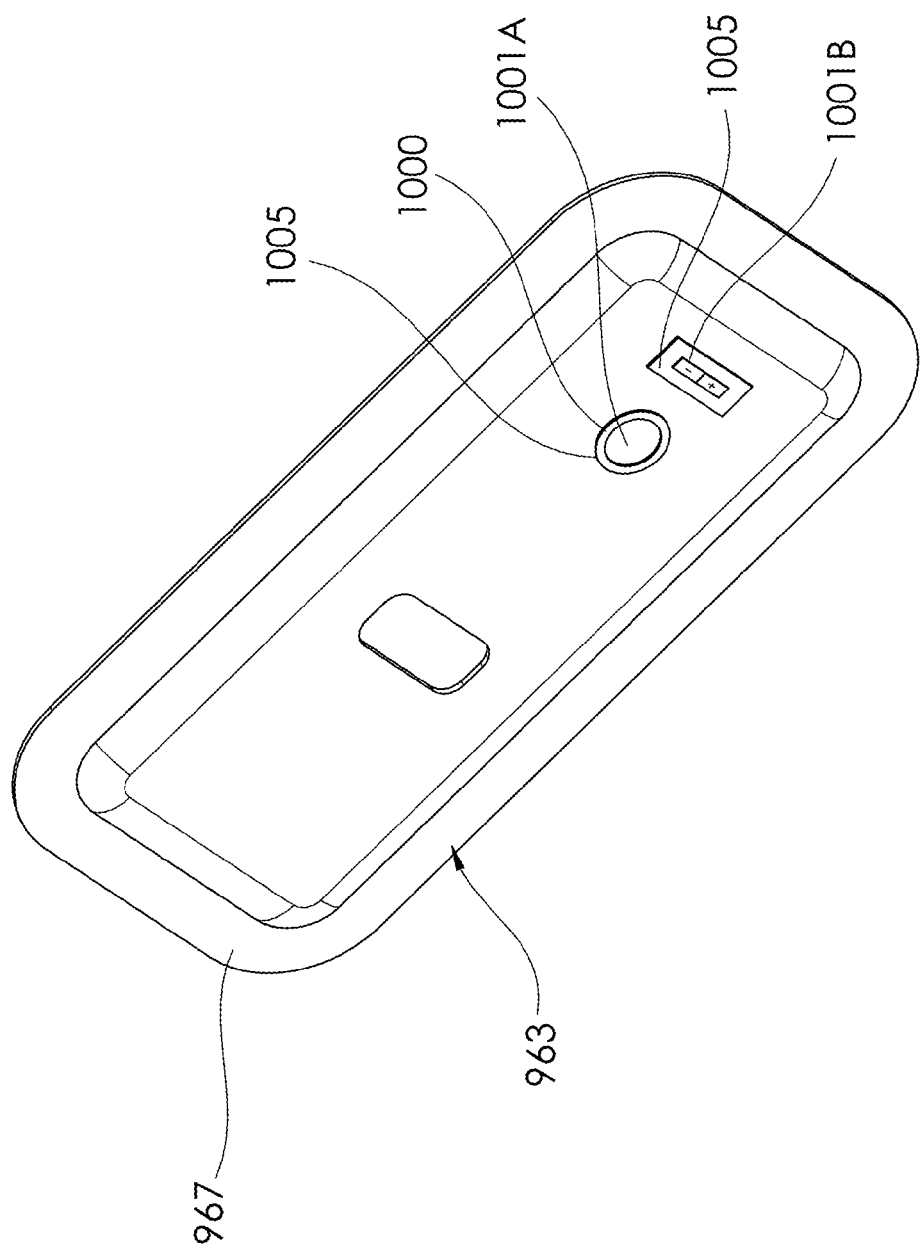
FIG. 103 is a top perspective view of the housing and additional input device of FIG. 102.

The input device 1000 may be positioned within the pocket 940 and/or the housing 963, may be positioned adjacent the pocket 940 and/or the housing 963, may form a part of the pocket 940 and/or the housing 963, or may be a separate element connected to the module 930, in various embodiments. In the embodiment of FIGS. 102-103, the input device 1000 is a separate device that is permanently or removably connected within the housing 963. The input device 1000 in this embodiment is in the form of a casing positioned within the end of the housing 963, proximate the narrowed portion 965 of the opening 942 (i.e., where the connector 935 of the module 930 is received), with the port 1004 having an opening facing into the pocket 940 defined by the housing 963. In this position, the module 930 can be inserted into the housing 963 so that the connector 935 is received within the port 1004, as shown schematically in FIG. 106. The input device 1000 may be permanently connected within the housing 963, such as by adhesive or other bonding technique, fasteners, integral forming, or other techniques, in one embodiment. The input device 1000 may be removably connected within the housing 963 in another embodiment. Such a removable input device 1000 may be removed from the housing for connection or disconnection with the module 930, as shown in FIGS. 107-110 and described below. Alternately, such a removable input device 1000 may be retained within the housing 963 as the module 930 is connected and disconnected, such as by a releasable retaining structure on the input device 1000 and/or the housing 963, a high-friction fit that is sufficient to retain the input device 1000 in place during activity or removing the module 930 from the port 1004, or other removable configuration. The housing 963 may also have features to facilitate access to the buttons 1001. For example, as shown in FIG. 103, the housing 963 has one or more openings 1005 on the outer wall 943 to permit access to the button(s) 1001. In another embodiment, the housing 963 may have one or more protrusions on the inner surface of the outer wall 943 adjacent to the button(s) 1001, so that force exerted on the housing 963 can reliably activate the button(s) 1001, similar to the protrusion 987 described above.

Figure 104:
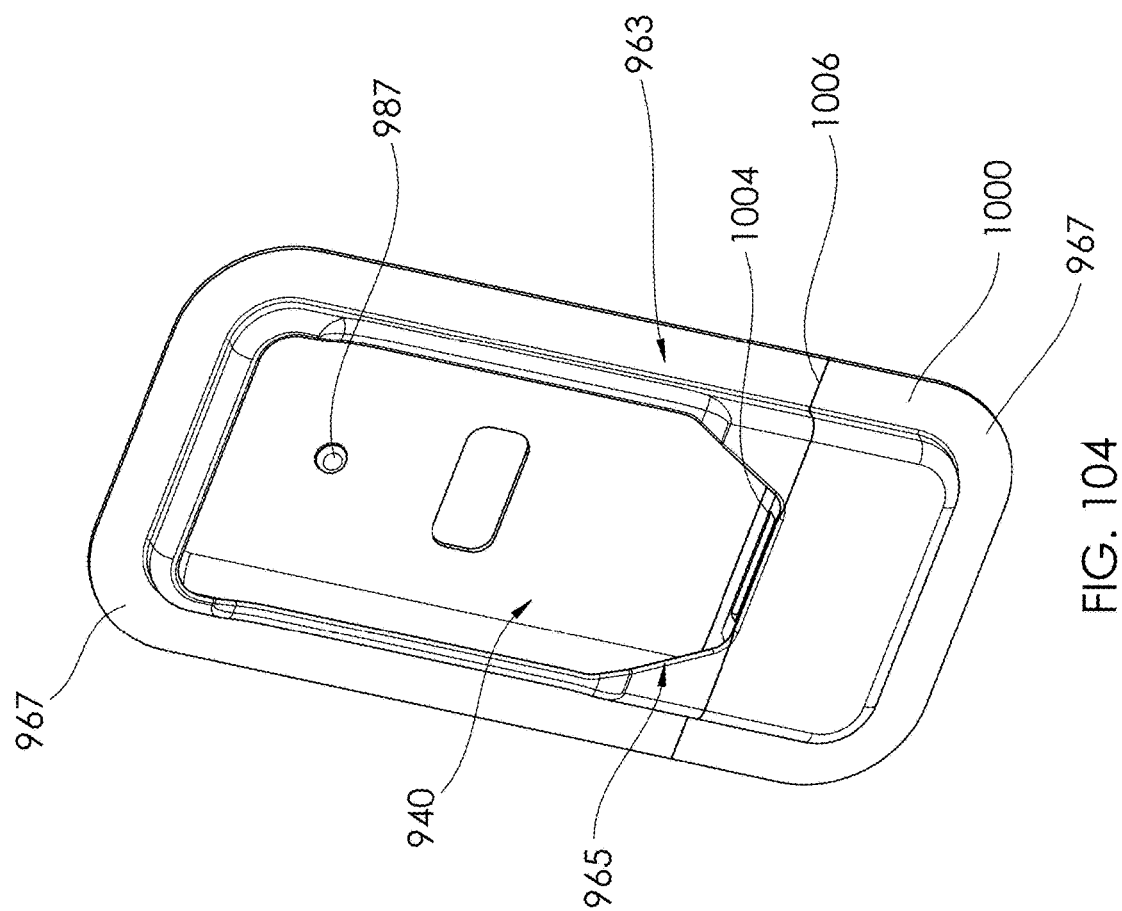
FIG. 104 is a bottom perspective view of one embodiment of a housing and additional input device that is usable in connection with a band and module according to aspects of the disclosure.
Figure 105:
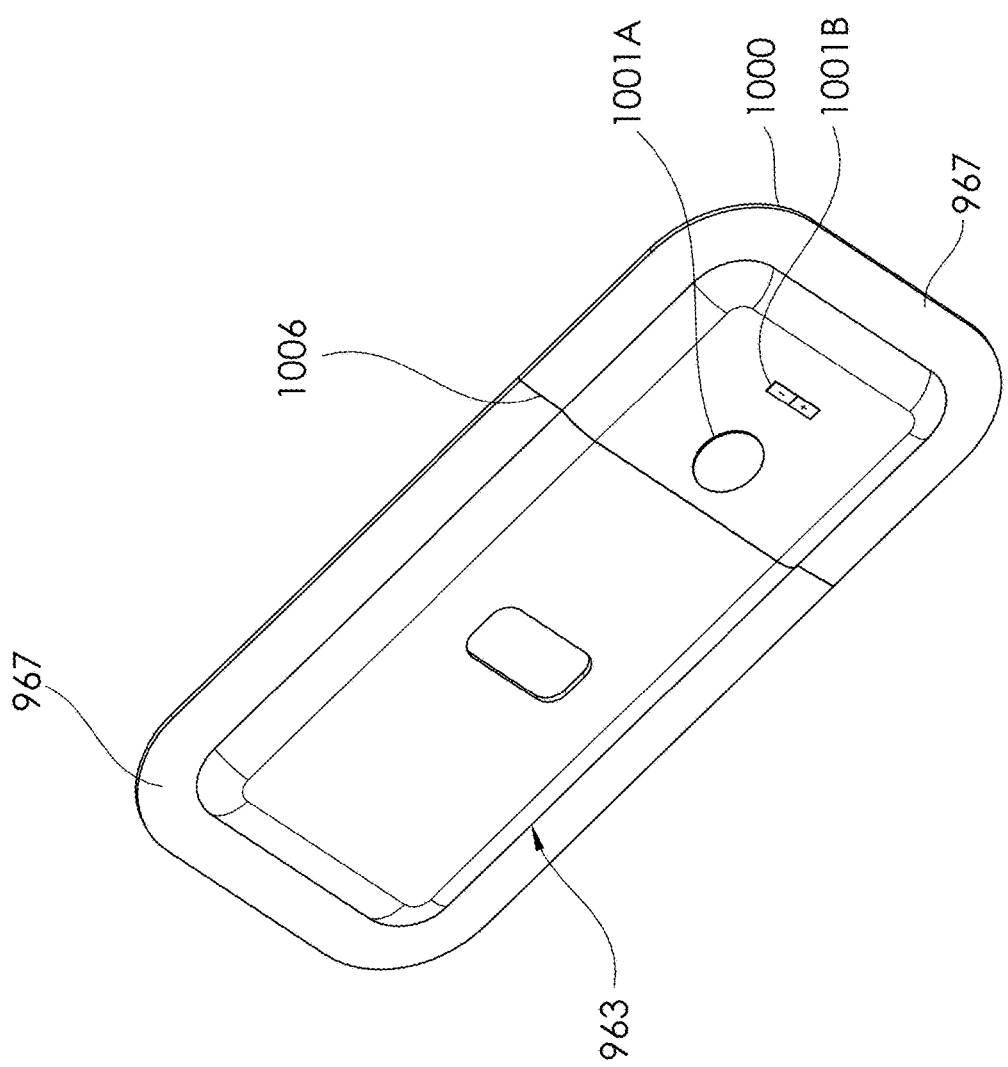
FIG. 105 is a top perspective view of the housing and additional input device of FIG. 104.
Figure 106:
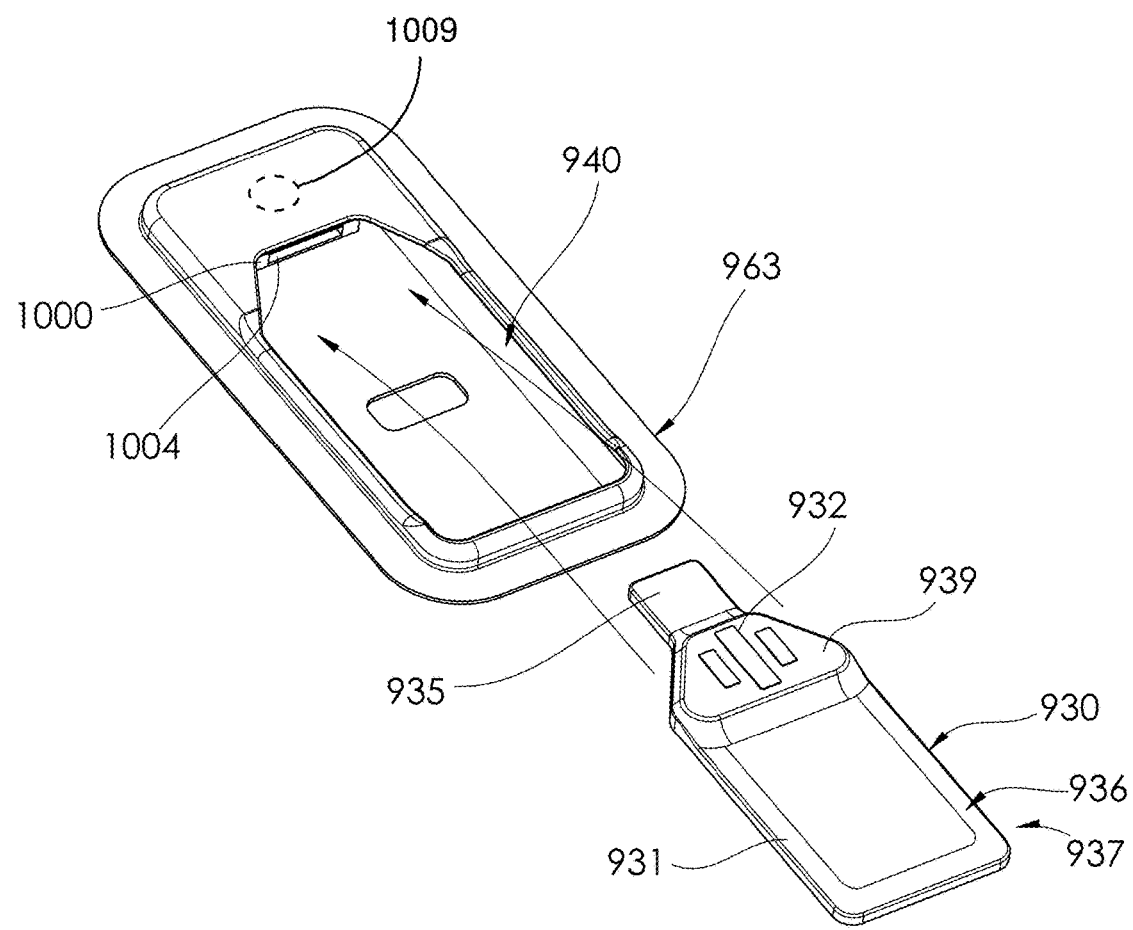
FIG. 106 is a bottom perspective view of the housing of FIG. 102 and the module of FIG. 60 being inserted into the housing.

In the embodiment of FIGS. 104-105, the input device 1000 forms a part of the housing 963 or forms part of a unitary structure with the housing 963. The input device 1000 in this embodiment forms an end of the housing 963 proximate the narrowed portion 965 of the opening 942, and has an outer shape and contour that are substantially contiguous with those of the housing 963. As shown in FIGS. 104-105, the input device 1000 has a flange 967 that is continuous with the flange 967 of the housing 963. The input device 1000 joins with the housing 963, and the housing 963 has an open end 1006 adjacent the input device 1000 in communication with the pocket 940, such that the port 1004 of the input device 1000 is placed in communication with the pocket 940 defined by the housing 963. In this configuration, the connector 935 of the module 930 is received within the port 1004 when the module 930 is inserted into the housing 963, as shown schematically in FIG. 106. The input device 1000 may be permanently connected within the housing 963 in one embodiment, or may be removably connected within the housing 963 in another embodiment, for example, by using one of the permanent or removable connection techniques described elsewhere herein. In this embodiment, the button(s) 1001 may be positioned on the outer surface of the input device 1000, as shown in FIG. 105.

Figure 107:
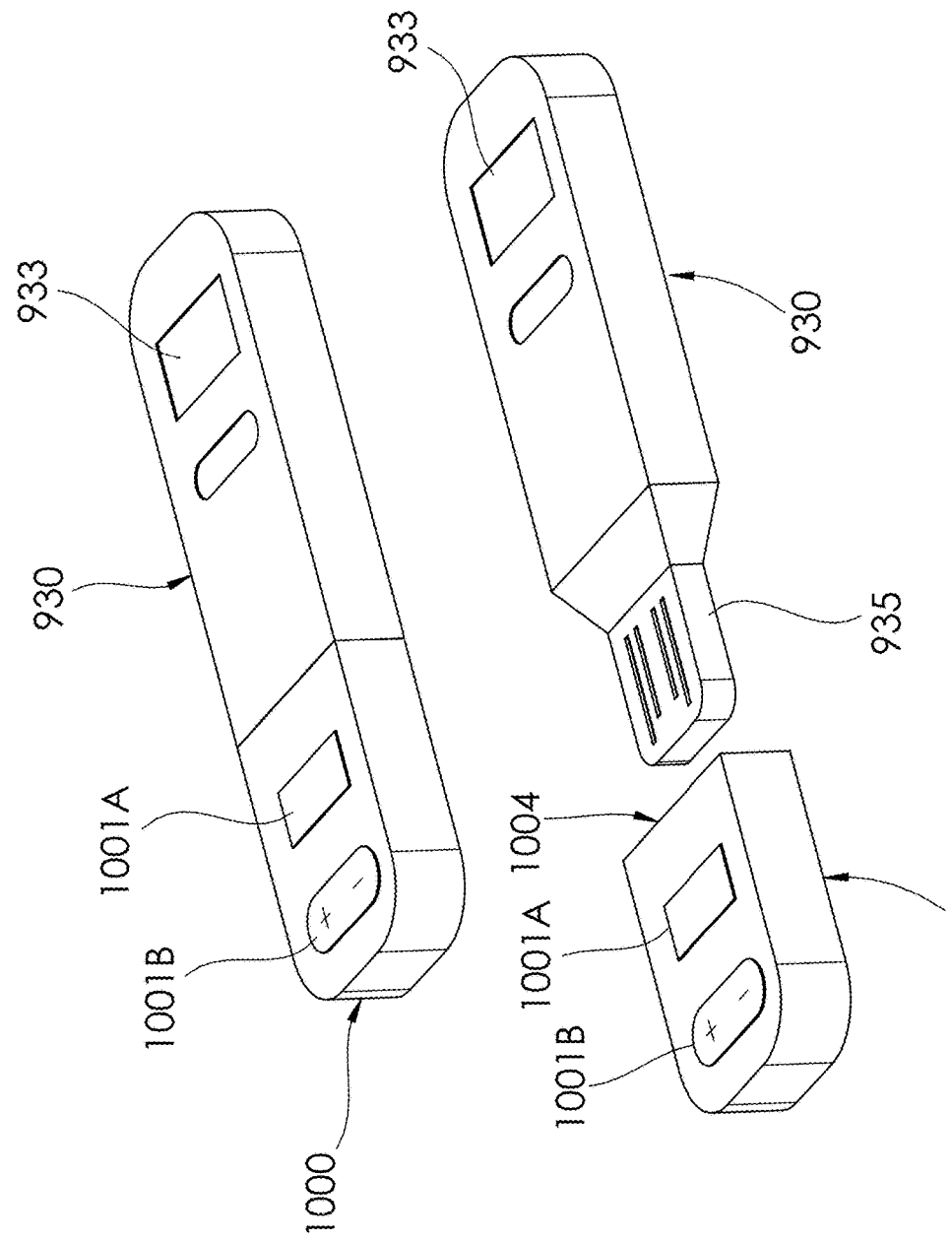
FIG. 107 is a perspective view and an exploded perspective view of another embodiment of an additional input device and a module according to aspects of the disclosure, showing a connection between the additional input device and the module.
Figure 108:
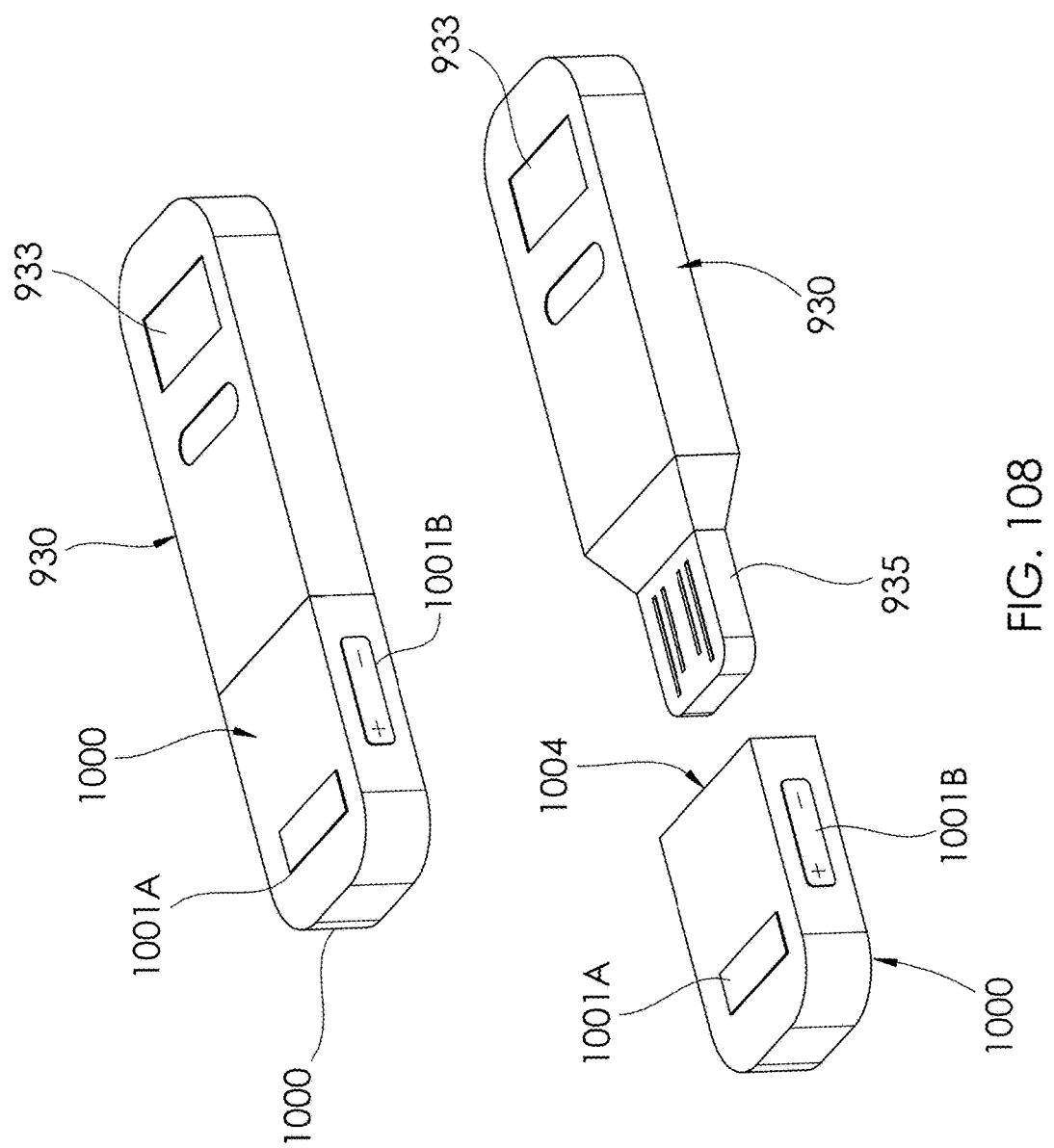
FIG. 108 is a perspective view and an exploded perspective view of another embodiment of an additional input device and a module according to aspects of the disclosure, showing a connection between the additional input device and the module.
Figure 109:
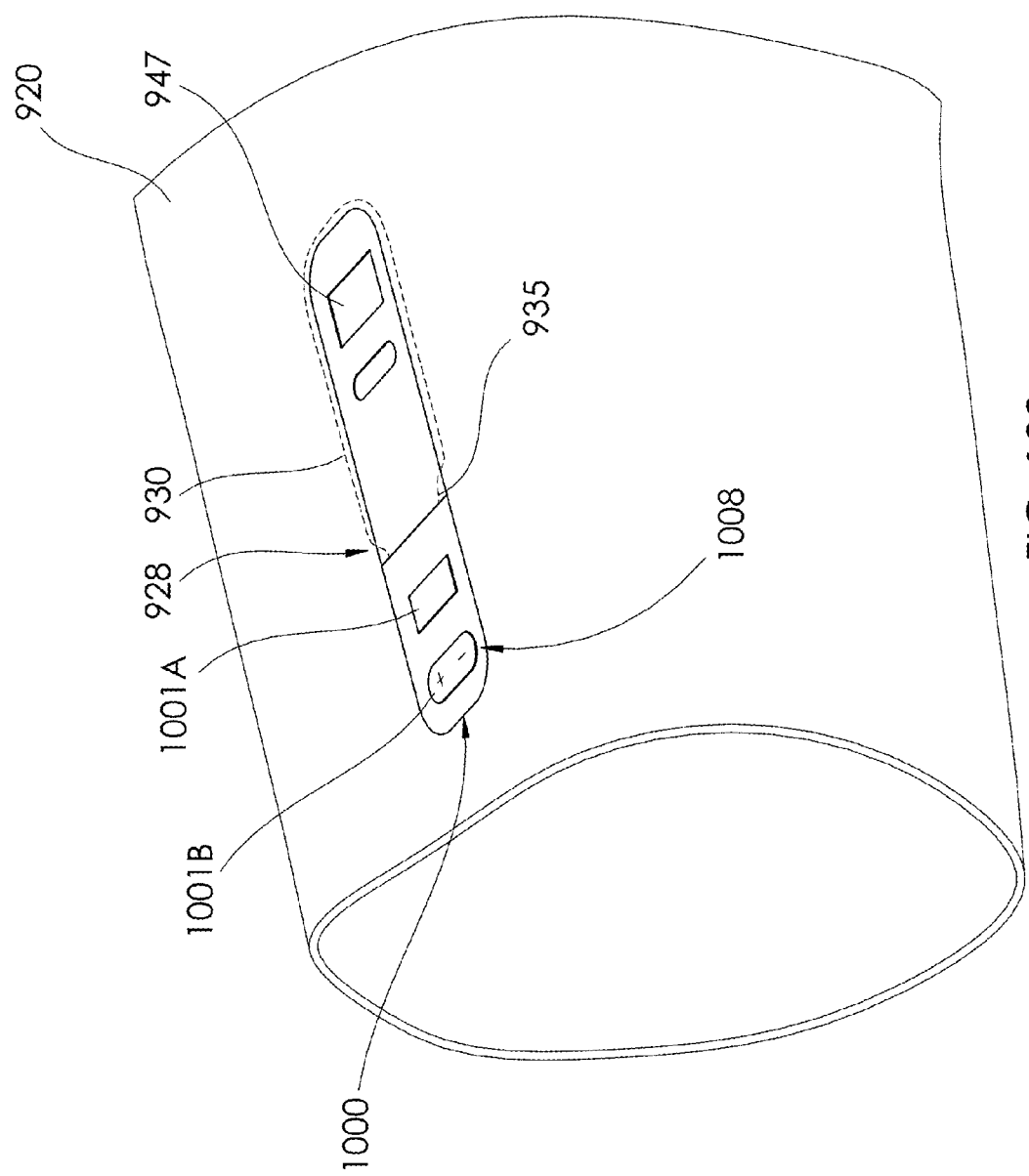
FIG. 109 is a perspective view of one embodiment of a band having an additional input device connected to the band, according to aspects of the disclosure.
Figure 110:
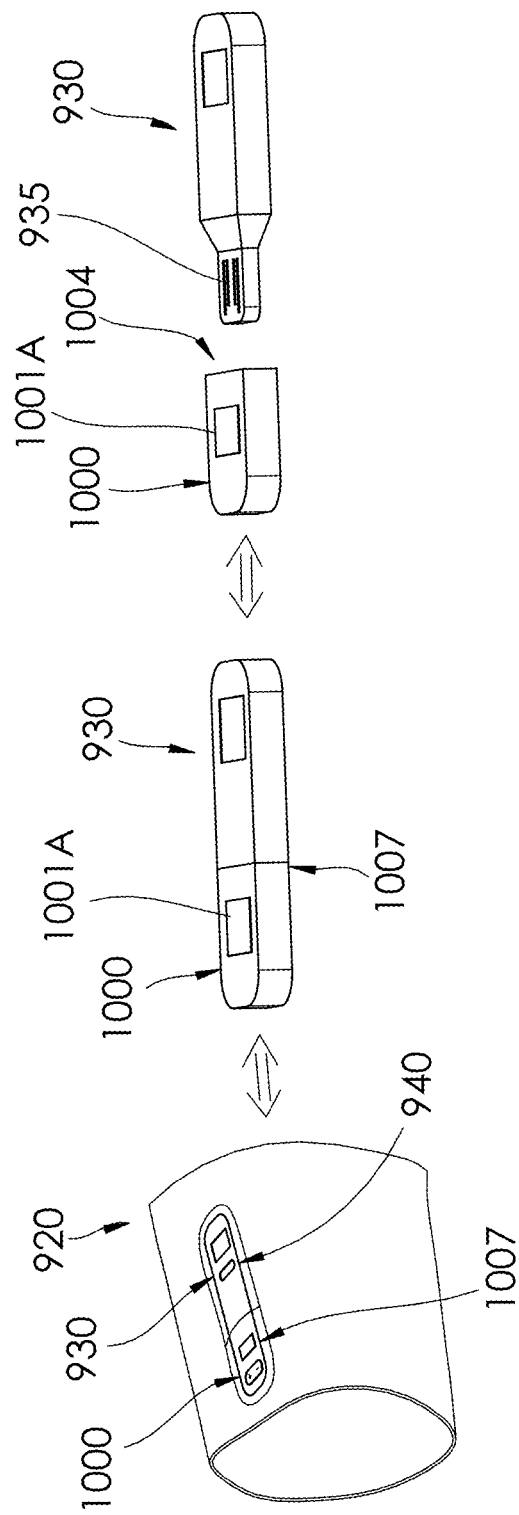
FIG. 110 is a schematic perspective view of another embodiment of a module, an additional input device, and a band according to aspects of the disclosure, showing the module being connected to the additional input device and then being connected to the band.

In the embodiments of FIGS. 107-108, the input device 1000 is a separate device that is configured for insertion into and removal from the housing 963 and the pocket 940 along with the module 930. The input device 1000 in each of these embodiments is in the form of a casing that is connected to the module 930 by inserting the connector 935 of the module 930 into the port 1004 outside the housing 963, and then inserting the module 930 and the input device 1000 simultaneously into the housing 963. Once inserted, the input device 1000 is positioned within the end of the housing 963, proximate the narrowed portion 965 of the opening 942, similar to the position shown in FIG. 102. Connection of the module 930 to the input device 1000 to form a connected structure 1007 and insertion of the connected structure 1007 into the pocket 940 defined by the housing 963 is shown schematically in FIG. 110. The input device 1000 of FIG. 107 differs from the input device 1000 of FIG. 108 primarily in the location of the volume control button 1001B, which is located on the top surface of the input device 1000 in the embodiment of FIG. 107 and is located on the side surface of the input device 1000 in the embodiment of FIG. 108. It is understood that the housing 963 and/or the band 920 may be configured for use with either of the input devices 1000 of FIGS. 107-108, such as by effective location of features for operating the button(s) 1001, including openings 1005, protrusions 987, indicia 1008, etc.

The input devices 1000 in FIGS. 102-110 are shown and described as being usable in connection with a band 920 as illustrated in FIGS. 68-70C and manufactured as illustrated in FIGS. 71-91. In other embodiments, the various embodiments of input devices 1000 described herein may be utilized with other embodiments of bands 920 as described herein, for example, the bands 920 shown in FIGS. 39A-B and manufactured as shown in FIGS. 18-38. It is understood that the input device 1000 and/or the band 920 may be modified to provide suitable functionality for such a combination.

As described above, the input device 1000 is configured for communication with an external device 1002 through the transmitter 1003, as shown in FIG. 111. The external device 1002 may include any components of the computer device 200 described above, and may be a mobile phone or other mobile device that can be carried by or positioned near a user during physical activity. As also described above, the input device 1000 may be configured to transmit signals to the external device with button input indicating the activation of the button(s) 1001, which includes the sequence and/or length of the button press(es) 1001. The external device 1002 may include software configured to receive the button input as input and take further action based on the button input. For example, the software on the external device 1002 may interpret specific sequences of button 1001 presses (e.g., a single, double, or triple-tap) as different input signals, and/or may interpret long-hold button 1001 presses as different from button taps. Further, the external device 1002 can be programmed to interpret and use the button input as different inputs for different purposes, and the device 1002 may include various preprogrammed and/or user-selected settings governing the interpretation of the button input. The external device 1002 may include various applications and functionality that are controlled and/or influenced by the button input, according to the settings.

The input device 1000 may be in communication with multiple external devices 1002, either simultaneously or alternatively, and the module 930 may be in communication with the input device 1000 and/or the external device 1002. The input device 1000 and/or the external device 1002 may also be in communication with an external camera 1008, such as a body-mounted camera that may be capable of video and/or still photo capture. The camera 1008 may be controlled directly by input from the input device 1000, or the button input may be used by the external device 1002 as instructions for controlling the camera 1008. The input device 1000 and/or the external device 1002 may also be in communication with one or more assemblies such as the assemblies 400, 304 shown in FIGS. 4-5 and described herein, for collection and/or communication of additional data. It is understood that the external device 1002 may receive button input from a different type of input device, for example, the module 930, an assembly 400 as shown in FIG. 4 or other wearable assembly (e.g., a smart watch), and that the methods, functions, and operation of the external device 1002 as described herein are not limited to use with an input device 1000 according to the embodiments described herein. For example, the functions and applications described below may be operated by the external device 1002 without input from the input device 1000 or any other input device. Still further, it is understood that some processing of information performed by the external device 1002 may include sending the information to another device (e.g., a server) for processing and receiving further information from the other device.

Figure 112:
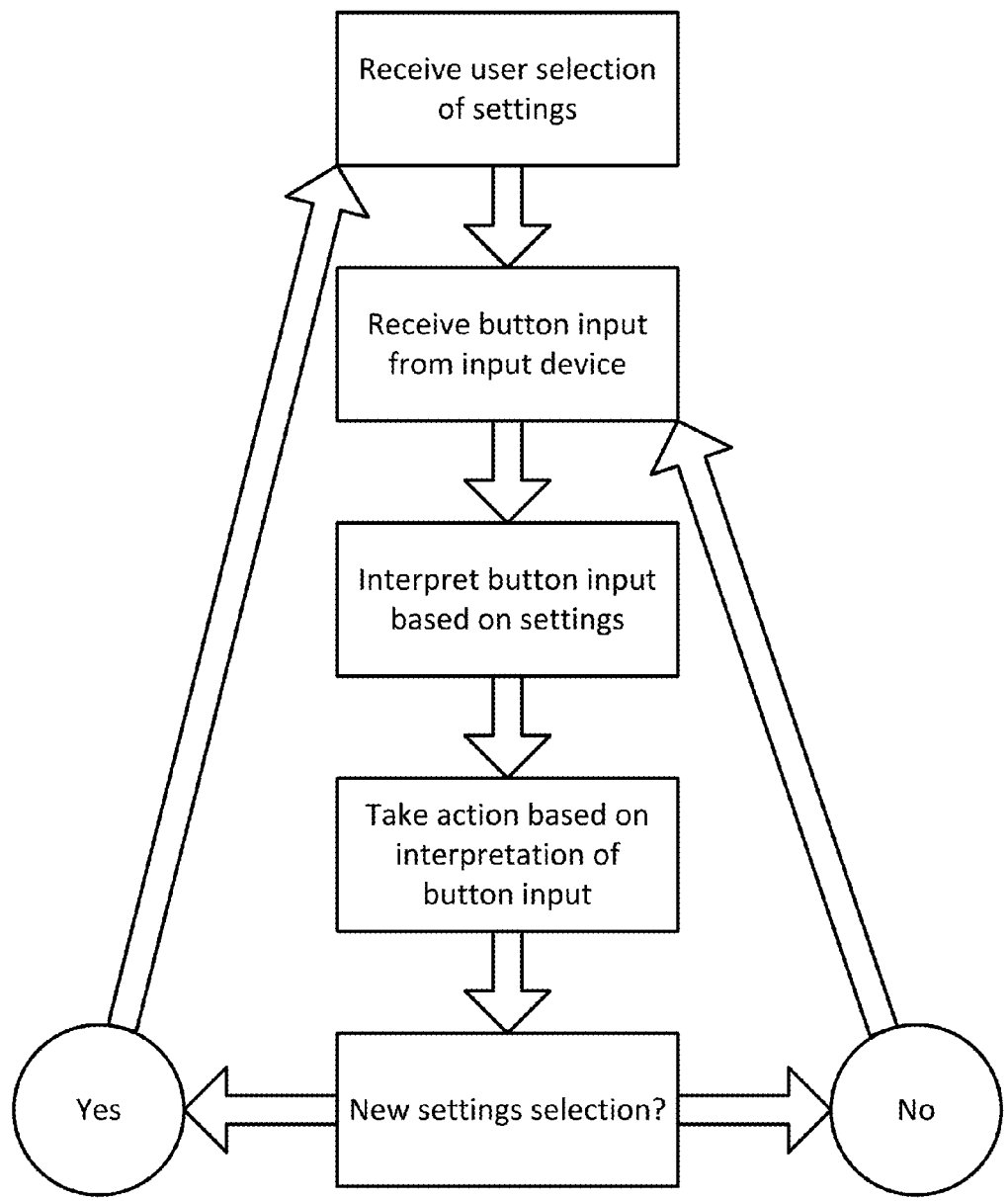
FIG. 112 is a flowchart showing one embodiment of a method of operation that can be used in connection with an external device and an additional input device according to aspects of the disclosure.

In one embodiment, the external device 1002 may operate as illustrated in FIG. 112. In this method of operation, the external device 1002 receives selection of one of a plurality of settings from the user, governing the functioning of the device 1002, such as through a user input of the device 1002, or through a specific sequence of button presses from the input device 1000. The settings may include one or more specific applications to operate as well. The external device 1002 then receives the button input from the input device 1000. The external device 1002 can then interpret the button input based on the settings selection and take one or more actions based on the interpretation of the button input. A non-exhaustive list of examples of actions that may be taken based on the button input includes: storing or deleting information; sending a signal to one or more other devices; initiating, answering, or ending a phone call; sending a text, picture, or video message; posting information to a website, social media outlet, blog, RSS feed, etc.; sharing information with a specified group of people and/or other devices; transmitting a location signal; controlling music and/or video being played by the external device 1002; controlling a camera associated with the external device 1002, including an integral camera of the external device 1002 or an external camera 1008; interacting with the module 930; transmitting data received from the module 930; powering the external device 1002 and/or the input device 1000 on or off; as well as other functions. After taking the action, the external device 1002 may continue to function using the same settings or may receive selection of other settings. Using the input device 1000 to transmit input to the external device 1002 may permit the user to control the external device 1002 without directly accessing the device 1002, or even if the device 1002 is not in the user's immediate possession (e.g., located in a gym bag on the bench during a sporting event). This greatly improves the versatility of the use of the external device 1002, as well as other components such as the camera 1008 and the module 930, which may be difficult or impossible to operate directly during certain physical activities.

Phone

One potential application or function that the external device 1002 may use in connection with the input device 1000 is operation of a telephone, such as a phone that is integrated within the external device 1002. For example, the button input may be used to place a call to a pre-selected number, answer an incoming call, switch to a held call, end a call, activate/deactivate speakerphone, change volume, and other functions. This enables the telephone to be operated without directly accessing the external device 1002, which may be difficult or clumsy during physical activity. A wireless headset or earpiece may be used in connection with the telephone as well. In one embodiment, the input device 1000 may include a dedicated button for volume control (button 1001B as described above), which may be used with a phone. The telephone operation may be used in connection with other functions or applications, such as the safety application(s) discussed herein. It is understood that the pre-selected phone number for a call, as well as the various control functions of the telephone with respect to the input device 1000, can be controlled by user settings.

Music

Another potential application or function that the external device 1002 may use in connection with the input device 1000 is operation of a music or video player, such as a music or video player that is integrated within the external device 1002 or controlled by the external device 1002. The button input may be used for functions such as play, pause, skip, repeat, forward, rewind, power on/off, selection of a specific song to play or a specific video or photograph to display, and volume control, among others. In one embodiment, the input device 1000 may include a dedicated button for volume control (button 1001B as described above), which may be used with a music or video player, or in another embodiment, sequences of the main button 1001A may control such features. It is understood that the pre-selected specific song, as well as the various control functions of the music or video player with respect to the input device 1000, can be controlled by user settings.

Camera

Another potential application or function that the external device 1002 may use in connection with the input device 1000 is operation of a music or video player, such as a music or video player that is integrated within the external device 1002 or controlled by the external device 1002. The button input may be used for functions such as taking a photo, series of photos, or video; transmitting, uploading, and/or sharing a photo or video; controlling camera or media settings such as exposure, sensitivity, filters, or video recording speed; and other functions. The camera operation may be used in connection with other functions or applications, such as the safety application(s) discussed herein. For example, the external device 1002 may be configured to activate the camera 1008 any time a safety issue is indicated, or when unexpected stops are detected along a running route, for safety and/or sharing purposes. It is understood that the various control functions of the camera with respect to the input device 1000 can be controlled by user settings.

Mapping

Another potential application or function that the external device 1002 may use in connection with the input device 1000 is operation of mapping features and/or applications of the external device. The button input may be used for functions such as accessing a map, setting a destination or waypoint, storing or transmitting a current location, finding the location of another user or device, or various other controls. The mapping operation may be used in connection with other functions or applications, such as the safety application(s) discussed herein. It is understood that the various control functions of the mapping features with respect to the input device 1000 can be controlled by user settings.

Activity Tracking and Sharing

Another potential application or function that the external device 1002 may use in connection with the input device 1000 is an activity tracking and/or sharing application, where users can share activity information with others, such as sharing among members of a designated group. Examples of such activity information include activity session information, photographs, text posts, locations, as well as other types of information. The button(s) 1001 can be used to quickly share information with others. For example, various button sequences may be used for tracking functions such as beginning or ending activity tracking, marking desired temporal points or locations during activity, switching from tracking one type of activity to another, displaying activity information on the external device 1002, or other functions; and various button sequences may also be used for sharing functions such as sharing activity session data, taking or sharing a photo or video, sharing a current location, detecting another user's location, or sending a pre-programmed text message to specified persons (e.g., "I'm starting/finishing my run"). It is understood that the content of such a pre-programmed message, as well as the various control functions of the application with respect to the input device 1000, can be controlled by user settings.

In one embodiment, the external device 1002 can obtain activity information shared by another user (e.g., one or more other runners), such as the location and speed of the other user(s), a planned running route, or other information, and then display and/or further process this information. Such further processing may include calculating a pace and/or a shortcut for the user to catch up to the other user, planning a route to meet the other user, transmitting the user's own information to the other user, etc. For example, if the user arrives late to an organized group run with a pre-planned route, the device 1002 can plot a route and pace for the user to catch up to the other runner(s) based on the pre-planned route and the other runner's position and speed. As another example, if a user has a friend competing in a large race, the device 1002 can locate the friend and set a pace for the user to catch the friend, based on the race route and the friend's location and speed. As a further example, the device 1002 could send a message to the other runner(s) in the previous examples to reduce their pace and/or take another route to facilitate the user catching up. Plotting of routes as described above may further incorporate safety features as described herein, such as by plotting routes that avoid known or suspected safety hazards based on safety information.

Figure 113:
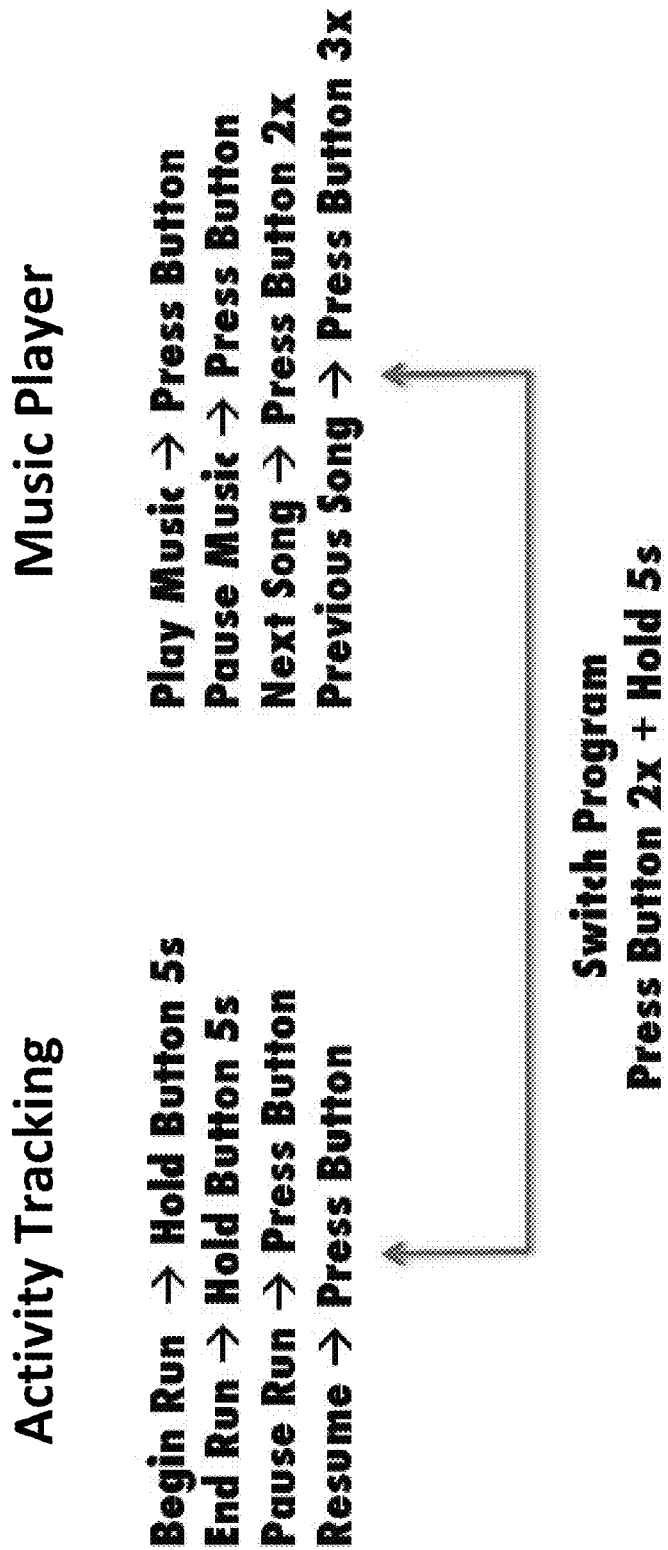
FIG. 113 is a flowchart showing another embodiment of a method of operation that can be used in connection with an external device and an additional input device according to aspects of the disclosure.

In another embodiment, the external device 1002 may combine the activity tracking and music player applications together, allowing the user to control both applications and switch between the two applications using only the input device 1000. FIG. 113 illustrates one example of a control scheme for controlling and switching between these two applications using the main button 1001A on the input device 1000. It is understood that the control scheme in FIG. 113 switches between control of these two applications, but that switching need not deactivate the de-selected application unless desired by the user. Other control schemes could be used in other embodiments, and the control scheme may be at least partially dictated by user-controlled settings. Control schemes similar to the example in FIG. 113 could be used in connection with other applications and functions of the external device 1002, for simultaneously controlling two or more different applications or functions and switching between such applications or functions, using the input device 1000.

In a further embodiment, the activity tracking application may include an activity selection setting, which permits the user to select an activity from the list, such that the device 1002 operates differently for different activity selections. For example, the device 1002 may have one set of user settings for interpreting button input for one activity and another set of user settings for interpreting button input for a different activity. As another example, the device 1002 and/or the module 930 may collect and interpret movement data differently based on different activity selections. As a further example, the device 1002 may instruct the input device 1000 to provide different types of haptic feedback for different purposes based on the activity selection. Other example selections may be used as well.

Safety Alert

Another potential application or function that the external device 1002 may use in connection with the input device 1000 is a safety alert application, which can alert others of potential safety concerns, such as attacks, accidents, crimes, fires, etc. In one embodiment, the external device 1002 may be programmed to contact others when signaled to do so by the input device 1000, such as alerting friends and/or family, alerting police or emergency services, etc. For example, specific button press sequences on the input device may control the device 1002 to send a pre-programmed text or other message (e.g., a call for help), transmit the user's location, initiate a phone call to a pre-selected recipient, transmitting and/or storing information regarding safety concerns, initiating an audible alarm (e.g., through speakers on the external device 1002), take a photo or video with the camera 1008, or other functions. An audible alarm may include a siren or other alert sound, music from a music player, or other audible alarm, and the device 1002 may automatically deactivate any headphones or similar equipment upon sounding the alarm. As one specific example, one button sequence may automatically share the user's location with others, and another button sequence may share the user's location with an indication of a safety issue, while a third button sequence may generate an emergency alert. It is understood that the various control functions of the application with respect to the input device 1000, including the identities of emergency contacts and the content of any automated messages, can be controlled by user settings.

In one embodiment, the devices 1000, 1002 may be used as part of a group or network of users to share safety information. For example, a user's device 1002 may share intended running information (e.g., intended distance, time of run, start and end points, etc.) with a designated group, to give the group a general idea of where the user will be at a specific time of day, in case a safety issue arises. A specific intended route may be shared as well. The device 1002 may also periodically send position updates to the group, which position updates can be performed automatically on a periodic basis, upon indication from the user (e.g., through the input device 1000), or upon detection that movement has changed (e.g., a stop or pause in running). Such a group may be configured to share all safety information with each other, and may be set up in advance as a temporary or persistent group. As another example, the external device 1002 may be configured to send emergency alerts or safety information to others in the group. As another example, the external device 1002 may be configured to take specified actions when an emergency alert is received from another user, such as automatically answering an emergency phone call or activating an audible alarm. In one embodiment, if another designated user sends out an emergency alert SMS message, the external device 1002 may be programmed to automatically answer any call from the other user within a specific time period following the alert message, or at any time until the other user sends a subsequent alert deactivation message. As a further example, the external device 1002 may be configured to alert the user when the user is in or approaching a potential hazard identified by another user in the network.

In another embodiment, the devices 1000, 1002 may be used as part of a safety information system. The safety information system may be operated in a network environment, which may include one or more servers and a number of other electronic devices. Communications through the safety information system may be made through a server or directly between devices. The system may collect and provide various types of safety information. For example, the safety information system can collect user-generated safety information from a plurality of different users/devices, including the external device 1002. Such safety information may include the locations and times of emergency alerts, locations and times of other potential safety issues, and gathered qualitative safety information. It is understood that the safety information may include positive safety information as well as negative safety information. Examples of different types of qualitative safety information include: areas where suspicious persons are known to congregate, areas that are isolated or desolate, areas with few or no street lights, areas with no sidewalks, popular pedestrian routes, areas that "feel" unsafe to the user, areas that frequently flood after rains, and other types of qualitative information. The qualitative information may include some quantitative component as well, such as a "danger" rating on a quantitative scale. The safety information may also include crime maps, which may be publicly accessible and/or privately generated based on crime data aggregation. The safety information may be categorized by location, time of day, whether a safety issue is temporary or persistent, type of safety issue (e.g., crime, fire, suspected threat, weather or environmental hazard, wildlife, etc.), quantitative danger rating, and other categorizations.

Figure 114:
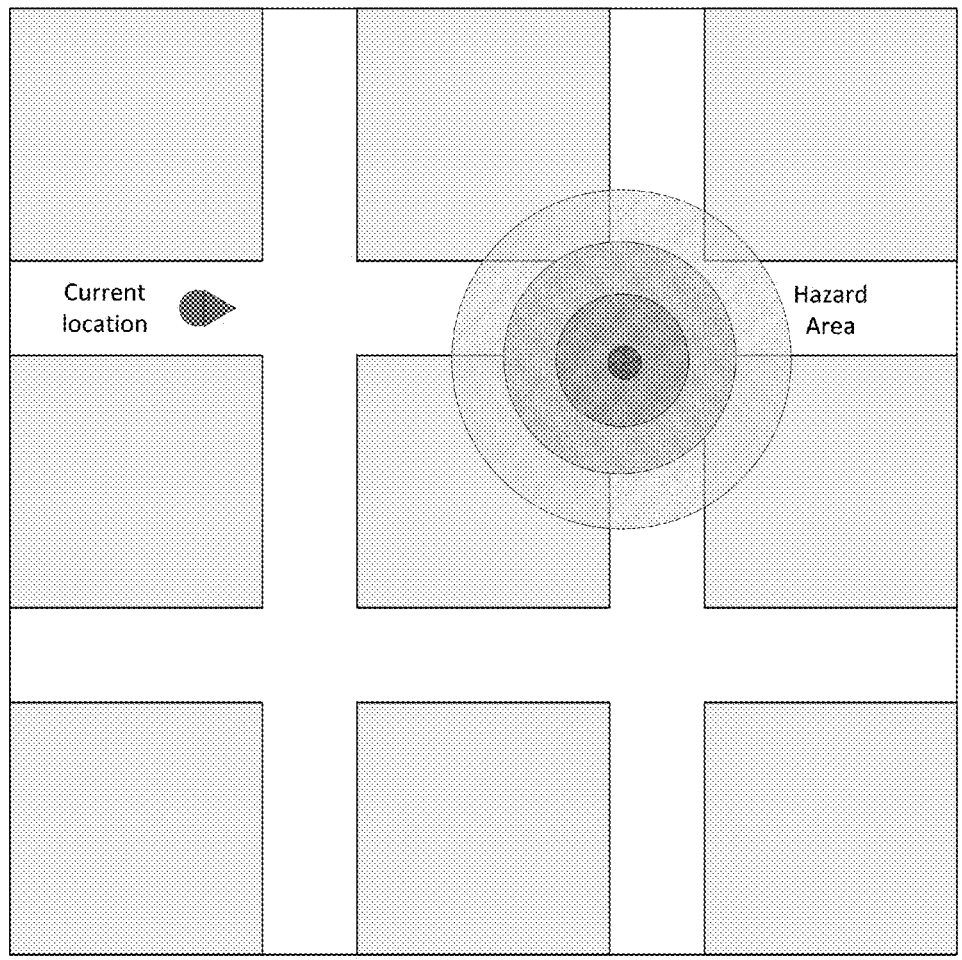
FIG. 114 illustrates one embodiment of a display of an external device being operated in conjunction with an additional input device according to aspects of the disclosure.
Figure 115:
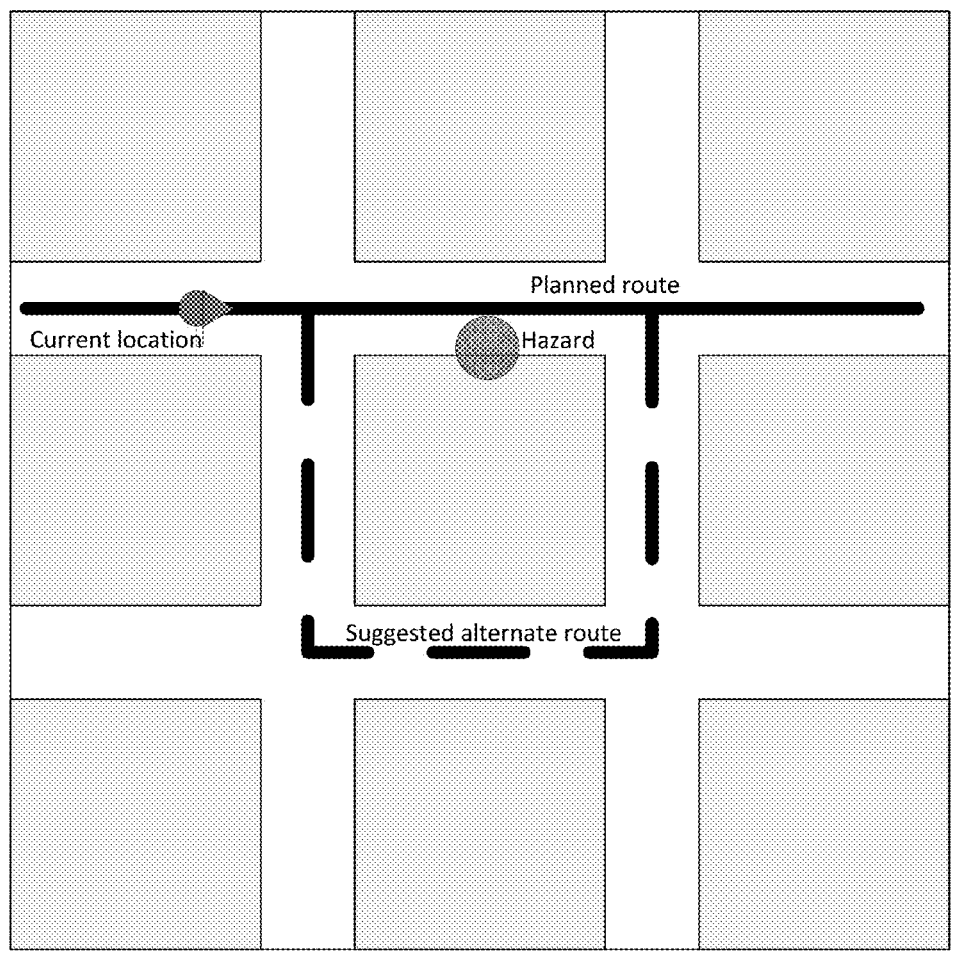
FIG. 115 illustrates another embodiment of a display of an external device being operated in conjunction with an additional input device according to aspects of the disclosure.

The safety information system may present or provide the safety information in a number of different ways. As one example, the device 1002 may generate an indication of a safety alert that has recently been generated by another user in the current area or along a planned route. As another example, the device 1002 may generate an indication that historical or aggregated safety information indicates that the present area, the area of a planned route, or the area the user is approaching includes a potential safety issue. FIG. 114 illustrates one example of a display on the external device 1002 indicating a potential safety hazard in an area near the user's location. An indication of a safety issue may factor in the current time or the time the user is expected to enter the area, if the safety issue is time-dependent, such as a recently-occurring event or a time of day when the safety issue is known or thought to exist based on historical information. An indication of a safety issue may also factor in a specific size of the relevant area (e.g., a radius around the user and/or around the safety issue). As another example, the device 1002 may generate a suggested action in response to a safety issue, such as turning around, suggesting an alternate route, taking cover, etc. Such suggested actions may be based on the nature of the safety issue, calculations performed by the device 1002 (e.g., alternate routes), public emergency notices (e.g., severe weather warnings), and other information. FIG. 115 illustrates one example of a display of the external device 1002 suggesting an alternate route to the user to avoid a safety hazard.

Route Recommendations

Another potential application or function that the external device 1002 may use in connection with the input device 1000 is a running route recommendation application, where the device 1002 can recommend running routes to the user based on various information including desired running location, desired start or end points, desired length of run, desired time of day of the run, safety information (as described above), other user-generated information such as route quality ratings (scenery, difficulty or ease of run, etc.), and other factors. In one embodiment, the user may input the desired run information into the device 1002, and the device generates a running route that conforms to the run information and avoids safety issues as discussed above. The device 1002 may dynamically alter the running route in progress based on new safety information, as also described above. The user may be able to share any information about the run with other users during or after a run as well, including safety information and route quality ratings or comments, which may be used by the device 1002 and/or other users' devices in generating future running routes. It is understood that the various control functions of the route recommendation application with respect to the input device 1000 can be controlled by user settings.

The route recommendation function of the devices 1000, 1002 can also be used in connection with a larger route recommendation system and network. The system may aggregate information from various users regarding specific running routes and use that information to generate future running routes based on user-defined criteria. For example, the system may make safety information and route quality ratings or comments available to users and their devices 1002. As another example, the system may develop and/or store "recommended" running routes in a specific area, and users who run the recommended routes can generate information regarding the route, such as safety and/or quality information. It is understood that such user-generated information may have a time-of-day component as well, such as safety issues that exist only at certain times of day or increased/decreased run quality at specific times of day. Thus, a route may only be recommended for specific times of day, or different quality/safety ratings for different times of day may be made available to the user. The system may further be configured to use only selected safety and/or quality information when providing a recommended route or when making such information available to the user, such as information of a certain category or quantitative/qualitative rating, or information generated by specific other users (e.g., a user's friends, other users with similar interests and preferences, other users of a specific gender, etc.). The system may alternately be configured to weigh such selected safety/quality information more or less heavily when providing a recommended route. For example, female users may desire route recommendations based on safety information generated by other female users, or runners who enjoy scenic routes may desire route recommendations based on quality information from other users with similar preferences.

Anti-Theft

Another potential application or function that the external device 1002 may use in connection with the input device 1000 is an anti-theft application, which can be used in the event of a theft or attempted theft of the external device 1002. For example, different button sequences on the input device 1000 may generate an alarm in the event of a theft attempt, lock the device 1002 to prevent access by others, generate an alert to law enforcement with a location of the device 1002, prevent powering off or deactivation of the device, or other anti-theft measures. It is understood that the various control functions of the anti-theft function with respect to the input device 1000 can be controlled by user settings.

The systems and networks described above, such as the safety information system, the route recommendation system, and emergency alerts, may access or communicate with other existing systems in connection with providing functionality. For example, such systems may exchange information with a public or private emergency service, such as gathering safety information from such services and/or transmitting emergency alerts to such services. Other examples of such cooperative information sharing may be used as well.

The various embodiments of athletic bands and other articles of apparel, housings, and modules described herein provide benefits over existing technology. For example, the configuration of the module and the pocket in which it is received can operate to place physiological sensors in close proximity to the user's skin, which can enhance the ability of such sensors to capture physiological data of the user. As another example, the structures of the band and/or housing described herein can control stretching of the elastic material in order to make pulling the band on and off an appendage quicker and easier; assist in preventing slippage of the band during use; facilitate moisture passage away from the electronic module during use; and increase durability and washability of the band, among other benefits described herein and/or recognized by those skilled in the art. As a further example, the additional input device as described herein provides enhanced ability for communication and interaction with an external device, as well as a simple interface for on-the-go operation of and communication with such an external device by an athlete in the middle of a competition or other athletic event. The various embodiments of manufacturing methods described herein also provide benefits over existing technology. For example, the manufacturing methods for the band as described herein create a durable structure that is efficient to produce. The various methods for operation of the module, the input device, and the external device described herein can enhance the performance monitoring operation of the module and provide enhanced functionality for a user in connection with use of the band and module. Still further benefits are recognizable by those skilled in the art.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. Terms such as "first," "second," "top," "bottom," etc., as used herein, are intended for illustrative purposes only and do not limit the embodiments in any way. Additionally, the term "plurality," as used herein, indicates any number greater than one, either disjunctively or conjunctively, as necessary, up to an infinite number. Further, "providing" an article or apparatus, as used herein, refers broadly to making the article available or accessible for future actions to be performed on the article and does not connote that the party providing the article has manufactured, produced, or supplied the article or that the party providing the article has ownership or control of the article. Accordingly, while specific embodiments have been illustrated and described, numerous modifications come to mind without significantly departing from the spirit of the invention.

What is claimed is:

1. A method comprising:
providing a main body piece formed of an elastic fabric material, the main body piece having a first portion having a first end, a second portion having a second end opposite the first end, and two side ends extending between the first and second ends;
placing a bonding material in contact with at least one of the first and second portions, wherein the bonding material is arranged in a plurality of lines extending in a first direction between the first and second ends, wherein the lines are spaced from each other in a second direction extending between the side ends;
folding the main body piece by moving the first and second ends together to define a folded main body piece, such that the first portion confronts the second portion, defining a fold line between the first and second portions, wherein the bonding material contacts the first and second portions and is positioned between the first and second portions;
heat pressing the folded main body piece to seal the bonding material between the first and second portions;
bending the folded main body piece and connecting the side ends together to form a band having a tubular body defining a central passage extending in an axial direction, wherein the band is configured to be worn on a user's body such that a portion of the user's body is received in the central passage, wherein the lines of the bonding material in the band extend in the axial direction; and
placing a plug between the first and second portions during the heat pressing, such that the plug defines a pocket connected to the band and having an access opening configured to receive an electronic module therein.

2. The method of claim 1, wherein the main body piece has a hole through the first portion, and wherein the hole defines the access opening.

3. The method of claim 2, wherein the main body piece is folded such that the first portion forms an inner surface of the band, and wherein the access opening is located on the inner surface of the band.

4. The method of claim 3, wherein the main body piece has a second hole through the first portion, and wherein the second hole defines a sensor opening in the pocket on the inner surface of the band, the sensor opening configured to permit a sensor permit a sensor of the electronic module to be placed in close proximity to skin of the user's body.

5. The method of claim 2, wherein the main body piece has a second hole through the second portion, wherein the second hole defines a display hole in an outer surface of the band configured to permit viewing a display of the electronic module through the second portion.

6. The method of claim 1, further comprising placing an additional piece of the elastic fabric material in contact with one of the first and second portions to further define the pocket of the band.

7. The method of claim 6, wherein the additional piece of the elastic fabric material comprises a trim piece positioned on an exterior surface of the folded main body piece and extending around the pocket, the additional piece further having a tongue connected to the trim piece and extending from the trim piece into the access opening.

8. The method of claim 1, further comprising placing a plurality of additional pieces of the elastic fabric material in contact with at least one of the first and second portions to further define the pocket of the band.

9. The method of claim 1, wherein each of the lines of bonding material is a broken line comprising a plurality of line segments separated by a plurality of gaps.

10. The method of claim 9, wherein the gaps of a first line are offset from the gaps of a second line adjacent to the first line, such that the gaps of the first line are aligned with the line segments of the second line, and the gaps of the second line are aligned with the line segments of the first line.

11. The method of claim 9, wherein the gaps in each line are staggered with respect to the gaps in each adjacent line.

12. The method of claim 1, wherein the lines are curved.

13. The method of claim 1, wherein the lines are straight.

14. The method of claim 1, further comprising applying a graphic to an outer surface of the band.

15. The method of claim 1, wherein the side ends are cut in an angular shape before the side ends are connected together, such that the band has a varying width.

16. The method of claim 1, wherein a first trim strip is connected to the band to cover the first and second ends, and a second trim strip is connected to the band to cover the side ends.

17. A method comprising:
providing a main body piece formed of an elastic fabric material, the main body piece having a first portion having a first end and a second portion having a second end opposite the first end and two side ends extending between the first and second ends, wherein the main body piece has a hole through the first portion;
placing a bonding material in contact with at least one of the first and second portions, wherein the bonding material is arranged in a plurality of lines extending in a first direction between the first and second ends, wherein the lines are spaced from each other in a second direction extending between the side ends, and wherein each of the lines of bonding material is a broken line comprising a plurality of line segments separated by a plurality of gaps;
folding the main body piece by moving the first and second ends together to define a folded main body piece, such that the first portion confronts the second portion, defining a fold line between the first and second portions, wherein the bonding material contacts the first and second portions and is positioned between the first and second portions, and wherein a first trim strip is connected to the folded main body piece to cover the first and second ends;
heat pressing the folded main body piece to seal the bonding material between the first and second portions, the heat pressing comprising placing a plug between the first and second portions during the heat pressing and pressing the folded main body piece between opposed dies, such that the plug defines a pocket connected to the folded main body piece and the hole defines an access opening on the inner surface of the folded main body piece configured to receive an electronic module therein; and
bending the folded main body piece and connecting the side ends together to form a band having a tubular body defining a central passage extending in an axial direction, wherein the first portion forms an inner surface of the band, such that the access opening is positioned on the inner surface, wherein a second trim strip is connected to the band to cover the side ends, wherein the band is configured to be worn on a user's body such that a portion of the user's body is received in the central passage, wherein the lines of the bonding material in the band extend in the axial direction.

18. The method of claim 17, wherein the main body piece has a second hole through the first portion, and wherein the second hole defines a sensor opening in the pocket on the inner surface of the band, the sensor opening configured to permit a sensor permit a sensor of the electronic module to be placed in close proximity to skin of the user's body.

19. A method comprising:
providing a main body piece formed of an elastic fabric material, the main body piece having a first portion having a first end and a second portion having a second end opposite the first end and two side ends extending between the first and second ends, the main body piece having a hole through the first portion;
placing a housing in contact with the main body piece, the housing being made from a polymer material having a rigidity greater than the elastic fabric material, the housing defining a cavity and having an access opening permitting access to the cavity;
folding the main body piece by moving the first and second ends together and connecting the first and second ends together to define a folded main body piece, such that the first portion confronts the second portion, defining a fold line between the first and second portions, wherein the housing is positioned between the first and second portions and a portion of the housing including the access opening is received in the hole through the first portion, such that the access opening is accessible; and
bending the folded main body piece and connecting the side ends together to form a band having a tubular body defining a central passage extending in an axial direction, wherein the band is configured to be worn on a user's body such that a portion of the user's body is received in the central passage, and wherein the housing defines a pocket that is configured to removably receive an electronic module through the access opening.

20. The method of claim 19, wherein the side ends are cut in an angular shape before the side ends are connected together, such that the band has a varying width.

21. The method of claim 19, wherein a first trim strip is connected to the band to cover the first and second ends, and a second trim strip is connected to the band to cover the side ends.

22. The method of claim 19, wherein the housing has a flange extending outwardly around at least a portion of a periphery of the housing, wherein the flange is positioned between the first and second portions after the main body piece is folded.

23. The method of claim 22, further comprising applying two opposed mold pieces to the folded main body piece to heat press the first and second portions around the flange of the housing.

24. The method of claim 23, further comprising applying a trim piece to the folded main body piece around the hole, wherein the mold pieces heat press the trim piece to the folded main body piece.

25. The method of claim 23, wherein the mold pieces each have an opening so that the mold pieces are configured to press only around the flange.

26. The method of claim 19, wherein the main body piece has a second hole through the second portion, and the housing has a window, wherein the second hole defines a display hole in an outer surface of the band that is aligned with the window and configured to permit viewing a display of the electronic module through the second portion.

27. The method of claim 26, further comprising placing a bonding material between the housing and the second portion around the window to bond the second portion to the housing such that the second hole is aligned with the window.

28. The method of claim 19, further comprising applying a graphic to an outer surface of the band.

29. A method comprising:
  providing a main body piece formed of an elastic fabric material, the main body piece having a first portion having a first end and a second portion having a second end opposite the first end and two side ends extending between the first and second ends, the main body piece having a hole through the first portion;
  placing a housing in contact with the main body piece, the housing being made from a polymer material having a rigidity greater than the elastic fabric material, the housing defining a cavity and having an access opening permitting access to the cavity, the housing further having a flange extending outwardly around at least a portion of a periphery of the housing;
  folding the main body piece by moving the first and second ends together and connecting the first and second ends together to define a folded main body piece, such that the first portion confronts the second portion, defining a fold line between the first and second portions, wherein a first trim strip is connected to the folded main body piece to cover the first and second ends, and wherein the flange of the housing is positioned between the first and second portions and a portion of the housing including the access opening is received in the hole through the first portion, such that the access opening is accessible; and
  bending the folded main body piece and connecting the side ends together to form a band having a tubular body defining a central passage extending in an axial direction, wherein the first portion forms an inner surface of the band, such that the access opening is positioned on the inner surface, wherein a second trim strip is connected to the band to cover the side ends, wherein the band is configured to be worn on a user's body such that a portion of the user's body is received in the central passage, and wherein the housing defines a pocket that is configured to removably receive an electronic module through the access opening.

\* \* \* \* \*